US009840715B1

(12) United States Patent
Deikman et al.

(10) Patent No.: US 9,840,715 B1
(45) Date of Patent: Dec. 12, 2017

(54) METHODS AND COMPOSITIONS FOR DELAYING SENESCENCE AND IMPROVING DISEASE TOLERANCE AND YIELD IN PLANTS

(75) Inventors: Jill Deikman, Davis, CA (US); Steven H. Schwartz, Davis, CA (US); Wei Zheng, Davis, CA (US); Suzan Herma Elisabeth Johanna Gabriels, Wageningen (NL); Michelle C. Hresko, Chesterfield, MO (US); Xiangqian Li, Chesterfield, MO (US); Nengbing Tao, O'Fallon, MO (US); Deryck J. Williams, University City, MO (US); Hui Xiong, Davis, CA (US)

(73) Assignee: Monsanto Technology LLC, St. Louis, MO (US)

( * ) Notice: Subject to any disclaimer, the term of this patent is extended or adjusted under 35 U.S.C. 154(b) by 268 days.

(21) Appl. No.: 13/614,446

(22) Filed: Sep. 13, 2012

Related U.S. Application Data

(60) Provisional application No. 61/534,351, filed on Sep. 13, 2011.

(51) Int. Cl.
C12N 15/113 (2010.01)
C12N 15/82 (2006.01)

(52) U.S. Cl.
CPC ..... *C12N 15/8218* (2013.01); *C12N 15/8266* (2013.01); *C12N 15/8282* (2013.01)

(58) Field of Classification Search
None
See application file for complete search history.

(56) References Cited

U.S. PATENT DOCUMENTS

| | | |
|---|---|---|
| 3,687,808 A | 8/1972 | De et al. |
| 3,850,752 A | 11/1974 | Schuurs et al. |
| 3,935,074 A | 1/1976 | Rubenstein et al. |
| 4,476,301 A | 10/1984 | Imbach et al. |
| 4,535,060 A | 8/1985 | Comai |
| 4,581,847 A | 4/1986 | Hibberd et al. |
| 4,761,373 A | 8/1988 | Anderson et al. |
| 4,769,061 A | 9/1988 | Comai |
| 4,810,648 A | 3/1989 | Stalker |
| 4,940,835 A | 7/1990 | Shah et al. |
| 4,971,908 A | 11/1990 | Kishore et al. |
| 5,004,863 A | 4/1991 | Umbeck |
| 5,013,659 A | 5/1991 | Bedbrook et al. |
| 5,015,580 A | 5/1991 | Christou et al. |
| 5,023,243 A | 6/1991 | Tullis |
| 5,034,506 A | 7/1991 | Summerton et al. |
| 5,094,945 A | 3/1992 | Comai |
| 5,141,870 A | 8/1992 | Bedbrook et al. |
| 5,145,783 A | 9/1992 | Kishore et al. |
| 5,159,135 A | 10/1992 | Umbeck |
| 5,166,315 A | 11/1992 | Summerton et al. |
| 5,177,196 A | 1/1993 | Meyer, Jr. et al. |
| 5,185,444 A | 2/1993 | Summerton et al. |
| 5,188,642 A | 2/1993 | Shah et al. |
| 5,188,897 A | 2/1993 | Suhadolnik et al. |
| 5,192,659 A | 3/1993 | Simons |
| 5,214,134 A | 5/1993 | Weis et al. |
| 5,216,141 A | 6/1993 | Benner |
| 5,235,033 A | 8/1993 | Summerton et al. |
| 5,264,562 A | 11/1993 | Matteucci |
| 5,264,564 A | 11/1993 | Matteucci |
| 5,304,732 A | 4/1994 | Anderson et al. |
| 5,310,667 A | 5/1994 | Eichholtz et al. |
| 5,312,910 A | 5/1994 | Kishore et al. |
| 5,331,107 A | 7/1994 | Anderson et al. |
| 5,378,824 A | 1/1995 | Bedbrook et al. |
| 5,399,676 A | 3/1995 | Froehler |
| 5,405,938 A | 4/1995 | Summerton et al. |
| 5,405,939 A | 4/1995 | Suhadolnik et al. |
| 5,416,011 A | 5/1995 | Hinchee et al. |
| 5,453,496 A | 9/1995 | Caruthers et al. |
| 5,455,233 A | 10/1995 | Spielvogel et al. |
| 5,463,174 A | 10/1995 | Moloney et al. |
| 5,463,175 A | 10/1995 | Barry et al. |
| 5,470,967 A | 11/1995 | Huie et al. |
| 5,476,925 A | 12/1995 | Letsinger et al. |
| 5,489,520 A | 2/1996 | Adams et al. |
| 5,489,677 A | 2/1996 | Sanghvi et al. |
| 5,491,288 A | 2/1996 | Chaubet et al. |
| 5,510,471 A | 4/1996 | Lebrun et al. |
| 5,519,126 A | 5/1996 | Hecht |

(Continued)

FOREIGN PATENT DOCUMENTS

CN 101914540 A 12/2010
EP 1416049 A1 5/2004

(Continued)

OTHER PUBLICATIONS

Momentive Performance Materials, Inc., 2003, "Silwet L-77 Spray Adjuvant for agricultural applications".*
Liu et al, 2000, Pest Manag., Sci., 56:861-866.*
Gao et al, 2008, Mol. Pharmaceutics, 6:651-658.*
Kim et al, 2009, Plant Cell Rep., 28:1159-1167.*
Jones-Rhoades et al., "MicroRNAs and Their Regulatory Roles in Plants", Annual Review of Plant Biology, 2006, pp. 19-53, vol. 57.
Reynolds et al., "Rational siRNA Design for RNA Interference", Nature Biotechnology, Mar. 2004, pp. 326-330, vol. 22 No. 3.
Pei et al., "On the Art of Identifying Effective and Specific siRNAs", Nature Methods, Sep. 2006, pp. 670-676, vol. 3 No. 9.

(Continued)

*Primary Examiner* — Jason Deveau Rosen
(74) *Attorney, Agent, or Firm* — Thompson Coburn LLP; Charles P. Romano

(57) ABSTRACT

The present invention provides novel compositions for use to enhance crop performance. Specifically, the present invention provides for delayed senescence and/or improved yield enhancement in various crops. The present invention also provides for combinations of compositions and methods that provide for delayed senescence and/or improved yield.

8 Claims, 4 Drawing Sheets

(56) References Cited

U.S. PATENT DOCUMENTS

| | | | |
|---|---|---|---|
| 5,536,821 A | 7/1996 | Agrawal et al. |
| 5,538,880 A | 7/1996 | Lundquist et al. |
| 5,541,306 A | 7/1996 | Agrawal et al. |
| 5,541,307 A | 7/1996 | Cook et al. |
| 5,550,111 A | 8/1996 | Suhadolnik et al. |
| 5,550,318 A | 8/1996 | Adams et al. |
| 5,561,225 A | 10/1996 | Maddry et al. |
| 5,561,236 A | 10/1996 | Leemans et al. |
| 5,563,253 A | 10/1996 | Agrawal et al. |
| 5,569,834 A | 10/1996 | Hinchee et al. |
| 5,571,799 A | 11/1996 | Tkachuk et al. |
| 5,587,361 A | 12/1996 | Cook et al. |
| 5,591,616 A | 1/1997 | Hiei et al. |
| 5,593,874 A | 1/1997 | Brown et al. |
| 5,596,086 A | 1/1997 | Matteucci et al. |
| 5,602,240 A | 2/1997 | De Mesmaeker et al. |
| 5,605,011 A | 2/1997 | Bedbrook et al. |
| 5,608,046 A | 3/1997 | Cook et al. |
| 5,610,289 A | 3/1997 | Cook et al. |
| 5,618,704 A | 4/1997 | Sanghvi et al. |
| 5,623,070 A | 4/1997 | Cook et al. |
| 5,625,050 A | 4/1997 | Beaton et al. |
| 5,627,061 A | 5/1997 | Barry et al. |
| 5,633,360 A | 5/1997 | Bischofberger et al. |
| 5,633,435 A | 5/1997 | Barry et al. |
| 5,633,448 A | 5/1997 | Lebrun et al. |
| 5,639,024 A | 6/1997 | Mueller et al. |
| 5,646,024 A | 7/1997 | Leemans et al. |
| 5,648,477 A | 7/1997 | Leemans et al. |
| 5,663,312 A | 9/1997 | Chaturvedula |
| 5,677,437 A | 10/1997 | Teng et al. |
| 5,677,439 A | 10/1997 | Weis et al. |
| 5,719,046 A | 2/1998 | Guerineau et al. |
| 5,721,138 A | 2/1998 | Lawn |
| 5,731,180 A | 3/1998 | Dietrich |
| 5,767,361 A | 6/1998 | Dietrich |
| 5,767,373 A | 6/1998 | Ward et al. |
| 5,780,708 A | 7/1998 | Lundquist et al. |
| 5,804,425 A | 9/1998 | Barry et al. |
| 5,824,877 A | 10/1998 | Hinchee et al. |
| 5,866,775 A | 2/1999 | Eichholtz et al. |
| 5,874,265 A | 2/1999 | Adams et al. |
| 5,879,903 A | 3/1999 | Strauch et al. |
| 5,914,451 A | 6/1999 | Martinell et al. |
| 5,919,675 A | 7/1999 | Adams et al. |
| 5,928,937 A | 7/1999 | Kakefuda et al. |
| 5,939,602 A | 8/1999 | Volrath et al. |
| 5,969,213 A | 10/1999 | Adams et al. |
| 5,981,840 A | 11/1999 | Zhao et al. |
| 5,985,793 A | 11/1999 | Sandbrink et al. |
| RE36,449 E | 12/1999 | Lebrun et al. |
| 6,040,497 A | 3/2000 | Spencer et al. |
| 6,056,938 A | 5/2000 | Unger et al. |
| 6,069,115 A | 5/2000 | Pallett et al. |
| 6,084,155 A | 7/2000 | Volrath et al. |
| 6,118,047 A | 9/2000 | Anderson et al. |
| 6,121,513 A | 9/2000 | Zhang et al. |
| 6,130,366 A | 10/2000 | Herrera-Estrella et al. |
| 6,153,812 A | 11/2000 | Fry et al. |
| 6,160,208 A | 12/2000 | Lundquist et al. |
| 6,177,616 B1 | 1/2001 | Bartsch et al. |
| 6,225,105 B1 | 5/2001 | Sathasivan et al. |
| 6,225,114 B1 | 5/2001 | Eichholtz et al. |
| 6,245,968 B1 | 6/2001 | Boudec et al. |
| 6,248,876 B1 | 6/2001 | Barry et al. |
| RE37,287 E | 7/2001 | Lebrun et al. |
| 6,268,549 B1 | 7/2001 | Sailland et al. |
| 6,271,359 B1 | 8/2001 | Norris et al. |
| 6,282,837 B1 | 9/2001 | Ward et al. |
| 6,288,306 B1 | 9/2001 | Ward et al. |
| 6,288,312 B1 | 9/2001 | Christou et al. |
| 6,294,714 B1 | 9/2001 | Matsunaga et al. |
| 6,326,193 B1 | 12/2001 | Liu et al. |
| 6,329,571 B1 | 12/2001 | Hiei |
| 6,348,185 B1 | 2/2002 | Piwnica-Worms |
| 6,365,807 B1 | 4/2002 | Christou et al. |
| 6,384,301 B1 | 5/2002 | Martinell et al. |
| 6,385,902 B1 | 5/2002 | Schipper et al. |
| 6,399,861 B1 | 6/2002 | Anderson et al. |
| 6,403,865 B1 | 6/2002 | Koziel et al. |
| 6,414,222 B1 | 7/2002 | Gengenbach et al. |
| 6,421,956 B1 | 7/2002 | Boukens et al. |
| 6,453,609 B1 | 9/2002 | Soli et al. |
| 6,506,559 B1 | 1/2003 | Fire et al. |
| 6,644,341 B1 | 11/2003 | Chemo et al. |
| 6,768,044 B1 | 7/2004 | Boudec et al. |
| 6,870,075 B1 * | 3/2005 | Beetham et al. ............. 800/278 |
| 6,992,237 B1 | 1/2006 | Habben et al. |
| 7,022,896 B1 | 4/2006 | Weeks et al. |
| 7,026,528 B2 | 4/2006 | Cheng et al. |
| RE39,247 E | 8/2006 | Barry et al. |
| 7,105,724 B2 | 9/2006 | Weeks et al. |
| 7,297,541 B2 | 11/2007 | Moshiri et al. |
| 7,304,209 B2 | 12/2007 | Zink et al. |
| 7,312,379 B2 | 12/2007 | Andrews et al. |
| 7,323,310 B2 | 1/2008 | Peters et al. |
| 7,371,927 B2 | 5/2008 | Yao et al. |
| 7,405,347 B2 | 7/2008 | Hammer et al. |
| 7,406,981 B2 | 8/2008 | Hemo et al. |
| 7,485,777 B2 | 2/2009 | Nakajima et al. |
| 7,525,013 B2 | 4/2009 | Hildebrand et al. |
| 7,622,301 B2 | 11/2009 | Ren et al. |
| 7,671,254 B2 | 3/2010 | Tranel et al. |
| 7,714,188 B2 | 5/2010 | Castle et al. |
| 7,838,263 B2 | 11/2010 | Dam et al. |
| 7,838,733 B2 | 11/2010 | Wright et al. |
| 7,842,856 B2 | 11/2010 | Tranel et al. |
| 7,884,262 B2 | 2/2011 | Clemente et al. |
| 7,910,805 B2 | 3/2011 | Duck et al. |
| 7,935,869 B2 | 5/2011 | Pallett et al. |
| 7,943,819 B2 | 5/2011 | Baum et al. |
| 7,973,218 B2 | 7/2011 | McCutchen et al. |
| 8,143,480 B2 | 3/2012 | Axtell et al. |
| 9,121,022 B2 | 9/2015 | Sammons et al. |
| 9,422,557 B2 | 8/2016 | Ader et al. |
| 2001/0042257 A1 | 11/2001 | Connor-Ward et al. |
| 2002/0114784 A1 | 8/2002 | Li et al. |
| 2003/0150017 A1 | 8/2003 | Mesa et al. |
| 2003/0167537 A1 | 9/2003 | Jiang |
| 2003/0235916 A1 | 12/2003 | Monahan et al. |
| 2004/0053289 A1 | 3/2004 | Christian et al. |
| 2004/0055041 A1 | 3/2004 | Labate et al. |
| 2004/0126845 A1 | 7/2004 | Eenennaam et al. |
| 2004/0133944 A1 | 7/2004 | Hake et al. |
| 2004/0147475 A1 | 7/2004 | Li et al. |
| 2004/0177399 A1 | 9/2004 | Hammer et al. |
| 2004/0244075 A1 | 12/2004 | Cai et al. |
| 2005/0026290 A1 * | 2/2005 | Ciardi ................ C12N 15/8249 435/468 |
| 2005/0239728 A1 * | 10/2005 | Pachuk ................ C12N 15/111 514/44 A |
| 2006/0021087 A1 | 1/2006 | Baum et al. |
| 2006/0111241 A1 | 5/2006 | Gerwick et al. |
| 2006/0130172 A1 | 6/2006 | Whaley et al. |
| 2006/0135758 A1 | 6/2006 | Wu |
| 2006/0200878 A1 | 9/2006 | Lutfiyya et al. |
| 2006/0247197 A1 | 11/2006 | Van De Craen et al. |
| 2006/0272049 A1 | 11/2006 | Waterhouse et al. |
| 2006/0276339 A1 | 12/2006 | Windsor et al. |
| 2007/0011775 A1 | 1/2007 | Allen et al. |
| 2007/0050863 A1 | 3/2007 | Tranel et al. |
| 2007/0124836 A1 | 5/2007 | Baum et al. |
| 2007/0199095 A1 | 8/2007 | Allen et al. |
| 2007/0250947 A1 | 10/2007 | Boukharov et al. |
| 2007/0259785 A1 | 11/2007 | Heck et al. |
| 2007/0281900 A1 | 12/2007 | Cui et al. |
| 2007/0300329 A1 | 12/2007 | Allen et al. |
| 2008/0022423 A1 | 1/2008 | Roberts et al. |
| 2008/0050342 A1 | 2/2008 | Fire et al. |
| 2008/0092256 A1 | 4/2008 | Kohn |
| 2008/0155716 A1 | 6/2008 | Sonnewald et al. |
| 2008/0214443 A1 | 9/2008 | Baum et al. |
| 2009/0011934 A1 | 1/2009 | Zawierucha et al. |
| 2009/0018016 A1 | 1/2009 | Duck et al. |

(56) References Cited

U.S. PATENT DOCUMENTS

| | | |
|---|---|---|
| 2009/0098614 A1 | 4/2009 | Zamore et al. |
| 2009/0137395 A1 | 5/2009 | Chicoine et al. |
| 2009/0165153 A1 | 6/2009 | Wang et al. |
| 2009/0165166 A1 | 6/2009 | Feng et al. |
| 2009/0188005 A1 | 7/2009 | Boukharov et al. |
| 2009/0205079 A1 | 8/2009 | Kumar et al. |
| 2009/0293148 A1 | 11/2009 | Ren et al. |
| 2009/0307803 A1 | 12/2009 | Baum et al. |
| 2010/0005551 A1 | 1/2010 | Roberts et al. |
| 2010/0068172 A1 | 3/2010 | Van De Craen |
| 2010/0071088 A1 | 3/2010 | Sela et al. |
| 2010/0100988 A1 | 4/2010 | Tranel et al. |
| 2010/0154083 A1 | 6/2010 | Ross et al. |
| 2010/0247578 A1 | 9/2010 | Salama |
| 2011/0035836 A1 | 2/2011 | Eudes et al. |
| 2011/0098180 A1 | 4/2011 | Michel et al. |
| 2011/0105327 A1 | 5/2011 | Nelson |
| 2011/0126310 A1 | 5/2011 | Feng et al. |
| 2011/0126311 A1 | 5/2011 | Velcheva et al. |
| 2011/0152346 A1 | 6/2011 | Karleson et al. |
| 2011/0152353 A1 | 6/2011 | Koizumi et al. |
| 2011/0160082 A1 | 6/2011 | Woo et al. |
| 2011/0166022 A1 | 7/2011 | Israels et al. |
| 2011/0166023 A1 | 7/2011 | Nettleton-Hammond et al. |
| 2011/0171287 A1 | 7/2011 | Saarma et al. |
| 2011/0177949 A1 | 7/2011 | Krapp et al. |
| 2011/0185444 A1 | 7/2011 | Li et al. |
| 2011/0185445 A1 | 7/2011 | Bogner et al. |
| 2011/0191897 A1 | 8/2011 | Poree et al. |
| 2011/0296555 A1 | 12/2011 | Ivashuta et al. |
| 2011/0296556 A1* | 12/2011 | Sammons et al. ............ 800/298 |
| 2012/0036594 A1 | 2/2012 | Cardoza et al. |
| 2012/0137387 A1 | 5/2012 | Baum et al. |
| 2012/0156784 A1 | 6/2012 | Adams, Jr. et al. |
| 2012/0164205 A1 | 6/2012 | Baum et al. |
| 2012/0185967 A1 | 7/2012 | Sela et al. |
| 2013/0003213 A1 | 1/2013 | Kabelac et al. |
| 2013/0041004 A1 | 2/2013 | Drager et al. |
| 2013/0047297 A1 | 2/2013 | Sammons et al. |
| 2013/0067618 A1 | 3/2013 | Ader et al. |
| 2013/0096073 A1 | 4/2013 | Sidelman |
| 2013/0097726 A1 | 4/2013 | Ader et al. |
| 2013/0212739 A1 | 8/2013 | Giritch et al. |
| 2013/0247247 A1 | 9/2013 | Ader et al. |
| 2013/0254940 A1 | 9/2013 | Ader et al. |
| 2013/0254941 A1 | 9/2013 | Ader et al. |
| 2013/0288895 A1 | 10/2013 | Ader et al. |
| 2013/0318657 A1 | 11/2013 | Avniel et al. |
| 2013/0318658 A1 | 11/2013 | Ader et al. |
| 2013/0326731 A1 | 12/2013 | Ader et al. |
| 2014/0018241 A1 | 1/2014 | Sammons et al. |
| 2014/0057789 A1 | 2/2014 | Sammons et al. |
| 2014/0109258 A1 | 4/2014 | Van De Craen et al. |
| 2014/0215656 A1 | 7/2014 | Crawford et al. |
| 2014/0230090 A1 | 8/2014 | Avniel et al. |
| 2014/0274712 A1 | 9/2014 | Finnessy et al. |
| 2014/0283211 A1 | 9/2014 | Crawford et al. |
| 2014/0296503 A1 | 10/2014 | Avniel et al. |

FOREIGN PATENT DOCUMENTS

| | | |
|---|---|---|
| EP | 2 530 159 A1 | 12/2012 |
| JP | 2006343473 A | 12/2006 |
| WO | 1989/11789 A1 | 12/1989 |
| WO | 96/05721 A1 | 2/1996 |
| WO | 1996/033270 A1 | 10/1996 |
| WO | 1996/038567 A2 | 12/1996 |
| WO | 1996/040964 A2 | 12/1996 |
| WO | 1999/024585 A1 | 5/1999 |
| WO | 1999/32619 A1 | 7/1999 |
| WO | 99/67367 A1 | 12/1999 |
| WO | 1999/61631 A1 | 12/1999 |
| WO | 30/32757 A2 | 6/2000 |
| WO | 2000/044914 A1 | 8/2000 |
| WO | 2002/14472 A2 | 2/2002 |
| WO | WO 03088738 A1 * | 10/2003 |
| WO | 2003/106636 A2 | 12/2003 |
| WO | 2004/005485 A2 | 1/2004 |
| WO | 2004/009761 A2 | 1/2004 |
| WO | 2004/022771 A2 | 3/2004 |
| WO | 2004/074443 A2 | 9/2004 |
| WO | 2005/003362 A2 | 1/2005 |
| WO | 2005/007860 | 1/2005 |
| WO | 2005/107437 A2 | 11/2005 |
| WO | 2005/110068 A2 | 11/2005 |
| WO | 2006/074400 A2 | 7/2006 |
| WO | 2006/138638 A1 | 12/2006 |
| WO | 2007/007316 A1 | 1/2007 |
| WO | 2007/035650 A2 | 3/2007 |
| WO | 2007/039454 A1 | 4/2007 |
| WO | 2007/051462 A2 | 5/2007 |
| WO | 2007/070389 A2 | 6/2007 |
| WO | 2007/074405 A2 | 7/2007 |
| WO | 2007/080126 A2 | 7/2007 |
| WO | 2007/080127 A2 | 7/2007 |
| WO | 2008/007100 A2 | 1/2008 |
| WO | 2008/063203 A2 | 5/2008 |
| WO | 2008/148223 A1 | 12/2008 |
| WO | 2009/046384 A1 | 4/2009 |
| WO | 2009/116558 A1 | 9/2009 |
| WO | 2009/125401 A2 | 10/2009 |
| WO | 2010/078912 A1 | 7/2010 |
| WO | 2010/104217 A1 | 9/2010 |
| WO | 2010/108611 A1 | 9/2010 |
| WO | 2010/112826 A2 | 10/2010 |
| WO | 2010/116122 A2 | 10/2010 |
| WO | 2010/119906 A1 | 10/2010 |
| WO | 2010/130970 A1 | 11/2010 |
| WO | 2011/001434 A1 | 1/2011 |
| WO | 2011/003776 A2 | 1/2011 |
| WO | 2011/067745 A2 | 6/2011 |
| WO | 2011/080674 A2 | 7/2011 |
| WO | 2011/112570 A1 | 9/2011 |
| WO | 2011/132127 A1 | 10/2011 |
| WO | 2012/001626 A1 | 1/2012 |
| WO | 2012/056401 A1 | 5/2012 |
| WO | 2012/092580 A2 | 7/2012 |
| WO | 2013/010691 A1 | 1/2013 |
| WO | 2013/025670 A2 | 2/2013 |
| WO | 2013/039990 A1 | 3/2013 |
| WO | 2013/040005 A1 | 3/2013 |
| WO | 2013/040021 A1 | 3/2013 |
| WO | 2013/040033 A1 | 3/2013 |
| WO | 2013/040049 A1 | 3/2013 |
| WO | 2013/040057 A1 | 3/2013 |
| WO | 2013/040116 A9 | 3/2013 |
| WO | 2013/040117 A1 | 3/2013 |
| WO | 2013/175480 A1 | 11/2013 |
| WO | 2014/106837 A2 | 7/2014 |
| WO | 2014/106838 A2 | 7/2014 |
| WO | 2014/151255 A1 | 9/2014 |
| WO | 2014/164761 A1 | 10/2014 |
| WO | 2014/164797 A1 | 10/2014 |
| WO | 2015/010026 A2 | 1/2015 |

OTHER PUBLICATIONS

Zhang et al., "Agrobacterium-mediated Transformation of Arabidopsis thaliana Using the Floral Dip Method", Nature Protocols, 2006, pp. 1-6, vol. 1 No. 2.
Brodersen et al., "The Diversity of RNA Silencing Pathways in Plants", Trends in Genetics, May 2006, pp. 268-280, vol. 22 No. 5.
Tomari et al., "Perspective: Machines for RNAi", Genes & Development, 2005, pp. 517-529, vol. 19.
Vaucheret, Hervé, "Post-transcriptional Small RNA Pathways in Plants: Mechanisms and Regulations", Genes & Development, 2006, pp. 759-771, vol. 20.
Meins, Jr. et al., "RNA Silencing Systems and Their Relevance to Plant Development", Annual Review of Cell and Developmental Biology, 2005, pp. 297-318, vol. 21.
Hamilton et al., "Two Classes of Short Interfering RNA in RNA Silencing", The European Molecular Biology Organization Journal, 2002, pp. 4671-4679, vol. 21, No. 17.

(56) References Cited

OTHER PUBLICATIONS

Du et al., "A Systematic Analysis of the Silencing Effects of an Active siRNA at All Single-nucleotide Mismatched Target Sites", Nucleic Acids Research, 2005, pp. 1671-1677, vol. 33 No. 5.
Concise Descriptions of Relevance filed by a third party on Nov. 29, 2012 in U.S. Appl. No. 13/042,856.
Hunter, Wayne B., "RNA Interference Strategies to Suppress Psyllids", International Plant and Animal Genome XIX, Jan. 15-19, 2001.
International Search Report and Written Opinion for PCT/US2011/027528 dated May 10, 2011.
Gan et al., "Bacterially Expressed dsRNA Protects Maize Against SCMV Infection", Plant Cell Reports, published online Aug. 24, 2010.
Tenllado et al., "Crude Extracts of Bacterially Expressed dsRNA can be used to Protect Plants Against Virus Infection" BMC Biotechnology, 2003, pp. 1-11, vol. 3 No. 3.
Sun et al., "Antisense Oligodeoxynucleotide Inhibition as a Potent Strategy in Plant Biology: Identification of SUSIBA2 as a Transcriptional Activator in Plant Sugar Signalling", The Plant Journal, 2005, pp. 128-138, vol. 44.
Baulcombe, David, "RNA Silencing and Heritable Epigenetic Effects in Tomato and Arabidopsis", Abstract 13th Annual Fall Symposium, Plant Genomes to Phenomes, Donald Danforth Plant Science Center, Sep. 28-30, 2011.
Himber et al., "Transitivity-dependent and -independent Cell-to-Cell Movement of RNA Silencing", The European Molecular Biology Organization Journal, 2003, pp. 4523-4533, vol. 22 No. 17.
Ryabov et al., "Cell-to-Cell, but Not Long-Distance, Spread of RNA Silencing That Is Induced in Individual Epidermal Cells", Journal of Virology, Mar. 2004, pp. 3149-3154, vol. 78 No. 6.
COST Action FA0806 progress report, "Plant virus control employing RNA-based vaccines: A novel non-transgenic strategy", 2010. European Cooperation in the field of Scientific and Technical Research, Memorandum of Understanding for COST Action FA0806, 2008.
Devgen, "The mini-Monsanto", KBC Securities, 2006.
Clough et al., "Floral dip: a simplified method for Agrobacterium-mediated transformation of Arabidopsis thaliana", The Plant Journal, 1998, pp. 735-743, vol. 16 No. 6.
Nowak et al., "A new and efficient method for inhibition of RNA viruses by DNA interference", The FEBS Journal, 2009, pp. 4372-4380, vol. 276.
Klahre et al., "High molecular weight RNAs and small interfering RNAs induce systemic posttranscriptional gene silencing in plants", PNAS, 2002, pp. 11981-11986, vol. 99 No. 18.
Liu et al., "Comparative study on the interaction of DNA with three different kinds of surfactants and the formation of multilayer films", Bioelectrochemistry, 2007, pp. 301-307, vol. 70.
Melnyk et al., "Intercellular and systemic movement of RNA silencing signals", The EMBO Journal, 2011, pp. 3553-3563, vol. 30.
Reddy et al., "Organosilicone Adjuvants Increased the Efficacy of Glyphosate for Control of Weeds in Citrus (*Citrus* spp.)", HortScience, 1992, pp. 1003-1005, vol. 27 No. 9.
Zhu et al., "Ingested RNA interference for managing the populations of the Colorado potato beetle, *Leptinotarsa decemlineata*", Pest Management Science, 2010, pp. 175-182, vol. 67.
Maas et al., "Mechanism and optimized conditions for PEG mediated DNA transfection into plant protoplasts", Plant Cell Reports, 1989, pp. 148-151, vol. 8.
Wardell, William L., "Floral Activity in Solutions of Deoxyribonucleic Acid Extracted from Tobacco Stems", Plant Physiology, 1976, pp. 855-861, vol. 57.
Wardell, William L., "Floral Induction of Vegetative Plants Supplied a Purified Fraction of Deoxyribonucleic Acid from Stems of Flowering Plants", Plant Physiology, 1977, pp. 885-891, vol. 60.
Hewezi et al., "Local infiltration of high- and low-molecular-weight RNA from silenced sunflower (*Helianthus annuus* L.) plants triggers post-transcriptional gene silencing in non-silenced plants", Plant Biotechnology Journal, 2005, pp. 81-89, vol. 3.
Zhao et al., "Phyllotreta striolata (Coleoptera: Chrysomelidae): Arginine kinase cloning and RNAi-based pest control", European Journal of Entomology, 2008, pp. 815-822, vol. 105.
Hannon, Gregory J., "RNA interference", Nature, 2002, pp. 244-251, vol. 418.
Tenllado, et al., "RNA interference as a new biotechnological tool for the control of virus diseases in plants", Virus Research, 2004, pp. 85-96, vol. 102.
Silwet L-77 Spray Adjuvant for agricultural applications, product description from Momentive Performance Materials, Inc., 2003.
Gong et al., "Silencing of Rieske iron-sulfur protein using chemically synthesised siRNA as a potential biopesticide against Plutella xylostella", Pest Management Science, 2011, pp. 514-520, vol. 67.
Dunoyer et al., "Small RNA Duplexes Function as Mobile Silencing Signals Between Plant Cells", Science, 2010, pp. 912-916, vol. 328.
Molnar et al., "Small Silencing RNAs in Plants Are Mobile and Direct Epigenetic Modification in Recipient Cells", Science, 2010, pp. 872-875, vol. 328.
Sun et al., "Sweet delivery—sugar translocators as ports of entry for antisense oligodeoxynucleotides in plant cells", The Plant Journal, 2007, pp. 1192-1198, vol. 52.
Voinnet et al., "Systemic Spread of Sequence-Specific Transgene RNA Degradation in Plants Is Initiated by Localized Introduction of Ectopic Promoterless DNA", Cell, 1998, pp. 177-187, vol. 95.
An et al., "Transient RNAi Induction against Endogenous Genes in Arabidopsis Protoplasts Using in Vitro-Prepared Double-Stranded RNA", Bioscience Biotechnology and Biochemistry, 2005, pp. 415-418, vol. 69 No. 2.
YouTube video by General Electric Company "Silwet Surfactants," screen shots taken on Jan. 11, 2012 of video of www.youtube_com/watch?v=WBw7nXMqHk8 (uploaded Jul. 13, 2009).
Artymovich, Katherine A., "Using RNA interference to increase crop yield and decrease pest damage", MMG 445 Basic Biotechnology, 2009, pp. 7-12, vol. 5.
Li et al., "The FAST technique: a simplified Agrobacterium-based transformation method for transient gene expression analysis in seedlings of Arabidopsis and other plant species", Plant Methods, 2009, vol. 5 No. 6.
Paungfoo-Lonhienne et al., "DNA Is Taken Up by Root Hairs and Pollen, and Stimulates Root and Pollen Tube Growth", Plant Physiology, 2010, pp. 799-805, vol. 153.
Paungfoo-Lonhienne et al., "DNA uptake by Arabidopsis induces changes in the expression of CLE peptides which control root morphology", Plant Signaling & Behavior, 2010, pp. 1112-1114, vol. 5 No. 9.
International Preliminary Report on Patentability for PCT/US2011/027528 dated Sep. 11, 2012.
Gaines et al., "Gene amplification confers glyphosate resistance in Amaranthus palmeri", PNAS, 2010, pp. 1029-1034, vol. 107 No. 3.
Kirkwood, Ralph C., "Use and Mode of Action of Adjuvants for Herbicides: A Review of some Current Work", Pesticide Science, 1993, pp. 93-102, vol. 38.
Kusaba et al., "Low glutelin content1: A Dominant Mutation That Supresses the Glutelin Multigene Family via RNA Silencing in Rice", The Plant Cell, 2003, pp. 1455-1467, vol. 15.
First Examination Report issued for New Zealand Application No. 601784 dated Apr. 23, 2013.
Unnamalai et al., "Cationic oligopeptide-mediated delivery of dsRNA for post-transcriptional gene silencing in plant cells", FEBS Letters, 2004, pp. 307-310, vol. 566.
Al-Kaff et al., "Plants rendered herbicide-susceptible by cauliflower mosaic virus-elicited suppression of a 35S promoter-regulated transgene", Nature Biotechnology, 2000, pp. 995-999, vol. 18.
Gao et al., "Nonviral Methods for siRNA Delivery", Molecular Pharmaceutics, 2008, pp. 651-658, vol. 6 No. 3.
Busch et al., "RNAi for discovery of novel crop protection products", Pflanzenschutz-Nachrichten Bayer, 2005, pp. 34-50, vol. 58 No. 1.
Roberts, Michael R., "Fast-track applications: The potential for direct delivery of proteins and nucleic acids to plant cells for the discovery of gene function", Plant Methods, 2005, vol. 1 No. 12.

(56) References Cited

OTHER PUBLICATIONS

Basu et al., "Weed genomics: new tools to understand weed biology", Trends in Plant Science, 2004, pp. 391-398, vol. 9 No. 8.
Tenllado et al., "Double-Stranded RNA-Mediated Interference with Plant Virus Infection", Journal of Virology, 2001, pp. 12288-12297, vol. 75 No. 24.
Bart et al., "A novel system for gene silencing using siRNAs in rice leaf and stem-derived protoplasts", Plant Methods, 2006, vol. 2 No. 13.
Fraley et al., "Liposome-mediated delivery of tobacco mosaic virus RNA into tobacco protoplasts: A sensitive assay for monitoring liposome-protoplast interactions", Proceedings of the National Academy of Sciences, 1982, pp. 1859-1863, vol. 79.
Tang et al., "Efficient delivery of small interfering RNA to plant cells by a nanosecond pulsed laser-induced stress wave for post-transcriptional gene silencing", Plant Science, 2006, pp. 375-381, vol. 171.
Waterhouse et al., "Exploring Plant Genomes by RNA-Induced Gene Silencing", Nature Reviews, Genetics, 2003, pp. 29-38, vol. 4.
Djanaguiraman et al., "Ethylene production under high temperature stress causes premature leaf senescence in soybean", Functional Plant Biology, 2010, pp. 1071-1084, vol. 37.
Bapat et al., "Ripening of fleshy fruit: Molecular insight and the role of ethylene." Biotechnology Advances, 2010, pp. 94-107, vol. 28.
Van Loon et al., "Ethylene as a modulator of disease resistance in plants", Trends in Plant Science, 2006, pp. 184-191, vol. 11 No. 4.
Thomas et al., "Five ways to stay green", 2000, Journal of Experimental Botany pp. 329-337, vol. 51, GMP Special Issue.
Hu et al., "Silencing of the LeSGR1 gene in tomato inhibits chlorophyll degradation and exhibits a stay-green phenotype." Biologia Plantarum, 2011, pp. 27-34, vol. 55 No. 1.
Lanahan et al., "The never ripe mutation blocks ethylene perception in tomato", The Plant Cell, 1994, pp. 521-530, vol. 6.
Montgomery et al., "Identification of an ethylene-responsive region in the promoter of a fruit ripening gene", Proceedings of the National Academy of Sciences, 1993, pp. 5939-5943, vol. 90.
Guzman et al., "Exploiting the Triple Response of Arabidopsis to Identify Ethylene-Related Mutants", The Plant Cell, 1990, pp. 513-523, vol. 2.
Thomas et al., "Size Constraints for Targeting Post-Transcriptional Gene Silencing and for RNA-Directed Methylation in Nicotiana Benthamiana using a Potato Virus X Vector", The Plant Journal, 2001, pp. 417-425, vol. 25 No. 4.
Chen et al., "Transfection and Expression of Plasmid DNA in Plant Cells by an Arginine-Rich Intracellular Delivery Peptide without Protoplast Preparation", FEBS Letters 581, 2007, pp. 1891-1897.
Kim et al., "Optimization of Conditions for Transient Agrobacterium-Mediated Gene Expression Assays in Arabidopsis", Plant Cell Reports, 2009, pp. 1159-1167, vol. 28.
Schweizer et al., "Double-stranded RNA interferes with gene function at the single-cell level in cereals", The Plant Journal, 2000, pp. 895-903, vol. 24, No. 6.
Office Action for U.S. Appl. No. 13/619,980 dated Apr. 7, 2016.
"Agricultural Chemical Usage 2006 Vegetables Summary", Agricultrual Statistics Board, Jul. 2007, pp. 1-372.
Kirkwood "Herbicides and Plants", Botanical Journal of Scotland, Jan. 1, 1993, pp. 447-462, vol. 46 Issue 3.
Kusaba, "RNA interference in crop plants," Curr Opin Biotechnol, 15(2):139-143 (2004).
Li et al., "The FAST technique: a simplified Agrobacterium-based transformation method for transient gene expression analysis in seedlings of Arabidopsis and other plant species," Plant Methods, 5(6):1-15 (2009).
Office Action for U.S. Appl. No. 13/612,985 dated Nov. 10, 2015.
Orbovic et al., "Foliar-Applied Surfactants and Urea Temporarily Reduce Carbon Assimilation of Grapefruit Leaves", Journal of the American Society for Horticultural Science, 2001, pp. 486-490, vol. 126.
Showalter "Structure and Function of Plant Cell Wall Proteins", The Plant Cell, Jan. 1993, pp. 9-23, vol. 5.
Stevens "Organosilicone Surfactants as Adjuvants for Agrochemicals", Journal of Pesticide Science, 1993, pp. 103-122, vol. 38.
Stevens et al., "New Formulation Technology—Sil Wet® Organosilicone Surfactants Have Physical and Physiological Properties Which Enhance the Performance of Sprays", Proceedings of the 9th Australian Weeds Conference, pp. 327-331 (1990).
Stock et al., "Possible Mechanisms for Surfactant-Induced Foliar Uptake of Agrochemicals", Pesticide Science, 1993, pp. 165-177, vol. 38.
Zhang et al., "Cationic Lipids and Polymers Mediated Vectors for Delivery of siRNA", Journal of Controlled Release, Oct. 18, 2007, pp. 1-10, vol. 123 Issue. 1.
Gelvin, "Agrobacterium-Mediated Plant Transformation: The Biology Behind the "Gene-Jockeying" Tool", Microbiology and Molecular Biology Reviews, Mar. 2003, p. 16-37, vol. 67 No. 1.
Somerville et al., "Plant Functional Genomics" Science, 285:380-383 (1999).
Warnasooriya et al., "Using transgenic modulation of protein synthesis and accumulation to probe protein signaling networks in Arabidopsis thaliana" Plant Signaling & Behavior, 6(9):1312-1321 (2011).
Zhai et al., "Establishing RNA Interference as a Reverse-Genetic Approach for Gene Functional Analysis in Protoplasts" Plant Physiology, 149:642-652 (2009).
Dalakouras et al., "Induction of Silencing in Plants by High-Pressure Spraying of in vitro-Synthesized Small RNAs", Frontiers in Plant Science, Aug. 2016, pp. 1-5, vol. 7, No. 1327.
Australian Government, Grains Research & Development Corporation, "Adjuvants: Oils, surfactants and other additives for farm chemicals", 2012, 52 pages.
AccuStandard, Inc., "Pesticide Standards Reference Guide", 2010, 116 pages.
Extended European Search Report dated Jun. 29, 2015, in European Patent Application No. 12831494.5.
Farooq et al., "Rice seed priming," IPRN, 30(2):45-48 (2005).
Final Office Action dated Nov. 7, 2013, in U.S. Appl. No. 13/042,856.
Fire et al., "Potent and specific genetic interference by double-stranded RNA in Caenorhabditis elegans," Nature, 391:806-811 (1998).
First Examination Report dated Jul. 28, 2014, in New Zealand Patent Application No. 627060.
First Office Action dated May 27, 2015, in Chinese Patent Application No. 201280054179.8.
Fukuhara et al., "Enigmatic Double-Stranded RNA in Japonica Rice," Plant Molecular Biology, 21:1121-1130 (1993).
Fukuhara et al., "The Unusual Structure of a Novel RNA Replicon in Rice," the Journal of Biological Chemistry, 270 (30):18147-18149 (1995).
Fukuhara et al., "The wide distribution of endomaviruses, large double-stranded RNA replicons with plasmid-like properties," Archives of Virology, 151:995-1002 (2006).
Further Examination Report issued in New Zealand Patent Application No. 601784 on May 16, 2014.
Ge et al., "Rapid vacuolar sequestration: the horseweed glyphosate resistance mechanism," Pest Management Sci., 66:345-348 (2010).
GenBank Accession No. AY545657.1, published 2004.
GenBank Accession No. DY640489, PU2_plate27_F03 PU2 Prunus persica cDNA similar to expressed mRNA inferred from Prunus persica hypothetical domain/motif containing IPR011005:Dihydropteroate synthase-like, MRNA sequence (2006) [Retrieved on Feb.4, 2013]. Retrieved from the internet <URL:http://www.ncbi.nlm.nih.gov/nucest/DY640489>.
GenBank Accession No. EU24568—"Amaranthus hypochondriacus acetolactate synthase (ALS) gene," (2007).
GenBank Accession No. FJ972198, Solanum lycopersicum cultivar Ailsa Craig dihydropterin pyrophosphokinase-dihydropteroate synthase (HPPK-DHPS) gene, complete cds (2010) [Retrieved on Nov. 26, 2012]. Retrieved from the internet,URL:http://www.ncbi.nlm.nih.gov/nuccore/FJ972198>.

(56) References Cited

OTHER PUBLICATIONS

GenBank accession No. GI:186478573, published Jan. 22, 2014.
GenEmbl FJ861243, published Feb. 3, 2010.
Gressel et al., "A Strategy to Provide Long-Term Control of Weedy Rice While Mitigating Herbicide Resistance Transgene Flow, and Its Potential Use for Other Crops with Related Weeds", Pest Management Science, 2009, pp. 723-731, vol. 65.
Gutensohn et al., "Functional analysis of the two *Arabidopsis* homologues of Toc34, a component of the chloroplast protein import apparatus," The Plant Journal, 23(6):771-783 (2000).
Haigh, "The Priming of Seeds: Investigation into a method of priming large quantities of seeds using salt solutions," Thesis submitted to Macquarie University (1983).
Han et al., "Molecular Basis for the Recognition of Primary microRNAs by the Drosha-DGCR8 Complex," Cell, 125 (5):887-901 (2006).
Hardegree, "Drying and storage effects on germination of primed grass seeds," Journal of Range Management, 47 (3):196-199 (1994).
Herman et al., "A three-component dicamba O-demethylase from Pseudomonas maltophilia, strain DI-6: gene isolation, characterization, and heterologous expression," J. Biol. Chem., 280: 24759-24767 (2005).
Hidayat et al., "Enhanced Metabolism of Fluazifop Acid in a Biotype of Digitaria sanguinalis Resistant to the Herbicide Fluazifop-P-Butyl," Pesticide Biochem. Physiol., 57:137-146 (1997).
Hirschberg et al., "Molecular Basis of Herbicide Resistance in Amaranthus hybridus," Science, 222:1346-1349 (1983).
Hoekema et al., "A binary plant vector strategy based on separation of vir- and T-region of the Agrobacterium tumefaciens Ti-plasmid," Nature, 303:179-180 (1983).
Hofgen et al., "Repression of Acetolactate Synthase Activity through Antisense Inhibition: Molecular and Biochemical Analysis of Transgenic Potato (Solanum tuberosum L. cv Desiree) Plants," Plant Physiol., 107(2):469-477 (1995).
Hsieh et al.,"A library of siRNA duplexes targeting the phosphoinositide 3-kinase pathway: determinants of gene silencing for use in cell-based screens," Nucleic Acids Res., 32(3):893-901 (2004).
Huesken et al., "Design of a genome-wide siRNA library using an artificial neural network," Nature Biotechnology, 23 (8): 995-1001 (2005).
Ichihara et al., "Thermodynamic instability of siRNA duplex is a prerequisite for dependable prediction of siRNA activities," Nucleic Acids Res., 35(18):e123 (2007).
International Preliminary Report on Patentability (Chapter II) dated Jul. 24, 2015, in International Application No. PCT/US2014/047204.
International Preliminary Report on Patentability dated Sep. 11, 2014, in International Application No. PCT/IL13/50447.
International Search Report and the Written Opinion dated Feb. 25, 2013, in International Application No. PCT/US12/54883.
International Search Report and the Written Opinion dated Feb. 27, 2013, in International Application No. PCT/US12/54814.
International Search Report and the Written Opinion dated Feb. 27, 2013, in International Application No. PCT/US12/54842.
International Search Report and the Written Opinion dated Feb. 27, 2013, in International Application No. PCT/US12/54862.
International Search Report and the Written Opinion dated Feb. 27, 2013, in International Application No. PCT/US12/54894.
International Search Report and the Written Opinion dated Feb. 27, 2013, in International Application No. PCT/US12/54974.
International Search Report and the Written Opinion dated Feb. 27, 2013, in International Application No. PCT/US12/54980.
International Search Report and the Written Opinion dated Jul. 15 2014, in International Application No. PCT/US2014/025305.
International Search Report and the Written Opinion dated Jul. 22 2014, in International Application No. PCT/IL2013/051083.
International Search Report and the Written Opinion dated Jul. 22 2014, in International Application No. PCT/IL2013/051085.
International Search Report and the Written Opinion dated Jul. 24 2014, in International Application No. PCT/US2014/026036.
International Search Report and the Written Opinion dated Oct. 1 2013, in International Application No. PCT/IL2013/050447.
International Search Report and Written Opinion dated Aug. 25, 2014, in International Application No. PCT/US2014/023503.
International Search Report and Written Opinion dated Aug. 27, 2014, in International Application No. PCT/US2014/023409.
International Search Report and Written Opinion dated Jul. 8 2015 in International Application No. PCT/US2015/011408.
International Search Report and Written Opinion dated Mar. 26, 2015, in International Application No. PCT/US2014/069353.
International Search Report dated Mar. 12, 2013 in International Application No. PCT/US12/54789.
Isaacs et al., "Engineered riboregulators enable post-transcriptional control of gene expression," Nature Biotechnology, 22(7):841-847 (2004).
Agrios, Plant Pathology (Second Edition), 2:466-470 (1978).
Alarcón-Reverte et al., "Resistance to ACCase-inhibiting herbicides in the weed Lolium multiflorum," Comm. Appl. Biol. Sci., 73(4):899-902 (2008).
Amarzguioui et al., "An algorithm for selection of functional siRNA sequences," Biochemical and Biophysical Research Communications, 316:1050-1058 (2004).
Ambrus et al., "The Diverse Roles of RNA Helicases in RNAi," Cell Cycle, 8(21):3500-3505 (2009).
Anonymous, "Do Monsanto Have the Next Big Thing?" Australian Herbicide Resistance Initiative (AHRI), retreived on Jan. 19, 2015, XP007922963.
Anonymous, "A handbook for high-level expression and purification of 6xHis-tagged proteins," The QIAexpressionist, (2003).
Aoki et al., "In Vivo Transfer Efficiency of Antisense Oligonucleotides into the Myocardium Using HVJ-Liposome Method," Biochem Biophys Res Commun, 231:540-545 (1997).
Arpaia et al., "Production of transgenic eggplant (Solanum melongena L) resistant to Colorado Potato Beetle (Leptinotarsa decemlineata Say)," (1997) Theor. Appl. Genet., 95:329-334 (1997).
Australian Patent Examination report No. 1 dated Nov. 11, 2013, in Australian Application No. 2011224570.
Axtell et al., "A Two-Hit Trigger for siRNA Biogenesis in Plants," Cell, 127:565?577 (2006).
Baerson et al., "Glyphosate-Resistant Goosegrass. Identification of a Mutation in the Target Enzyme 5-Enolpyruvylshikimate-3-Phosphate Synthase," Plant Physiol., 129(3):1265-1275 (2002).
Bai et al, "Naturally Occurring Broad-Spectrum Powdery Mildew Resistance in a Central American Tomato Accession is Caused by Loss of Mb Function," MPMI, 21(1):30-39 (2008).
Banerjee et al., "Efficient production of transgenic potato (S. tuberosum L ssp. andigena) plants via Agrobacterium tumefaciens-mediated transformation," Plant Sci., 170:732 738 (2006).
Bayer et al., "Programmable ligand-controlled riboregulators of eukaryotic gene expression," Nature Biotechnol., 23 (3):337-343 (2005).
Beal, et al., "Second Structural Motif for Recognition of DNA by Oligonucleotide-Directed Triple-Helix Formation," Science, 251:1360-1363 (1992).
Becker et al., "Fertile transgenic wheat from microprojectile bombardment of scutellar tissue," The Plant Journal, 5 (2):299-307 (1994).
Bhargava et al., "Long double-stranded RNA-mediated RNA interference as a tool to achieve site-specific silencing of hypothalamic neuropeptides," Brain Research Protocols, 13:115-125 (2004).
Boletta et al., "High Efficient Non-Viral Gene Delivery to the Rat Kidney by Novel Polycationic Vectors," J. Am Soc. Nephrol., 7:1728 (1996).
Bolognesi et al., "Characterizing the Mechanism of Action of Double-Stranded RNA Activity against Western Corn Rootworm(Diabrotica virgifera virgifera LeConte)," PLoS ONE 7(10):e47534 (2012).

(56) References Cited

OTHER PUBLICATIONS

Bolter et al., "A chloroplastic inner envelope membrane protease is essential for plant development," FEBS Letters, 580:789-794 (2006).
Bourgeois et al., "Field and Producer Survey of Accase Resistant Wild Oat in Manitoba," Canadian Journal of Plant Science, 709-7 15 (1997).
Breaker et al., "A DNA enzyme with Mg2+-dependent RNA phosphoesterase activity," Chemistry and Biology, 2:655-660 (1995).
Brugière et al., "Glutamine Synthetase in the Phloem Plays a Major Role in Controlling Proline Production," The Plant Cell, 11:1995-2011(1999).
Busi et al., "Gene Flow Increases the Initial Frequency of Herbicide Resistance Alleles in Unselected Lolium Rigidum Populations", Agriculture, Ecosystems and Environments, 2011, pp. 403-409, vol. 142.
Butler et al., "Priming and re-drying improve the survival of mature seeds of Digitalis purpurea during storage," Annals of Botany, 103:1261-1270 (2009).
Bytebier et al., "T-DNA organization in tumor cultures and transgenic plants of the monocotyledon Asparagus officinalis," Proc. Natl. Acad. Sci. U.S.A., 84:5345-5349 (1987).
Chabbouh et al. "Cucumber mosaic virus in artichoke," FAO Plant Protection Bulletin, 38:52-53 (1990).
Chakravarty et al., "Genetic Transformation in Potato: Approaches and Strategies," Amer J Potato Res, 84:301 311 (2007).
Chang et al., "Cellular Internalization of Fluorescent Proteins via Arginine-Rich Intracellular Delivery Peptide in Plant Cells", Plant Cell Physiology, 2005, pp. 482-488, vol. 46.
Chee et al., "Transformation of Soybean (Glycine max) by Infecting Germinating Seeds with Agrobacterium tumefaciens," Plant Physiol., 91:1212-1218 (1989).
Chen et al., "In Vivo Analysis of the Role of atTic20 in Protein Import into Chloroplasts," The Plant Cell, 14:641-654 (2002).
Cheng et al., "Production of fertile transgenic peanut (Arachis hypogaea L.) plants using Agrobacterium tumefaciens," Plant Cell Reports, 15:653-657 (1996).
Chi et al., "The Function of RH22, a DEAD RNA Helicase, in the Biogenesis of the 50S Ribosomal Subunits of *Arabidapsis* Chloroplasts," Plant Physiology, 158:693-707 (2012).
Chinese Office Action dated Aug. 28, 2013 in Chinese Application No. 201180012795.2.
Chupp et al, "Chapter 8: White Rust," Vegetable Diseases and Their Control, The Ronald Press Company, New York, pp. 267-269 (1960).
Colbourne et al. "The Ecoresponsive Genome of Daphnia pulex," Science, 331(6017):555-561 (2011).
Colombian Office Action dated Aug. 2, 2013 in Application No. 12 152898.
Colombian Office Action dated Feb. 21, 2014 in Application No. 12 152898.
Communication pursuant to Article 94(3) EPC dated Jun. 26, 2015, as received in European Patent Application No. 11 753 9163.
Dalmay et al., "An RNA-Depenedent RNA Polymerase Gene in *Arabidopsis* Is Required for Posttranscriptional Gene Silencing Mediated by a Transgene but Not by a Virus," Cell, 101:543-553 (2000).
Datebase EMBL CBIB Daphnia—XP-002732239 (2011).
Davidson et al., "Engineering regulatory RNAs," TRENDS in Biotechnology, 23(3):109-112 (2005).
De Block, et al. "Engineering herbicide resistance in plants by expression of a detoxifying enzyme," EMBO J. 6(9):2513-2519 (1987).
De Framond, "MINI-Ti: A New Vector Strategy for Plant Genetic Engineering," Nature Biotechnology, 1:262-269 (1983).
della-Cioppa et al., "Import of a precursor protein into chloroplasts is inhibited by the herbicide glyphosate," The EMBO Journal, 7(5):1299-1305 (1988).

Diallo et al., "Long Endogenous dsRNAs Can Induce Complete Gene Silencing in Mammalian Cells and Primary Cultures," Oligonucleotides, 13:381-392 (2003).
Ellington et al., "In vitro selection of RNA molecules that bind specific ligands," Nature, 346:818-822 (1990).
Emery et al., "Radial Patterning of *Arabidopsis* Shoots by Class III HD-ZIP and KANADI Genes," Current Biology, 13:1768-1774 (2003).
Eurasian Office Action dated Feb. 24, 2014, in Application No. 201201264.
European Supplemental Search Report dated Oct. 8, 2013 in Application No. 117539163.
Ui-Tei et al., "Guidelines for the selection of highly effective siRNA sequences for mammalian and chick RNA interference," Nucleic Acids Res., 32(3): 936-948 (2004).
Urayama et al., "Knock-down of OsDCL2 in Rice Negatively Affects Maintenance of the Endogenous dsRNA Virus, *Oryza sativa* Endomavirus," Plant and Cell Physiology, 51(1):58-67 (2010).
van de Wetering et al., "Specific inhibition of gene expression using a stably integrated, inducible small-interfering-RNA vector," EMBO Rep., 4(6):609-615 (2003).
Vasil et al., "Herbicide Resistant Fertile Transgenic Wheat Plants Obtained by Microprojectile Bombardment of Regenerable Embryogenic Callus," Bio/Technology,10:667-674 (1992).
Vencill et al., "Resistance of Weeds to Herbicides," Herbicides and Environment, 29:585-594 (2011).
Verma et al. "Modified oligonucleotides: synthesis and strategy for users," Annu. Rev. Biochem., 67:99-134 (1998).
Vermeulen et al, "The Contributions of dsRNA Structure to Dicer Specificity and Efficiency," RNA, 11(5):674-682 (2005).
Vert et al., "An accurate and interpretable model for siRNA efficacy prediction," BMC Bioinformatics, 7:520 (2006).
Wakelin et al., "A target-site mutation is present in a glyphosate-resistant Lolium rigidum population," Weed Res. (Oxford), 46(5):432-440 (2006).
Walton et al., "Prediction of antisense oligonucleotide binding affinity to a structured RNA target," Biotechnol Bioeng 65(1):1-9 (1999).
Wan et al., "Generation of Large Numbers Of Independently Transformed Fertile Barley Plants," Plant Physiol., 104:37-48 (1994).
Waterhouse et al., "Virus resistance and gene silencing in plants can be induced by simultaneous expression of sense and antisense RNA," Proc Natl Acad Sci USA, 95:13959-13964 (1998).
Welch et al., "Expression of ribozymes in gene transfer systems to modulate target RNA levels," Curr Opin Biotechnol. 9(5):486-496 (1998).
Written Opinion dated May 8, 2014, in International Application No. PCT/IL2013/050447.
Written Opinion dated Sep. 4, 2014, in Singapore Patent Application No. 201206152-9.
Zagnitko, "Lolium regidum clone LS1 acetyl-CoA carboxylase mRNA, partial cds; nuclear gene for plastid product," GenBank: AF359516.1, 2 pages (2001).
Zagnitko, et al., "An isoleucine/leucine residue in the carboxyltransferase domain of acetyl-CoA carboxylase is critical for interaction with aryloxyphenoxypropionate and cyclohexanedione inhibitors," PNAS, 98(12):6617-6622 (2001).
Zhang et al., "A novel rice gene, NRR responds to macronutrient deficiency and regulates root growth," Mol Plant, 5(1):63-72 (2012).
Zhang et al., "DEG: a database of essential genes," Nucleic Acids Res., 32:D271-D272 (2004).
Zhang et al., "Transgenic rice plants produced by electroporation-mediated plasmid uptake into protoplasts," The Plant Cell Rep., 7:379-384 (1988).
Wang et al., "A Web-Based Design Center for Vector-Based siRNA and siRNA Cassette", BioInformatic Applications Note, 2004, pp. 1818-1820, vol. 20 No. 11.
Kozomara et al, "miRBase: Annotating High Confidence MicroRNAs Using Deep Sequencing Data", Nucleic Acids Research, 2014, p. D68-D73, vol. 42.

(56) References Cited

OTHER PUBLICATIONS

Mallory et al, "MicroRNA Control of PHABULOSA in Leaf Development: Importance of Pairing to the MicroRNA 5'Region", The EMBO Journal, 2004, pp. 3356-3364, vol. 23 No. 16.
Lu et al., "Novel and Mechanical Stress-Responsive MicroRNAs in Populus Trichocarpa That Are Absent from *Arabidopsis*", the Plant Cell, Aug. 2005, pp. 2186-2203, vol. 17.
Mansoor et al, "Engineering Novel Traits in Plants Through RNA Interference", Trends in Plant Science, 2006, pp. 559-565, vol. 11, No. 11.
Khan et al., "Matriconditioning of Vegetable Seeds to Improve Stand Establishment in Early Field Plantings," .1 Amer. Soc. Hon. Sci., 1 17(1):41-47 (1992).
Ji et al., "Regulation of small RNA stability: methylation and beyond," Cell Research, 22:624-636 (2012).
Jofre-Garfias et al., "Agrobacerium-Mediated Transformation of Amaranthus Hypochondriacus: Light-And Tissue-Specific Expression of a Pea Chlorophyll A/B-Binding Protein Promoter," Plant Cell Reports, 16:847-852 (1997).
Josse et al., "A DELLA in Disguise: SPATULA Restrains the Growth of the Developing Arabidopsis Seedling," Plant Cell, 23:1337-1351 (2011).
Kam et al., "Nanotube Molecular Transporters:? Internalization of Carbon Nanotube?Protein Conjugates into Mammalian Cells," J. Am. Chem. Soc., 126(22):6850-6851 (2004).
Katoh et al., "Specific residues at every third position of siRNA shape its efficient RNAi activity," Nucleic Acids Res., 35(4): e27 (2007).
Kertbundit et al., "In vivo random β-glucuronidase gene fusions in *Arabidopsis thaliana*," Proc. Natl. Acad. Sci. U S A., 88:5212-5216 (1991).
Khachigian, "DNAzymes: Cutting a path to a new class of therapeutics," Curr Opin Mol Ther 4(2):119-121 (2002).
Khodakovskaya et al., "Carbon Nanotubes Are Able to Penetrate Plant Seed Coat and Dramatically Affect Seed Germination and Plant Growth," ACS Nano, 3(10):3221-3227 (2009).
Kim et al., "Synthetic dsRNA Dicer substrates enhance RNAi potency and efficacy," Nature Biotechnology, 23(2):222-226 (2005).
Kronenwett et al., "Oligodeoxyribonucleotide Uptake in Primary Human Hematopoietic Cells Is Enhanced by Cationic Lipids and Depends on the Hematopoietic Cell Subset," Blood, 91(3):852-862 (1998).
Lavigne et al., "Enhanced antisense inhibition of human immunodeficiency virus type 1 in cell cultures by DLS delivery system," Biochem Biophys Res Commun, 237:566-571 (1997).
Lee et al., "Aptamer Database," Nucleic Acids Research, 32:D95-D100 (2004).
Leopold et al., "Chapter 4: Moisture as a Regulator of Physiological Reaction in Seeds," Seed Moisture, CSSA Special Publication No. 14, pp. 51-69 (1989).
Li et al., "Establishment of a highly efficient transformation system for pepper (Capsicum annuum L.)," Plant Cell Reports, 21: 785-788 (2003).
Liu et al., "Carbon Nanotubes as Molecular Transporters for Walled Plant Cells," Nano Letters, 9(3):1007-1010 (2009).
Liu et al., "DNAzyme-mediated recovery of small recombinant RNAs from a 5S rRNA-derived chimera expressed in *Escherichia coli*," BMC Biotechnology, 10:85 (2010).
Llave et al., "Endogenous and Silencing-Associated Small RNAs in Plants," the Plant Cell, 14:1605-1619 (2002).
Lu et al., "OligoWalk: an online siRNA design tool utilizing hybridization thermodynamics," Nucleic Acids Research, 36:W104-W108 (2008).
Lu et al., "RNA silencing in plants by the expression of siRNA duplexes," Nucleic Acids Res., 32(21):e171 (2004).
Luft, "Making sense out of antisense oligodeoxynucleotide delivery: getting there is half the fun," J Mol Med, 76:75-76 (1998).

Mackenzie et al, "Transgenic Nicotiana Debneyii Expressing Viral Coat Protein Are Resistant to Potato Virus S Infection," Journal of General Virology, 71:2167-2170 (1990).
Maher III et al., "Inhibition of DNA binding proteins by oligonucleotide-directed triple helix formation," Science, 245(4919):725-730 (1989).
Mandal et al., "Adenine riboswitches and gene activation by disruption of a transcription terminator," Nature Struct. Mol. Biol., 11(1):29-35 (2004).
Mandal et al., "Gene Regulation by Riboswitches," Nature Reviews I Molecular Cell Biology, 5:451-463 (2004).
Manoharan, "Oligonucleotide Conjugates as Potential Antisense Drugs with Improved Uptake, Biodistribution, Targeted Delivery, and Mechanism of Action," Antisense & Nucleic Acid Drug Development, 12:103-128 (2002).
Masoud et al., "Constitutive expression of an inducible β-1,3-glucanase in alfalfa reduces disease severity caused by the oomycete pathogen Phytophthora megasperma f. sp medicaginis, but does not reduce disease severity of chitincontaining fungi," Transgenic Research, 5:313-323 (1996).
Matveeva et al., "Prediction of antisense oligonucleotide efficacy by in vitro methods," Nature Biotechnology, 16:1374-1375 (1998).
Meinke, et al., "Identifying essential genes in *Arabidopsis thaliana*," Trends Plant Sci., 13(9):483-491 (2008).
Misawa et al., "Expression of an Erwinia phytoene desaturase gene not only confers multiple resistance to herbicides interfering with carotenoid biosynthesis but also alters xanthophyll metabolism in transgenic plants," the Plant Journal, 6(4):481-489 (1994).
Misawa et al., "Functional expression of the Erwinia uredovora carotenoid biosynthesis gene crtI in transgenic plants showing an increase of ?-carotene biosynthesis activity and resistance to the bleaching herbicide norflurazon," The Plant Journal, 4(5):833-840 (1993).
Miura et al., "The Balance between Protein Synthesis and Degradation in Chloroplasts Determined Leaf Variegation in *Arabidopsis* yellow variegated Mutants," the Plant Cell, 19:1313-1328 (2007).
Molina et al, "Inhibition of Protoporphyrinogen Oxidase Expression in *Arabidopsis* Causes a Lesion-Mimic Phenotype That Induces Systemic Acquired Resistance," The Plant Journal, 1 7(6):667-678 (1999).
Molnar et al., "Plant Virus-Derived Small Interfering RNAs Originate Predominantly from Highly Structured Single-Stranded Viral RNAs," Journal of Virology, 79(12):7812-7818 (2005).
Moriyama et al., "Double-stranded RNA in rice: a novel RNA replicon in plants," Molecular & General Genetics, 248(3):364-369 (1995).
Moriyama et al., "Stringently and developmentally regulated levels of a cytoplasmic double-stranded RNA and its high-efficiency transmission via egg and pollen in rice," Plant Molecular Biology, 31:713-719 (1996).
Morrissey et al., "Potent and persistent in vivo anti-HBV activity of chemically modified siRNAs," Nat Biotechnol. 23(8):1002-1007 (2005).
Moser et al., "Sequence-Specific Cleavage of Double Helical DNA by Triple Helix Formation," Science, 238:645-646 (1987).
Non-Final Office Action dated Apr. 11, 2013, in U.S. Appl. No. 13/042,856.
Non-Final Office Action dated Aug. 12, 2015, in U.S. Appl. No. 13/612,936.
Non-Final Office Action dated Aug. 13, 2015, in U.S. Appl. No. 13/612,929.
Non-Final Office Action dated Jul. 23, 2015, in U.S. Appl. No. 14/335,135.
Non-Final Office Action dated Jul. 30, 2014, in U.S. Appl. No. 13/042,856.
Non-Final Office Action dated Jun. 5, 2015, in U.S. Appl. No. 13/612,948.
Non-Final Office Action dated Jun. 8, 2015, in U.S. Appl. No. 13/612,941.
Non-Final Office Action dated May 15, 2015, in U.S. Appl. No. 14/608,951.
Non-Final Office Action dated May 22, 2015, in U.S. Appl. No. 13/612,985.

(56) References Cited

OTHER PUBLICATIONS

Office Action dated Feb. 17, 2014, in Mexican Patent Application No. MX/a/2012/010479.
Office Action for UA Application No. 201211548 dated Jul. 23, 2015.
Office Action dated Jan. 6, 2015, in Japanese Patent Application No. 2012-557165.
Office Action dated Nov. 19, 2014, in Eurasian Patent Application No. 201201264/28.
Office Action dated Nov. 3, 2014, in Chinese Patent Application No. 201180012795.2.
Office Action dated Oct. 8, 2014, in Mexican Patent Application MX/a/2012/010479.
Paddison et al., "Stable suppression of gene expression by RNAi in mammalian cells," Proc. Natl Acad. Sci. USA, 99(3):1443-1448 (2002).
Palauqui et al., "Activation of systemic acquired silencing by localised introduction of DNA," Current Biology, 9:59-66 (1999).
Parera et al., "Dehydration Rate after Solid Matrix Priming Alters Seed Performance of Shrunken-2 Corn," J. Amer. Soc. Hort. Sci., 119(3):629-635 (1994).
Peretz et al., "A Universal Expression/Silencing Vector in Plants," Plant Physiology, 145:1251-1263 (2007).
Pomprom et al., "Glutamine synthetase mutation conferring target-site-based resistance to glufosinate in soybean cell selections," Pest Manag Sci, 2009; 65(2):216-222 (2009).
Pratt et al, "Amaranthus Rudis and a. Tuberculatus, One Species or Two?," Journal of the Torrey Botanical Society, 128(3):282-296 (2001).
Preston et al., "Multiple effects of a naturally occurring proline to threonine substitution within acetolactate synthase in two herbicide-resistant populations of Lactuca serriola," Pesticide Biochem. Physiol., 84(3):227-235 (2006).
Qiwei,"Progress in DNA interference," Progress in Veterinary Medicine, 30(1):71-75 (2009).
Rajur et al., "Covalent Protein-Oligonucleotide Conjugates for Efficient Delivery of Antisense Molecules," Bioconjug Chem., 8:935-940 (1997).
Reddy et al., "Aminomethylphosphonic Acid Accumulation in Plant Species Treated with Glyphosate," J. Agric. Food Chem., 56(6):2125-2130 (2008).
Reither et al., "Specificity of DNA triple helix formation analyzed by a FRET assay," BMC Biochemistry, 3:27 (2002).
Riggins et al., "Characterization of De Nova Transcriptome for Waterhemp (Amaranthus Tuberculalus) Using Gs-Flx 454 Pyrosequeneing And Its Application for Studies of Herbicide Target-Site Genes," Pest Manag. Sci., 66:1042-1052 (2010).
Rose et al, "Functional Polarity Is Introduced by Dicer Processing of Short Substrate RNAs," Nucleic Acids Research, 33(13):4140-4156 (2005).
Santoro et al. "A general purpose RNA-cleaving DNA enzyme," Proc. Natl. Acad. Sci. USA, 94:4262-4266 (1997).
Sathasivan et al., "Nucleotide sequence of a mutant acetolactate synthase gene from an imidazolinone-resistant *Arabidopsis thaliana* var. Columbia," Nucleic Acids Research, 18(8):2188-2193 (1990).
Schwab et al., "RNA silencing amplification in plants: Size matters," PNAS, 107(34):14945-14946 (2010).
Schwember et al., "Drying Rates following Priming Affect Temperature Sensitivity of Germination and Longevity of Lettuce Seeds," HortScience, 40(3):778-781 (2005).
Second Chinese Office Action issued in Chinese Patent Application No. 201180012795.2, dated Jun. 10, 2014.
Seidman et al., "The potential for gene repair via triple helix formation," J Clin Invest., 112(4):487-494 (2003).
Selvarani et al., "Evaluation of seed priming methods to improve seed vigour of onion (Allium cepa cv. Aggregatum) and carrot (Daucus carota)," Journal of Agricultural Technology, 7(3):857-867 (2011).

Senthil-Kumar et al., "A Systematic Study to Determine the Extent of Gene Silencing in Nicotiana Benthamiana and Other Solanaccac Species When Heterologous Gene Sequences Are Used for Virus-Induced Gene Silencing", New Phylologist, 176:782-791 (2007).
Sharma et al., "A simple and efficient Agrobacterium-mediated procedure for transformation of tomato," J. Biosci., 3493):423 433 (2009).
Sijen et al., "On the Role of RNA Amplification in dsRNA-Triggered Gene Silencing," Cell, 107:465-476 (2001).
Singh et al., "Absorption and translocation of glyphosate with conventional and organosilicone adjuvants," Weed Biology and Management, 8:104-111 (2008).
Snead et al, "Molecular Basis for Improved Gene Silencing by Dicer Substrate Interfering RNA Compared With Other siRNA Variants," Nucleic Acids Research, 41(12):6209-6221 (2013).
Steeves et al., "Transgenic soybeans expressing siRNAs specific to a major sperm protein gene suppress Heterodera glycines reproduction," Funct. Plant Biol., 33:991-999 (2006).
Strat et al., "Specific and nontoxic silencing in mammalian cells with expressed long dsRNAs," Nucleic Acids Research, 34(13):3803-3810 (2006).
Street, "Why is DNA (and not RNA) a Stable Storage Form for Genetic Information?," Biochemistry Revisited, pp. 1-4 (2008).
Sudarsan et al., "Metabolite-binding RNA domains are present in the genes of eukaryotes," RNA, 9:644-647 (2003).
Sun et al., "A Highly efficient Transformation Protocol for Micro-Tom, a Model Cultivar for Tomato Functional Genomics," Plant Cell Physiol., 47(3):426-431 (2006).
Supplementary European Search Report for EP 1283156T8 dated Jan. 29, 2015.
Supplementary European Search Report for EP 12832415.9 dated Jan. 21, 2015.
Sutton et al., "Activity of Mesotrione on Resistant Weeds in Maize," Pest Manag. Sci., 58:981-984 (2002).
Takasaki et al., "An Effective Method for Selecting siRNA Target Sequences in Mammalian Cells," Cell Cycle, 3:790-795 (2004).
Tank Mixing Chemicals Applied to Peanut Crops: Are the Chemicals. Compatible?, College of Agriculture & Life Sciences, NC State University, AGW-653, pp. 1-11 (2004).
Taylor, "Seed Storage, Germination and Quality," The Physiology of Vegetable Crops, pp. 1-36 (1997).
Templeton et al., "Improved DNA: liposome complexes for increased systemic delivery and gene expression," Nature Biotechnology, 15:647-652 (1997).
Tepfer, "Risk assessment of virus resistant transgenic plants," Annual Review of Phytopathology, 40:467-491 (2002).
The Seed Biology Place, Website Gerhard Leubner Lab Royal Holloway, University of London, http://www.seedbiology.de/seedtechnology.asp, last updated May 2, 2012.
Thompson, et al., "CLUSTAL W: improving the sensitivity of progressive multiple sequence alignment through sequence weighting, position-specific gap penalties and weight matrix choice," Nucl. Acids Res, 22(22):4673-4680 (1994).
Timmons et al. "Specific interference by ingested dsRNA," Nature, 395:854 (1998).
Topfer et al., "Uptake and Transient Expression of Chimeric Genes in Seed-Derived Embryos," Plant Cell, 1:133-139 (1989).
Toriyama et al., "Transgenic Rice Plants After Direct Gene Transfer Into Protoplasts", Biotechnology, 1988, pp. 1072-1074, vol. 6.
Tran et al., "Control of specific gene expression in mammalian cells by co-expression of long complementary RNAs," FEBS Lett.;573(1-3):127-134 (2004).
Tranel et al., "Resistance of Weeds to ALS-Inhibiting Herbicides: What Have We Learned?," Weed Science, 50:700-712 (2002).
Tuschl, "Expanding small RNA interference," Nature Biotechnol., 20: 446-448 (2002).
Tuschl, "RNA Interference and Small Interfering RNAs," ChemBiochem. 2(4):239-245 (2001).

\* cited by examiner

SEQUENCE LISTING

<160> NUMBER OF SEQ ID NOS: 659

<210> SEQ ID NO 1
<211> LENGTH: 1473
<212> TYPE: DNA
<213> ORGANISM: Canola

<400> SEQUENCE: 1

```
tgaatggctg aacgccagct ctatacgact actataggga aagctggtac gcctgcaggt      60
accggtccgg aattcccggg tcgacccacg cgtccgaggg ggaagtggta ccggaagcct     120
ttcccgttg caaggtttgg gtcgtgctgc tcgacgacac ttgtctgcga ttcttgatga      180
gttttgggga catttatatg attttcatgg gcaattagtt gctgaagcca gggcaaagaa     240
actagaccag ttgtttggcg ctgatcaaaa gtcaccctct cctgtgaaag tggattcttt     300
tgtaagggac aacactagca gtggatattg catgtcacca acaacaaagg gattggaatc     360
acagatgaat tcgagtttgt atgattcact gaagcagcag aggacacctg aagtatcga     420
ttctttatat ggactacaaa gaggttcatc accgtcatca tcaccgttgg tcaaccgtat     480
gcagatgttg actgcatatg gtaacactcc caataataat aatgcttatg aattgagtga     540
agaagatac tccagcctgc gtgctccatc gtcctcagag tctcgggaac accaacaacc     600
agctacaatt catggatacc agattaagtc ctacgttgac aatttggcaa agaaaggct     660
tgaagcttta cagtcccgtg gagagatccc aacatctcga tctatggccc tgggttcttt     720
gagctacaca cagcaactgg cttagcctt gaaacagaag tcccagaatg gtctaacccc     780
tggaccagct cctgggtttg agaactttgc tgggtctaga acgtatcgc gacaatccga     840
aagatcttac tacggtgttc catcttctgg aaacaccgat tctgtaaacg cagtagttgc     900
taatgagaag aagtatagta gcatgccaga tatatctgga ttgtctatgt caccgggcat     960
cctgccttcg ccaaacaaca agagtgggta ctgggatgca tcaactggag gaggaggagc    1020
agggtatagc gcttcttcgt atggtcggtt aagcaatgaa tcatcatcat tatattctaa    1080
tttggggtca agggttggag tagcctcagg ttatgaaacc atgtctcagt caagaggagg    1140
ctacagagat gcatatacgt tgccacagag tgcaacaaca gggactggat cgctttggtc    1200
cagacagccc tttgagcagt ttggtgtagc ggagaggaac ggcgctgttg gtgaggaagt    1260
caggaataga tcagctccga taaatataga caacaacaac aacgcttcta ccgtcgatgc    1320
agaggctaag cttcttcagt cgttcaggaa ctgtatactg aagcttatta aactggaagg    1380
atcggaatgg ttgtttgggc aaagcgatgg agtcgatgaa gaactgattg acaaggtagc    1440
tgcgagagag aagtttatct atgaagctga aac                                 1473
```

<210> SEQ ID NO 2
<211> LENGTH: 4315
<212> TYPE: DNA
<213> ORGANISM: Corn

<400> SEQUENCE: 2

```
atggatgcac cggatgttca acagagcatg ggatataagg agtccagggg tggtatgcct      60
aagttttcc atgcccttgg accagcactc ctgatttcaa tgggttacat tgatctcggg     120
aagtgggtgg cagccgttga agctggttct tgttttggat tcgacctggt gttgctggct     180
ctcctttca atttcactgc cattgtatgt cagtaccttg ctgcttgcat ggcactgtc      240
acagggaaga atcttgcaga gatatgccac caagagtaca accagccaac atgtatattc     300
cttggtgttc aagctggatt gtctttgttg acgtcagagc tgactatgat ttttggcata     360
gcactcggat tcaacctcct gtttgaatat gatgatctca tcacagggat atgctttgca     420
acagtggtac ctaatctgct accatatgct atatcccacc tgggaaagaa gatggaaggg     480
acaataaatg cctgcatagc aggatttgca cttcttagtt atgtgcttgg cttattggtt     540
agccagccac aaattcctct cacgatgaat gtaatattcc ccaagatcag tggtgagagt     600
```

```
gcttactctc tgatggcgct tcttggtgca aacataatgg cacacaactt ctacattcat      660
tcatcagttg tccagggtca gaaaaagtca tctgcagttg gtcttggagc cttatttcac      720
gaccaccttt tttcaatatt gttcattttt actggaatct ttatggtgaa ctatgttcta      780
atgaactctg cagcagcgga atctactaat actcttctca ttaccttcca agatgttgta      840
gagctaatga atcagatatt tgtaaaccct ctggcaccaa ctatattttt agtggttctt      900
ctcttctcca gccacatcat ctcgctgaca tctgctatcg gtagccaagt gatttcacac      960
catttattcg gtataaacct tcctctttct ggacatcgtc tcctactgaa ggtttttgcc     1020
atagttccta ctctgtactg ggcgaaagtt gcaggagctg aagggatata ccaattatta     1080
attatatgcc agattattca agccatgctt cttccatctt cagtcgtccc actttttcgt     1140
gttgcttcat caagatcaat aatgggagcc catagagtgt ctttgcatct ggagatactg     1200 gttttcttg catttctcct tatgctattt tcaaatatca tatttgtggc agaaatgcta      1260
tttggcgaca gtgggtggat gaacaatctg aaaggatata ctggaagccc tgtggtgctc     1320
ccatataccg ttttagtttt agttgcactt atatctgtgg cttttcact gtacctggct      1380 gttacaccat tgagatctgg aagtcatgaa gctgaatccc atgaatggtc tgtgcattct     1440
cagagagaac tcttgaatac ttctcaagaa agggaagatg ttaaggtgga caatgttaca     1500
tatgaggaag atcaaagatc agatgttgtc ccttctccca gggatgtgcc tgacagccat     1560
ccggaactgg ccttggacta tattgatact tctgacactg ctgtagaatc tgatcacgac     1620
tctcaacaat ctactgctta tgcatccact gctcctgaaa cctgctcctc cccgtcgttt     1680
actcgcgagg agtcaaaatc agttgttgca gtcaactggc cggagccttt ggagaaggtt     1740
cctacttcta ctgtgatgga ggaaagcaca gtagaaaatg tggtctctag gatcacgact     1800
gaaagagatg ttttagtaga aacagatgtt gtctcgggca aggataagga agatatccgt     1860
actttggagt ctgagaagtc aattgttgat agcacccat  atgtgtctga tgacggtccg     1920
ccatccctta ctttcagcag gggaaagggc tcagatgcag gaaatggcag tggtagtctc     1980
tcaaggttat ctggtttggg ccgtgcagca aggagacagc tagctgctac tcttgatgag     2040 ttctggggc atctgtttga ttaccatggt aagctcactc aagaagctag caccaaaaag      2100
tttggtatct tgcttgggat agaccttaga acacctagca catctgtaag aacggataaa     2160
caagctgctg aaatacttaa gagcccactg gtgagagact caatgcgggg ggcagctttt     2220
ttgtcaagct cagtggacat gatgtccct aagaatgaaa cgtcgaattt ggaacttgca      2280
tatgggcttc agagggggacc tggcatggga ttgtcaagct ggtctcaggg tatgcagcta     2340
ccaaatacac agctgcagag ctcaagcaat agcctacttg agcagagtgc aagattaaac     2400
tcaaatttta gttcatctta ttcagacaac aatcagttct accaacctgc aacaattcat     2460
ggataccagc tcacatctta cctgaaacag atgaatgcca gcccaagcct ttactctagc     2520
atgccgctgg acccacaacg gcttccaaaa tcatctgtgt ctgctgtgcc aaactatgct     2580
gattccatga tgcatgctcg taatcataac ctgcttgctt cactgggtgg tactactaca     2640
cagcttcctg caacatcccg cgtaggctca atgatgcctg aaagatcgta ttatgatcct     2700
tccagcgttg atgggaatga aaacgctggt tcacctgctt actcaaaaaa gtaccacagc     2760
tcacctgata tgtctggaat aatcgctgca agtagagctg cactcttgaa tgaagcaaag     2820
ttgggtgctg ccattggacc acagtcatac ctcagcaggc tggcggcaga aagatctcaa     2880
tatgcaagct caacagccag gcccgcggct ccattagcat ttgacgagct ttcacctcct     2940
```

```
aagctccaga gtgatatctt ctcggcgcag tcaagcatga gaccaagtgc tagatccctt    3000
tgggctaagc aaccatttga gcaattgttc ggcatgtcaa gtgcagagct cagtaaaggt    3060
gacttcaatc ttccaggcag atcaggtggc gtggccaagg atgatttctc ttataaggaa    3120
tctgagacga agcttcttca gtccctcagg ctctgcatca tgaagctcct taagctagag    3180
ggatcagggt ggctgttcaa gcaaaatggt ggttgtgatg aagatctaat cgaccgagtc    3240
gctgcagccg agaagctatt gatgcaaggg actgccgaga tcaactgct gcttcatggt     3300 ggtgatctcc agcaacattc ttccgaccag gccggcatcc agtacatgcg cacgcttccc    3360
aactgcgggg aggactgtgt ttggcgcgcg tcactcgtcg ttagtttcgg tgtctggtgt    3420
gtccgccgag tgctggacat gtctctggtg aaagcaggc cagaactttg gggcaagtat     3480
acctatgtcc ttaaccgtct tcaggggatc ttggaccctg cgttctccaa gcctcggggt    3540
gctctgacaa tatgcacctg ccttcagaaa gacaccgag tgcgcaatag cccacccac      3600 agtgggctaa cagccatggg cccggtcccc acaccgatcc ggggcgcctt cacgaccgca    3660
ggcgtggttc tggagatgat caaggacgtg gaggctgcgg tctcaggccg caagggcagg    3720
agcggcacgg cggcgggcga cgtcgccttc cccaagggga aggagaacct ggcctccgtg    3780
ctgaagcggt acaagcggcg gctcgccagc aagggccagt agcgcgcggg tgtcagacag    3840
gcaggcgatc gcaagcaatg ttaggaggag cctgactatt gttctccagg ggggctgcca    3900
ctggcgccgg cctccctgag ccctggattt tttcgttgca cgacgttcct agggaccggt    3960
ggttgcccga tggtcgtctt ggtcccttcc agcaggtttt ttttttcctt ccctctttct    4020
gttggtttct ttttgttggc tttgtgatgt tttgtaaggg gcaactaggg tatgtgctca    4080
gaaggactca agatgtacac gcgaagatgt actagtctgc tgatgcagcg ttgtaaagtc    4140
cacactctgc aggttaaccc tttttggggc cgtcaagtgt tagtgcgtgc cctatgtatg    4200
ttaatcaccc ctgcagagag gttgcgaata ctgaactact cacagacctg cacctgtcga    4260
gatcgtttgt aatatccgac gtcttgttca gaattgttct cactcttttt tgccc         4315
```

<210> SEQ ID NO 3
<211> LENGTH: 2003
<212> TYPE: DNA
<213> ORGANISM: Corn

<400> SEQUENCE: 3

```
tagtttatcc gacctttaac atttctgaat ttaaaccggc aaattaaccc agacgaacag      60
atgacaagaa tttcaaaaaa aaaaaaaaaa gcgtaagcac cacagttctt gaaatcagga     120
ctggtccaca aacccactc ttgccacccc gtgacagcag gaaacagtac acagtagcgc      180
ataaccttcc aagaaaattt aattaataaa cccgaagaag ccaagaggga agggaaaaaa    240
aaagaaagaa aaaaaactga cacataagaa aagagcagcg agcaagctga aggtgaaagc     300
cacagcagct cgtccccttc cccccacttc ttcctcagat aaggagaggc cccaggccag     360
agaaaaaagc atcgaatttc ccccgttaa ttggcctgag ccctcagccg tctaccagca      420
gcagctagag gtacgattct cgcattgctt gctccctgcg cctgccctcg atttttgctg     480
ttttttcgag ctcctcttcc agttcttttg ccgtgttgga accgcatcta tgcagcctag    540
cgcggggtac tagcgtgatt cggtcagtgg atcccgtcgg gctgctgctt cctcgcggct    600
gatttgcgag aggaagcagg tccccgggaa gcgatctcat ttttcgttat ttttttagct    660
ccctacacca aagaccagag tcagatccga ggctacccgc cgcccggca aggatttac     720 ccggccggag ctctgcaaca tcggtgggat cgatggctgc gacctccacg agctccggtg    780
```

```
cccacgaatc gaagtcagca gcgccgtgtg gactgagtca cgtgcctggt tcgccgtcct    840
gtccgacgct tctcacctcg agagcccgtc gctgttgcct cggactcgag ggagctggcg    900
gcgcaaacgc cgtgcggcca aaatcgagat ccccaccatc cgaatcgagg tcctctctac    960
cagaatcagt tcccgccgcc gcgtcgaggt agctgtcacc caaattgagc tttccgtcgc   1020
tgctggatgt gttggaatcg gaagcttcgg gcgcatagct tgagctcgct caagtgtatc   1080
gagcaagcaa accaagcgtt gggggtcttg ctttgcgcct tgccgcgct  agcttagcct   1140 atctatccgt gctaggaatc cccctccctt tcggtgtgat gttttttgact tgccactgcc   1200 tggtgttgct gggctgctt  ttctcttctc ctttggggct ctgaatgaag actgaagaaa   1260
tcgaaagaga ggaaagctac gcctgagtcg gggaacgcct acgaagtaag ttttggctta   1320
aaggtggaag cttttgaggt ttctccttgc gaaataaatg ctttttttcga tgttatttga   1380 tggatttggt tggtactcgg tcaaaaggtg ttcttggttt gcccttttcta tgctctggct   1440 gctgttgcaa ctgcaacttc cctttcccttt agagtttggc gctctaaaag ttggttcact   1500
ttgcacgaag gatttctgtt tcttgttgct gattgggttg tttggatcta tctgcaggca   1560
gacaagctag gttttactgc ttcattgagc acaaagatcc gctgacctct tgctcttggt   1620
aaaaatccaa cctttcttgt attgttttct tcctgggaaa acctccttgt ggtgcataaa   1680
cttcgtagta cactctgcca tttctggaga ggaagctgag aactactatc catatctggc   1740
acgacccttg tcaagaacca tggctgttca catgccatga agctgcttga actggaggca   1800
cctaaatgct gtggattgtt cctatgcaga tgattggatc agtggtttca ggcttcgggg   1860
ggttcgatca gatgttgtat gaataatagc aggattgctt gagagactat agtttgggta   1920
ctgtttgctt ctgtatttac tggtacggtt tcctactgat ctgcggctgc gcaggaaggc   1980
attctctttt ttgccgtacc atg                                             2003

<210> SEQ ID NO 4
<211> LENGTH: 4372
<212> TYPE: DNA
<213> ORGANISM: Cucumber

<400> SEQUENCE: 4
atggaatcta cgacattgcg tacaactcat cagtccgctg ctattcatag gtttatacct     60
ttcattgcac ctgcactcct ggtttcaatt agttatgttg accctggaaa gtgggcagca    120
actgttgaag gaggtgctcg gtttggcttt gatttgcttg tgctagtgct tcttttcaat    180
cttgctgcta ttttatgcca gtatctctca gctagcattg gtgtagtcac cggaagaggt    240
cttgcccaga tatgcagcga ggagtatgat aagtgtacat gtttcttcct gggaatccaa    300
gcagaggctt ctgtgattct gttagacctt aacatgatct tgggcatttc acatggactt    360
aatcttctac ttgggtggga cctcttcaca tgtgtccttt tgacgggtgt tgctgctgct    420
ttatttcctc cttttgctga ccttcaggaa gatggcaggg caaagttcct gtatatatgt    480
atggcgggat ttgtactgct ctctttggtt cttggagtat taatcagtca acctgaaatc    540
ccactttcca tgaatctcat gccgacaagg ttaaacgggg aaagtgcctt tactcttatg    600
agtcttcttg gagcaagtgt catgcctcac aatttttatg tgcattcttc tattgtgcag    660
cagcaccaga gtccacccaa tatttccaaa gaagttttgt gttacaatca tttgtttgct    720
attttctgca tattcagtgg aatctatgtg gtgaataacg ttctcatgaa ctcagctgca    780
aatgtattct atagcagtgg ccttgctttg cacacccttc cagatgcatt atctttagtg    840
```

```
gagcaggtat ttgggagctc agtggtatat gttctcttct tactcgttct gtttctatca    900
aatcaaatca cagctctcac atggagtctt ggtggtcaac ttgtcctgac caatttctta    960
aaattggata ttcctggttg ctccattgt gctacaatta ggattattgc cattattcca    1020
gcgctctgct gtgtctggag ttcaggcgct gaagggatgt atcaacttct tatattttct    1080
caggttatgg tagctctatt gcttccatct tctgtgattc ccctctatcg tgttgcttca    1140
tcaagaacaa taatgggtgc cttcaaaata tcgcagcttg tggaatttat agcaattggt    1200
atctttattg gaatattagg actgaaaatt atatttgttg tagagatgat ttttggtaac    1260
agtgattggg tagttaattt gaggtggaac atggggagtg gtatgtcaat cccatttgtg    1320
gttctcctta ttactgcttg ttcatcgttt tgtctgatgc tatggttggc agctactcca    1380
ttaaaatctg ctactactat tgcccaatta gatgctgaag tattgaactg ggatatgcca    1440
gaagttatac ctgattcatc tgaagagagg gaaaacatag atttggggaa aagttcaaac    1500
agtgccgaac ctatagaaag tcattctgac ctatctacaa caaagtttga ttttaatttg    1560
cctgaaaata ttatggaacc tgatcaggtt cttggttcag ttaatcaaaa cgagaatcga    1620
tctagtggtg tagttccaag ctcccccaaaa tatgtacaag aggaacttga atccactgag    1680
gagttagtct catcctcaac tgtgactcgc gatgttcctg attcaacatt ggctgacaaa    1740
aaggtcttaa aaatagagcc agtggagccc gttgaaaaga ctgttggact cgatggtgat    1800
ttgcgttctg agaaggatga ttatgaggtt gataactggg aggctgaaga gtcaatgaaa    1860
gagatttctg gaatataccc atcctcaaca tctgagggtc ctggttcttt tagaagtatt    1920
ggtgggaaaa gcgaagaagg tgggaatggc actggtagtc tttcaaggtt agctggcctt    1980
gggcgtgctg caaggcgcca acttactgga atacttgatg aattttgggg acaattgtat    2040
gatttccatg gggtggctac tcaagatgca aaggttaaga aactagattt gttgctgggt    2100
attacctctc tgaaattgga tgctgttggt aaagattttc ctcactcatc acctcttgga    2160
tgcaaaacat ctgatccaat ttcttccagt ttgtacgact cccccaagag tcagagggta    2220
caaagtgggt tagaaccacc ctatgggata caaaagggga accaaccatt gtggtctaac    2280
cacatgcagc tttgggatgc gtatgtgaat aattctagcc ataatgctct ggactctgga    2340
gtgaagcgat attctagttt gcgcagtttg ccgtctactg agagttggga ttatcagcct    2400
gccacagtcc atggctatca gctaacttac ctgagtagaa tggcaaagga cagaagttct    2460
ggtaattcga atggtcagtt ggattcgtca ggctctaaat atcataccttt gggtggtggt    2520 ggtgcaggct tgcgagactc agttgcattt gcaatggggc aaaagttgca aaatggctta    2580
ggtgcttgtc agcaggctgc tcccccagga ttttccaaca tcaaagtatc caggaaacct    2640
tcttccgaat ctgaaaggca atattatgat ctttctcctt ctggaactgg tgagaattta    2700
gtgagtgtat ctaacacaaa gaaataccat agcttgccgg atattcaccg tgatcagcac    2760
acatcagata agagttctca gtgggataat gcaactgttt atggaacatc aattggtaaa    2820
ataacagctc gtggagtgtc ctttgcaaat tctggatcaa gatcagtcgc tccttttagca    2880 tttgatgaac tatctcctgc aaatgtctac agtggtgcat tatcaccaca aatgaatcct    2940
catttggatt ctggatcttt ctggcataga cagccttctg agcaatttgg cttggataaa    3000
aatagcaact ccgagagtaa aggaattggg aggctgcatt caattagtca agaagcttct    3060
ttcgttgtta attcagaggc caggcttctc cagtccttca gagactgcat tgtcaaactt    3120
cttaaattgg aaggatcaga ctggttattt gggcaaagtg atggtactga cgaggaacta    3180
attgactgtg tagctgccag ggagaaattt ctttatgaag ctgaggcaag ggagatgggt    3240
```

| | |
|---|---|
| cgggtggtcc gtatgaaaga atctccttca ttttctcctg ataggagacc aggttctgga | 3300 |
| atgaagaacg atacaaattt ctccaatgtt tctatatcct ctgtacctca ttgtggagaa | 3360 |
| ggttgtattt ggagatcaga tctgattgta agttttggtg tatggtgcat tcaccgaatt | 3420 |
| ctggatctct cacttatgga aagtcggcct gaactgtggg gaaaatatac ctatgtactc | 3480 |
| aatcgtcttc agggtattat cgatcctgca ttttcgaagc ctcgtgtacc aatgccgcca | 3540 |
| tgcttctgcc ttcaaattcc ccaagcattc cagcagaggt caagcccaca aattgcaaac | 3600 |
| ggaatgttgc ctcctgctgc aaaacctggc aagggaaaat gcaccactgc ggcaatgctt | 3660 |
| ctggatatgg tcaaggatgt ggagatagcc atctcttgcc gaaaaggccg aactggtaca | 3720 |
| gctgccggtg acgtagcttt cccaaagggg aaggagaact tggcttcagt cctcaaacgc | 3780 |
| tacaagcgtc gattatccaa taaaccagtt gccactcacg aagtatcatc tatctcacgc | 3840 |
| aagctttcag caacatccgt tccttatagc tcatagtatt tacccaaaaa tggtgatcaa | 3900 |
| atcacccagc tgtttaattt tggaaagcag ctcatggttc ggaacgagat gccctcatct | 3960 |
| tggtctttac tctctctctc aaaacattat caaggctctt tgctgcgaat tttcttctca | 4020 |
| catgttaaaa atgattagga tgtgactcaa tggacccctta gttgcagcaa aactcaggaa | 4080 |
| actggtgcaa acccaaagtt gattgttatg gtggttgcac tagttacttg tatcaaagta | 4140 |
| attgctggag gagagatcac aaggtgactt tgaaaagttc aaaaaaaaaa aaatgttagt | 4200 |
| atatagcaga cagaggctaa tgtgctgtat atattgtctg tgcaaaactt tctgaaacat | 4260 |
| ttcaaatatc tttccacaaa agctatttta gatcttgttg tttgttgtta gatgatgcag | 4320 |
| aaactttgtt ttgttgcccg tttcggtgag tcaaaagata actacatcct ct | 4372 |

<210> SEQ ID NO 5
<211> LENGTH: 3768
<212> TYPE: DNA
<213> ORGANISM: Cucumber

<400> SEQUENCE: 5

| | |
|---|---|
| atggaatcta cgacattgca tacaactcat cagtcgggtg ctattcatag gtttatacct | 60 |
| ttcattgcac ctgcacttct agtttcaatt agttatgttg accctggaaa gtgggctgca | 120 |
| actgttgaag gaggtgctcg gtttggcttt gatttgtttg tgttagtgct tcttttcaat | 180 |
| cttgctgcta ttttatgcca gtatctctca gctagcattg gtgtggtcac tggaagaggt | 240 |
| cttgcccaga tatgcaacga ggagtatgat aagtgtacat gtttcttcct gggaatccaa | 300 |
| gcagaggctt ctgtgattct gttagacctt aacatgatct tgggcatttc aaatggactt | 360 |
| aatcttctac ttgggtggga cctcttcaca tgtgtccttt tgacgggtgt tgctgctgct | 420 |
| ttatttcctc cttttgctga ccttctggaa gatggcaggg caagttcct ctatatatgt | 480 |
| atggcgggat ttgtactgct ctctttggtt cttggagtat taatcagtca acctgaaatc | 540 |
| ccactttcca tgaatctcat gccgacaagg ttaaatgggg aaagtgcctt tactcttatg | 600 |
| agtcttcttg gagcaagtgt catgccacac aatttttatg tgcattcttc tattgtgcag | 660 |
| cagcaccaga gtccaccaaa tatttccaaa gaagtttcgt gttataatca tttgtttgct | 720 |
| atttcctgca tattcagtgg aatttatgtg gtgaataacg ttctcatgaa ctcagctgca | 780 |
| aatgtattct atagcagtgg tcttgctttg cacaccttta cagatgcatt gtctttaatg | 840 |
| gagcaggtat ttgggagctc agtggtatat gttctcttct tacttgtttt gtttctatca | 900 |
| aatcaaatca cagctctcac atggagtctt ggtggtcaac tggttctgac caatttctta | 960 |

-continued

```
aaattagata ttcctggttg gctccattgt gctacaatta ggattattgc cattattcca      1020
gcactatgct gtgtctggag ttcgggtgct gaagggatgt atcaacttct tatattttct      1080
caggttatgg tagctctatt gcttccatct tctgtgattc ccctctatcg tgttgcttca      1140
tcaagaacaa taatgggtgc cctcaaaata tcgcagcttg tggaatttat agcaattggt      1200
atctttattg gaatattagg actgaaaatt atatttgttg tagagatgat ttttggtaac      1260
agtgattggg tagttaactt gaggtggaac atggggagtg gtatgtcaat cccatttgtg      1320
gttcttctta ttactgcttg ttcatcgttt tgtctgatgc tatggttggc agctacccca      1380
ttaaaatctg ctactactat tgcccaatta gatgctcaag tattgaactg ggatatggca      1440
gaggttagac ccgattcatc tgaagagagg gaaaacatag atttggggaa aagttcatac      1500
agtgccgagc ctatagaaag tcattctgac ctatcttcaa caaagtttga ttttaatttg      1560
cctgaaaata ttatggaacc tgatcaggtt cttggttcag ttaatcaaaa cgagaatcga      1620
tctagtactg tagttccaag ctccccaaaa tatgtacaag aggaacttga atccactgag      1680
gagttagtct catcctcaat tgtgactcac gatgttcctg attcaacatt ggctgacaaa      1740
aaggtcttaa aaatagagtc agtggaggcc gttgaaaaga ctgttggact cgatggtgat      1800
ttgcgttctg agaaggatga ttatgaggtt gataactggg aggctgaaga gtcactgaaa      1860
gagatctctg gaatataccc atcctcaaca tctgagggtc ctggttcttt tagaagtatt      1920
ggtgggagaa gtgaagaagg tgggaatgga actggtagtc tttcaaggtt agctggcctc      1980
gggcgtgctg caaggcgcca acttactgga attcttgatg aattttgggg acaattgtat      2040
gatttccatg gggtgcctac tcaagatgca aaggttaaga actagatttt gttactgggt      2100
tttacctctc tgaaattgga tgctgttggt aaagattttc ctcactcatc acctattgga      2160
tgcaaaacat ccgatccaat ttcttctagt ttgtacgact cccccaagag tcagagggta      2220
caaagtgggt tagaaccacc ctatgggata caaaagggc accagccatt gtggtctaac      2280
cacatgcagc attgggatgc atatgtgaat aattctagcc ataatgctct ggactctgga      2340
gtgaagcgat attctagttt gcgcagtttg ccttctactg agagttggga ttatcagcct      2400
gccacagtcc atggctatca gttaacttat ctgagtagaa tggcaaagga cagaagttct      2460
ggtaattcga acggtcagtt ggattcatca ggctctaaat atcataccttt gggtggtggt      2520 ggtgcaggct tgcgagactc agttgcattt gcaatgggc aaaagttgca aaatggcttg      2580
ggtgcttgtc agcaggcggc tcccccaggt ttttccaaca tcacagtatc caggaaacct      2640
tcttccgaat ctgaaaggaa atattatgat cattctcttt ctggaactgg tgagaattta      2700
gtgagtgtat ctaacacaaa gaaataccat agcttaccgg atattcaccg tgatcagcac      2760
acatcagata gagttctca gtgggataat gtgagtggtt atggaacatc tattggtaga      2820
ataacagctc gtggagtgtc cacaaattct ggatcaagat tagtttctcc tttagcatt      2880 gatgaactat ctcctgcaaa tgtctacagt ggtgcattat caccacaaat gaatcctcat      2940
ctggattctg gatctttctg gcatagacag ccttctgagc aatttggctt ggacaaaaat      3000
agcaactccg agagtaaagg aattgggagg ctgcattcaa ttagtcacga agcttctttt      3060
gttgttaatt cagaggccag gcttctccag tccttcagag actgcattgt caaacttctg      3120
aaattagaag gatcagactg gttatttggg caaagtgatg gtgctgacga ggagctaatt      3180
gattgtgtag ctgccaggga gaaatttctt tatgaagctg aggcaaggga gatgggtcgg      3240
gtggtccgca tgaaagaatc tccttcattt tctcctgata ggagaccagg ttctggaatg      3300
aagaatgata caaatttctc caatgttttct atttcctctg tacctcattg tggagaaggc      3360
```

```
tgtatttgga gatcagattt gattggtatt atcgatcctg cattttcgaa gcctcgtata    3420
ccgatgccac catgcttctg cctccaaatt ccccaagcat tccagcagag gtcaagccca    3480
caaattgcaa atggaatgtt gcctcctgct gcaaaacctg gcaagggaaa atgcaccact    3540
gctgcaatgc ttctggatat ggtcaaggat gtggagatag ccatctcttg ccgaaaaggt    3600
cgaactggta cagcagccgg cgacgtagct ttcccaaagg ggaaggagaa cttggcttca    3660
gtcctcaaac gctacaagcg ccgattatcc aataaaccag ttgccactca cgaagtatca    3720
tctatttcac gcaagatttc agcaacatcc gttccttata gctcatag                3768
```

<210> SEQ ID NO 6
<211> LENGTH: 1189
<212> TYPE: DNA
<213> ORGANISM: Lactuca sativa
<220> FEATURE:
<221> NAME/KEY: unsure
<222> LOCATION: (1)..(1189)
<223> OTHER INFORMATION: unsure at all n locations

<400> SEQUENCE: 6

```
gagaagaggt attacagtat gccagatatt gccgggttga ttcgtaatcg ggagtctaaa      60
gttctacccg aaagagagag cgggtcgaga tacccccccc tgggtatccg ggcccaggat     120
caggcccagg cccaggcccg gtgtacaggt ccgggacaat ctcgggttat ggcgggttgt     180
cttattctaa tttgtcccgg gatgctgctg cttaccaacc cgtttccagt tacgggccag     240
ggattgggtt aggggtaggg ttcggtcggg gtcagacac gtggtcaatg tggtcaaaac      300
aaccgtctga acaatttggt gtggctgaaa aggttaattt gaacactcaa gaagctttta     360
ttacatctgg agtagatgct gaagcaaatc ttttgaagtc atttaggttg tgtattgtaa     420
aactgttgaa gcttgaaggg tctgaatggt tgtttaagca gaatggtggg ttagatgagg     480
atcttgttga ccgggtggct gcccgggaga gatttctgta tgaaattgag ggcaatgagg     540
tgacccgggc agctgcccgt ggtggtgggg ccaaagttga tgaagctgaa tacaataagt     600
atttagtgac atcggttcca aattgtggtg agggttgtgt atggagaatt gagttgataa     660
aaagctttgg tgtttggtgt atacatagaa ttctcgagct ttctttaatg gaaagtaggc     720
ccgaactttg ggggaataca catatgttct caatcgtctt cagggaataa ttgagccgtc     780
attctcgaaa cctcgtacac catcaagtcc cgtgtttctg tcttcagctt ccggaagcat     840
accacctgcg atcatctccg cccaaatcca tcaccagtct gccgcctccg gtgaaacaga     900
gcagagggaa aaccaccacc gccgccagtc tgttggacat agtaaaagac gtggagaccg     960
ccatctcttg ccggaaaggc cgaccgggta ctgccgccgg tgacgtggcg ttcccgaaag    1020
ggaaagaaaa cctggcgtct gttctncaaa gatacaagcg gcggttgatg gcggtggctc    1080
cggacgggta tagccggagc ccgtaagtct ccggcgactt tgtgtgttg gtttattgag     1140 ttgtttgata ttgatgaaca gctcgaagtt ctactctttt ggtatttac                1189
```

<210> SEQ ID NO 7
<211> LENGTH: 5154
<212> TYPE: DNA
<213> ORGANISM: Rice

<400> SEQUENCE: 7

```
acagttccac taaaaaaatc cacttcacct agcagccgct ctcacctcca cgcgctctcc     60
gccaccggag cacgagcgcg actgccacca cctccaccgg attcatctcc gcctcttgcc    120
```

```
gcggcaaagc cccccagct tggattcctc tgtttttttt tccttttgc gtacgaatct    180 cttgtatatc cctctcctgt atgttgcgag aaatcaatct agtccgaatg gtgtgctcct    240
gcgtgctgga gtagtctagg tataccagtt ttgttctcca aagcatttgg gattgggttg    300 aatgaacat ctatggtcca cgctaggtcc gcccctggct gtgatggatg gagcttagag    360
caggggcaac ctagatcagg ggtgtctccc tgggggtttt tcatggtgct gtggatgttc    420
actagctttg gagggtttga ttagggcctc ttgggtcata acaggagggt tttaagggac    480
ctggatttgg taaagcattt ttcaggcatg tgatgcttct tggggaggat ttcatggtgt    540
tgtggatgtt caccagcttt ggagggtttg attagggctg cttgggtcac aacaggaggg    600
ctttagggat ctgaatttgg tagtcatttc aggcatgtga tgcttcttgg ggaggatttc    660
atggtgttgt ggatggatgt cccccaggtt tggatggtta gacttcttcg atcaccacaa    720
gagctttgaa gagacctgag tggataagca tttgatcctt cttggaggtg tttcatggtg    780
ttctagatgt tcaccagctt cggagggttt gattagactg cttgagttaa cagtgttcaa    840
gggactgaat ttgataagca tgtcgggcat ttgatccagt ggtgtggatt cgtatccatc    900
ttttgttgtt ataagatttg ctgccacaaa aaatggaagg tgtgcacggt atagaatctc    960
tggctactgg agatggttgg catcatcttt cccgtaccct tggaccggtg ctcctgatct   1020
cgatggggta tattgacctt gggaagtggg tggaaacgat agatgccggg tctcggtttg   1080
gctatgatct cgtaatactg gtgttgcttt tcaacttgtc ggccattctg tgccagtatc   1140
tgtcgatgtg tatcggcatg gtcactggga aaaatcttgc ggagatttgc cgcgaggagt   1200
acagtccatc aatatgtgtc atccttggta ttcaggcagg attgtccttg ctaaccgcgg   1260
aactaaccat gctttcaggc atatcagtcg gattcaacct ggtctttgaa tatgatgatc   1320
ctatcgcagg cttatatttt gctagtgttg tggtcaattt gctaccttac actatgtctt   1380
atctgggcaa acggatggct gggacattga atgcatgcgt agcaggcttt gcacttcttt   1440
gttttgtgct tggtttatta gtcagtcaac caaaaattcc agttgatatg aatgcaatgt   1500
tccccaagtt gagtggtgaa agtgcttatt ccttgatggc gcttcttggc ggaaatgtaa   1560
tagcgcacaa tttttatgtt cattcatcag ttgtacaggg ccaaagacaa tctacaactc   1620
tttcccttgg tgctctgttc cacgatcacc tgttctcaat attgtttatt ttcactgggg   1680
ttttccttgt gaattatgtc ctgatgggct cagcagcagt tgaatccaat aatactctgg   1740
ttacttttca agattctgta gatttaatga accagatgtt catgaatccg atggcaccaa   1800
ttgttttttt agtgatccct atccttttcga gtcatgtcat ctcattgaca tctattattg   1860
gcagccacgc aattttgaag aatttctttg gtgtaaactt gcctcattct gctcatcatc   1920
tgctactaaa ggccgttgcc atggttccta ctatgtacta tgcaaaggtt gcaggttctg   1980
aagggatata tcagttactc attatctgcc cagttatcca agctatgttc cttccttcat   2040
ctgttattcc tgttttccgt gtttcctcat caagagttat aatgagcaga tataaaatat   2100 cttttgtacgt tgaaatattg gccatcctag catttcttct tttgctgttc acaaatatca   2160
tttttgctgc ggaaatcctg tttggtgata gtacctggac aaacaacttg aaagggaaca   2220
ctggaagccc tgttgtactt ccgcatgcca ttgtagttct aatttcttgt gcatcaatta   2280
cttttacgct gttcctggct gtcactccac tgaagtcagc aagtaatgaa cctgaaactc   2340
aggagctatc tgagcactct cagagagaag atccagatac tacttatcaa agagaagcaa   2400
gtaatgaacc tgaaactcag gagctatctg agcactctca gagagaagat ccagatacta   2460
cttatcaaat agaagtaagt aatgaacgtg aaactcagca gctatctgag cactctcaga   2520
```

```
tagaagatcc agatactttt tatcatagag aggagctttc tctggttgaa cagaaagaag    2580
atcatacgac ttctactatt aatgctattc ccaggatttc atcagaaagt tatcaaacat    2640
cagctttgga gcataatgac tttcctgaca tcactgtgga gtctggtcat ggcactcagc    2700
agcttactgc ttttgtgcca attattccgg aggtctcatc gtctatcaaa cataaggaac    2760
caaaatcagt agttattgac cagacggaac cagtgccaaa ggtttgtact gccacagtag    2820
tagaacataa cactgctgag aacatcaaaa tgaagagtac aacttcaaag catgtccaag    2880
aagaagcagg agctagcatg gactatgata ctgaggcttc ttataatgcg gaagtcagca    2940
agtcttctgg aaacaaggca cctccaattt ctgatgaccc aacatctctt actttgagca    3000
aggggagaga ctctgatgct ggttatcgtg gcagtaacct ctcaagactg cctggttttgg   3060 gtcgtgcagc aaggaggcaa ttagcagcga ttcttgatga gttctgggga catctctttg    3120
attatcatgg taagctaacg caagaagcta atgcaggaag gttcaacttt ctgctaggac    3180
catacccgaa agcagttaga agtgataacc aagccatcga agcttctagg agcccccttga   3240 tgagagatgc aatacgagga tcagctacca tacagaaatc atgggactca cgtgctaagg    3300
aagtctctag tccaggcttt aattttgtgc ttcagatggg tcgcattgga tcatcaaact    3360
ggtctgagag catgcgttta tctaatgctg acatcccaag gccaactagc accttgtttg    3420
aacaaaatac tcagttttat tcaaattata atgtcccatc ttaccctgac aatcagttct    3480
atcaacctgc taccattcat ggctatcacc tggcaacctc tttgaaaagt atgaatgcaa    3540
gtcacagcac gcactccagc atttcactag atccacggcg acttcctaga tcatctgaat    3600
ctgctggttc taactacgca gattctgcaa ggtatgctcg taaccaagat gtaattggtt    3660
cacagggaac cgcttcgcaa aacacaacaa tgagctgttt agatacaatg acagtggaga    3720
gagcttttta caatcctgcc tctgttaatg agattgaagg ggttggttca tctgcttact    3780
caaagaagta ccatagttca cctgacatat ctgcactaat tgctgcaagt aggaattatt    3840
tgccaaatga agtaaatttg ggaggtgctg ctggaagcag ttcatacttc agtaatttgg    3900
catgtgaaag atcacaatat gtgaacttgg gatccagttc cacagctcaa tttgcactta    3960
gcaagcactc acaacctaat ttccatagag acacatcatc tatgcagtca agtgtgaacc    4020
caagtactga atccatttgg gcccagcagc cgtttgaaca attactcggt gtatcaagag    4080
cagagttgaa taagggcgag ggtaacaccg accagagatc aagtggtgtc accaaacacg    4140
atttctctaa caagaatat gaggtgaaac ttcttcaatc actcagattt tgcatcatga    4200
agctcttgaa actggaagga tcaggatggc tctttgagca aaatggtggc tgtgatgaaa    4260
aattaattga tcaagttgct gtagctgaga gagtttcaca acataccact gaaaatcagt    4320
tatctgctga tctccagctc catagttctg atgaagactt gcagccactg caaggaatg    4380 ataacaggga tgccaattgc atgagcctac tgcccaagtg tggagatgat tgtgtttggc    4440 aggccccct gattgtcagt tttggtgttt ggtgcatccg ccagattctg aacctgtgcc    4500
ttgtcgaaag taggccagaa ctttggggca agtatacata tgttcttaat cgtctccagg    4560
gaatacttga tcctgcattt tccaagcctc agaaacccat gaaaggatgc gtatgccttc    4620
aaaaagttgc caagcccatc tctggtactt tcaccactgc tggtatgatc ttggagatga    4680
ttaaagacgt ggaacaagcc atttctagcc gcaagggccg aagcggcaca gcagcaggag    4740
acgttgcttt tccaaagggg aaggagaacc tagcttctgt ccttaagcga tacaagcgta    4800
ggctctcgaa caagacatct gcaggacaat agcgtggcag cgagctttct tttgtttctt    4860
```

| | |
|---|---|
| gtttgtatag ggttcttggg gctgctccac aaagttctgt ttttttgtgc tcctcaaacc | 4920 |
| ttgggttttt tcgatgcaca cgatctccag agtgcctgag agcttcttga tctttggtca | 4980 |
| tttttgcaca tgttgtttat gaagtggcca agggtgaatg gtataccttg tttattcatc | 5040 |
| ttatcagcga gatctcaaca gtagatgata tttgctggag cagcaacatt gtaaagttct | 5100 |
| ttttccagat gaacattctg aagtccgctg gcttggcttt ctgaaatctc cact | 5154 |

<210> SEQ ID NO 8
<211> LENGTH: 4791
<212> TYPE: DNA
<213> ORGANISM: Rice

<400> SEQUENCE: 8

| | |
|---|---|
| ggtttccccc aatttcctcc cgcaatttct acttgttctt ggctcctctc tgctgttctt | 60 |
| agcctcgccg cgatggcgta gtcttggaga agatcagatc catctcgagt tcgattgggg | 120 |
| tttttttttt ctctcttgag atttccatga ttggtggtgg agttcatcgg caaggaattc | 180 |
| agcagaagag atcagattct gtacacagtt cgtcttcttg ctcggtgact aagctgggtt | 240 |
| aggagaggag gaaaagaaaa tctttttttt ttttttgcg gcgccatgga tgggcagcag | 300 |
| ctacgtagct cggaatctcc ggcgagcggc ggcggcggag tcaccggcgg cggcgcgcca | 360 |
| catctgttcc acgcgctcgg gccggcgctg ctgatctcga ttgggtacat tgacctcggg | 420 |
| aaatgggtgg ccgcggtgga ggcagggtca cggttcggcc ttgacctcgt gctgctggcc | 480 |
| ctcctcttca acttcatggc catcctgtgc cagtatctcg cggcttgcat tggcacggtc | 540 |
| accggggagga gcctcgccga gatctgccac caagaataca gcaggccaac atgcatcttt | 600 |
| ctgggtgttc aagcaggatt gtccttgttg acatcagaat tgacgatgat ttttgggata | 660 |
| gcacttggat tcaatcttct atttgaatat gatgatctca tcactgggat atgttttgca | 720 |
| accgttgttc ctaatctgct accatatgct atatcacacc tgggaaagaa gatggtgggg | 780 |
| acattaaatg cttgcattgc aggctttgcg cttctttgct acgttcttgg tttattggtc | 840 |
| agccaaccac aaattcctct gacaacgaat gtaattttcc ccaagctcag tggtgaaagt | 900 |
| gcttattctc tgatggctct tcttggtgca aacgtaatgg cacacaactt ttacatccat | 960 |
| tcatcagttg ttcagggtca gaaaagatct gcctttgctg ttggtgcctt atttcatgat | 1020 |
| cacttgtttt cagtattatt tatttttact ggaattttc tggtgaatca tgttctaatg | 1080 |
| aactctgcag cagctgattc cactaacacc cttcttctca ccttccaaga tgttgtagaa | 1140 |
| ctaatgaacc agatatttgt aaaccctatg gctccaacta tatttctagt ggttcttctc | 1200 |
| ttctctagcc acatcatctc gttgacatct gctattggta gccaagtgat ttcgcagcat | 1260 |
| ttgtttggca ttaatcttcc tctctctgga catcatctga tactgaaggc ttttgccata | 1320 |
| gttcctgctc tgtactgtgc taaggttgca ggtgctgaag aatataccca attactgata | 1380 |
| atctgccaga ttatccaggc catgctcctt ccatcatcag tcgtgccact cttccgtgtt | 1440 |
| gcctcatcaa gattgataat gggtgcccac agagtgtctt tgcatctgga gatattaaca | 1500 |
| tttcttgcat ttctcctcat gctgttttcg aatatcatct ttatggcaga aatgctgttt | 1560 |
| ggtgacagtg gttggctgaa cactctgaaa gggaatactg gaagccctgt ggtgttccaa | 1620 |
| tctacggttc tcatcacggt ggcttgtgtc tctgttgcat tttcactcta catggctgtt | 1680 |
| acaccactga aatcaggaag ccatgaagct gaattgcagc aggaatggtc tgtgccttct | 1740 |
| cagaaagagc tcttgaatac tactcaagac agagaagaga cttgtgcggg caatgttacc | 1800 |
| tatgaggaag atcagagatc tgatgttgtc ccttctccta ggattcagcc tgtggattgt | 1860 |

```
ctgaaatcag ctctggacta cattgatagt tcggacacag ctatagaatc tgatcatgat    1920
tctcaacatt ccactgctca tacatctacc gctcctgaat cctgtcactc tccatcattc    1980
attcctgaag agtcaaaatc agttgttgct gttgactggc cagagcctct ggagccaatt    2040
tctaatgcta ttgtggctga ggaaagtaca gtagagagtg tggactccaa gagcacaggc    2100
gaaagggata ttgaagtaga accagctctt ttgatggaca atgataagga ggctccaaat    2160
attctagagt ctgacaacaa gccacttgga ggcaataatc cttcctgtgc atcggatgat    2220
ggcccaccat ctcttacctt cagcaggggg aaaggctcag atgcaggcaa tggcagcggg    2280
agtctctcga ggttatctgg tttgggccgt gcagcaagga ggcaactagc agccatactt    2340
gatgagttct gggggcatct ctttgattac catgggaaac tcactcaaga agctagctct    2400
aaaaggtttg acatcttgct tgggctagac gtaagaacac ctagctcaac tgtaagagca    2460
gacagtcaag ctaatgaaat cccgaagagt cccatggtac gagacaattt acaagggtct    2520
gccttcttgg gaagttcaag ggatctgatg tctactaaga atgagatgtc gaatttggat    2580
ctgacatatg ggcttcagat gggcaataac attgggtcat cagcctggtc tcagggcatg    2640
cagttaccaa gtacccaact gcagagttca agcaacagct tactcgatca aggtgcaaga    2700
ttaaattcaa attttagcac gccatcatac gcagacaaca accaattcta ccaacctgca    2760
acgattcatg ggtatcagct cgcatcatac ctaaaacaga tgaatgctaa tcgaaatcct    2820
tactctagca tgccattgga cccacagcga cttccaaaat cttctgcatc ggctgtgcca    2880
acctatgtcg attctgtcat gcatgctcgt aaccagaact tgcttgcttc attgggagct    2940
actccttcac agatcgcagc aacatcccgg ataggtacta tgatggcaga aagatcctat    3000
tatgtcccct tccactcttga cgggaatgaa aatgctggtt catcagctta ctcaaagaag    3060
taccacagct caccagacat atctgcactg attgctgcaa gcaggagtgc tctgttgaat    3120
gaatcaaagt tgggtggtgg taccattgga tcccagtcgt accttagcag gcttgcatcg    3180
gaaagatctc agtatacaaa ctcggtggcc aggcctgcag ctcccttggc gtttgatgag    3240
ctctctccac ctaagctccc aggggatatc ttctcaatgc aacaaagccc aaacccaagt    3300
gcaagatccc tttgggctaa gcaaccttt gagcagctgt ttggtgtgtc gagtgcggag    3360
ctcactaaaa gcgagttcaa ccctgcaggc agatcgggtg gcatgaccaa ggatgatttc    3420
tcttacaagg agtctgaggc gaagcttctt cagtctctta gattctgcat ctcgaagctc    3480
ctgaagctag aaggatcagg gtggctgttc aagcaaaatg gtggcagcga cgaagatctg    3540
attgatcaag ttgctgcggt agagaagcta ttgcaacaag gaaccagtga caaccaactg    3600
ctgcttggtg atactcagca accaccatgt gataaggcag acatccagta catgcgcgta    3660
ctgcctaact gcgagacga ctgcatctgg cgcgcctccc tcgttgtcag cttcggtgtc    3720
tggtgcatcc gccgggtgct agacctgtct ctggtggaaa gcaggccaga actttgggc    3780 aagtatacct atgttctcaa ccgtcttcag ggcatcctgg atcctgcatt ctccaagcct    3840
cggagtgctc tcagcgcgtg tgcgtgcctt cacagagata tccgggtgct caacagcctg    3900
cgccacagta gcctggtagc aacaaactcc attccaaggc aaatccgagg ttccttcacc    3960
accgcatctg tggtcctgga gatgatcaag gatgtggaga ccgcagtctc agggcgcaag    4020
ggcaggagtg gcaccgcagc tgggatgtc gccttcccca aggggaagga gaacctggcc    4080
tccgtgctga agcgatacaa gcggaggctc tcgagcaagg acaacaata taaggcatc    4140 tgggcagcgt gatcctgtcg cgttttaggg ggactttgac cattgttctt caaggatggc    4200
```

```
agccagccat ggtggcttgc cctccctgag ccctggattt tttcgttgca caacgtttgc    4260
agggacctga ggaattggcc aacacttctg gtcccttcca tcatatttcg ttttttttttg   4320 tttctttctt gtttttttt ttttttttgc atgtgatgtg ttgtataatg gtaactgttc    4380
atgtgccaga agaacaacca ccaaaatgta aacagatgt agtcagctga tgcaccattg    4440
taaagtttag tctctgcatt ttaaccttt ttttgggggt cattgacaaa ctgaatgaat    4500
gccctgtgta atctctcttc agagaggatg ccaagactga gaaaaagctt ttgccagatt   4560
tccagattcc ttgtgttcat ctaatatctg tcatgtctct cacattttct ccagcttatg    4620
atctttttgt ctcgttggca tttgatagcg tgtgctggag atgtctaccg tatatgtgga    4680
ttactgtatt aagcttctgg gaccggtgta tatatataat ttgtatggat agagataaag    4740
aaatactaac tcgatatgga ttagttatat cctaatgttt ctctaaacac c             4791
```

<210> SEQ ID NO 9
<211> LENGTH: 2000
<212> TYPE: DNA
<213> ORGANISM: Rice

<400> SEQUENCE: 9

```
aaaatgtaaa aattatatga atagatttgt cttgaaaaat actttcataa aagtatacat      60
atatcacttt tcaatgaata tttttatata aataagaagt caaagttgtg ttttggagac     120
cgtgtcgata tcctaaacga cttcctttat gagtatggag ggagtatgtg aataggcatg     180
gtggtaatgg gacatgccac cagcattaaa tctaaaggcc taaagtctga gcgcacatgg    240
tggtaatggg acatgccacc agcattaaac ctaaaggcct aaagtctaag cgcacattga    300
tgacaaggac gatgaacgtc actggaccca tggcctcctc aactcccgt cctccgtctc     360 atgcttaagg catgacgatg tgcaccggat ttgactctca tgcagaaaag aggcaaacaa    420
ggagaattga taccgaccgg cacgaattcc tcctcccata aattgtcatt ggtgatggaa   480
aaggagacca tgaggctgct atatatgag ctttgattgg cacctaacat ggtgaagcga    540
tcatgtttct cacccacctt atgtgtaggt acgtcatatg acacatcatc tggttagtac    600
ccataggtaa caactagtgt tgttgcttat aacaccgtgt cctagcacct agccatcaac    660
atcgatattg accgttgcca cgatctcctc ctagtgatgt tatcgtgctt cattgttgac    720
gggtggcttt gctcaggggc gtccttaggc ccatgcgggc tgtgcgaccg aacagggccc    780
ccaaatttca agggccctaa aatattaagt atacccaata tataataata ttaaatgctt    840
caattttagt aaaactaagc ccccaaaaca atgcaaaagg tgaatgatcc attttccaat    900
ttccatcgta cagtcgtccg tgtcgtcgaa gtcccaacgc acgtcgctt cgtctcctct     960 cctcagttac taggccacta ggatccattt taatatttcg cacggggacc caatttgtcc   1020
gggatgcccc tggctttgct catgacaaag acacgagtgt gtgtcgtggg cgtgggatgc   1080
tgccaaactc acgaggagga ggcaccataa tcctgcgacc tagcatgggc tgctgccgac   1140
tgattttctc gtgtcgtctc gtctgcaagc tcatcctggt gggagcacag cacagcagag   1200
agctagacga actcacaacc ccaggtgaac gtggtcaagt tgctcaacat acacgtgcaa    1260
agctacttta gctcctagag gttttgcatg ggtttaaggg tgcctctcct acgcacgacg    1320
acgacgaaaa caggaaaggg tgggtgggca cgcttttgca gctgaactcc ccgagataga   1380
gcggtttgat ggaacccgag agacaaagga gacaacggcg tgtgtttggt taattcggca    1440
gcatcttcgg cacgggacca ggcgtagtat cgcgtatatg ccctcgtctc gactccgccg    1500
taatctgatt cggccgcggt cttcttctgg agaatattat gcttgctcat tttatgctgt    1560
```

```
gtttagttgg tgaaaagaaa atttttaagt gtcacattaa actttgatt ggatgttaaa      1620 atgagttctc agacacgatt aaaaaactaa tttcataact tggttggaaa ccgcgagatg      1680
aatttattaa gtctaattaa tctttcatta gcacatatat gttactgtag cacttatgat      1740
taatcatgga ttaattaaac tcaaaatatt cgtatcgcga ttttcataca aactgtataa      1800
ttaatttttt ttaatttata tttaatgctt atatatgtgt ctaaaatttg atgggaattt      1860
tttgagaaaa aaagtttagg gaactaaggt gtccctcctt tccaaacacc acctaaacag      1920
gcctttacaa tctacaaaaa aggcacgggc atagcacgag ctttgccctt ttttctcgcg      1980
ctcgcacatc ctctctttcc                                                 2000

<210> SEQ ID NO 10
<211> LENGTH: 2000
<212> TYPE: DNA
<213> ORGANISM: Rice

<400> SEQUENCE: 10
gatcctaatg aacatatgta cggttcagcc gtgcttcatg catatgccat cgtttgatcg        60
actgatatga tcccaaaatt cccaattaag gtttattcga tttcaatcaa tattagtgta       120
gcttaatact gtgtatttga tttatttct tgaattatag tgagccaata ggtacaattg       180
ttgtgaacta gtgatatgta tttctcgcga cgtgattgac tagtaacttt atgcttgata       240
tgtgctacca cctttttctct caggtaatgc taccatagcc agcgaccttt cctcgctttt       300
attagtacaa tgtagtttta ttgatcactg ttgccaattt catatattta tttcaaaaat       360
tgtatttatt actagctgat tattcttttt tggggaaaac tctgactgat tgtgaatcat       420
atatatcatg catggcgcca tgattctttt agagctaagg aggcttaaaa cagttaaccc       480
cgacatctag ttttaatag tcttacaaaa accatttcaa ttgattttca acagttttgc       540
aagtcggccg attgatattt tggcttgaag acataaacca gtagtgattt tctcttatct       600
ctaaaaagat tcataaccat gaaagtttag aggttatttt ttttggtaaa gtgtactttc       660
attaattgtg tttaaaccgt cattaatgac cttatctaat tattgcacga attgttagag       720
atgactgcta caaattaatc atcagaggtt gcctttttt ataatattga gtgagacttc       780
cggttgagct cttaataaat tttcagattc agatcaaaat attttaacaaa ctcattaaat       840 cccaaaacta tgtcacggaa aaaagatcc ttcattcaat ttcatacaac aacaatacaa       900
actttcatct catgccttcc aaaaataaag aaaaaatgca tatccaaaac gtgggaatgc       960
gaaaagtagc ctatgccaaa cagcattact actgtcaacc tcaaagctag cttgcaaatt      1020
aaaaggattg gccacgttga cactttcaag tcctctccaa cagtgaaagc acaacatggg      1080
caaagtacca ataaaaagtg ataatgttat aatcttgttg ctttgctatg caaccttgct      1140
tatttctaat taataacagt gccttttgaa ttattggaga gcaccatcac accacaccac      1200
acatggtagc aagttcatta ccatacttca attgctgaaa gtcttccatg tctttgactt      1260
aattagacac tgttaagtga tagttgtatt agtactagtt acatccattg ttggtgactg      1320
agaagccata aaagtaaagt cacattattc ccaagaggga cttctcattt aggcttcctt      1380
cttttcagtt gaacgaactc agctcattct aatagggtaa tgaagataac cattaatgca      1440
taattactta agtggagtac ttactattat aaagtatttt ttttaaaaaa atatttaata      1500
ttaacaaaac ttgtaagtag aaactttta tataaaatat aaggtttgac aattcagaaa      1560
acatgctaac attaaacaaa gggagtagta ctagcatgta ggactatcac tgactggtgc      1620
```

| atggaccaag tccatccact gctgaacatg gggaacaaca ctacacagta agcacagaat | 1680 |
| cttccaaata atataaacaa aaagatcaga aattttttta agaaaacaaa aaaaaataaa | 1740 |
| aaaaatagtg aagaaaaaga gctagggaga ggagagagaa agagagaaag ctgaaagctg | 1800 |
| tgaaagaaaa gcctctgctg ctctctgcta gcttcttctc ctcctcctcc tccccttct | 1860 |
| ccccgtagat aaggaggacc cggggaaaaa ggggaggcaa aaagctgcga ttttccgcta | 1920 |
| attaaccccg gggattagct gcccaagaac aggaggaggt acgattcttg cattacttca | 1980 |
| ccccacgcga ttccctcccc | 2000 |

<210> SEQ ID NO 11
<211> LENGTH: 4629
<212> TYPE: DNA
<213> ORGANISM: Glycine max

<400> SEQUENCE: 11

| ggtggttaat cttaatctga gtgtgtgaga tctacttagt agtggtagtg gcagatgaag | 60 |
| aagagagaag aagcagtgaa ggatttgaga agttcgagtg ggaagtgatg atgatggatg | 120 |
| tgtttgggaa ccctttttga aattgagaat cgccagagct gtttatgaag tttggcctca | 180 |
| aattggattg attttcagtc atgttgagga gatgaatgga atttttaata gtggtgtgtt | 240 |
| gtgaaaagat tttgtgatgg tataccttga cttgatcgaa aacctcggtc ttgttagtat | 300 |
| cggatgtgct atatgttcaa cttttttgcaa gttgcaagtg attttagcag cttagtttat | 360 |
| atttgaagct gctaacatat ctatgattgt aataaataaa taaatacaat cttttgatag | 420 |
| aaatatagtt aagttgcagt tatggaattg tctatgggtc attaggtttt agctacttca | 480 |
| aagtggttgt cctgtcctga gtatcatatt tttccagtag ccttattgtt gctagtatgg | 540 |
| tatcgaagag taaaatggaa gcagggacat tgagtcctaa ccaccctcct tgctttcttc | 600 |
| gtcagtcact tcctgctgtt gcacctatgc ttctgatttc aacaggatat gttgaccctg | 660 |
| gaaagtgggt agccactgtt gaaggtggtg cacggtttgg gtttgatctg atggctgtca | 720 |
| tgcttatttt caattttgct gctatcttct gtcagtacat atctgcaagg attggtgcga | 780 |
| ttactggaaa aagtctagct cagatttgca gtgatgagta tgatacatgg acatgcatgc | 840 |
| tccttggagt tcaaacagaa cttttcagtga aatgctaga ccttaacatg atcttgggca | 900 |
| tggcacaagg attaaatctt attttttgggt gggacttgtt cacttgtgtc ttttaactg | 960 |
| ctactggtgc tgttttcat atacttctct cagttctcct tgacattgag aaggcaaaaa | 1020 |
| tcctaggacc gtttgttgct ggttttgtat tgcttgcttt tatacttgga ctgcttatca | 1080 |
| atcaaccgga aattccattt tccatgaatg gaataccaac aaggttgagt ggggagagtg | 1140 |
| catttgtgct aatgagtctt ctaggagcaa atcttgtacc tcacaacttt taccttcatt | 1200 |
| cctctattgt acagtggcat cagggattga caagcatttc taagaatgct ttgtgtcata | 1260 |
| accactttt ggccatatta tgtgtttcca gtggtcttta tttggtaaat aatatgctga | 1320 |
| tgaccgcctc agcaaatgag ttctacagta cagatcctgt tctgcttact ttcaggatg | 1380 |
| cattgtcacc catggaacag gtcttacgta gcccaatagc tctgcttggg ttttgctca | 1440 |
| ttttgtttct tgcaaatcaa accacagcat taacttggag tttaggcgga gaagtagtag | 1500 |
| tgcgtaattt cttaaaattg gatattccag gttggcttca ttatgctaca attagagtga | 1560 |
| ttgctgtttt gcctgccctt tattgtgtct ggagttcagg agctgagggg atgtatcagc | 1620 |
| tactattatc cacacaagtt ttggtagctc tgcaacttcc atcttttgtg atccctcttt | 1680 |
| ttcgagttgc cacatctaga tcaataatgg gtgtacacaa gatatcccag tttctggaac | 1740 |

```
ttttggcatc gatcatattc attggtatgc ttggcttgaa tattgtcttc gtggtagaaa    1800
tgatattcgg caatagtgac tgggcaagtg atttgagatg gaatgttggg agtggtgtgt    1860
ctgtctcata tttagttctt cttaccgctg ctattacatc gttatgtttg atgctttggt    1920
tagccgccac acctttaaga tctgccagtg tccaattaga tgctcagaca tggaactggg    1980
atatgccaga gactctgcca actcctccag ttgttgggga ggaattgtat ttaactgaaa    2040
aaaagtgtca tgaagatgta tctaagcatg tggaggaaca cacaccagct gtagcaaaaa    2100
gcttggacta ctcagatgta tcacttccaa gttttcatcc tgatctacct gaatctttaa    2160
tggaacctga accccatgtg aatgctgtaa gggataatta ttctcttata tcgacttcca    2220
catcagagtt agaggcagta tatgctgtag ttaatgagac ttctgattct tgtttggaag    2280
acaccaaaac cataacaatg gaaacaaacg ctgaaaggga tgacgatgat tcatgggaaa    2340
ctgaagaacc ttctggagtg gtatcagcca gtgttccatc ttcaacatca gatggccctg    2400
catcattcag gagtcttaat ggcaaaagtg atgaaggagg gaatagctgt ggaagtcttt    2460
caagaataga aggcttaggg cgtgcagcaa ggcgtcagct agctactgtt cttaatgaat    2520
tctggggaca actatatgat ttgcatggac aagtaaccca ggaggcaaag ctgggaaaa    2580 ttgacctttt gctgggagtg ggtgtagatt caaggcccac cagttccttg caaaaagtgg    2640
atgcatgtgg aaaggattat tctgaatact tagtatctgt cagaggtaga gcttctgacg    2700
cattaatgaa ctctgcttca tatgattctt ccaagcagcc tatgatgcaa agtaattcag    2760
agtcttatgg ccttcaaagg agttcttcct caatgtgggc aaatcccatc caattattgg    2820
atgcatatgt acagaactct agccacaatc tcctcgattc tggtgagagg cgctattcaa    2880
gtgtgcgtaa tctacattca tcagaagctt gggattatca accagctacc atacatggtt    2940
atcagactgc atcctatctt agccggcttg gtaaagacag aaattctgct aacttaaatt    3000
gtcaggtgga cttgtcatca ctgaaatccc cttccatagt taatacaaag tacagggatt    3060
cacttgcatt tgctttgggg aaaaggttgc aaagtggctc aggtgtgggc caaccccag    3120 ggttcccaaa tgtagctgtc tctagagatt cccaattaca atctgagagg ttttattatg    3180
acttatgctc ttctggatct gcagataata cagtcaattc agttaatact aaaaagtacc    3240
acagtttgcc agacatttca ggatactcca tcccccacag ggctggttat gtgtctgata    3300
aaaatgctcc aagggatggt tctgttggat atggatcttt tgctagtagg acgtgctatg    3360
accaatcatt atatttaaat tctggatcaa gaacaggagg tcatttggcc ttcaatgaac    3420
ttcctttgtc tgaagtttac aacaaggcac tctcttcaca gttgagttct ggttttgata    3480
ctggatccct ccggtctaga ttgccttatg agcagtttgg ggtagctgag aaaattccta    3540
atgttgcaat ggaagctgtt ggaaataggc taatgcaat tgctcaagaa actacttcat    3600
ttgtggatat agagggaaa cttcttcagt ctattagact ttgcattgtg aagctcttga    3660
aactggatgg gtctgattgg ttgtttagac agaatggtgg agccgatgag gatctgatag    3720
attctgttgc tgcaagggag aagttgtttt atgaaattga aaccagggag atgaatcagg    3780
tcattcatat ggatgaagct cattattttc cttctgatag gaaatttggt tcttcaatga    3840
agagtaatgg ggcatattct tcaggttttt cggtgtcttc ggttccaaat tgcgggcagg    3900
gatgtatatg gaaaacagat ttaataataa gctttggagt atggtgtatc cacagtattc    3960
ttaacctctc aattgtagaa agccggccgg agctttgggg gaaatacacc tatgttctca    4020
atcgcctcca gggcatcatt gatccagctt tccttaagcc tcggagtccc ttggctccat    4080
```

| | |
|---|---|
| gcttctgcct tcaagttcag caaaagttaa gcccccatct ttcaaatggg atactacccc | 4140 |
| caacgactac aaaaccaggc cagggcaaat gcacaactgc atcaacgttg cttgaactta | 4200 |
| tcaaggaagt ggagcttgcc atctctggca ggaaaggacg taccggaact gccgcaggcg | 4260 |
| atgtggcttt ccctatgggg aaggaaaatt tggcgtctgt tctcaaacgg tacaagcgga | 4320 |
| ggctatctaa caagcccgtt ggcactaatg gagggacagg ttcacgcaag atccccacat | 4380 |
| tagcaccata caaccaataa tagcattttg cgttaacaaa atcagcgtta gttgggctgt | 4440 |
| tttgtaattt attttcttta gcagctcatg ctgtcaaaga atgttgtctt ctccgtgtat | 4500 |
| catattccat tccctgctga cattgtagca aattttatcc acgtatgtta catacacgta | 4560 |
| gggcaaaatg tactatattc aagtgcagca aaatcaacat gaaaaatggt tagatggaaa | 4620 |
| attagtcat | 4629 |

<210> SEQ ID NO 12
<211> LENGTH: 4525
<212> TYPE: DNA
<213> ORGANISM: Glycine max

<400> SEQUENCE: 12

| | |
|---|---|
| taacatcttg gtggatgact tgtaaattgt aatagatgga atgttttgct agtaatatag | 60 |
| tatttatcta gcagcaatat aatttatggc tcgctgagca ttggtacttc caattgcttg | 120 |
| tagacctaat cctggtggta ctagtagaag aggaagaatg gaagcagaga ctttgaacgc | 180 |
| aaatcaccct cccggttttc ttcaccggtc gcttcctgct gttgtgccta tgcttttgat | 240 |
| ttcaatagga tatgttgacc ctggaaagtg ggtggcaatt gctgaaggag gtgcacgatt | 300 |
| tgggttcgat ctgatggcct tcacacttat ctttaatctt gctgccatct tctgtcagta | 360 |
| catagcagca aaaattggtg ttatcacagg aaaagatctt gctcagattt gcagtgatga | 420 |
| gtacgataat tggacgtgca tgcttcttgg agttcaagca gaactttcgg tgattatgct | 480 |
| agaccttaac atgatattgg gcatggcaca tggattaaat attctttttg ggtgggactt | 540 |
| gttcacttgt gtcttttaa ctgctactgg tgctgttttc catctccttc tttttgtcat | 600 |
| ccttgacatt gagaaggcaa agatcctggg actgttgtg tcaggttttg tatttctttc | 660 |
| atttgtactt ggaacactca ttaatcaacc agacattcca ttatccatta atggaatact | 720 |
| aacaaagttg aatggggaga gtgcatttgt gctgatgagt ctattaggag caattcttgt | 780 |
| gcctcacaac ttctaccttc attcctctat tgtacagtgg catcagggat caactaccat | 840 |
| ttctaaggat gcttttgtgtc ataaccattt tttggccatc atgtgtgtct tcagtggcct | 900 |
| ttatttggtc aataatgtgc tgatgaatgc tgcagcaaat gagttctaca gtatgggtct | 960 |
| tgttttgact acttttcagg acgcattatc gccaatggaa caggtgttgc gtagtccaat | 1020 |
| agccatgctt gcttttttac tcattctgtt tttttcaaat caaccacag cattaacttg | 1080 |
| gagtttcggt ggagaagtag tagtgcgaaa tttcttaaaa ttggatattc cgggttggct | 1140 |
| tcattatgct acaattagag taattgctgt tctgcctgcc ctttattgcg tttggaattc | 1200 |
| aggagctgaa gggatgtatc aactacttat attcactcag attgtggtag ctctgcaact | 1260 |
| tccttcttct gtgatccccc ttttttcggat cgcctcatct agatcaataa tgggggtaca | 1320 |
| caagatccct caatttgtgg aattttggc attgatcata ttcattggga tgcttggctt | 1380 |
| gaatattgtc tttgttgtag aaatggtatt tggcagtagt gattgggtgg gcaatttgag | 1440 |
| atggaatgtg gagactggtg tgtctctctc ttatttggtc cttctgtgca ctgcttttgc | 1500 |
| atctttctgt ctgatgcttt ggttagctgc cacaccttta aaatctgcaa gtgttcaatt | 1560 |

```
ggatgatcag gcatggaact gggacatgcc acaagccata ccaaagtcac ggattgataa    1620
cgaggaaaca gatttaaaag aaacaagata tcatggagat gcatcagttc aggtgaagga    1680
accatcacca gttctagcaa ggaccctgga atactcagat gtaccaattg caagttttca    1740
tcatgatcta cctgaaacta tcatggagcc tgatgttcct gtgactactg taagggagac    1800
tcatccattt acatcatttc ctttctcccc aacttctgtt gttaaggaat cagcttccac    1860
ttcagaatca gaggcagtac cagctgtaag taatgagact tctgatatta tattgggaga    1920
ttccaaaact ttgaaaacag aaactactgc ccctgttgag aaaactgtag aagttgaggg    1980
agattcaaat gccgaagggg atgatgatta tggagattca tgggaaactg aagaaatacc    2040
aaaagtggtc tcactagccc catcttcagc atcagatggc ccagcatcat tcaggagcct    2100
tagtgggaaa agtgatgatg gagggaatag cattggaagt cttcaagat tagcaggttt    2160 agggcgcggt gcaagacgtc aactagctgc tattcttgat gaattctggg gacaacttt    2220 tcatttccat ggtcaattta cccaggaagc taaggccaag aaacttgatg ttttactggg    2280
agtagattca acactcactg gttctttgca aaaaatggat tcatgtaagg catgttatga    2340
atacttcaaa tctgtaggaa gtagagctcc agatacttta atgaactctg ctccatatga    2400
atctcccagg ctgaatagga tgcaaagtaa tttagaggct tcctttgggc tcaaaggag    2460 ttcttcctca ctgcaggcaa atcctgtcca gtttatggat gaatatgttc agacctccag    2520
ccgcaatctc cttgatgctg gtgaaaggcg ctattttagt gtgcacaatc tacctacatc    2580
tgcagcctgg gattatcagc cagctaccat acatggttat caggtttcat catatattaa    2640
tcaagttggt aaagacacaa attctgataa attaaatggt ctgagggaat ccccttccat    2700
gggtaataca aacaactaca ggaattctat tgcatttgct ttgggtaaaa agttgcaaaa    2760
cggttctggt ttaagccaac ccccaggatt cccgaacatt gctgtctcta agaatagcca    2820
attgccatct gagaggtcct attatgattc tcgcccttcc ggacctgtgg atagtacagt    2880
cagttcagtc tatgctaaga agttccacag cttgccagac atttcaggat atgccatccc    2940
tcacagggat gtttacctgt ctgataaaag tgctccatgg gatgattctg ttggtggata    3000
tagatcttct gcaagtagga ctcattatga accgtcatta tattcaaatt ctggatcaag    3060
tacaggagct cctttagcct ttgatgtact ctctccatca aaagtctacg gtggtgtact    3120
ttcttctcag ttgagttctg gttttggcac tggatccctc tggtccagac agcctttga    3180 gcagtttggg gtggatgata aaattcataa tgctgcaaca aagatgttg gaaataggcc    3240 tagtgcaact actcatgaaa ttacttcagt tgtggatatt gatggcaagc ttcttcaatc    3300
ttttagacaa tgtatttga aactcttaaa attggaaggg tctgattggt tgtttaaaca    3360
gaatgatggg gctgatgaag atctgattga ccgtgttgct gcaagggaga aatttgttta    3420
tgaaattgaa accacagaga tgaaccgcaa tcatatggga gaaactcgat atctttcttc    3480
tgatgggaag gcttgttctt caatgaagaa taatgaggca aattggtcta gttttctgt    3540 aacctcaatc cctaactgtg gggaaggatg tgtttggaga gcagatataa taataagctt    3600
tggagtgtgg tgtatcaaac gtgttctgga cctctcccta atggagagcc gaccagagct    3660 gtggggaag tacacttatg tactcaatcg cctccagggc atcattgatc tggctttctc    3720
caagcctcgt agtcccatga ccccatgctt ttgccttcaa gttccatga cttaccagca    3780 gaagtcaagc tcgcctcctt ccaatgggat gctgcccct gcgtcaaaac cgggccgtgg    3840
aaaatgcaca actgcatcag tggtgtttga gatggtcaag gatgtggaga tagcaatctc    3900
```

-continued

| | |
|---|---|
| cagccggaaa ggtcgcacag gaaccgctgc tggtgacgta gccttcccaa agggaaagga | 3960 |
| gaatttggca tctgttctca aacggtataa gcgtagatta tccaacaaac cagttggcac | 4020 |
| tactcaagaa gggattcgca agatatactt gtagcatttt gcctttcact acgcattaac | 4080 |
| ataagcagtg ttccttgggc tgttttgatt tgtgaagcag ttcatgctgt agatcaaagg | 4140 |
| attaccatag gaagttcctc gccacaagac tgctgtctcc gtgtaccaat cctcactgca | 4200 |
| gatttatt cctgtaatg ttatatacac atagggttag agttactata tgtaattgca | 4260 |
| acaaaaaatc aaaggaaaaa gatggttaga tggaaactga cttctaccat tttggcttat | 4320 |
| ttttcattac ttcactcgct actgcatgca aggtggggaa acaaaatggg aagaaaattg | 4380 |
| tcgacatctt gtcatcttaa cagggaaaaa aattatcgat gtgttttaa ttttgtttt | 4440 |
| ttttattaag gtacctgtta tggttgccaa attttcgttt tcatcaagtc tttcaagcgt | 4500 |
| taaaatgatg gaagtggtta cgttt | 4525 |

<210> SEQ ID NO 13
<211> LENGTH: 4005
<212> TYPE: DNA
<213> ORGANISM: Glycine max

<400> SEQUENCE: 13

| | |
|---|---|
| atggaagcag agactttgaa tgcaaatcac cctcccggtt ttcttcaccg gtcgctcccc | 60 |
| gctgttgtgc ctatccttt gatttcaata ggatatgttg accctggaaa gtgggtggca | 120 |
| attgctgaag gaggtgcacg atttgggttc gatctgatgg ccttcatgct tatctttaat | 180 |
| tttgcagcca tcttctgtca gtacatatca gcaaaaattg tgttatcac aggaaaggat | 240 |
| cttgctcaga tttgcagtga tgagtacgat aattggacat gcatgcttct tggagttcag | 300 |
| gcagaacttt cggtgattat gctagacctt aacatgatat tgggcatggc acatggatta | 360 |
| aatattcttt tgggtggga cttgttcact tgtgtctttt taattgctac tggtgctgtt | 420 |
| ttccatctcc ttcttttgc cctcctggac attgagaagg tgaagatcct gggcctgttt | 480 |
| gtgtcaggtt ttgtatttct ttcgtttgta cttggaacac tcattaatca accagacatt | 540 |
| ccattatcca ttaatggaat actaacaaag ttgagtgggg agagtgcatt tgtgctgatg | 600 |
| agtctattag gagcaactct tgtgcctcac aacttctacc ttcattcctc tattgtacag | 660 |
| tggcatcagg gatcaactac catttctaag gatgctttat gtcataacca ttttttggcc | 720 |
| atcatgtgtg tcttcagtgg cctttatttg gtaaataatg tgctgatgaa tgctgcagca | 780 |
| aatgagttct acagtatggg tcttgttttg actactttc aggatgcatt atcaccaatg | 840 |
| gaacaggtgt tgcgtagtcc aatagccatg cttgcttttt tactcattct gtttttttca | 900 |
| aatcaaacca cagcattaac ttggagtttt ggtggagaag tagttgtgca agtttctta | 960 |
| aaattggata ttccgggttg gcttcattat gctacaatta gagtaattgc tgttctgcct | 1020 |
| gcccttatt gtgtttggag ttcaggagct gaagggatgt atcaactact tatattcact | 1080 |
| cagattgttg tagctctgca acttccatct tctgtgatcc cccttttcg gatcgcctca | 1140 |
| tctagatcaa taatgggggt acacaagatc cctcaatttg tggaattttt ggcattgatc | 1200 |
| atattcattg ggatgcttgg cttgaatatt gtctttgttg tagaaatgat atttggcagt | 1260 |
| agtgattggg tggcaattt gagatggaat gtggggactg gtgtgtctct ctcttatttg | 1320 |
| gttcttcttt gcactgcgtt tgcatcattc tgtctgatgc tttggttagc tgccacacct | 1380 |
| ttaaagtctg ctagtgttca attggatgat cagcaatgga actgggacat gccacaggcc | 1440 |
| gtaccaaaat cacggattga taacgaggaa acagatttaa aagaaacaag atatcaagga | 1500 |

```
gatgcatcag ttcaggggaa ggaaccatca ccagctctag caaggaccct ggaatattca   1560
gatgtaccag ttgcaagttt tcatcttgat ctacctgaaa ctatcatgga gcctgatgtt   1620
cctgtgacta ctgtaaggga gactcatcca tttacatcat ttccttgctc cccaacatct   1680
gttaaggaat cagcttccac ttcagaatcg gaggcagtac cagctgtaag taatgagact   1740
tctgatatta tattgggaca ttccaaaact ttgaaaacag aaactactgc ccctgttgag   1800
aaaactgtag aaattgaggg agattcaaat gccgaagggg atgatgatga tggagattca   1860
tgggaaactg aagaaataca aaagtggtc tcactagccc catcttcagc atcagatggc   1920
ccagcatcat tcaggagcct tagtgggaaa agtgatgatg gagggaatag cattggtagt   1980
ctttcgagat tagcaggttt agggcgcggt gcaagacgtc aactagctgc tattcttgat   2040
gaattctggg gacaactttta tggtttccat ggtcaattta cccaggaagc taaggccaag   2100
aaacttgatg ttttactggg aatagattca agactcactg gttctttgca aagaatggat   2160
ccatgtggaa aggaatattc tgaatattta atatctgtag gaagtagagc tccagatact   2220
ttaatgaact ctgctccata tgaatctccc aggcagaata ggatccaaag taatttagat   2280
gcttcctatg ggcctcaaag gagttcttcc tcactgcggg caaatcctgt ccagtttatg   2340
gatgaatatg ttcagacctc cagccgcaat ctcctcgatg ctggtgaaag gcgctattcc   2400
agtgtgcgca atttacctac gtctgcagcc tgggattatc agccagctac tatacatggt   2460
tatcaggttt catcgtatat taatcaggtt ggtaaagaca caaattctga taacttaaat   2520
ggtctgaggg aatccccttc catgggtaat acgaaccact acaggaattc tatgggtaat   2580
acgaactaca ggaattctat tgcatttgct ttgggtaaaa agttgcaaaa tggttcaggt   2640
ttaagccaac ccccagggtt ccagaacatt gctgtctcta agaatagcca attgccatct   2700
gagaggtcct attatgattc tcgcccttcc ggacctgtgg atagtacagt cagttcagtc   2760
aatgctaaaa agtaccacag cttgccagat atttcaggat atgccattcc tcacagggat   2820
gtttacatgt ctgataagag tgctccatgg gatggttctg ttggtggata tagatcttct   2880
gcaagtagga ctcattatga accgtcatta tattcaaact ctggatcaag acaggagct   2940 cctttagcct ttgatgtact ctctccatca aaagcctaca gtgatgaact ttcttctcag   3000
ttgagttctg gttttggcac tggatccctc tggtccagac agccttttga gcagtttggg   3060
gtggatgata aaattcataa tgctgcaaca gaagatgttg gaaataggcc tagtgcaact   3120
actcaagaaa ctacttcagt ggtggatata gatggcaaac ttcttcaatc ttttagacaa   3180 tgtatttttga aactcttaaa attggaaggg tctgattggt gtgtttaaaca gaatgatggg   3240 gctgatgaag atctgattga tcgtgttgct gcaagggaga aatttgttta tgaaattgaa   3300
accacagaga tgaaccgcaa tcatatggga gaaactcgat atctttcttc tgatgggaat   3360
ttttccgtaa cctcaatccc taactgtgga gatggatgtg tatggagagc agacataata   3420
ataagctttg gggtgtggtg tatcaaacgt gttcttgacc tctcattaat ggagagccgg   3480
ccagagctgt gggggaagta cacttatgta ctcaatcgcc tccagggcat cattgatctg   3540
gctttctcca agcctcgtag tcccatgacc ccatgctttt gccttcaagt tcccatgact   3600
taccagcaga agtcaggctc acctccttcc aatgggatgc tgcccctgc atcaaaacca   3660 ggccgtggaa aatgcacaac tgcgtcagtg gtgtttgaga tggtcaagga tgtggagata   3720
gcaatctcta gccggaaagg tcgcacagga actgctgctg gtgatgtagc tttcccaaag   3780
ggaaaggaga atttggcatc tgttctcaaa cggtataagc gtagattatc caataaacca   3840
```

```
gttggcacta ctcaagaagg gattcgcaag attcccacat cagcaccata caacttttca    3900
tgctgtagat caaaggatta ccaatttcct cgccacaaga ctgctgtctc catgtaccaa    3960
tcctcgccgc agatttatt tccttgtaat gttatataca cgtag                     4005

<210> SEQ ID NO 14
<211> LENGTH: 2003
<212> TYPE: DNA
<213> ORGANISM: Glycine max

<400> SEQUENCE: 14
agacacctca ctgttttaaa actgcataac ataatccaaa atatgaatct ctgtagaagg      60
agatagggta ctaagggtag caatttctag ttcaggatca tgtcaacaaa ttcagcaaca     120
acagttagtt agattattag aagaagacca ataggaataa gaatggctac aaaactaggc     180
cctatcggta gaggacagag agagtgagga acaagagtat cagaaagaaa ccgccaccat     240
aataataaat aattatttat ttataaatat ataaaaatat ggataatact ttttcagaca     300
accgatttaa ttattatctc ttttaattga aaattgaggt gtgatctggt ttaagaatga     360
agtcatgaat atttaccttg aagagcttac agacaataat taattgaatt accaaataaa     420
attcataata tcttgttatg ctaaaataaa taaataaatt tgaatgaaaa tgaatataaa     480
aacaaataaa ggtaagagaa aaaaaaatac tagttggact aaaagactgt taatagcaat     540
tttttataga gacttttttgg aacacattta tgaaatgaaa ctttctcttc tttgtttctt     600
ttctggcttc attcactcat gctttctctc tcttgaatgt ggcctagaaa gttgaaaccc     660
ttcacccatg tcataaattt tctttttttct tttccttagc tgctctctct ccatgttcac     720
ataagttagt agtagcactt acatcattaa atatgctaaa ttattaaaca ataaattaat     780
atataattta tttaatgttt atatacatga tcccgtgaga tctactttgc aggagtaaat     840
agcatagctg ggatagagac ttgtggcagc tgaaaagaaa ttcagagaaa ggtaaagatt     900
tcagaaccct aataaccact ctcagactct ttaggaactg ttctgttgta cggtcttctt     960
aattcattct cagtcctgaa accccccatca tcgtccttgt cgaaattcgt gcaactgttt    1020
tttttcttcc tctttttctct ttcttcttttc ttcttcttcg tgtgtttctt cttgcaacag    1080
atccacgcca acgctttcag ttcctcttttt tatctatttc atgaccgtac acgccgtagg    1140 gttttttgttt tgtttcttcg tttctcagca ttttttttagc gttttgtttt cttcttaaaga    1200 tctatttttgt tgttgttatt actatttatg attattataa ttataattat aattataatt    1260
atttaactat ggtggatgct gtaatttgtt gttttgggtgg ttttttttttg tttgttaaag    1320 caaattcaag aaagataaaa tgattttgtt gcgttggttt tttattttct tgtaatcaac    1380
cgttgtgctg atgaattttt aaggtatttg ttgtttctat tggtatggtg gctgtgttat    1440
tgttgtttac gtgaactaat tcgatgcagg atttgaggag tccaaggagg ttgatttatc    1500 aggggggtgct ttgctggatt agcattgaga gtctcaagag ggtgtttggt ttgggaagtt    1560
tgagatggat tggattggct ttcagtcatg tgaaggagat gagtggaata atttgtaaga    1620
ctgtagtgaa gaaattttgg tatggcgtgc aggttgactt tagtgataag tcagatttgt    1680
gtctgacata gtatcacagt taatgttgga acatcactgg ctggttgatg ctgggatacg    1740
aggtggagaa gctagttgtt gaattgttga aggtgtcttg gactggcttg caggttgaaa    1800 gtccttttgtc ttttaattat ctttgaagcg gctaacatct tggtgatgac ttgtaaattg    1860
tagtagatag aatgttgct agtaataatg gtatttatct agcagtaata taattatgt     1920 ctctctgagt attggtgctt ccaagtgttt ctccaagtgt cataagcctt aatcttggtg    1980
```

```
gtactagtag aagagtaaaa atg                                            2003
```

<210> SEQ ID NO 15
<211> LENGTH: 2003
<212> TYPE: DNA
<213> ORGANISM: Glycine max

<400> SEQUENCE: 15

```
ggattacatt acgaatatta acactagcat tgataaaatc cacaatcatc atttattgta      60
gacacctcac tgttttagta aaattgcata ataacatt ttttttattt ataaatatat       120
aaataaattt tataaaagat aacaatgaga tattgattac aggagcacta gattcaattc     180
tcatgtttga atgtgaatga aaatagtaat tgaaaaatca tcaaatttag tccatcaatt     240
ttttttaatg gagattgctt actaataaaa gcgagtagat attccttatg aataatatga     300
taaccaattt tttattaaaa aattagacat aagtaataat taagaattaa aattgtgatg     360
gtagaatatt aattgagtgt gaaatagaag ttttaaatat ctttcggtta aaataaaaaa     420
gacaaataaa agagaaaaat actaaaaaac gttaatagcg ttttttcgttt tttgagatac     480
ttattggaac acatttatga aatatgaaac ttttctttcc ttcttttctc gcttcattca     540
ctcacacttt ctctctcttc aatgtggcct agaaagttga aacccttcac ccatgccata     600
aatttttctt ttctttctt agctttctct cagctttccg ggaaaatctc tctctccatt      660
ttcacataag ttagtagtag taccttacat cattacctat gctaaattat taaacaatga     720
attaattaat ttgatttaat gtttatatat atgatccgtg agatctactt tgcaggagta     780
aatagcacag ctgagacaga gacttgtggc agctgaaaag aaattcagag aaaaggtaga     840
gagatttcag aaccctaata acaactactc tcagactctg gtgaaactgt ttttctgttg     900
tattgtacgg tcttttttaat tcttagtcgt gaaaccccaa tcatcgtcct cgtcgaaatt     960
cgtgcttctg ttttcccc tatttttctc tttcttcttc cttcttcctg tgtttcttct      1020
tgcatcagat ccacgccaac tctttcagtt cctcttttt ttatctattt catgaccgta     1080
cacagggtag ggttttttgtt ttgcttccaa gttttctcaac atttttttagc gttttgtttt     1140
cttctagaga tctaattttt tgttgttgtt aattatgtaa cttttttttt tataaaaaat     1200
attaattatt agtttgttag cagagactaa gaagatagaa tccaccattt ttttctcctt     1260
ccttttttaa ccacccaacc aaccttatat ctccttgata aattggtaat tatttaactg     1320
tggtggatgc tgtaaacttt gttgctgtgg tggtctttt gttaccgttt tttttttggtg     1380
cttttttaaat caaatttaag aaagataaaa tgattttttt ttgtgttgtt gatggatttt     1440
tttcactgta atttgttatt tctattatgg cggttgtgtt gttgtttatg tgaactaatt     1500
cgatgcagga tttgaggagt tcgaggaggt tgatttatca tggagtgctt tgttttggaa     1560
gtttgagatg gattggattg atttatcaat gagtggaatc atttgtaagg ttgtggtgaa     1620
gagattttgg gatgggaagc aggttgactt tactaatgaa gtcagattta tgcatgatat     1680
atgatcatag ttgatgttgg aacatcatcc gctgggttgc tgttggggta cgaggaagag     1740
aagctagttg ttgaattgtt gaaggtgtct tggactggct tgcaagttga aagtcctttg     1800
tcctttaatt atatgggatta ttatggttaa tgtttgaagc tgctaacatc ttggtggatg     1860
acttgtaaat tgtaatagat ggaatgtttt gctagtaata tagtatttat ctagcagcaa     1920
tataatttat ggctcgctga gcattggtac ttccaattgc ttgtagacct aatcctggtg     1980
gtactagtag aagaggaaga atg                                            2003
```

<210> SEQ ID NO 16
<211> LENGTH: 2003
<212> TYPE: DNA
<213> ORGANISM: Glycine max

<400> SEQUENCE: 16

```
cgtttgtaaa attgttcttt atttaactta atcttaatta aaacaacaac agaaacaaaa      60
caaaaattat caaattatct gcaggatcta ttttctatat gtttatttgc aactttacta     120
aatgaaaact ccattcaaaa ataatttata ttgaccatga ctatttacta ttcagagtat     180
cctctctggc actacaacta ccaatttgac ttttgtatct tattgctagg aaagaatcta     240
tatccaccct atttaaacca ttaatataca aatacactta cgcacaaaca ttcaaaagag     300
tattcaaaac ataattcaac ataaaaaaaa atgtatctaa tatgtagtgt gttttggatc     360
aacattgaca actcattata ctttaatgat ttaaagtctc aaattatata aaaaaaaggc     420
ggaaactaat atatttaaca catctacctg gatggacgaa tgtccaagca tggagatgga     480
ttgctcttta cttgtgaaag gtttccttca aatatggtaa aaattgttaa tagaataaac     540
aacaaacatt attttgatgt gagtgaaatg actgattttt ttttaagtaa agtccctaat     600
aaagaagaag aaaaacttct aaaaatgact aattagattt tctagtaaat aaatattaat     660
aacggacaaa gtataacgat aaatagccga cacatacaga aaatataaat aagatgtcat     720
ttaatactca atggacattt cataaattcg gctgagacag ttaaattgta atctttgtat     780
ttatccattt cccctttatct ctaaacttta gagagaataa tgaatatttt tggaaaatgg     840
cgaagaagaa tatattttaa acattttccc cccctttggg aagagaagtg cgaatgagat     900
agaggcagct ataaataaat gaaacagtaa gtgtcgtttt taggagttac agttactagc     960
ctcctttga agattctcat cctttctctc tcctcgtgtt cacccatacc ttacataata    1020
ataccccggtt tactttccca gaacctcctc tctcttaata tgaatataaa aatttaaaaa    1080
tatatatact attatttatc tgaatgtatg aatggtggtt aatcttaatc tgagtgtgtg    1140
agatctactt agtagtggta gtggcagatg aagaagagag aagaagcagt gaaggtaaac    1200
atttcttcag aaccctaact gtacggtcat catcatcgtc cttgaatttc gtgctaaatg    1260
ttccttccta aggcttcatc agatccacgc caacgttttc attacttctt gaacttttcc    1320
attcagtgag ggtcaggct tttttacctc tcttctcttat tctccttggg attccggagc    1380
tgagttctgt ttcgctactt gtcttatggt ttttggttgc ttgcgtgcta tttgttaccg    1440
ctttctactg ttaattaatt aattgtaacg aagatagtgt gaatataaag tttctgttt    1500
tactttggtg ctaatgttgt tacattggtc aatttgatga tgcaggattt gagaagttcg    1560
agtgggaagt gatgatgatg gatgtgtttg ggaacccttt ttgaaattga gaatcgccag    1620
agctgtttat gaagtttggc ctcaaattgg attgattttc agtcatgttg aggagatgaa    1680
tggaattttt aatagtggtg tgttgtgaaa agattttgtg atggtatacc ttgacttgat    1740
cgaaaacctc ggtcttgtta gtatcggatg tgctatatgt tcaactttttt gcaagttgca    1800
agtgattta gcagcttagt ttatatttga agctgctaac atatctatga ttgtaataaa    1860
taaataaata caatcttttg atagaaatat agttaagttg cagttatgga attgtctatg    1920
ggtcattagg ttttagctac ttcaaagtgg ttgtcctgtc ctgagtatca tatttttcca    1980
gtagccttat tgttgctagt atg                                             2003
```

<210> SEQ ID NO 17
<211> LENGTH: 4294

<212> TYPE: DNA
<213> ORGANISM: Tomato

<400> SEQUENCE: 17

```
cttgttcatg tcaaatgggt tgctaagtga tgctgtagtg ctagtttact gcgatctctg        60
ggcttgctaa ccatttaaat caaataatgg agtctgaaac tctgactaga gaatataggc       120
agcccagcat gcttcagcga gtactttctg cttctgtgcc aatgctgttg attgcagttg       180
gctatgttga tcctgggaaa tgggctgcaa tggttgatgg aggagcccga tttgggtttg       240
atttggtcat gctagtactc ttgttcaatt ttgctgccat tctgtgccag tatctgtctg       300
cttgtatagc cttggttaca gaccgagatc ttgcgcagat ttgcagtgaa gaatatgaca       360
aagttacatg catattccta ggaattcaag ctgaggtttc gatgattgct ttggacctca       420
caatggtttt gggcactgcc catgggctta atgttgtgtt tggagttgac ctgtttagct       480
gtgttttcct gactgcaacc ggtgccattt tgtttccact gcttgcttct ctctttgaca       540
atggcagtgc aaaattctta tgtattggct gggcaagctc tgtactgctc tcttatgttt       600
ttggagtggt tataactcta cctgaaactc cattctccat tggtggtgtg ctgaataagt       660
ttagtggaga gagtgcattt gcattgatga gtcttcttgg agcaagtatt atgcctcaca       720
attttttacct ccattcttct attgtacagc aaggtaagga atcaacagag cttccaggg       780
gagctctgtg tcaggaccat tttttttgcca ttgtttcat attcagtggc attttcctgg       840
tcaactatgc cgcgatgaat tcagcagcga atgtgtctta cagtactggc ctttgttgc       900
tgacatttca ggacacattg tcattgctcg atcaggtttt cagaagctca gttgcaccat       960
tcaccataat gctggttaca tttatttcca atcaagttac accactaact tgggatcttg      1020
gtagacaagc agttgtgcat gacttatttg gaatggacat cccaggctgg cttcatcatg      1080
tgacgatcag agttatttcc attgtcccag ctctttattg tgtatggagt tcaggagctg      1140
aaggcctata tcagttactt atactgacac aggttgtggt ggctcttgtc cttccatctt      1200
ctgtcatacc cctgttcaga gttgcttctt ccagatcaat tatgggtatc cacaaaattt      1260
ctcagttaat ggagttctta tctcttggca catttattgg cttacttggc ctaaagatta      1320
tatttgtcat agagatgata tttggaaata gtgattgggt taataatttg aagtggaata      1380
ttgggagtag tgtgtctact ccatatgttt ttctcctcat cgcagcctct ttatgtcttt      1440
gtctgatgct gtggttagca gttactcctc tgaaatctgc aagttccagg ttcgatgctc      1500
aggcgtttct gcaaacgcat gtgcctgagc catattcaga gtgtaatcaa cttggtgcga      1560
gtaatgctat gtttggtcta gtagaaggat cctcccaaaa gcaagaaggt gcatttcatg      1620
tggaaaaatc cttggtaacc catccagatt tatcaactaa agatcctgat caactcttgc      1680
cagaatctct cttggatttt gaaaaggtcc atcagttggc tactattgat gagagcaaat      1740
ctgaaacaac attttcagct cctgctgtcg ttcatcctga ggtacctgta tcagcaggag      1800
caagtcccag tgtgaaaagt gttttgtaatg aggtttctgg tgttgtatca gtggatacca      1860
gtgtcttcaa tactgaaact gtggatgtcg cagagaagac tctcagaatt gaaggggaca      1920
tggcaaatga cagggatgat ggagattcgt gggaagagcc tgaagaggca atcaaaggag      1980
tatctgagaa cgctcaatct tttattttctg atggtccggg gtcatacaaa agtctaagtg      2040
gaaaactaga ggacacgggg agtggtacag gaagtctatc aagattagca ggtcttggtc      2100
gtgcagctag gaggcagtta acagaagctc taaatgagtt ttgggggcag cttttttgatt      2160
accatggcat ggcaacagca gaagcgaagt ccaagaaact ggatataata cttggtctgg      2220
```

```
attcaaagat gaatccaaaa cctgcccctg catcattaaa agttgaaagc agtgcgtata    2280
ttccatcggg gagtgcaagg ataccagagc ctctgatcaa ctcgcatgtg tactctccca    2340
agcagcaatt tgcgtctaac attgtggact ctgcttatag agtcccaaag gagccatctt    2400
cgacatcttc tatgtggtct aaccatatga aattagtagg tgcatatgtg caaagttcca    2460
acagcaacat gcttgactca ggggagaggc gctattctag tatgcggatt ccagcgactt    2520
ctgctggcta tgatcagcag cctgccactg tgcatggata tcagattact gcttacctta    2580
atcaacttgc gaaagaaaga ggatctgatt atttaaatgg gcaactggag tcaccatctc    2640
ctcgttctgt atcatcactg acgtcaaact atgcagaacc attggctcgt gtttcggggc    2700
aaaaacctca gagtggagtc agtagtcgag caccacctgg ttttggaaat gtccctgtag    2760
gccgaaataa ttcgatgcag cccactaaca ctacttctgt cgaccatagc tctactgaaa    2820
ctgctgaaag cgtggctggt tcagccaact ctaagaagta ctacagcttg cctgatatct    2880
cagggcgcta tgttcctcgc caagattcta tagtgtcaga tgcgagagct caatggtaca    2940
attccatggg attcggacaa tctggtggtc gatctacata cgaacaagcc tatatgagtg    3000
gttcactaag ggcaggtggt cctcagaggt atgaacattc tcctaaagtc tgcagagatg    3060
cattctcctt gcagtacagc tccaattcag ggactggatc cctgtggtct agacagcctt    3120
ttgagcaatt tggtgtagct ggtaagccag atgttggtag cggcgatcat ggaactgtgc    3180
tgagttcctc tgctcaagag agtacatcta cggttgactt ggaagctaag ctgcttcagt    3240
ctttcagaag ttgtattgtg aaacttttga aactggaagg atctgagtgg ttatttaggc    3300
aagatgatgg ggctgatgag gatcttatag gtcggattgc tgcaagagag aaatttctct    3360
atgaagctga aactagggag ataagtagat tgaccaacat tggtgaatca cacttctctt    3420
ccaacaggaa acccggttct gccccaaaac ctgaagagat ggattacacc aagttcttgg    3480
tgatgtcagt tccccactgc ggagaaggtt gtgtttggaa agtagatctg attataagct    3540
tcggtgtgtg gtgcattcac agaattcttg agctttcact tatggaaagt aggccagagt    3600
tgtgggcaa atatacctat gttctcaacc gtcttcaggg catagtagat ctggcatttt    3660
caaagcccca ttctccgacg agccattgtt tttgtcttca aattccggct ggccgccagc    3720
aaaaggcaag ccccctcca atttctaatg gaaacttgcc gccacaagca aaacagggtc    3780
gaggaaaatg cacgactgca gcaatgctct tagagatgat caaagacgtg gagacagcaa    3840
tttcctgtcg aaagggacga acgggcactg cagcagggga tgtagccttt cctaaaggaa    3900
aagagaacct ggcatccgtc ctcaagcgct ataaacgtcg attatccaat aagccggtag    3960
gaaaccagga ggtggctgga gtcgccggac cgcgcaaagt aacgctgtct gcctcatcac    4020
cccctttcgt cttgtaacgc tcttttctca gttcatagca aatgactggt gagatcacca    4080
ttgttagact tgttcttagt ttctgtgaat tatccccccc tccccaacta tacctcccct    4140
gcacctcatg tgtattttga atctttgcag cttattcacc cccatccctt gtacctcaat    4200
ctgtatacat aggataaaat gttgtaacga ggttactgta aaactgcaat ggtgaaatga    4260
aacgggctaa aaggcgggaa aagatgttat taca                                4294
```

<210> SEQ ID NO 18
<211> LENGTH: 2000
<212> TYPE: DNA
<213> ORGANISM: Tomato

<400> SEQUENCE: 18

```
cttggcaggt aaaactgaac gaaaaggata caaacgagaa atatagtaat aaaacgagag      60
```

```
atacgacaat aaaaccaaaa acccaactaa ctagcgcgcg aaattctgaa cttggcaggt      120
aaaactgaac gaaaaaatac aaatgaaaaa tatagtaata aaacaacttt taccgaattt      180
cttcgacata attctctcaa aacaccttaa tatactgtat tttatttacg tatgtatcta      240
tgctgaatat aatggagaaa aaaaccgatt aaaaaactat cttttagtt cactttctc       300 cttcatagct tttggactca cattagtgaa gtgaaactct caacttttc tctctctc       360 caagatagct ttaagaccct acccacccc ttacatgacc cccttttccc cataatatat      420
atataaatac agtaatatat atgtatatat atatagtttc tctctctaca gtagtcacag      480
ctcacacacc ataactctcc atctctctag gatatgtatt atgtacaggt tcctctcttt      540
atctcttagt agtatatata gatattagag cttccttaaa agcttctgat ctgaactctg      600
agcactgaaa tttatagaga agaagactga agaaaaccca tccagaaaag gaaggaaaac      660
tatttgaaga aggtataaaa aagaaatgga aaaccctaat ggtctacaca cccacttggg      720
taaattttat cattttttt aattttactg ttatgggtat gtttagatat aggtataagg      780
attatatgtt ttggaatctt gaaataaaaa tttggtcttt ataggatatg tttgtatcag      840
atccgatgaa gtgggtattg agttttttgc tgattgtttt gatttgttgt attgggttgt      900
gttaaaaagg ttggagaagt gttatttatg gggttttggt ttttggttg gaaaaagatt      960 tgatcttctt ttatataaat ttgatggggt tttgtagttt tgtgtaataa agatctggat     1020
ggttgaggag gagaaggtgt ttcatttgca gttctcttct tttctttttg aaaagtggta     1080
ttgcttttga agtcaagttg atgttttttt ttgtttcaaa atgcaggata tttttgttaa     1140
agcaatcatg tttagttta gatgccaggc tgtaacatgg agtttactga gtgttttaat     1200 tattttttg ggcaagttga ctaattttga aatatatgaa taatgctgga ttggtttgtg     1260
aattgtgatc tcagtgaagg tttgccaaat ttttgtgttc catgtttctc gcgctacagg     1320
acactgtgat gtatgttagg tcgtgaaaga tccaatttttt ttctgttggg tagtttatca     1380
acttcagcat ttttgtcttt taactggaat taacatgtat atagttttag tttggatata     1440 atgcttctc cagctgtttt aagtgtttga tagtcatggt tacctagttt tttctgtaac     1500
tacaatttga atacttgact gaagttttgg tatttaactc aattcagaaa tcagaatcgg     1560
caatcggatt attgacggat gcaaaggtgt taatgcggtg tatttggttg gagttggtgg     1620 attagcaac tcgaaaagac ttccatcttt ataaggcgca cttctcaaag ttattgttcg      1680
aagttggttg attttagcag cttgaaaaga ctcttaataa attgcttttg tcaagttctt     1740
catgtccatt gcttttgggt gcaaacttgc tcaaaattct ccagagataa cgaggggttt     1800
tggtatcctg ttctaactgt gctacattga gctacagtct acagttggag ctgcagctgc     1860
tacatagaaa agctgtgtgg tcggaacttg gaacttcact ggttggattg tgagcttgtt     1920
catgtcaaat gggttgctaa gtgatgctgt agtgctagtt tactgcgatc tctgggcttg     1980
ctaaccattt aaatcaaata                                                 2000
```

<210> SEQ ID NO 19
<211> LENGTH: 21
<212> TYPE: DNA
<213> ORGANISM: Unknown
<220> FEATURE:
<223> OTHER INFORMATION: Sequence listing for 58620.

<400> SEQUENCE: 19

```
ttttgcttga acagccaccc t                                                 21
```

```
<210> SEQ ID NO 20
<211> LENGTH: 21
<212> TYPE: DNA
<213> ORGANISM: Unknown
<220> FEATURE:
<223> OTHER INFORMATION: Sequence listing for 58620.

<400> SEQUENCE: 20
tttggggcaa gtatacctat g                                              21

<210> SEQ ID NO 21
<211> LENGTH: 21
<212> TYPE: DNA
<213> ORGANISM: Unknown
<220> FEATURE:
<223> OTHER INFORMATION: Sequence listing for 58620.

<400> SEQUENCE: 21
tttgggccgt gcagcaagga g                                              21

<210> SEQ ID NO 22
<211> LENGTH: 21
<212> TYPE: DNA
<213> ORGANISM: Unknown
<220> FEATURE:
<223> OTHER INFORMATION: Sequence listing for 58620.

<400> SEQUENCE: 22
tttgcttgaa cagccaccct g                                              21

<210> SEQ ID NO 23
<211> LENGTH: 21
<212> TYPE: DNA
<213> ORGANISM: Unknown
<220> FEATURE:
<223> OTHER INFORMATION: Sequence listing for 58620.

<400> SEQUENCE: 23
tttgaatatg atgatctcat c                                              21

<210> SEQ ID NO 24
<211> LENGTH: 21
<212> TYPE: DNA
<213> ORGANISM: Unknown
<220> FEATURE:
<223> OTHER INFORMATION: Sequence listing for 58620.

<400> SEQUENCE: 24
tttcttaaaa ttggatattc c                                              21

<210> SEQ ID NO 25
<211> LENGTH: 21
<212> TYPE: DNA
<213> ORGANISM: Unknown
<220> FEATURE:
<223> OTHER INFORMATION: Sequence listing for 58620.

<400> SEQUENCE: 25
ttggggcaag tatacctatg t                                              21

<210> SEQ ID NO 26
<211> LENGTH: 21
<212> TYPE: DNA
<213> ORGANISM: Unknown
<220> FEATURE:
<223> OTHER INFORMATION: Sequence listing for 58620.
```

```
<400> SEQUENCE: 26
ttgcttgaac agccaccctg a                                              21

<210> SEQ ID NO 27
<211> LENGTH: 21
<212> TYPE: DNA
<213> ORGANISM: Unknown
<220> FEATURE:
<223> OTHER INFORMATION: Sequence listing for 58620.

<400> SEQUENCE: 27
ttgcttagcc caaagggatc t                                              21

<210> SEQ ID NO 28
<211> LENGTH: 21
<212> TYPE: DNA
<213> ORGANISM: Unknown
<220> FEATURE:
<223> OTHER INFORMATION: Sequence listing for 58620.

<400> SEQUENCE: 28
ttgctgcacg gcccaaacca g                                              21

<210> SEQ ID NO 29
<211> LENGTH: 21
<212> TYPE: DNA
<213> ORGANISM: Unknown
<220> FEATURE:
<223> OTHER INFORMATION: Sequence listing for 58620.

<400> SEQUENCE: 29
ttgccccaaa gttctggcct g                                              21

<210> SEQ ID NO 30
<211> LENGTH: 21
<212> TYPE: DNA
<213> ORGANISM: Unknown
<220> FEATURE:
<223> OTHER INFORMATION: Sequence listing for 58620.

<400> SEQUENCE: 30
ttgatgagtt ctgggggcat c                                              21

<210> SEQ ID NO 31
<211> LENGTH: 21
<212> TYPE: DNA
<213> ORGANISM: Unknown
<220> FEATURE:
<223> OTHER INFORMATION: Sequence listing for 58620.

<400> SEQUENCE: 31
ttgaatatga tgatctcatc a                                              21

<210> SEQ ID NO 32
<211> LENGTH: 21
<212> TYPE: DNA
<213> ORGANISM: Unknown
<220> FEATURE:
<223> OTHER INFORMATION: Sequence listing for 58620.

<400> SEQUENCE: 32
ttctggcctg ctttccacca g                                              21

<210> SEQ ID NO 33
```

```
-continued

<211> LENGTH: 21
<212> TYPE: DNA
<213> ORGANISM: Unknown
<220> FEATURE:
<223> OTHER INFORMATION: Sequence listing for 58620.

<400> SEQUENCE: 33
ttctccttcc ccttggggaa g                                              21

<210> SEQ ID NO 34
<211> LENGTH: 21
<212> TYPE: DNA
<213> ORGANISM: Unknown
<220> FEATURE:
<223> OTHER INFORMATION: Sequence listing for 58620.

<400> SEQUENCE: 34
ttctcaaccg tcttcagggc a                                              21

<210> SEQ ID NO 35
<211> LENGTH: 21
<212> TYPE: DNA
<213> ORGANISM: Unknown
<220> FEATURE:
<223> OTHER INFORMATION: Sequence listing for 58620.

<400> SEQUENCE: 35
ttctaatgaa ctctgcagca g                                              21

<210> SEQ ID NO 36
<211> LENGTH: 21
<212> TYPE: DNA
<213> ORGANISM: Unknown
<220> FEATURE:
<223> OTHER INFORMATION: Sequence listing for 58620.

<400> SEQUENCE: 36
ttccccaagg ggaaggagaa c                                              21

<210> SEQ ID NO 37
<211> LENGTH: 21
<212> TYPE: DNA
<213> ORGANISM: Unknown
<220> FEATURE:
<223> OTHER INFORMATION: Sequence listing for 58620.

<400> SEQUENCE: 37
ttcagcacgg aggccaggtt c                                              21

<210> SEQ ID NO 38
<211> LENGTH: 21
<212> TYPE: DNA
<213> ORGANISM: Unknown
<220> FEATURE:
<223> OTHER INFORMATION: Sequence listing for 58620.

<400> SEQUENCE: 38
ttatctggtt tgggccgtgc a                                              21

<210> SEQ ID NO 39
<211> LENGTH: 21
<212> TYPE: DNA
<213> ORGANISM: Unknown
<220> FEATURE:
<223> OTHER INFORMATION: Sequence listing for 58620.

<400> SEQUENCE: 39
```

```
tgttctcaac cgtcttcagg g                                               21

<210> SEQ ID NO 40
<211> LENGTH: 21
<212> TYPE: DNA
<213> ORGANISM: Unknown
<220> FEATURE:
<223> OTHER INFORMATION: Sequence listing for 58620.

<400> SEQUENCE: 40
tgttctaatg aactctgcag c                                               21

<210> SEQ ID NO 41
<211> LENGTH: 21
<212> TYPE: DNA
<213> ORGANISM: Unknown
<220> FEATURE:
<223> OTHER INFORMATION: Sequence listing for 58620.

<400> SEQUENCE: 41
tgtctctggt ggaaagcagg c                                               21

<210> SEQ ID NO 42
<211> LENGTH: 21
<212> TYPE: DNA
<213> ORGANISM: Unknown
<220> FEATURE:
<223> OTHER INFORMATION: Sequence listing for 58620.

<400> SEQUENCE: 42
tggtttgggc cgtgcagcaa g                                               21

<210> SEQ ID NO 43
<211> LENGTH: 21
<212> TYPE: DNA
<213> ORGANISM: Unknown
<220> FEATURE:
<223> OTHER INFORMATION: Sequence listing for 58620.

<400> SEQUENCE: 43
tggtggaaag caggccagaa c                                               21

<210> SEQ ID NO 44
<211> LENGTH: 21
<212> TYPE: DNA
<213> ORGANISM: Unknown
<220> FEATURE:
<223> OTHER INFORMATION: Sequence listing for 58620.

<400> SEQUENCE: 44
tggtcaagga tgtggagata g                                               21

<210> SEQ ID NO 45
<211> LENGTH: 21
<212> TYPE: DNA
<213> ORGANISM: Unknown
<220> FEATURE:
<223> OTHER INFORMATION: Sequence listing for 58620.

<400> SEQUENCE: 45
tggctgttca agcaaaatgg t                                               21

<210> SEQ ID NO 46
<211> LENGTH: 21
<212> TYPE: DNA
```

```
<213> ORGANISM: Unknown
<220> FEATURE:
<223> OTHER INFORMATION: Sequence listing for 58620.

<400> SEQUENCE: 46
tggcctgctt tccaccagag a                                              21

<210> SEQ ID NO 47
<211> LENGTH: 21
<212> TYPE: DNA
<213> ORGANISM: Unknown
<220> FEATURE:
<223> OTHER INFORMATION: Sequence listing for 58620.

<400> SEQUENCE: 47
tggaaagcag gccagaactt t                                              21

<210> SEQ ID NO 48
<211> LENGTH: 21
<212> TYPE: DNA
<213> ORGANISM: Unknown
<220> FEATURE:
<223> OTHER INFORMATION: Sequence listing for 58620.

<400> SEQUENCE: 48
tgcttgaaca gccaccctga t                                              21

<210> SEQ ID NO 49
<211> LENGTH: 21
<212> TYPE: DNA
<213> ORGANISM: Unknown
<220> FEATURE:
<223> OTHER INFORMATION: Sequence listing for 58620.

<400> SEQUENCE: 49
tgctgcagag ttcattagaa c                                              21

<210> SEQ ID NO 50
<211> LENGTH: 21
<212> TYPE: DNA
<213> ORGANISM: Unknown
<220> FEATURE:
<223> OTHER INFORMATION: Sequence listing for 58620.

<400> SEQUENCE: 50
tgctgcacgg cccaaaccag a                                              21

<210> SEQ ID NO 51
<211> LENGTH: 21
<212> TYPE: DNA
<213> ORGANISM: Unknown
<220> FEATURE:
<223> OTHER INFORMATION: Sequence listing for 58620.

<400> SEQUENCE: 51
tgccctgaag acggttgaga a                                              21

<210> SEQ ID NO 52
<211> LENGTH: 21
<212> TYPE: DNA
<213> ORGANISM: Unknown
<220> FEATURE:
<223> OTHER INFORMATION: Sequence listing for 58620.

<400> SEQUENCE: 52
tgccccaaag ttctggcctg c                                              21
```

<210> SEQ ID NO 53
<211> LENGTH: 21
<212> TYPE: DNA
<213> ORGANISM: Unknown
<220> FEATURE:
<223> OTHER INFORMATION: Sequence listing for 58620.

<400> SEQUENCE: 53
tgcccaagat catgttaagg t                                              21

<210> SEQ ID NO 54
<211> LENGTH: 21
<212> TYPE: DNA
<213> ORGANISM: Unknown
<220> FEATURE:
<223> OTHER INFORMATION: Sequence listing for 58620.

<400> SEQUENCE: 54
tgcacggccc aaaccagata a                                              21

<210> SEQ ID NO 55
<211> LENGTH: 21
<212> TYPE: DNA
<213> ORGANISM: Unknown
<220> FEATURE:
<223> OTHER INFORMATION: Sequence listing for 58620.

<400> SEQUENCE: 55
tgcaacgaaa aaatccaggg c                                              21

<210> SEQ ID NO 56
<211> LENGTH: 21
<212> TYPE: DNA
<213> ORGANISM: Unknown
<220> FEATURE:
<223> OTHER INFORMATION: Sequence listing for 58620.

<400> SEQUENCE: 56
tgatgagttc tggggggcatc t                                             21

<210> SEQ ID NO 57
<211> LENGTH: 21
<212> TYPE: DNA
<213> ORGANISM: Unknown
<220> FEATURE:
<223> OTHER INFORMATION: Sequence listing for 58620.

<400> SEQUENCE: 57
tgatgagatc atcatattca a                                              21

<210> SEQ ID NO 58
<211> LENGTH: 21
<212> TYPE: DNA
<213> ORGANISM: Unknown
<220> FEATURE:
<223> OTHER INFORMATION: Sequence listing for 58620.

<400> SEQUENCE: 58
tgagccctgg atttttttcgt t                                             21

<210> SEQ ID NO 59
<211> LENGTH: 21
<212> TYPE: DNA
<213> ORGANISM: Unknown
<220> FEATURE:

<223> OTHER INFORMATION: Sequence listing for 58620.

<400> SEQUENCE: 59
tgaatatgat gatctcatca c                                          21

<210> SEQ ID NO 60
<211> LENGTH: 21
<212> TYPE: DNA
<213> ORGANISM: Unknown
<220> FEATURE:
<223> OTHER INFORMATION: Sequence listing for 58620.

<400> SEQUENCE: 60
tgaagacggt tgagaacata g                                          21

<210> SEQ ID NO 61
<211> LENGTH: 21
<212> TYPE: DNA
<213> ORGANISM: Unknown
<220> FEATURE:
<223> OTHER INFORMATION: Sequence listing for 58620.

<400> SEQUENCE: 61
tctggtttgg gccgtgcagc a                                          21

<210> SEQ ID NO 62
<211> LENGTH: 21
<212> TYPE: DNA
<213> ORGANISM: Unknown
<220> FEATURE:
<223> OTHER INFORMATION: Sequence listing for 58620.

<400> SEQUENCE: 62
tctggtggaa agcaggccag a                                          21

<210> SEQ ID NO 63
<211> LENGTH: 21
<212> TYPE: DNA
<213> ORGANISM: Unknown
<220> FEATURE:
<223> OTHER INFORMATION: Sequence listing for 58620.

<400> SEQUENCE: 63
tctggcctgc tttccaccag a                                          21

<210> SEQ ID NO 64
<211> LENGTH: 21
<212> TYPE: DNA
<213> ORGANISM: Unknown
<220> FEATURE:
<223> OTHER INFORMATION: Sequence listing for 58620.

<400> SEQUENCE: 64
tctgctacca tatgctatat c                                          21

<210> SEQ ID NO 65
<211> LENGTH: 21
<212> TYPE: DNA
<213> ORGANISM: Unknown
<220> FEATURE:
<223> OTHER INFORMATION: Sequence listing for 58620.

<400> SEQUENCE: 65
tctctggtgg aaagcaggcc a                                          21

-continued

```
<210> SEQ ID NO 66
<211> LENGTH: 21
<212> TYPE: DNA
<213> ORGANISM: Unknown
<220> FEATURE:
<223> OTHER INFORMATION: Sequence listing for 58620.

<400> SEQUENCE: 66
tctccttccc cttggggaag g                                              21

<210> SEQ ID NO 67
<211> LENGTH: 21
<212> TYPE: DNA
<213> ORGANISM: Unknown
<220> FEATURE:
<223> OTHER INFORMATION: Sequence listing for 58620.

<400> SEQUENCE: 67
tctccagatg caaagacact c                                              21

<210> SEQ ID NO 68
<211> LENGTH: 21
<212> TYPE: DNA
<213> ORGANISM: Unknown
<220> FEATURE:
<223> OTHER INFORMATION: Sequence listing for 58620.

<400> SEQUENCE: 68
tctcaaccgt cttcagggca t                                              21

<210> SEQ ID NO 69
<211> LENGTH: 21
<212> TYPE: DNA
<213> ORGANISM: Unknown
<220> FEATURE:
<223> OTHER INFORMATION: Sequence listing for 58620.

<400> SEQUENCE: 69
tctaatgaac tctgcagcag c                                              21

<210> SEQ ID NO 70
<211> LENGTH: 21
<212> TYPE: DNA
<213> ORGANISM: Unknown
<220> FEATURE:
<223> OTHER INFORMATION: Sequence listing for 58620.

<400> SEQUENCE: 70
tcgccttccc caaggggaag g                                              21

<210> SEQ ID NO 71
<211> LENGTH: 21
<212> TYPE: DNA
<213> ORGANISM: Unknown
<220> FEATURE:
<223> OTHER INFORMATION: Sequence listing for 58620.

<400> SEQUENCE: 71
tccttgctgc acggcccaaa c                                              21

<210> SEQ ID NO 72
<211> LENGTH: 21
<212> TYPE: DNA
<213> ORGANISM: Unknown
<220> FEATURE:
<223> OTHER INFORMATION: Sequence listing for 58620.
```

<400> SEQUENCE: 72
tccttcccct tggggaaggc g                                        21

<210> SEQ ID NO 73
<211> LENGTH: 21
<212> TYPE: DNA
<213> ORGANISM: Unknown
<220> FEATURE:
<223> OTHER INFORMATION: Sequence listing for 58620.

<400> SEQUENCE: 73
tccctgagcc ctggattttt t                                        21

<210> SEQ ID NO 74
<211> LENGTH: 21
<212> TYPE: DNA
<213> ORGANISM: Unknown
<220> FEATURE:
<223> OTHER INFORMATION: Sequence listing for 58620.

<400> SEQUENCE: 74
tccccaaggg gaaggagaac c                                        21

<210> SEQ ID NO 75
<211> LENGTH: 21
<212> TYPE: DNA
<213> ORGANISM: Unknown
<220> FEATURE:
<223> OTHER INFORMATION: Sequence listing for 58620.

<400> SEQUENCE: 75
tcagggtggc tgttcaagca a                                        21

<210> SEQ ID NO 76
<211> LENGTH: 21
<212> TYPE: DNA
<213> ORGANISM: Unknown
<220> FEATURE:
<223> OTHER INFORMATION: Sequence listing for 58620.

<400> SEQUENCE: 76
tcagcacgga ggccaggttc t                                        21

<210> SEQ ID NO 77
<211> LENGTH: 21
<212> TYPE: DNA
<213> ORGANISM: Unknown
<220> FEATURE:
<223> OTHER INFORMATION: Sequence listing for 58620.

<400> SEQUENCE: 77
tatgttgacc ctggaaagtg g                                        21

<210> SEQ ID NO 78
<211> LENGTH: 21
<212> TYPE: DNA
<213> ORGANISM: Unknown
<220> FEATURE:
<223> OTHER INFORMATION: Sequence listing for 58620.

<400> SEQUENCE: 78
tatgttctca accgtcttca g                                        21

<210> SEQ ID NO 79
<211> LENGTH: 21

```
<212> TYPE: DNA
<213> ORGANISM: Unknown
<220> FEATURE:
<223> OTHER INFORMATION: Sequence listing for 58620.

<400> SEQUENCE: 79
tatctggttt gggccgtgca g                                              21

<210> SEQ ID NO 80
<211> LENGTH: 21
<212> TYPE: DNA
<213> ORGANISM: Unknown
<220> FEATURE:
<223> OTHER INFORMATION: Sequence listing for 58620.

<400> SEQUENCE: 80
tatctccaga tgcaaagaca c                                              21

<210> SEQ ID NO 81
<211> LENGTH: 21
<212> TYPE: DNA
<213> ORGANISM: Unknown
<220> FEATURE:
<223> OTHER INFORMATION: Sequence listing for 58620.

<400> SEQUENCE: 81
tatctccaca tccttgacca t                                              21

<210> SEQ ID NO 82
<211> LENGTH: 21
<212> TYPE: DNA
<213> ORGANISM: Unknown
<220> FEATURE:
<223> OTHER INFORMATION: Sequence listing for 58620.

<400> SEQUENCE: 82
tatagcatat ggtagcagat t                                              21

<210> SEQ ID NO 83
<211> LENGTH: 21
<212> TYPE: DNA
<213> ORGANISM: Unknown
<220> FEATURE:
<223> OTHER INFORMATION: Sequence listing for 58620.

<400> SEQUENCE: 83
tatacttgcc ccaaagttct g                                              21

<210> SEQ ID NO 84
<211> LENGTH: 21
<212> TYPE: DNA
<213> ORGANISM: Unknown
<220> FEATURE:
<223> OTHER INFORMATION: Sequence listing for 58620.

<400> SEQUENCE: 84
tatacctatg ttctcaaccg t                                              21

<210> SEQ ID NO 85
<211> LENGTH: 21
<212> TYPE: DNA
<213> ORGANISM: Unknown
<220> FEATURE:
<223> OTHER INFORMATION: Sequence listing for 58620.

<400> SEQUENCE: 85
```
taggtatact tgccccaaag t                                         21

<210> SEQ ID NO 86
<211> LENGTH: 21
<212> TYPE: DNA
<213> ORGANISM: Unknown
<220> FEATURE:
<223> OTHER INFORMATION: Sequence listing for 58620.

<400> SEQUENCE: 86
tagcatatgg tagcagatta g                                         21

<210> SEQ ID NO 87
<211> LENGTH: 21
<212> TYPE: DNA
<213> ORGANISM: Unknown
<220> FEATURE:
<223> OTHER INFORMATION: Sequence listing for 58620.

<400> SEQUENCE: 87
tagaccttaa catgatcttg g                                         21

<210> SEQ ID NO 88
<211> LENGTH: 21
<212> TYPE: DNA
<213> ORGANISM: Unknown
<220> FEATURE:
<223> OTHER INFORMATION: Sequence listing for 58620.

<400> SEQUENCE: 88
tacttgcccc aaagttctgg c                                         21

<210> SEQ ID NO 89
<211> LENGTH: 21
<212> TYPE: DNA
<213> ORGANISM: Unknown
<220> FEATURE:
<223> OTHER INFORMATION: Sequence listing for 58620.

<400> SEQUENCE: 89
tacctatgtt ctcaaccgtc t                                         21

<210> SEQ ID NO 90
<211> LENGTH: 21
<212> TYPE: DNA
<213> ORGANISM: Unknown
<220> FEATURE:
<223> OTHER INFORMATION: Sequence listing for 58620.

<400> SEQUENCE: 90
taatctgcta ccatatgcta t                                         21

<210> SEQ ID NO 91
<211> LENGTH: 21
<212> TYPE: DNA
<213> ORGANISM: Unknown
<220> FEATURE:
<223> OTHER INFORMATION: Sequence listing for 58620.

<400> SEQUENCE: 91
gtttgggccg tgcagcaagg a                                         21

<210> SEQ ID NO 92
<211> LENGTH: 21
<212> TYPE: DNA
<213> ORGANISM: Unknown

-continued

<220> FEATURE:
<223> OTHER INFORMATION: Sequence listing for 58620.

<400> SEQUENCE: 92
gttgcttagc ccaaagggat c                                              21

<210> SEQ ID NO 93
<211> LENGTH: 21
<212> TYPE: DNA
<213> ORGANISM: Unknown
<220> FEATURE:
<223> OTHER INFORMATION: Sequence listing for 58620.

<400> SEQUENCE: 93
gttctggcct gctttccacc a                                              21

<210> SEQ ID NO 94
<211> LENGTH: 21
<212> TYPE: DNA
<213> ORGANISM: Unknown
<220> FEATURE:
<223> OTHER INFORMATION: Sequence listing for 58620.

<400> SEQUENCE: 94
gttctccttc cccttgggga a                                              21

<210> SEQ ID NO 95
<211> LENGTH: 21
<212> TYPE: DNA
<213> ORGANISM: Unknown
<220> FEATURE:
<223> OTHER INFORMATION: Sequence listing for 58620.

<400> SEQUENCE: 95
gttctcaacc gtcttcaggg c                                              21

<210> SEQ ID NO 96
<211> LENGTH: 21
<212> TYPE: DNA
<213> ORGANISM: Unknown
<220> FEATURE:
<223> OTHER INFORMATION: Sequence listing for 58620.

<400> SEQUENCE: 96
gttctaatga actctgcagc a                                              21

<210> SEQ ID NO 97
<211> LENGTH: 21
<212> TYPE: DNA
<213> ORGANISM: Unknown
<220> FEATURE:
<223> OTHER INFORMATION: Sequence listing for 58620.

<400> SEQUENCE: 97
gttatctggt ttgggccgtg c                                              21

<210> SEQ ID NO 98
<211> LENGTH: 21
<212> TYPE: DNA
<213> ORGANISM: Unknown
<220> FEATURE:
<223> OTHER INFORMATION: Sequence listing for 58620.

<400> SEQUENCE: 98
gtgtctttgc atctggagat a                                              21

<210> SEQ ID NO 99
<211> LENGTH: 21
<212> TYPE: DNA
<213> ORGANISM: Unknown
<220> FEATURE:
<223> OTHER INFORMATION: Sequence listing for 58620.

<400> SEQUENCE: 99
gtggctgttc aagcaaaatg g                                    21

<210> SEQ ID NO 100
<211> LENGTH: 21
<212> TYPE: DNA
<213> ORGANISM: Unknown
<220> FEATURE:
<223> OTHER INFORMATION: Sequence listing for 58620.

<400> SEQUENCE: 100
gtggaaagca ggccagaact t                                    21

<210> SEQ ID NO 101
<211> LENGTH: 21
<212> TYPE: DNA
<213> ORGANISM: Unknown
<220> FEATURE:
<223> OTHER INFORMATION: Sequence listing for 58620.

<400> SEQUENCE: 101
gtgcaacgaa aaatccagg g                                     21

<210> SEQ ID NO 102
<211> LENGTH: 21
<212> TYPE: DNA
<213> ORGANISM: Unknown
<220> FEATURE:
<223> OTHER INFORMATION: Sequence listing for 58620.

<400> SEQUENCE: 102
gtgatgagat catcatattc a                                    21

<210> SEQ ID NO 103
<211> LENGTH: 21
<212> TYPE: DNA
<213> ORGANISM: Unknown
<220> FEATURE:
<223> OTHER INFORMATION: Sequence listing for 58620.

<400> SEQUENCE: 103
gtctctggtg gaaagcaggc c                                    21

<210> SEQ ID NO 104
<211> LENGTH: 21
<212> TYPE: DNA
<213> ORGANISM: Unknown
<220> FEATURE:
<223> OTHER INFORMATION: Sequence listing for 58620.

<400> SEQUENCE: 104
gtcgccttcc ccaaggggaa g                                    21

<210> SEQ ID NO 105
<211> LENGTH: 21
<212> TYPE: DNA
<213> ORGANISM: Unknown
<220> FEATURE:
<223> OTHER INFORMATION: Sequence listing for 58620.

```
<400> SEQUENCE: 105
gtatacttgc cccaaagttc t                                                  21

<210> SEQ ID NO 106
<211> LENGTH: 21
<212> TYPE: DNA
<213> ORGANISM: Unknown
<220> FEATURE:
<223> OTHER INFORMATION: Sequence listing for 58620.

<400> SEQUENCE: 106
ggtttgggcc gtgcagcaag g                                                  21

<210> SEQ ID NO 107
<211> LENGTH: 21
<212> TYPE: DNA
<213> ORGANISM: Unknown
<220> FEATURE:
<223> OTHER INFORMATION: Sequence listing for 58620.

<400> SEQUENCE: 107
ggttgcttag cccaaaggga t                                                  21

<210> SEQ ID NO 108
<211> LENGTH: 21
<212> TYPE: DNA
<213> ORGANISM: Unknown
<220> FEATURE:
<223> OTHER INFORMATION: Sequence listing for 58620.

<400> SEQUENCE: 108
ggttctcctt ccccttgggg a                                                  21

<210> SEQ ID NO 109
<211> LENGTH: 21
<212> TYPE: DNA
<213> ORGANISM: Unknown
<220> FEATURE:
<223> OTHER INFORMATION: Sequence listing for 58620.

<400> SEQUENCE: 109
ggttatctgg tttgggccgt g                                                  21

<210> SEQ ID NO 110
<211> LENGTH: 21
<212> TYPE: DNA
<213> ORGANISM: Unknown
<220> FEATURE:
<223> OTHER INFORMATION: Sequence listing for 58620.

<400> SEQUENCE: 110
ggtggctgtt caagcaaaat g                                                  21

<210> SEQ ID NO 111
<211> LENGTH: 21
<212> TYPE: DNA
<213> ORGANISM: Unknown
<220> FEATURE:
<223> OTHER INFORMATION: Sequence listing for 58620.

<400> SEQUENCE: 111
ggtggaaagc aggccagaac t                                                  21

<210> SEQ ID NO 112
```

```
<211> LENGTH: 21
<212> TYPE: DNA
<213> ORGANISM: Unknown
<220> FEATURE:
<223> OTHER INFORMATION: Sequence listing for 58620.

<400> SEQUENCE: 112
ggtcaaggat gtggagatag c                                              21

<210> SEQ ID NO 113
<211> LENGTH: 21
<212> TYPE: DNA
<213> ORGANISM: Unknown
<220> FEATURE:
<223> OTHER INFORMATION: Sequence listing for 58620.

<400> SEQUENCE: 113
ggtatacttg ccccaaagtt c                                              21

<210> SEQ ID NO 114
<211> LENGTH: 21
<212> TYPE: DNA
<213> ORGANISM: Unknown
<220> FEATURE:
<223> OTHER INFORMATION: Sequence listing for 58620.

<400> SEQUENCE: 114
gggtggctgt tcaagcaaaa t                                              21

<210> SEQ ID NO 115
<211> LENGTH: 21
<212> TYPE: DNA
<213> ORGANISM: Unknown
<220> FEATURE:
<223> OTHER INFORMATION: Sequence listing for 58620.

<400> SEQUENCE: 115
ggggaaggag aacctggcct c                                              21

<210> SEQ ID NO 116
<211> LENGTH: 21
<212> TYPE: DNA
<213> ORGANISM: Unknown
<220> FEATURE:
<223> OTHER INFORMATION: Sequence listing for 58620.

<400> SEQUENCE: 116
gggaaggaga acctggcctc c                                              21

<210> SEQ ID NO 117
<211> LENGTH: 21
<212> TYPE: DNA
<213> ORGANISM: Unknown
<220> FEATURE:
<223> OTHER INFORMATION: Sequence listing for 58620.

<400> SEQUENCE: 117
ggctgttcaa gcaaaatggt g                                              21

<210> SEQ ID NO 118
<211> LENGTH: 21
<212> TYPE: DNA
<213> ORGANISM: Unknown
<220> FEATURE:
<223> OTHER INFORMATION: Sequence listing for 58620.

<400> SEQUENCE: 118
```

-continued ggcctgcttt ccaccagaga c      21

<210> SEQ ID NO 119
<211> LENGTH: 21
<212> TYPE: DNA
<213> ORGANISM: Unknown
<220> FEATURE:
<223> OTHER INFORMATION: Sequence listing for 58620.

<400> SEQUENCE: 119
ggccaggttc tccttcccct t      21

<210> SEQ ID NO 120
<211> LENGTH: 21
<212> TYPE: DNA
<213> ORGANISM: Unknown
<220> FEATURE:
<223> OTHER INFORMATION: Sequence listing for 58620.

<400> SEQUENCE: 120
ggccagaact ttggggcaag t      21

<210> SEQ ID NO 121
<211> LENGTH: 21
<212> TYPE: DNA
<213> ORGANISM: Unknown
<220> FEATURE:
<223> OTHER INFORMATION: Sequence listing for 58620.

<400> SEQUENCE: 121
ggatcagggt ggctgttcaa g      21

<210> SEQ ID NO 122
<211> LENGTH: 21
<212> TYPE: DNA
<213> ORGANISM: Unknown
<220> FEATURE:
<223> OTHER INFORMATION: Sequence listing for 58620.

<400> SEQUENCE: 122
ggaggccagg ttctccttcc c      21

<210> SEQ ID NO 123
<211> LENGTH: 21
<212> TYPE: DNA
<213> ORGANISM: Unknown
<220> FEATURE:
<223> OTHER INFORMATION: Sequence listing for 58620.

<400> SEQUENCE: 123
ggagaacctg gcctccgtgc t      21

<210> SEQ ID NO 124
<211> LENGTH: 21
<212> TYPE: DNA
<213> ORGANISM: Unknown
<220> FEATURE:
<223> OTHER INFORMATION: Sequence listing for 58620.

<400> SEQUENCE: 124
ggaatatcca attttaagaa a      21

<210> SEQ ID NO 125
<211> LENGTH: 21
<212> TYPE: DNA

```
<213> ORGANISM: Unknown
<220> FEATURE:
<223> OTHER INFORMATION: Sequence listing for 58620.

<400> SEQUENCE: 125
ggaaggagaa cctggcctcc g                                              21

<210> SEQ ID NO 126
<211> LENGTH: 21
<212> TYPE: DNA
<213> ORGANISM: Unknown
<220> FEATURE:
<223> OTHER INFORMATION: Sequence listing for 58620.

<400> SEQUENCE: 126
ggaaagcagg ccagaacttt g                                              21

<210> SEQ ID NO 127
<211> LENGTH: 21
<212> TYPE: DNA
<213> ORGANISM: Unknown
<220> FEATURE:
<223> OTHER INFORMATION: Sequence listing for 58620.

<400> SEQUENCE: 127
gcttgaacag ccaccctgat c                                              21

<210> SEQ ID NO 128
<211> LENGTH: 21
<212> TYPE: DNA
<213> ORGANISM: Unknown
<220> FEATURE:
<223> OTHER INFORMATION: Sequence listing for 58620.

<400> SEQUENCE: 128
gcttcagcac ggaggccagg t                                              21

<210> SEQ ID NO 129
<211> LENGTH: 21
<212> TYPE: DNA
<213> ORGANISM: Unknown
<220> FEATURE:
<223> OTHER INFORMATION: Sequence listing for 58620.

<400> SEQUENCE: 129
gctgttcaag caaaatggtg g                                              21

<210> SEQ ID NO 130
<211> LENGTH: 21
<212> TYPE: DNA
<213> ORGANISM: Unknown
<220> FEATURE:
<223> OTHER INFORMATION: Sequence listing for 58620.

<400> SEQUENCE: 130
gctgctgcag agttcattag a                                              21

<210> SEQ ID NO 131
<211> LENGTH: 21
<212> TYPE: DNA
<213> ORGANISM: Unknown
<220> FEATURE:
<223> OTHER INFORMATION: Sequence listing for 58620.

<400> SEQUENCE: 131
gctgcagagt tcattagaac a                                              21
```

<210> SEQ ID NO 132
<211> LENGTH: 21
<212> TYPE: DNA
<213> ORGANISM: Unknown
<220> FEATURE:
<223> OTHER INFORMATION: Sequence listing for 58620.

<400> SEQUENCE: 132
gctgcacggc ccaaaccaga t                                              21

<210> SEQ ID NO 133
<211> LENGTH: 21
<212> TYPE: DNA
<213> ORGANISM: Unknown
<220> FEATURE:
<223> OTHER INFORMATION: Sequence listing for 58620.

<400> SEQUENCE: 133
gctatctcca catccttgac c                                              21

<210> SEQ ID NO 134
<211> LENGTH: 21
<212> TYPE: DNA
<213> ORGANISM: Unknown
<220> FEATURE:
<223> OTHER INFORMATION: Sequence listing for 58620.

<400> SEQUENCE: 134
gccttcccca aggggaagga g                                              21

<210> SEQ ID NO 135
<211> LENGTH: 21
<212> TYPE: DNA
<213> ORGANISM: Unknown
<220> FEATURE:
<223> OTHER INFORMATION: Sequence listing for 58620.

<400> SEQUENCE: 135
gcctgctttc caccagagac a                                              21

<210> SEQ ID NO 136
<211> LENGTH: 21
<212> TYPE: DNA
<213> ORGANISM: Unknown
<220> FEATURE:
<223> OTHER INFORMATION: Sequence listing for 58620.

<400> SEQUENCE: 136
gccctggatt ttttcgttgc a                                              21

<210> SEQ ID NO 137
<211> LENGTH: 21
<212> TYPE: DNA
<213> ORGANISM: Unknown
<220> FEATURE:
<223> OTHER INFORMATION: Sequence listing for 58620.

<400> SEQUENCE: 137
gccctgaaga cggttgagaa c                                              21

<210> SEQ ID NO 138
<211> LENGTH: 21
<212> TYPE: DNA
<213> ORGANISM: Unknown
<220> FEATURE:

<223> OTHER INFORMATION: Sequence listing for 58620.

<400> SEQUENCE: 138
gccccaaagt tctggcctgc t                                              21

<210> SEQ ID NO 139
<211> LENGTH: 21
<212> TYPE: DNA
<213> ORGANISM: Unknown
<220> FEATURE:
<223> OTHER INFORMATION: Sequence listing for 58620.

<400> SEQUENCE: 139
gcccaagatc atgttaaggt c                                              21

<210> SEQ ID NO 140
<211> LENGTH: 21
<212> TYPE: DNA
<213> ORGANISM: Unknown
<220> FEATURE:
<223> OTHER INFORMATION: Sequence listing for 58620.

<400> SEQUENCE: 140
gccattctgt gccagtatct g                                              21

<210> SEQ ID NO 141
<211> LENGTH: 21
<212> TYPE: DNA
<213> ORGANISM: Unknown
<220> FEATURE:
<223> OTHER INFORMATION: Sequence listing for 58620.

<400> SEQUENCE: 141
gccaggttct ccttcccctt g                                              21

<210> SEQ ID NO 142
<211> LENGTH: 21
<212> TYPE: DNA
<213> ORGANISM: Unknown
<220> FEATURE:
<223> OTHER INFORMATION: Sequence listing for 58620.

<400> SEQUENCE: 142
gccagaactt tggggcaagt a                                              21

<210> SEQ ID NO 143
<211> LENGTH: 21
<212> TYPE: DNA
<213> ORGANISM: Unknown
<220> FEATURE:
<223> OTHER INFORMATION: Sequence listing for 58620.

<400> SEQUENCE: 143
gcaggccaga actttggggc a                                              21

<210> SEQ ID NO 144
<211> LENGTH: 21
<212> TYPE: DNA
<213> ORGANISM: Unknown
<220> FEATURE:
<223> OTHER INFORMATION: Sequence listing for 58620.

<400> SEQUENCE: 144
gcacggccca aaccagataa c                                              21

```
<210> SEQ ID NO 145
<211> LENGTH: 21
<212> TYPE: DNA
<213> ORGANISM: Unknown
<220> FEATURE:
<223> OTHER INFORMATION: Sequence listing for 58620.

<400> SEQUENCE: 145
gcacggaggc caggttctcc t                                               21

<210> SEQ ID NO 146
<211> LENGTH: 21
<212> TYPE: DNA
<213> ORGANISM: Unknown
<220> FEATURE:
<223> OTHER INFORMATION: Sequence listing for 58620.

<400> SEQUENCE: 146
gcaacgaaaa aatccagggc t                                               21

<210> SEQ ID NO 147
<211> LENGTH: 21
<212> TYPE: DNA
<213> ORGANISM: Unknown
<220> FEATURE:
<223> OTHER INFORMATION: Sequence listing for 58620.

<400> SEQUENCE: 147
gattatccaa taaaccagtt g                                               21

<210> SEQ ID NO 148
<211> LENGTH: 21
<212> TYPE: DNA
<213> ORGANISM: Unknown
<220> FEATURE:
<223> OTHER INFORMATION: Sequence listing for 58620.

<400> SEQUENCE: 148
gatgccccca gaactcatca a                                               21

<210> SEQ ID NO 149
<211> LENGTH: 21
<212> TYPE: DNA
<213> ORGANISM: Unknown
<220> FEATURE:
<223> OTHER INFORMATION: Sequence listing for 58620.

<400> SEQUENCE: 149
gatgagatca tcatattcaa a                                               21

<210> SEQ ID NO 150
<211> LENGTH: 21
<212> TYPE: DNA
<213> ORGANISM: Unknown
<220> FEATURE:
<223> OTHER INFORMATION: Sequence listing for 58620.

<400> SEQUENCE: 150
gatccctttg ggctaagcaa c                                               21

<210> SEQ ID NO 151
<211> LENGTH: 21
<212> TYPE: DNA
<213> ORGANISM: Unknown
<220> FEATURE:
<223> OTHER INFORMATION: Sequence listing for 58620.
```

<400> SEQUENCE: 151
gatcagggtg gctgttcaag c                                                    21

<210> SEQ ID NO 152
<211> LENGTH: 21
<212> TYPE: DNA
<213> ORGANISM: Unknown
<220> FEATURE:
<223> OTHER INFORMATION: Sequence listing for 58620.

<400> SEQUENCE: 152
gatatagcat atggtagcag a                                                    21

<210> SEQ ID NO 153
<211> LENGTH: 21
<212> TYPE: DNA
<213> ORGANISM: Unknown
<220> FEATURE:
<223> OTHER INFORMATION: Sequence listing for 58620.

<400> SEQUENCE: 153
gagtgtcttt gcatctggag a                                                    21

<210> SEQ ID NO 154
<211> LENGTH: 21
<212> TYPE: DNA
<213> ORGANISM: Unknown
<220> FEATURE:
<223> OTHER INFORMATION: Sequence listing for 58620.

<400> SEQUENCE: 154
gaggccaggt tctccttccc c                                                    21

<210> SEQ ID NO 155
<211> LENGTH: 21
<212> TYPE: DNA
<213> ORGANISM: Unknown
<220> FEATURE:
<223> OTHER INFORMATION: Sequence listing for 58620.

<400> SEQUENCE: 155
gagccctgga tttttctgtt g                                                    21

<210> SEQ ID NO 156
<211> LENGTH: 21
<212> TYPE: DNA
<213> ORGANISM: Unknown
<220> FEATURE:
<223> OTHER INFORMATION: Sequence listing for 58620.

<400> SEQUENCE: 156
gagaacctgg cctccgtgct g                                                    21

<210> SEQ ID NO 157
<211> LENGTH: 21
<212> TYPE: DNA
<213> ORGANISM: Unknown
<220> FEATURE:
<223> OTHER INFORMATION: Sequence listing for 58620.

<400> SEQUENCE: 157
gacggttgag aacataggta t                                                    21

<210> SEQ ID NO 158
<211> LENGTH: 21

```
<212> TYPE: DNA
<213> ORGANISM: Unknown
<220> FEATURE:
<223> OTHER INFORMATION: Sequence listing for 58620.

<400> SEQUENCE: 158
gaccttaaca tgatcttggg c                                              21

<210> SEQ ID NO 159
<211> LENGTH: 21
<212> TYPE: DNA
<213> ORGANISM: Unknown
<220> FEATURE:
<223> OTHER INFORMATION: Sequence listing for 58620.

<400> SEQUENCE: 159
gacagatact ggcacagaat g                                              21

<210> SEQ ID NO 160
<211> LENGTH: 21
<212> TYPE: DNA
<213> ORGANISM: Unknown
<220> FEATURE:
<223> OTHER INFORMATION: Sequence listing for 58620.

<400> SEQUENCE: 160
gaatatccaa ttttaagaaa t                                              21

<210> SEQ ID NO 161
<211> LENGTH: 21
<212> TYPE: DNA
<213> ORGANISM: Unknown
<220> FEATURE:
<223> OTHER INFORMATION: Sequence listing for 58620.

<400> SEQUENCE: 161
gaaggagaac ctggcctccg t                                              21

<210> SEQ ID NO 162
<211> LENGTH: 21
<212> TYPE: DNA
<213> ORGANISM: Unknown
<220> FEATURE:
<223> OTHER INFORMATION: Sequence listing for 58620.

<400> SEQUENCE: 162
gaagacggtt gagaacatag g                                              21

<210> SEQ ID NO 163
<211> LENGTH: 21
<212> TYPE: DNA
<213> ORGANISM: Unknown
<220> FEATURE:
<223> OTHER INFORMATION: Sequence listing for 58620.

<400> SEQUENCE: 163
gaactttggg gcaagtatac c                                              21

<210> SEQ ID NO 164
<211> LENGTH: 21
<212> TYPE: DNA
<213> ORGANISM: Unknown
<220> FEATURE:
<223> OTHER INFORMATION: Sequence listing for 58620.

<400> SEQUENCE: 164
```

```
gaacctggcc tccgtgctga a                                              21

<210> SEQ ID NO 165
<211> LENGTH: 21
<212> TYPE: DNA
<213> ORGANISM: Unknown
<220> FEATURE:
<223> OTHER INFORMATION: Sequence listing for 58620.

<400> SEQUENCE: 165
gaaagcaggc cagaactttg g                                              21

<210> SEQ ID NO 166
<211> LENGTH: 21
<212> TYPE: DNA
<213> ORGANISM: Unknown
<220> FEATURE:
<223> OTHER INFORMATION: Sequence listing for 58620.

<400> SEQUENCE: 166
gaaaaaatcc agggctcagg g                                              21

<210> SEQ ID NO 167
<211> LENGTH: 21
<212> TYPE: DNA
<213> ORGANISM: Unknown
<220> FEATURE:
<223> OTHER INFORMATION: Sequence listing for 58620.

<400> SEQUENCE: 167
ctttggggca agtataccta t                                              21

<210> SEQ ID NO 168
<211> LENGTH: 21
<212> TYPE: DNA
<213> ORGANISM: Unknown
<220> FEATURE:
<223> OTHER INFORMATION: Sequence listing for 58620.

<400> SEQUENCE: 168
cttgctgcac ggcccaaacc a                                              21

<210> SEQ ID NO 169
<211> LENGTH: 21
<212> TYPE: DNA
<213> ORGANISM: Unknown
<220> FEATURE:
<223> OTHER INFORMATION: Sequence listing for 58620.

<400> SEQUENCE: 169
cttgccccaa agttctggcc t                                              21

<210> SEQ ID NO 170
<211> LENGTH: 21
<212> TYPE: DNA
<213> ORGANISM: Unknown
<220> FEATURE:
<223> OTHER INFORMATION: Sequence listing for 58620.

<400> SEQUENCE: 170
cttgatgagt tctgggggca t                                              21

<210> SEQ ID NO 171
<211> LENGTH: 21
<212> TYPE: DNA
<213> ORGANISM: Unknown
```

```
<220> FEATURE:
<223> OTHER INFORMATION: Sequence listing for 58620.

<400> SEQUENCE: 171
cttgaacagc caccctgatc c                                              21

<210> SEQ ID NO 172
<211> LENGTH: 21
<212> TYPE: DNA
<213> ORGANISM: Unknown
<220> FEATURE:
<223> OTHER INFORMATION: Sequence listing for 58620.

<400> SEQUENCE: 172
cttccccttg gggaaggcga c                                              21

<210> SEQ ID NO 173
<211> LENGTH: 21
<212> TYPE: DNA
<213> ORGANISM: Unknown
<220> FEATURE:
<223> OTHER INFORMATION: Sequence listing for 58620.

<400> SEQUENCE: 173
cttccccaag gggaaggaga a                                              21

<210> SEQ ID NO 174
<211> LENGTH: 21
<212> TYPE: DNA
<213> ORGANISM: Unknown
<220> FEATURE:
<223> OTHER INFORMATION: Sequence listing for 58620.

<400> SEQUENCE: 174
cttcagcacg gaggccaggt t                                              21

<210> SEQ ID NO 175
<211> LENGTH: 21
<212> TYPE: DNA
<213> ORGANISM: Unknown
<220> FEATURE:
<223> OTHER INFORMATION: Sequence listing for 58620.

<400> SEQUENCE: 175
ctggtttggg ccgtgcagca a                                              21

<210> SEQ ID NO 176
<211> LENGTH: 21
<212> TYPE: DNA
<213> ORGANISM: Unknown
<220> FEATURE:
<223> OTHER INFORMATION: Sequence listing for 58620.

<400> SEQUENCE: 176
ctggtggaaa gcaggccaga a                                              21

<210> SEQ ID NO 177
<211> LENGTH: 21
<212> TYPE: DNA
<213> ORGANISM: Unknown
<220> FEATURE:
<223> OTHER INFORMATION: Sequence listing for 58620.

<400> SEQUENCE: 177
ctggcctgct ttccaccaga g                                              21
```

<210> SEQ ID NO 178
<211> LENGTH: 21
<212> TYPE: DNA
<213> ORGANISM: Unknown
<220> FEATURE:
<223> OTHER INFORMATION: Sequence listing for 58620.

<400> SEQUENCE: 178
ctgctgcaga gttcattaga a                                              21

<210> SEQ ID NO 179
<211> LENGTH: 21
<212> TYPE: DNA
<213> ORGANISM: Unknown
<220> FEATURE:
<223> OTHER INFORMATION: Sequence listing for 58620.

<400> SEQUENCE: 179
ctgcagagtt cattagaaca t                                              21

<210> SEQ ID NO 180
<211> LENGTH: 21
<212> TYPE: DNA
<213> ORGANISM: Unknown
<220> FEATURE:
<223> OTHER INFORMATION: Sequence listing for 58620.

<400> SEQUENCE: 180
ctgcacggcc caaaccagat a                                              21

<210> SEQ ID NO 181
<211> LENGTH: 21
<212> TYPE: DNA
<213> ORGANISM: Unknown
<220> FEATURE:
<223> OTHER INFORMATION: Sequence listing for 58620.

<400> SEQUENCE: 181
ctgagccctg gattttttcg t                                              21

<210> SEQ ID NO 182
<211> LENGTH: 21
<212> TYPE: DNA
<213> ORGANISM: Unknown
<220> FEATURE:
<223> OTHER INFORMATION: Sequence listing for 58620.

<400> SEQUENCE: 182
ctgaagacgg ttgagaacat a                                              21

<210> SEQ ID NO 183
<211> LENGTH: 21
<212> TYPE: DNA
<213> ORGANISM: Unknown
<220> FEATURE:
<223> OTHER INFORMATION: Sequence listing for 58620.

<400> SEQUENCE: 183
ctctggtgga aagcaggcca g                                              21

<210> SEQ ID NO 184
<211> LENGTH: 21
<212> TYPE: DNA
<213> ORGANISM: Unknown
<220> FEATURE:
<223> OTHER INFORMATION: Sequence listing for 58620.

```
<400> SEQUENCE: 184
ctccttgctg cacggcccaa a                                              21

<210> SEQ ID NO 185
<211> LENGTH: 21
<212> TYPE: DNA
<213> ORGANISM: Unknown
<220> FEATURE:
<223> OTHER INFORMATION: Sequence listing for 58620.

<400> SEQUENCE: 185
ctccttcccc ttggggaagg c                                              21

<210> SEQ ID NO 186
<211> LENGTH: 21
<212> TYPE: DNA
<213> ORGANISM: Unknown
<220> FEATURE:
<223> OTHER INFORMATION: Sequence listing for 58620.

<400> SEQUENCE: 186
ctccctgagc cctggatttt t                                              21

<210> SEQ ID NO 187
<211> LENGTH: 21
<212> TYPE: DNA
<213> ORGANISM: Unknown
<220> FEATURE:
<223> OTHER INFORMATION: Sequence listing for 58620.

<400> SEQUENCE: 187
ctccagatgc aaagacactc t                                              21

<210> SEQ ID NO 188
<211> LENGTH: 21
<212> TYPE: DNA
<213> ORGANISM: Unknown
<220> FEATURE:
<223> OTHER INFORMATION: Sequence listing for 58620.

<400> SEQUENCE: 188
ctatgttctc aaccgtcttc a                                              21

<210> SEQ ID NO 189
<211> LENGTH: 21
<212> TYPE: DNA
<213> ORGANISM: Unknown
<220> FEATURE:
<223> OTHER INFORMATION: Sequence listing for 58620.

<400> SEQUENCE: 189
ctatctccac atccttgacc a                                              21

<210> SEQ ID NO 190
<211> LENGTH: 21
<212> TYPE: DNA
<213> ORGANISM: Unknown
<220> FEATURE:
<223> OTHER INFORMATION: Sequence listing for 58620.

<400> SEQUENCE: 190
ctaatctgct accatatgct a                                              21

<210> SEQ ID NO 191
```

```
<211> LENGTH: 21
<212> TYPE: DNA
<213> ORGANISM: Unknown
<220> FEATURE:
<223> OTHER INFORMATION: Sequence listing for 58620.

<400> SEQUENCE: 191
cggaggccag gttctccttc c                                              21

<210> SEQ ID NO 192
<211> LENGTH: 21
<212> TYPE: DNA
<213> ORGANISM: Unknown
<220> FEATURE:
<223> OTHER INFORMATION: Sequence listing for 58620.

<400> SEQUENCE: 192
cgcttcagca cggaggccag g                                              21

<210> SEQ ID NO 193
<211> LENGTH: 21
<212> TYPE: DNA
<213> ORGANISM: Unknown
<220> FEATURE:
<223> OTHER INFORMATION: Sequence listing for 58620.

<400> SEQUENCE: 193
cgccttcccc aaggggaagg a                                              21

<210> SEQ ID NO 194
<211> LENGTH: 21
<212> TYPE: DNA
<213> ORGANISM: Unknown
<220> FEATURE:
<223> OTHER INFORMATION: Sequence listing for 58620.

<400> SEQUENCE: 194
cgaaaaaatc cagggctcag g                                              21

<210> SEQ ID NO 195
<211> LENGTH: 21
<212> TYPE: DNA
<213> ORGANISM: Unknown
<220> FEATURE:
<223> OTHER INFORMATION: Sequence listing for 58620.

<400> SEQUENCE: 195
ccttgctgca cggcccaaac c                                              21

<210> SEQ ID NO 196
<211> LENGTH: 21
<212> TYPE: DNA
<213> ORGANISM: Unknown
<220> FEATURE:
<223> OTHER INFORMATION: Sequence listing for 58620.

<400> SEQUENCE: 196
ccttcccctt ggggaaggcg a                                              21

<210> SEQ ID NO 197
<211> LENGTH: 21
<212> TYPE: DNA
<213> ORGANISM: Unknown
<220> FEATURE:
<223> OTHER INFORMATION: Sequence listing for 58620.

<400> SEQUENCE: 197
```

```
ccttccccaa ggggaaggag a                                                21

<210> SEQ ID NO 198
<211> LENGTH: 21
<212> TYPE: DNA
<213> ORGANISM: Unknown
<220> FEATURE:
<223> OTHER INFORMATION: Sequence listing for 58620.

<400> SEQUENCE: 198
ccttaacatg atcttgggca t                                                21

<210> SEQ ID NO 199
<211> LENGTH: 21
<212> TYPE: DNA
<213> ORGANISM: Unknown
<220> FEATURE:
<223> OTHER INFORMATION: Sequence listing for 58620.

<400> SEQUENCE: 199
cctggcctcc gtgctgaagc g                                                21

<210> SEQ ID NO 200
<211> LENGTH: 21
<212> TYPE: DNA
<213> ORGANISM: Unknown
<220> FEATURE:
<223> OTHER INFORMATION: Sequence listing for 58620.

<400> SEQUENCE: 200
cctgagccct ggatttttc g                                                 21

<210> SEQ ID NO 201
<211> LENGTH: 21
<212> TYPE: DNA
<213> ORGANISM: Unknown
<220> FEATURE:
<223> OTHER INFORMATION: Sequence listing for 58620.

<400> SEQUENCE: 201
cctgaagacg gttgagaaca t                                                21

<210> SEQ ID NO 202
<211> LENGTH: 21
<212> TYPE: DNA
<213> ORGANISM: Unknown
<220> FEATURE:
<223> OTHER INFORMATION: Sequence listing for 58620.

<400> SEQUENCE: 202
cctccctgag ccctggattt t                                                21

<210> SEQ ID NO 203
<211> LENGTH: 21
<212> TYPE: DNA
<213> ORGANISM: Unknown
<220> FEATURE:
<223> OTHER INFORMATION: Sequence listing for 58620.

<400> SEQUENCE: 203
cctatgttct caaccgtctt c                                                21

<210> SEQ ID NO 204
<211> LENGTH: 21
<212> TYPE: DNA
```

```
<213> ORGANISM: Unknown
<220> FEATURE:
<223> OTHER INFORMATION: Sequence listing for 58620.

<400> SEQUENCE: 204
cctaatctgc taccatatgc t                                              21

<210> SEQ ID NO 205
<211> LENGTH: 21
<212> TYPE: DNA
<213> ORGANISM: Unknown
<220> FEATURE:
<223> OTHER INFORMATION: Sequence listing for 58620.

<400> SEQUENCE: 205
ccctggattt tttcgttgca c                                              21

<210> SEQ ID NO 206
<211> LENGTH: 21
<212> TYPE: DNA
<213> ORGANISM: Unknown
<220> FEATURE:
<223> OTHER INFORMATION: Sequence listing for 58620.

<400> SEQUENCE: 206
ccctgagccc tggatttttt c                                              21

<210> SEQ ID NO 207
<211> LENGTH: 21
<212> TYPE: DNA
<213> ORGANISM: Unknown
<220> FEATURE:
<223> OTHER INFORMATION: Sequence listing for 58620.

<400> SEQUENCE: 207
ccctgaagac ggttgagaac a                                              21

<210> SEQ ID NO 208
<211> LENGTH: 21
<212> TYPE: DNA
<213> ORGANISM: Unknown
<220> FEATURE:
<223> OTHER INFORMATION: Sequence listing for 58620.

<400> SEQUENCE: 208
ccccaagggg aaggagaacc t                                              21

<210> SEQ ID NO 209
<211> LENGTH: 21
<212> TYPE: DNA
<213> ORGANISM: Unknown
<220> FEATURE:
<223> OTHER INFORMATION: Sequence listing for 58620.

<400> SEQUENCE: 209
ccccaaagtt ctggcctgct t                                              21

<210> SEQ ID NO 210
<211> LENGTH: 21
<212> TYPE: DNA
<213> ORGANISM: Unknown
<220> FEATURE:
<223> OTHER INFORMATION: Sequence listing for 58620.

<400> SEQUENCE: 210
cccactttcc agggtcaaca t                                              21
```

```
<210> SEQ ID NO 211
<211> LENGTH: 21
<212> TYPE: DNA
<213> ORGANISM: Unknown
<220> FEATURE:
<223> OTHER INFORMATION: Sequence listing for 58620.

<400> SEQUENCE: 211
cccaagggga aggagaacct g                                              21

<210> SEQ ID NO 212
<211> LENGTH: 21
<212> TYPE: DNA
<213> ORGANISM: Unknown
<220> FEATURE:
<223> OTHER INFORMATION: Sequence listing for 58620.

<400> SEQUENCE: 212
cccaagatca tgttaaggtc t                                              21

<210> SEQ ID NO 213
<211> LENGTH: 21
<212> TYPE: DNA
<213> ORGANISM: Unknown
<220> FEATURE:
<223> OTHER INFORMATION: Sequence listing for 58620.

<400> SEQUENCE: 213
cccaaagttc tggcctgctt t                                              21

<210> SEQ ID NO 214
<211> LENGTH: 21
<212> TYPE: DNA
<213> ORGANISM: Unknown
<220> FEATURE:
<223> OTHER INFORMATION: Sequence listing for 58620.

<400> SEQUENCE: 214 ccatttgct tgaacagcca c                                               21

<210> SEQ ID NO 215
<211> LENGTH: 21
<212> TYPE: DNA
<213> ORGANISM: Unknown
<220> FEATURE:
<223> OTHER INFORMATION: Sequence listing for 58620.

<400> SEQUENCE: 215
ccattctgtg ccagtatctg t                                              21

<210> SEQ ID NO 216
<211> LENGTH: 21
<212> TYPE: DNA
<213> ORGANISM: Unknown
<220> FEATURE:
<223> OTHER INFORMATION: Sequence listing for 58620.

<400> SEQUENCE: 216
ccaggttctc cttccccttg g                                              21

<210> SEQ ID NO 217
<211> LENGTH: 21
<212> TYPE: DNA
<213> ORGANISM: Unknown
<220> FEATURE:
```

<223> OTHER INFORMATION: Sequence listing for 58620.

<400> SEQUENCE: 217 ccagaactttt ggggcaagta t                                        21

<210> SEQ ID NO 218
<211> LENGTH: 21
<212> TYPE: DNA
<213> ORGANISM: Unknown
<220> FEATURE:
<223> OTHER INFORMATION: Sequence listing for 58620.

<400> SEQUENCE: 218
ccactttcca gggtcaacat a                                         21

<210> SEQ ID NO 219
<211> LENGTH: 21
<212> TYPE: DNA
<213> ORGANISM: Unknown
<220> FEATURE:
<223> OTHER INFORMATION: Sequence listing for 58620.

<400> SEQUENCE: 219
ccaccatttt gcttgaacag c                                         21

<210> SEQ ID NO 220
<211> LENGTH: 21
<212> TYPE: DNA
<213> ORGANISM: Unknown
<220> FEATURE:
<223> OTHER INFORMATION: Sequence listing for 58620.

<400> SEQUENCE: 220
ccaaggggaa ggagaacctg g                                         21

<210> SEQ ID NO 221
<211> LENGTH: 21
<212> TYPE: DNA
<213> ORGANISM: Unknown
<220> FEATURE:
<223> OTHER INFORMATION: Sequence listing for 58620.

<400> SEQUENCE: 221
ccaagatcat gttaaggtct a                                         21

<210> SEQ ID NO 222
<211> LENGTH: 21
<212> TYPE: DNA
<213> ORGANISM: Unknown
<220> FEATURE:
<223> OTHER INFORMATION: Sequence listing for 58620.

<400> SEQUENCE: 222
ccaaagttct ggcctgcttt c                                         21

<210> SEQ ID NO 223
<211> LENGTH: 21
<212> TYPE: DNA
<213> ORGANISM: Unknown
<220> FEATURE:
<223> OTHER INFORMATION: Sequence listing for 58620.

<400> SEQUENCE: 223
cattttgctt gaacagccac c                                         21

```
<210> SEQ ID NO 224
<211> LENGTH: 21
<212> TYPE: DNA
<213> ORGANISM: Unknown
<220> FEATURE:
<223> OTHER INFORMATION: Sequence listing for 58620.

<400> SEQUENCE: 224
cattctgtgc cagtatctgt c                                              21

<210> SEQ ID NO 225
<211> LENGTH: 21
<212> TYPE: DNA
<213> ORGANISM: Unknown
<220> FEATURE:
<223> OTHER INFORMATION: Sequence listing for 58620.

<400> SEQUENCE: 225
cataggtata cttgccccaa a                                              21

<210> SEQ ID NO 226
<211> LENGTH: 21
<212> TYPE: DNA
<213> ORGANISM: Unknown
<220> FEATURE:
<223> OTHER INFORMATION: Sequence listing for 58620.

<400> SEQUENCE: 226
caggttctcc ttccccttgg g                                              21

<210> SEQ ID NO 227
<211> LENGTH: 21
<212> TYPE: DNA
<213> ORGANISM: Unknown
<220> FEATURE:
<223> OTHER INFORMATION: Sequence listing for 58620.

<400> SEQUENCE: 227
cagggtggct gttcaagcaa a                                              21

<210> SEQ ID NO 228
<211> LENGTH: 21
<212> TYPE: DNA
<213> ORGANISM: Unknown
<220> FEATURE:
<223> OTHER INFORMATION: Sequence listing for 58620.

<400> SEQUENCE: 228
caggccagaa ctttggggca a                                              21

<210> SEQ ID NO 229
<211> LENGTH: 21
<212> TYPE: DNA
<213> ORGANISM: Unknown
<220> FEATURE:
<223> OTHER INFORMATION: Sequence listing for 58620.

<400> SEQUENCE: 229
cagcacggag gccaggttct c                                              21

<210> SEQ ID NO 230
<211> LENGTH: 21
<212> TYPE: DNA
<213> ORGANISM: Unknown
<220> FEATURE:
<223> OTHER INFORMATION: Sequence listing for 58620.
```

<400> SEQUENCE: 230
cagatactgg cacagaatgg c                                          21

<210> SEQ ID NO 231
<211> LENGTH: 21
<212> TYPE: DNA
<213> ORGANISM: Unknown
<220> FEATURE:
<223> OTHER INFORMATION: Sequence listing for 58620.

<400> SEQUENCE: 231
cagaactttg gggcaagtat a                                          21

<210> SEQ ID NO 232
<211> LENGTH: 21
<212> TYPE: DNA
<213> ORGANISM: Unknown
<220> FEATURE:
<223> OTHER INFORMATION: Sequence listing for 58620.

<400> SEQUENCE: 232
cacggcccaa accagataac c                                          21

<210> SEQ ID NO 233
<211> LENGTH: 21
<212> TYPE: DNA
<213> ORGANISM: Unknown
<220> FEATURE:
<223> OTHER INFORMATION: Sequence listing for 58620.

<400> SEQUENCE: 233
cacggaggcc aggttctcct t                                          21

<210> SEQ ID NO 234
<211> LENGTH: 21
<212> TYPE: DNA
<213> ORGANISM: Unknown
<220> FEATURE:
<223> OTHER INFORMATION: Sequence listing for 58620.

<400> SEQUENCE: 234
caccattttg cttgaacagc c                                          21

<210> SEQ ID NO 235
<211> LENGTH: 21
<212> TYPE: DNA
<213> ORGANISM: Unknown
<220> FEATURE:
<223> OTHER INFORMATION: Sequence listing for 58620.

<400> SEQUENCE: 235
caaggggaag gagaacctgg c                                          21

<210> SEQ ID NO 236
<211> LENGTH: 21
<212> TYPE: DNA
<213> ORGANISM: Unknown
<220> FEATURE:
<223> OTHER INFORMATION: Sequence listing for 58620.

<400> SEQUENCE: 236
caactggttt attggataat c                                          21

<210> SEQ ID NO 237
<211> LENGTH: 21

```
<212> TYPE: DNA
<213> ORGANISM: Unknown
<220> FEATURE:
<223> OTHER INFORMATION: Sequence listing for 58620.

<400> SEQUENCE: 237
caacgaaaaa atccagggct c                                              21

<210> SEQ ID NO 238
<211> LENGTH: 21
<212> TYPE: DNA
<213> ORGANISM: Unknown
<220> FEATURE:
<223> OTHER INFORMATION: Sequence listing for 58620.

<400> SEQUENCE: 238
caaagttctg gcctgctttc c                                              21

<210> SEQ ID NO 239
<211> LENGTH: 21
<212> TYPE: DNA
<213> ORGANISM: Unknown
<220> FEATURE:
<223> OTHER INFORMATION: Sequence listing for 58620.

<400> SEQUENCE: 239
attttgcttg aacagccacc c                                              21

<210> SEQ ID NO 240
<211> LENGTH: 21
<212> TYPE: DNA
<213> ORGANISM: Unknown
<220> FEATURE:
<223> OTHER INFORMATION: Sequence listing for 58620.

<400> SEQUENCE: 240
atttcttaaa attggatatt c                                              21

<210> SEQ ID NO 241
<211> LENGTH: 21
<212> TYPE: DNA
<213> ORGANISM: Unknown
<220> FEATURE:
<223> OTHER INFORMATION: Sequence listing for 58620.

<400> SEQUENCE: 241
atgttgaccc tggaaagtgg g                                              21

<210> SEQ ID NO 242
<211> LENGTH: 21
<212> TYPE: DNA
<213> ORGANISM: Unknown
<220> FEATURE:
<223> OTHER INFORMATION: Sequence listing for 58620.

<400> SEQUENCE: 242
atgttctcaa ccgtcttcag g                                              21

<210> SEQ ID NO 243
<211> LENGTH: 21
<212> TYPE: DNA
<213> ORGANISM: Unknown
<220> FEATURE:
<223> OTHER INFORMATION: Sequence listing for 58620.

<400> SEQUENCE: 243
```

-continued atgttctaat gaactctgca g                                              21

<210> SEQ ID NO 244
<211> LENGTH: 21
<212> TYPE: DNA
<213> ORGANISM: Unknown
<220> FEATURE:
<223> OTHER INFORMATION: Sequence listing for 58620.

<400> SEQUENCE: 244
atggtcaagg atgtggagat a                                              21

<210> SEQ ID NO 245
<211> LENGTH: 21
<212> TYPE: DNA
<213> ORGANISM: Unknown
<220> FEATURE:
<223> OTHER INFORMATION: Sequence listing for 58620.

<400> SEQUENCE: 245
atgccctgaa gacggttgag a                                              21

<210> SEQ ID NO 246
<211> LENGTH: 21
<212> TYPE: DNA
<213> ORGANISM: Unknown
<220> FEATURE:
<223> OTHER INFORMATION: Sequence listing for 58620.

<400> SEQUENCE: 246
atgcccccag aactcatcaa g                                              21

<210> SEQ ID NO 247
<211> LENGTH: 21
<212> TYPE: DNA
<213> ORGANISM: Unknown
<220> FEATURE:
<223> OTHER INFORMATION: Sequence listing for 58620.

<400> SEQUENCE: 247
atgcccaaga tcatgttaag g                                              21

<210> SEQ ID NO 248
<211> LENGTH: 21
<212> TYPE: DNA
<213> ORGANISM: Unknown
<220> FEATURE:
<223> OTHER INFORMATION: Sequence listing for 58620.

<400> SEQUENCE: 248
atgagtcttc ttggagcaag t                                              21

<210> SEQ ID NO 249
<211> LENGTH: 21
<212> TYPE: DNA
<213> ORGANISM: Unknown
<220> FEATURE:
<223> OTHER INFORMATION: Sequence listing for 58620.

<400> SEQUENCE: 249
atctggtttg ggccgtgcag c                                              21

<210> SEQ ID NO 250
<211> LENGTH: 21
<212> TYPE: DNA
<213> ORGANISM: Unknown

<220> FEATURE:
<223> OTHER INFORMATION: Sequence listing for 58620.

<400> SEQUENCE: 250
atctgctacc atatgctata t                                              21

<210> SEQ ID NO 251
<211> LENGTH: 21
<212> TYPE: DNA
<213> ORGANISM: Unknown
<220> FEATURE:
<223> OTHER INFORMATION: Sequence listing for 58620.

<400> SEQUENCE: 251
atctccagat gcaaagacac t                                              21

<210> SEQ ID NO 252
<211> LENGTH: 21
<212> TYPE: DNA
<213> ORGANISM: Unknown
<220> FEATURE:
<223> OTHER INFORMATION: Sequence listing for 58620.

<400> SEQUENCE: 252
atccctttgg gctaagcaac c                                              21

<210> SEQ ID NO 253
<211> LENGTH: 21
<212> TYPE: DNA
<213> ORGANISM: Unknown
<220> FEATURE:
<223> OTHER INFORMATION: Sequence listing for 58620.

<400> SEQUENCE: 253
atcagggtgg ctgttcaagc a                                              21

<210> SEQ ID NO 254
<211> LENGTH: 21
<212> TYPE: DNA
<213> ORGANISM: Unknown
<220> FEATURE:
<223> OTHER INFORMATION: Sequence listing for 58620.

<400> SEQUENCE: 254
atatagcata tggtagcaga t                                              21

<210> SEQ ID NO 255
<211> LENGTH: 21
<212> TYPE: DNA
<213> ORGANISM: Unknown
<220> FEATURE:
<223> OTHER INFORMATION: Sequence listing for 58620.

<400> SEQUENCE: 255
ataggtatac ttgccccaaa g                                              21

<210> SEQ ID NO 256
<211> LENGTH: 21
<212> TYPE: DNA
<213> ORGANISM: Unknown
<220> FEATURE:
<223> OTHER INFORMATION: Sequence listing for 58620.

<400> SEQUENCE: 256
atagcatatg gtagcagatt a                                              21

<210> SEQ ID NO 257
<211> LENGTH: 21
<212> TYPE: DNA
<213> ORGANISM: Unknown
<220> FEATURE:
<223> OTHER INFORMATION: Sequence listing for 58620.

<400> SEQUENCE: 257
atacttgccc caaagttctg g					21

<210> SEQ ID NO 258
<211> LENGTH: 21
<212> TYPE: DNA
<213> ORGANISM: Unknown
<220> FEATURE:
<223> OTHER INFORMATION: Sequence listing for 58620.

<400> SEQUENCE: 258
atacctatgt tctcaaccgt c					21

<210> SEQ ID NO 259
<211> LENGTH: 21
<212> TYPE: DNA
<213> ORGANISM: Unknown
<220> FEATURE:
<223> OTHER INFORMATION: Sequence listing for 58620.

<400> SEQUENCE: 259
agttctggcc tgctttccac c					21

<210> SEQ ID NO 260
<211> LENGTH: 21
<212> TYPE: DNA
<213> ORGANISM: Unknown
<220> FEATURE:
<223> OTHER INFORMATION: Sequence listing for 58620.

<400> SEQUENCE: 260
agtgtctttg catctggaga t					21

<210> SEQ ID NO 261
<211> LENGTH: 21
<212> TYPE: DNA
<213> ORGANISM: Unknown
<220> FEATURE:
<223> OTHER INFORMATION: Sequence listing for 58620.

<400> SEQUENCE: 261
aggttctcct tccccttggg g					21

<210> SEQ ID NO 262
<211> LENGTH: 21
<212> TYPE: DNA
<213> ORGANISM: Unknown
<220> FEATURE:
<223> OTHER INFORMATION: Sequence listing for 58620.

<400> SEQUENCE: 262
aggttatctg gtttgggccg t					21

<210> SEQ ID NO 263
<211> LENGTH: 21
<212> TYPE: DNA
<213> ORGANISM: Unknown
<220> FEATURE:
<223> OTHER INFORMATION: Sequence listing for 58620.

<400> SEQUENCE: 263
aggtatactt gccccaaagt t                                              21

<210> SEQ ID NO 264
<211> LENGTH: 21
<212> TYPE: DNA
<213> ORGANISM: Unknown
<220> FEATURE:
<223> OTHER INFORMATION: Sequence listing for 58620.

<400> SEQUENCE: 264
agggtggctg ttcaagcaaa a                                              21

<210> SEQ ID NO 265
<211> LENGTH: 21
<212> TYPE: DNA
<213> ORGANISM: Unknown
<220> FEATURE:
<223> OTHER INFORMATION: Sequence listing for 58620.

<400> SEQUENCE: 265
aggggaagga gaacctggcc t                                              21

<210> SEQ ID NO 266
<211> LENGTH: 21
<212> TYPE: DNA
<213> ORGANISM: Unknown
<220> FEATURE:
<223> OTHER INFORMATION: Sequence listing for 58620.

<400> SEQUENCE: 266
aggccaggtt ctccttcccc t                                              21

<210> SEQ ID NO 267
<211> LENGTH: 21
<212> TYPE: DNA
<213> ORGANISM: Unknown
<220> FEATURE:
<223> OTHER INFORMATION: Sequence listing for 58620.

<400> SEQUENCE: 267
aggccagaac tttggggcaa g                                              21

<210> SEQ ID NO 268
<211> LENGTH: 21
<212> TYPE: DNA
<213> ORGANISM: Unknown
<220> FEATURE:
<223> OTHER INFORMATION: Sequence listing for 58620.

<400> SEQUENCE: 268
aggagaacct ggcctccgtg c                                              21

<210> SEQ ID NO 269
<211> LENGTH: 21
<212> TYPE: DNA
<213> ORGANISM: Unknown
<220> FEATURE:
<223> OTHER INFORMATION: Sequence listing for 58620.

<400> SEQUENCE: 269
agccctggat ttttcgttg c                                               21

<210> SEQ ID NO 270

```
<211> LENGTH: 21
<212> TYPE: DNA
<213> ORGANISM: Unknown
<220> FEATURE:
<223> OTHER INFORMATION: Sequence listing for 58620.

<400> SEQUENCE: 270
agcatatggt agcagattag g                                    21

<210> SEQ ID NO 271
<211> LENGTH: 21
<212> TYPE: DNA
<213> ORGANISM: Unknown
<220> FEATURE:
<223> OTHER INFORMATION: Sequence listing for 58620.

<400> SEQUENCE: 271
agcaggccag aactttgggg c                                    21

<210> SEQ ID NO 272
<211> LENGTH: 21
<212> TYPE: DNA
<213> ORGANISM: Unknown
<220> FEATURE:
<223> OTHER INFORMATION: Sequence listing for 58620.

<400> SEQUENCE: 272
agcacggagg ccaggttctc c                                    21

<210> SEQ ID NO 273
<211> LENGTH: 21
<212> TYPE: DNA
<213> ORGANISM: Unknown
<220> FEATURE:
<223> OTHER INFORMATION: Sequence listing for 58620.

<400> SEQUENCE: 273
agatgccccc agaactcatc a                                    21

<210> SEQ ID NO 274
<211> LENGTH: 21
<212> TYPE: DNA
<213> ORGANISM: Unknown
<220> FEATURE:
<223> OTHER INFORMATION: Sequence listing for 58620.

<400> SEQUENCE: 274
agatcccttt gggctaagca a                                    21

<210> SEQ ID NO 275
<211> LENGTH: 21
<212> TYPE: DNA
<213> ORGANISM: Unknown
<220> FEATURE:
<223> OTHER INFORMATION: Sequence listing for 58620.

<400> SEQUENCE: 275
agagtgtctt tgcatctgga g                                    21

<210> SEQ ID NO 276
<211> LENGTH: 21
<212> TYPE: DNA
<213> ORGANISM: Unknown
<220> FEATURE:
<223> OTHER INFORMATION: Sequence listing for 58620.

<400> SEQUENCE: 276
```
agacggttga gaacataggt a                                              21

<210> SEQ ID NO 277
<211> LENGTH: 21
<212> TYPE: DNA
<213> ORGANISM: Unknown
<220> FEATURE:
<223> OTHER INFORMATION: Sequence listing for 58620.

<400> SEQUENCE: 277
agaccttaac atgatcttgg g                                              21

<210> SEQ ID NO 278
<211> LENGTH: 21
<212> TYPE: DNA
<213> ORGANISM: Unknown
<220> FEATURE:
<223> OTHER INFORMATION: Sequence listing for 58620.

<400> SEQUENCE: 278
agaactttgg ggcaagtata c                                              21

<210> SEQ ID NO 279
<211> LENGTH: 21
<212> TYPE: DNA
<213> ORGANISM: Unknown
<220> FEATURE:
<223> OTHER INFORMATION: Sequence listing for 58620.

<400> SEQUENCE: 279
agaacctggc ctccgtgctg a                                              21

<210> SEQ ID NO 280
<211> LENGTH: 21
<212> TYPE: DNA
<213> ORGANISM: Unknown
<220> FEATURE:
<223> OTHER INFORMATION: Sequence listing for 58620.

<400> SEQUENCE: 280
actttggggc aagtatacct a                                              21

<210> SEQ ID NO 281
<211> LENGTH: 21
<212> TYPE: DNA
<213> ORGANISM: Unknown
<220> FEATURE:
<223> OTHER INFORMATION: Sequence listing for 58620.

<400> SEQUENCE: 281
acttgctcca agaagactca t                                              21

<210> SEQ ID NO 282
<211> LENGTH: 21
<212> TYPE: DNA
<213> ORGANISM: Unknown
<220> FEATURE:
<223> OTHER INFORMATION: Sequence listing for 58620.

<400> SEQUENCE: 282
acttgcccca aagttctggc c                                              21

<210> SEQ ID NO 283
<211> LENGTH: 21
<212> TYPE: DNA

```
<213> ORGANISM: Unknown
<220> FEATURE:
<223> OTHER INFORMATION: Sequence listing for 58620.

<400> SEQUENCE: 283
acggttgaga acataggtat a                                              21

<210> SEQ ID NO 284
<211> LENGTH: 21
<212> TYPE: DNA
<213> ORGANISM: Unknown
<220> FEATURE:
<223> OTHER INFORMATION: Sequence listing for 58620.

<400> SEQUENCE: 284
acggcccaaa ccagataacc t                                              21

<210> SEQ ID NO 285
<211> LENGTH: 21
<212> TYPE: DNA
<213> ORGANISM: Unknown
<220> FEATURE:
<223> OTHER INFORMATION: Sequence listing for 58620.

<400> SEQUENCE: 285
acggaggcca ggttctcctt c                                              21

<210> SEQ ID NO 286
<211> LENGTH: 21
<212> TYPE: DNA
<213> ORGANISM: Unknown
<220> FEATURE:
<223> OTHER INFORMATION: Sequence listing for 58620.

<400> SEQUENCE: 286
acgaaaaaat ccagggctca g                                              21

<210> SEQ ID NO 287
<211> LENGTH: 21
<212> TYPE: DNA
<213> ORGANISM: Unknown
<220> FEATURE:
<223> OTHER INFORMATION: Sequence listing for 58620.

<400> SEQUENCE: 287
accttaacat gatcttgggc a                                              21

<210> SEQ ID NO 288
<211> LENGTH: 21
<212> TYPE: DNA
<213> ORGANISM: Unknown
<220> FEATURE:
<223> OTHER INFORMATION: Sequence listing for 58620.

<400> SEQUENCE: 288
acctggcctc cgtgctgaag c                                              21

<210> SEQ ID NO 289
<211> LENGTH: 21
<212> TYPE: DNA
<213> ORGANISM: Unknown
<220> FEATURE:
<223> OTHER INFORMATION: Sequence listing for 58620.

<400> SEQUENCE: 289
acctatgttc tcaaccgtct t                                              21
```

<210> SEQ ID NO 290
<211> LENGTH: 21
<212> TYPE: DNA
<213> ORGANISM: Unknown
<220> FEATURE:
<223> OTHER INFORMATION: Sequence listing for 58620.

<400> SEQUENCE: 290
accattttgc ttgaacagcc a                                              21

<210> SEQ ID NO 291
<211> LENGTH: 21
<212> TYPE: DNA
<213> ORGANISM: Unknown
<220> FEATURE:
<223> OTHER INFORMATION: Sequence listing for 58620.

<400> SEQUENCE: 291
acataggtat acttgcccca a                                              21

<210> SEQ ID NO 292
<211> LENGTH: 21
<212> TYPE: DNA
<213> ORGANISM: Unknown
<220> FEATURE:
<223> OTHER INFORMATION: Sequence listing for 58620.

<400> SEQUENCE: 292
acagatactg gcacagaatg g                                              21

<210> SEQ ID NO 293
<211> LENGTH: 21
<212> TYPE: DNA
<213> ORGANISM: Unknown
<220> FEATURE:
<223> OTHER INFORMATION: Sequence listing for 58620.

<400> SEQUENCE: 293
aatttcttaa aattggatat t                                              21

<210> SEQ ID NO 294
<211> LENGTH: 21
<212> TYPE: DNA
<213> ORGANISM: Unknown
<220> FEATURE:
<223> OTHER INFORMATION: Sequence listing for 58620.

<400> SEQUENCE: 294
aatctgctac catatgctat a                                              21

<210> SEQ ID NO 295
<211> LENGTH: 21
<212> TYPE: DNA
<213> ORGANISM: Unknown
<220> FEATURE:
<223> OTHER INFORMATION: Sequence listing for 58620.

<400> SEQUENCE: 295
aatatccaat tttaagaaat t                                              21

<210> SEQ ID NO 296
<211> LENGTH: 21
<212> TYPE: DNA
<213> ORGANISM: Unknown
<220> FEATURE:

```
<223> OTHER INFORMATION: Sequence listing for 58620.

<400> SEQUENCE: 296
aagttctggc ctgctttcca c                                              21

<210> SEQ ID NO 297
<211> LENGTH: 21
<212> TYPE: DNA
<213> ORGANISM: Unknown
<220> FEATURE:
<223> OTHER INFORMATION: Sequence listing for 58620.

<400> SEQUENCE: 297
aaggggaagg agaacctggc c                                              21

<210> SEQ ID NO 298
<211> LENGTH: 21
<212> TYPE: DNA
<213> ORGANISM: Unknown
<220> FEATURE:
<223> OTHER INFORMATION: Sequence listing for 58620.

<400> SEQUENCE: 298
aaggagaacc tggcctccgt g                                              21

<210> SEQ ID NO 299
<211> LENGTH: 21
<212> TYPE: DNA
<213> ORGANISM: Unknown
<220> FEATURE:
<223> OTHER INFORMATION: Sequence listing for 58620.

<400> SEQUENCE: 299
aagcaggcca gaactttggg g                                              21

<210> SEQ ID NO 300
<211> LENGTH: 21
<212> TYPE: DNA
<213> ORGANISM: Unknown
<220> FEATURE:
<223> OTHER INFORMATION: Sequence listing for 58620.

<400> SEQUENCE: 300
aagacggttg agaacatagg t                                              21

<210> SEQ ID NO 301
<211> LENGTH: 21
<212> TYPE: DNA
<213> ORGANISM: Unknown
<220> FEATURE:
<223> OTHER INFORMATION: Sequence listing for 58620.

<400> SEQUENCE: 301
aactttgggg caagtatacc t                                              21

<210> SEQ ID NO 302
<211> LENGTH: 21
<212> TYPE: DNA
<213> ORGANISM: Unknown
<220> FEATURE:
<223> OTHER INFORMATION: Sequence listing for 58620.

<400> SEQUENCE: 302
aacgaaaaaa tccagggctc a                                              21
```

```
<210> SEQ ID NO 303
<211> LENGTH: 21
<212> TYPE: DNA
<213> ORGANISM: Unknown
<220> FEATURE:
<223> OTHER INFORMATION: Sequence listing for 58620.

<400> SEQUENCE: 303
aacctggcct ccgtgctgaa g                                              21

<210> SEQ ID NO 304
<211> LENGTH: 21
<212> TYPE: DNA
<213> ORGANISM: Unknown
<220> FEATURE:
<223> OTHER INFORMATION: Sequence listing for 58620.

<400> SEQUENCE: 304
aaagttctgg cctgctttcc a                                              21

<210> SEQ ID NO 305
<211> LENGTH: 21
<212> TYPE: DNA
<213> ORGANISM: Unknown
<220> FEATURE:
<223> OTHER INFORMATION: Sequence listing for 58620.

<400> SEQUENCE: 305
aaagcaggcc agaactttgg g                                              21

<210> SEQ ID NO 306
<211> LENGTH: 21
<212> TYPE: DNA
<213> ORGANISM: Unknown
<220> FEATURE:
<223> OTHER INFORMATION: Sequence listing for 58620.

<400> SEQUENCE: 306
aaaatccagg gctcagggag g                                              21

<210> SEQ ID NO 307
<211> LENGTH: 21
<212> TYPE: DNA
<213> ORGANISM: Unknown
<220> FEATURE:
<223> OTHER INFORMATION: Sequence listing for 58620.

<400> SEQUENCE: 307
aaaaatccag gctcaggga g                                               21

<210> SEQ ID NO 308
<211> LENGTH: 21
<212> TYPE: DNA
<213> ORGANISM: Unknown
<220> FEATURE:
<223> OTHER INFORMATION: Sequence listing for 58620.

<400> SEQUENCE: 308
aaaaaatcca gggctcaggg a                                              21

<210> SEQ ID NO 309
<211> LENGTH: 201
<212> TYPE: DNA
<213> ORGANISM: Canola

<400> SEQUENCE: 309
```

```
tgaatggctg aacgccagct ctatacgact actatagggA aagctggtac gcctgcaggt    60
accggtccgg aattcccggg tcgacccacg cgtccgaggg ggaagtggta ccggaagcct   120
ttcccggttg caaggtttgg gtcgtgctgc tcgacgacac ttgtctgcga ttcttgatga   180
gttttgggga catttatatg a                                             201

<210> SEQ ID NO 310
<211> LENGTH: 201
<212> TYPE: DNA
<213> ORGANISM: Canola

<400> SEQUENCE: 310
gatgagtttt ggggacattt atatgatttt catgggcaat tagttgctga agccagggca    60
aagaaactag accagttgtt tggcgctgat caaaagtcac cctctcctgt gaaagtggat   120
tcttttgtaa gggacaacac tagcagtgga tattgcatgt caccaacaac aaagggattg   180
gaatcacaga tgaattcgag t                                             201

<210> SEQ ID NO 311
<211> LENGTH: 201
<212> TYPE: DNA
<213> ORGANISM: Canola

<400> SEQUENCE: 311
gattggaatc acagatgaat tcgagtttgt atgattcact gaagcagcag aggacacctg    60
gaagtatcga ttctttatat ggactacaaa gaggttcatc accgtcatca tcaccgttgg   120
tcaaccgtat gcagatgttg actgcatatg gtaacactcc caataataat aatgcttatg   180
aattgagtga aagaagatac t                                             201

<210> SEQ ID NO 312
<211> LENGTH: 201
<212> TYPE: DNA
<213> ORGANISM: Canola

<400> SEQUENCE: 312
ttatgaattg agtgaaagaa gatactccag cctgcgtgct ccatcgtcct cagagtctcg    60
ggaacaccaa caaccagcta caattcatgg ataccagatt aagtcctacg ttgacaattt   120
ggcaaaagaa aggcttgaag ctttacagtc ccgtggagag atcccaacat ctcgatctat   180
ggccctgggt tctttgagct a                                             201

<210> SEQ ID NO 313
<211> LENGTH: 201
<212> TYPE: DNA
<213> ORGANISM: Canola

<400> SEQUENCE: 313
tctatggccc tgggttcttt gagctacaca cagcaactgg ctttagcctt gaaacagaag    60
tcccagaatg gtctaacccc tggaccagct cctgggtttg agaactttgc tgggtctaga   120
aacgtatcgc gacaatccga agatcttac tacggtgttc catcttctgg aaacaccgat   180
tctgtaaacg cagtagttgc t                                             201

<210> SEQ ID NO 314
<211> LENGTH: 201
<212> TYPE: DNA
<213> ORGANISM: Canola

<400> SEQUENCE: 314
```

-continued

```
ccgattctgt aaacgcagta gttgctaatg agaagaagta tagtagcatg ccagatatat    60
ctggattgtc tatgtcaccg ggcatcctgc cttcgccaaa caacaagagt gggtactggg   120
atgcatcaac tggaggagga ggagcagggt atagcgcttc ttcgtatggt cggttaagca   180
atgaatcatc atcattatat t                                             201
```

<210> SEQ ID NO 315
<211> LENGTH: 201
<212> TYPE: DNA
<213> ORGANISM: Canola

<400> SEQUENCE: 315

```
aagcaatgaa tcatcatcat tatattctaa tttggggtca agggttggag tagcctcagg    60
ttatgaaacc atgtctcagt caagaggagg ctacagagat gcatatacgt tgccacagag   120
tgcaacaaca gggactggat cgctttggtc cagacagccc tttgagcagt ttggtgtagc   180
ggagaggaac ggcgctgttg g                                             201
```

<210> SEQ ID NO 316
<211> LENGTH: 201
<212> TYPE: DNA
<213> ORGANISM: Canola

<400> SEQUENCE: 316

```
gtagcggaga ggaacggcgc tgttggtgag gaagtcagga atagatcagc tccgataaat    60
atagacaaca acaacaacgc ttctaccgtc gatgcagagg ctaagcttct tcagtcgttc   120
aggaactgta tactgaagct tattaaactg gaaggatcgg aatggttgtt tgggcaaagc   180
gatggagtcg atgaagaact g                                             201
```

<210> SEQ ID NO 317
<211> LENGTH: 201
<212> TYPE: DNA
<213> ORGANISM: Corn

<400> SEQUENCE: 317

```
atggatgcac cggatgttca acagagcatg ggatataagg agtccagggg tggtatgcct    60 aagttttttcc atgcccttgg accagcactc ctgatttcaa tgggttacat tgatctcggg   120
aagtgggtgg cagccgttga agctggttct tgttttggat tcgacctggt gttgctggct   180
ctccttttca atttcactgc c                                             201
```

<210> SEQ ID NO 318
<211> LENGTH: 201
<212> TYPE: DNA
<213> ORGANISM: Corn

<400> SEQUENCE: 318

```
tggctctcct tttcaatttc actgccattg tatgtcagta ccttgctgct tgcattggca    60
ctgtcacagg gaagaatctt gcagagatat gccaccaaga gtacaaccag ccaacatgta   120
tattccttgg tgttcaagct ggattgtctt tgttgacgtc agagctgact atgattttttg   180 gcatagcact cggattcaac c                                             201
```

<210> SEQ ID NO 319
<211> LENGTH: 201
<212> TYPE: DNA
<213> ORGANISM: Corn

```
<400> SEQUENCE: 319
ttttggcata gcactcggat tcaacctcct gtttgaatat gatgatctca tcacagggat    60
atgctttgca acagtggtac ctaatctgct accatatgct atatcccacc tgggaaagaa   120
gatggaaggg acaataaatg cctgcatagc aggatttgca cttcttagtt atgtgcttgg   180
cttattggtt agccagccac a                                             201

<210> SEQ ID NO 320
<211> LENGTH: 201
<212> TYPE: DNA
<213> ORGANISM: Corn

<400> SEQUENCE: 320
cttggcttat tggttagcca gccacaaatt cctctcacga tgaatgtaat attccccaag    60
atcagtggtg agagtgctta ctctctgatg gcgcttcttg gtgcaaacat aatggcacac   120
aacttctaca ttcattcatc agttgtccag ggtcagaaaa agtcatctgc agttggtctt   180
ggagccttat ttcacgacca c                                             201

<210> SEQ ID NO 321
<211> LENGTH: 201
<212> TYPE: DNA
<213> ORGANISM: Corn

<400> SEQUENCE: 321
gtcttggagc cttatttcac gaccaccttt tttcaatatt gttcattttt actggaatct    60
ttatggtgaa ctatgttcta atgaactctg cagcagcgga atctactaat actcttctca   120
ttaccttcca agatgttgta gagctaatga atcagatatt tgtaaaccct ctggcaccaa   180
ctatattttt agtggttctt c                                             201

<210> SEQ ID NO 322
<211> LENGTH: 201
<212> TYPE: DNA
<213> ORGANISM: Corn

<400> SEQUENCE: 322
accaactata tttttagtgg ttcttctctt ctccagccac atcatctcgc tgacatctgc    60
tatcggtagc caagtgattt cacaccattt attcggtata aaccttcctc tttctggaca   120
tcgtctccta ctgaaggttt tgccatagt tcctactctg tactgggcga aagttgcagg   180
agctgaaggg atataccaat t                                             201

<210> SEQ ID NO 323
<211> LENGTH: 201
<212> TYPE: DNA
<213> ORGANISM: Corn

<400> SEQUENCE: 323
gcaggagctg aagggatata ccaattatta attatatgcc agattattca agccatgctt    60
cttccatctt cagtcgtccc acttttcgt gttgcttcat caagatcaat aatgggagcc   120
catagagtgt ctttgcatct ggagatactg gttttcttg catttctcct tatgctattt   180
tcaaatatca tatttgtggc a                                             201

<210> SEQ ID NO 324
<211> LENGTH: 201
<212> TYPE: DNA
<213> ORGANISM: Corn
```

<400> SEQUENCE: 324

```
tattttcaaa tatcatattt gtggcagaaa tgctatttgg cgacagtggg tggatgaaca      60
atctgaaagg atatactgga agccctgtgg tgctcccata taccgtttta gttttagttg     120
cacttatatc tgtggctttt tcactgtacc tggctgttac accattgaga tctggaagtc     180
atgaagctga atcccatgaa t                                               201
```

<210> SEQ ID NO 325
<211> LENGTH: 201
<212> TYPE: DNA
<213> ORGANISM: Corn

<400> SEQUENCE: 325

```
aagtcatgaa gctgaatccc atgaatggtc tgtgcattct cagagagaac tcttgaatac      60
ttctcaagaa agggaagatg ttaaggtgga caatgttaca tatgaggaag atcaaagatc     120
agatgttgtc ccttctccca gggatgtgcc tgacagccat ccggaactgg ccttggacta     180
tattgatact tctgacactg c                                               201
```

<210> SEQ ID NO 326
<211> LENGTH: 201
<212> TYPE: DNA
<213> ORGANISM: Corn

<400> SEQUENCE: 326

```
gactatattg atacttctga cactgctgta gaatctgatc acgactctca acaatctact      60
gcttatgcat ccactgctcc tgaaacctgc tcctccccgt cgtttactcg cgaggagtca     120
aaatcagttg ttgcagtcaa ctggccggag cctttggaga aggttcctac ttctactgtg     180
atggaggaaa gcacagtaga a                                               201
```

<210> SEQ ID NO 327
<211> LENGTH: 201
<212> TYPE: DNA
<213> ORGANISM: Corn

<400> SEQUENCE: 327

```
ctgtgatgga ggaaagcaca gtagaaaatg tggtctctag gatcacgact gaaagagatg      60
ttttagtaga aacagatgtt gtctcgggca aggataagga agatatccgt actttggagt     120
ctgagaagtc aattgttgat agcacccat atgtgtctga tgacggtccg ccatcccta      180
ctttcagcag gggaaagggc t                                               201
```

<210> SEQ ID NO 328
<211> LENGTH: 201
<212> TYPE: DNA
<213> ORGANISM: Corn

<400> SEQUENCE: 328

```
ccttactttc agcaggggaa agggctcaga tgcaggaaat ggcagtggta gtctctcaag      60
gttatctggt ttgggccgtg cagcaaggag acagctagct gctactcttg atgagttctg     120
ggggcatctg tttgattacc atggtaagct cactcaagaa gctagcacca aaaagtttgg     180
tatcttgctt gggatagacc t                                               201
```

<210> SEQ ID NO 329
<211> LENGTH: 201
<212> TYPE: DNA

<213> ORGANISM: Corn

<400> SEQUENCE: 329

```
tttggtatct tgcttgggat agaccttaga acacctagca catctgtaag aacggataaa    60
caagctgctg aaatacttaa gagcccactg gtgagagact caatgcgggg ggcagctttt   120
ttgtcaagct cagtggacat gatgtcccct aagaatgaaa cgtcgaattt ggaacttgca   180
tatgggcttc agagggacc t                                              201
```

<210> SEQ ID NO 330
<211> LENGTH: 201
<212> TYPE: DNA
<213> ORGANISM: Corn

<400> SEQUENCE: 330

```
ttgcatatgg gcttcagagg ggacctggca tgggattgtc aagctggtct cagggtatgc    60
agctaccaaa tacacagctg cagagctcaa gcaatagcct acttgagcag agtgcaagat   120
taaactcaaa ttttagttca tcttattcag acaacaatca gttctaccaa cctgcaacaa   180
ttcatggata ccagctcaca t                                             201
```

<210> SEQ ID NO 331
<211> LENGTH: 201
<212> TYPE: DNA
<213> ORGANISM: Corn

<400> SEQUENCE: 331

```
aacaattcat ggataccagc tcacatctta cctgaaacag atgaatgcca gcccaagcct    60
ttactctagc atgccgctgg acccacaacg gcttccaaaa tcatctgtgt ctgctgtgcc   120
aaactatgct gattccatga tgcatgctcg taatcataac ctgcttgctt cactgggtgg   180
tactactaca cagcttcctg c                                             201
```

<210> SEQ ID NO 332
<211> LENGTH: 201
<212> TYPE: DNA
<213> ORGANISM: Corn

<400> SEQUENCE: 332

```
ggtggtacta ctacacagct tcctgcaaca tcccgcgtag gctcaatgat gcctgaaaga    60
tcgtattatg atccttccag cgttgatggg aatgaaaacg ctggttcacc tgcttactca   120
aaaaagtacc acagctcacc tgatatgtct ggaataatcg ctgcaagtag agctgcactc   180
ttgaatgaag caaagttggg t                                             201
```

<210> SEQ ID NO 333
<211> LENGTH: 201
<212> TYPE: DNA
<213> ORGANISM: Corn

<400> SEQUENCE: 333

```
cactcttgaa tgaagcaaag ttgggtgctg ccattggacc acagtcatac ctcagcaggc    60
tggcggcaga aagatctcaa tatgcaagct caacagccag gccgcggct ccattagcat   120
ttgacgagct ttcacctcct aagctccaga gtgatatctt ctcggcgcag tcaagcatga   180
gaccaagtgc tagatccctt t                                             201
```

<210> SEQ ID NO 334
<211> LENGTH: 201

<212> TYPE: DNA
<213> ORGANISM: Corn

<400> SEQUENCE: 334

```
catgagacca agtgctagat ccctttgggc taagcaacca tttgagcaat tgttcggcat      60
gtcaagtgca gagctcagta aaggtgactt caatcttcca ggcagatcag gtggcgtggc     120
caaggatgat ttctcttata aggaatctga gacgaagctt cttcagtccc tcaggctctg     180
catcatgaag ctccttaagc t                                               201
```

<210> SEQ ID NO 335
<211> LENGTH: 201
<212> TYPE: DNA
<213> ORGANISM: Corn

<400> SEQUENCE: 335

```
ctctgcatca tgaagctcct taagctagag ggatcagggt ggctgttcaa gcaaaatggt      60
ggttgtgatg aagatctaat cgaccgagtc gctgcagccg agaagctatt gatgcaaggg     120
actgccgaga atcaactgct gcttcatggt ggtgatctcc agcaacattc ttccgaccag     180
gccggcatcc agtacatgcg c                                               201
```

<210> SEQ ID NO 336
<211> LENGTH: 201
<212> TYPE: DNA
<213> ORGANISM: Corn

<400> SEQUENCE: 336

```
accaggccgg catccagtac atgcgcacgc ttcccaactg cggggaggac tgtgtttggc      60
gcgcgtcact cgtcgttagt ttcggtgtct ggtgtgtccg ccgagtgctg acatgtctc     120
tggtggaaag caggccagaa ctttggggca agtataccta tgtccttaac cgtcttcagg     180
ggatcttgga ccctgcgttc t                                               201
```

<210> SEQ ID NO 337
<211> LENGTH: 201
<212> TYPE: DNA
<213> ORGANISM: Corn

<400> SEQUENCE: 337

```
tcagggatc ttggaccctg cgttctccaa gcctcgggt gctctgacaa tatgcacctg       60
ccttcagaaa gacaccagag tgcgcaatag cccaccccac agtgggctaa cagccatggg    120
cccggtcccc acaccgatcc ggggcgcctt cacgaccgca ggcgtggttc tggagatgat    180
caaggacgtg gaggctgcgg t                                               201
```

<210> SEQ ID NO 338
<211> LENGTH: 201
<212> TYPE: DNA
<213> ORGANISM: Corn

<400> SEQUENCE: 338

```
atgatcaagg acgtggaggc tgcggtctca ggccgcaagg gcaggagcgg cacggcggcg      60
ggcgacgtcg ccttccccaa ggggaaggag aacctggcct ccgtgctgaa gcggtacaag    120
cggcggctcg ccagcaaggg ccagtagcgc gcgggtgtca gacaggcagg cgatcgcaag    180
caatgttagg aggagcctga c                                               201
```

<210> SEQ ID NO 339

```
<211> LENGTH: 201
<212> TYPE: DNA
<213> ORGANISM: Corn

<400> SEQUENCE: 339
gcaagcaatg ttaggaggag cctgactatt gttctccagg ggggctgcca ctggcgccgg    60
cctccctgag ccctggattt tttcgttgca cgacgttcct agggaccggt ggttgcccga   120
tggtcgtctt ggtcccttcc agcaggtttt tttttccttt ccctctttct gttggtttct   180
ttttgttggc tttgtgatgt t                                             201

<210> SEQ ID NO 340
<211> LENGTH: 201
<212> TYPE: DNA
<213> ORGANISM: Corn

<400> SEQUENCE: 340 tttcttttg ttggctttgt gatgttttgt aagggcaac tagggtatgt gctcagaagg      60
actcaagatg tacacgcgaa gatgtactag tctgctgatg cagcgttgta aagtccacac   120
tctgcaggtt aacccttttt ggggccgtca agtgttagtg cgtgccctat gtatgttaat   180 caccctgca gagaggttgc g                                              201

<210> SEQ ID NO 341
<211> LENGTH: 201
<212> TYPE: DNA
<213> ORGANISM: Corn

<400> SEQUENCE: 341
tagtttatcc gacctttaac atttctgaat ttaaaccggc aaattaaccc agacgaacag    60
atgacaagaa tttcaaaaaa aaaaaaaaaa gcgtaagcac cacagttctt gaaatcagga   120
ctggtccaca aaacccactc ttgccacccc gtgacagcag gaaacagtac acagtagcgc   180
ataaccttcc aagaaaattt a                                             201

<210> SEQ ID NO 342
<211> LENGTH: 201
<212> TYPE: DNA
<213> ORGANISM: Corn

<400> SEQUENCE: 342
agcgcataac cttccaagaa aatttaatta ataaacccga agaagccaag agggaaggga    60 aaaaaaaga aagaaaaaaa actgacacat aagaaaagag cagcgagcaa gctgaaggtg    120
aaagccacag cagctcgtcc ccttccccccc acttcttcct cagataagga gaggcccag   180 gccagagaaa aaagcatcga a                                             201

<210> SEQ ID NO 343
<211> LENGTH: 201
<212> TYPE: DNA
<213> ORGANISM: Corn

<400> SEQUENCE: 343
cccaggccag agaaaaaagc atcgaatttc ccccgttaa ttggcctgag ccctcagccg     60
tctaccagca gcagctagag gtacgattct cgcattgctt gctccctgcg cctgccctcg   120 attttttgctg ttttttcgag ctcctcttcc agttcttttg ccgtgttgga accgcatcta   180
tgcagcctag cgcggggtac t                                             201
```

<210> SEQ ID NO 344
<211> LENGTH: 201
<212> TYPE: DNA
<213> ORGANISM: Corn

<400> SEQUENCE: 344

| | | | | | |
|---|---|---|---|---|---|
| atctatgcag | cctagcgcgg | ggtactagcg | tgattcggtc | agtggatccc | gtcgggctgc | 60 |
| tgcttcctcg | cggctgattt | gcgagaggaa | gcaggtcccc | gggaagcgat | ctcattttc | 120 |
| gttatttttt | tagctcccta | caccaaagac | cagagtcaga | tccgaggcta | cccgccgccc | 180 |
| cggcaaggat | tttacccggc | c | | | | 201 |

<210> SEQ ID NO 345
<211> LENGTH: 201
<212> TYPE: DNA
<213> ORGANISM: Corn

<400> SEQUENCE: 345

| | | | | | |
|---|---|---|---|---|---|
| cgccccggca | aggattttac | ccggccggag | ctctgcaaca | tcggtgggat | cgatggctgc | 60 |
| gacctccacg | agctccggtg | cccacgaatc | gaagtcagca | gcgccgtgtg | gactgagtca | 120 |
| cgtgcctggt | tcgccgtcct | gtccgacgct | tctcacctcg | agagcccgtc | gctgttgcct | 180 |
| cggactcgag | ggagctggcg | g | | | | 201 |

<210> SEQ ID NO 346
<211> LENGTH: 201
<212> TYPE: DNA
<213> ORGANISM: Corn

<400> SEQUENCE: 346

| | | | | | |
|---|---|---|---|---|---|
| tgcctcggac | tcgagggagc | tggcggcgca | aacgccgtgc | ggccaaaatc | gagatcccca | 60 |
| ccatccgaat | cgaggtcctc | tctaccagaa | tcagttcccg | ccgccgcgtc | gaggtagctg | 120 |
| tcacccaaat | tgagctttcc | gtcgctgctg | gatgtgttgg | aatcggaagc | ttcgggcgca | 180 |
| tagcttgagc | tcgctcaagt | g | | | | 201 |

<210> SEQ ID NO 347
<211> LENGTH: 201
<212> TYPE: DNA
<213> ORGANISM: Corn

<400> SEQUENCE: 347

| | | | | | |
|---|---|---|---|---|---|
| gcgcatagct | tgagctcgct | caagtgtatc | gagcaagcaa | accaagcgtt | gggggtcttg | 60 |
| cttttgcgcct | ttgccgcgct | agcttagcct | atctatccgt | gctaggaatc | ccctcccctt | 120 |
| tcggtgtgat | gttttgact | tgccactgcc | tggtgttgct | ggggctgctt | ttctcttctc | 180 |
| ctttggggct | ctgaatgaag | a | | | | 201 |

<210> SEQ ID NO 348
<211> LENGTH: 201
<212> TYPE: DNA
<213> ORGANISM: Corn

<400> SEQUENCE: 348

| | | | | | |
|---|---|---|---|---|---|
| ttctcctttg | gggctctgaa | tgaagactga | agaaatcgaa | agagaggaaa | gctacgcctg | 60 |
| agtcggggaa | cgcctacgaa | gtaagttttg | gcttaaaggt | ggaagctttt | gaggtttctc | 120 |
| cttgcgaaat | aaatgctttt | ttcgatgtta | tttgatggat | ttggttggta | ctcggtcaaa | 180 |
| aggtgttctt | ggtttgccct | t | | | | 201 |

<210> SEQ ID NO 349
<211> LENGTH: 201
<212> TYPE: DNA
<213> ORGANISM: Corn

<400> SEQUENCE: 349

```
tcaaaaggtg ttcttggttt gcccttcta tgctctggct gctgttgcaa ctgcaacttc      60
cctttccctt agagtttggc gctctaaaag ttggttcact ttgcacgaag gatttctgtt    120
tcttgttgct gattgggttg tttggatcta tctgcaggca gacaagctag gttttactgc   180
ttcattgagc acaaagatcc g                                              201
```

<210> SEQ ID NO 350
<211> LENGTH: 201
<212> TYPE: DNA
<213> ORGANISM: Corn

<400> SEQUENCE: 350

```
actgcttcat tgagcacaaa gatccgctga cctcttgctc ttggtaaaaa tccaaccttt     60
cttgtattgt ttcttcctg ggaaaacctc cttgtggtgc ataaacttcg tagtacactc   120
tgccatttct ggagaggaag ctgagaacta ctatccatat ctggcacgac ccttgtcaag   180
aaccatggct gttcacatgc c                                              201
```

<210> SEQ ID NO 351
<211> LENGTH: 201
<212> TYPE: DNA
<213> ORGANISM: Corn

<400> SEQUENCE: 351

```
tcaagaacca tggctgttca catgccatga agctgcttga actggaggca cctaaatgct     60
gtggattgtt cctatgcaga tgattggatc agtggtttca ggcttcgggg ggttcgatca   120
gatgttgtat gaataatagc aggattgctt gagagactat agtttgggta ctgtttgctt   180
ctgtatttac tggtacggtt t                                              201
```

<210> SEQ ID NO 352
<211> LENGTH: 201
<212> TYPE: DNA
<213> ORGANISM: Cucumber

<400> SEQUENCE: 352

```
atggaatcta cgacattgcg tacaactcat cagtccgctg ctattcatag gtttataccct    60 ttcattgcac ctgcactcct ggtttcaatt agttatgttg accctggaaa gtgggcagca   120
actgttgaag gaggtgctcg gtttggcttt gatttgcttg tgctagtgct tcttttcaat   180
cttgctgcta ttttatgcca g                                              201
```

<210> SEQ ID NO 353
<211> LENGTH: 201
<212> TYPE: DNA
<213> ORGANISM: Cucumber

<400> SEQUENCE: 353

```
tcaatcttgc tgctattta tgccagtatc tctcagctag cattggtgta gtcaccggaa      60
gaggtcttgc ccagatatgc agcgaggagt atgataagtg tacatgtttc ttcctgggaa   120
tccaagcaga ggcttctgtg attctgttag accttaacat gatcttgggc atttcacatg   180
gacttaatct tctacttggg t                                              201
```

<210> SEQ ID NO 354
<211> LENGTH: 201
<212> TYPE: DNA
<213> ORGANISM: Cucumber

<400> SEQUENCE: 354

```
acatggactt aatcttctac ttgggtggga cctcttcaca tgtgtccttt tgacgggtgt    60
tgctgctgct ttatttcctc cttttgctga ccttcaggaa gatggcaggg caaagttcct   120
gtatatatgt atggcgggat ttgtactgct ctctttggtt cttggagtat taatcagtca   180
acctgaaatc ccactttcca t                                             201
```

<210> SEQ ID NO 355
<211> LENGTH: 201
<212> TYPE: DNA
<213> ORGANISM: Cucumber

<400> SEQUENCE: 355

```
agtcaacctg aaatcccact ttccatgaat ctcatgccga caaggttaaa cggggaaagt    60
gcctttactc ttatgagtct tcttggagca agtgtcatgc ctcacaattt ttatgtgcat   120
tcttctattg tgcagcagca ccagagtcca cccaatattt ccaaagaagt tttgtgttac   180
aatcatttgt ttgctatttt c                                             201
```

<210> SEQ ID NO 356
<211> LENGTH: 201
<212> TYPE: DNA
<213> ORGANISM: Cucumber

<400> SEQUENCE: 356

```
gttacaatca tttgtttgct attttctgca tattcagtgg aatctatgtg gtgaataacg    60
ttctcatgaa ctcagctgca aatgtattct atagcagtgg ccttgctttg cacacctttc   120
cagatgcatt atctttagtg gagcaggtat ttgggagctc agtggtatat gttctcttct   180
tactcgttct gtttctatca a                                             201
```

<210> SEQ ID NO 357
<211> LENGTH: 201
<212> TYPE: DNA
<213> ORGANISM: Cucumber

<400> SEQUENCE: 357

```
cttcttactc gttctgtttc tatcaaatca aatcacagct ctcacatgga gtcttggtgg    60
tcaacttgtc ctgaccaatt tcttaaaatt ggatattcct ggttggctcc attgtgctac   120
aattaggatt attgccatta ttccagcgct ctgctgtgtc tggagttcag gcgctgaagg   180
gatgtatcaa cttcttatat t                                             201
```

<210> SEQ ID NO 358
<211> LENGTH: 201
<212> TYPE: DNA
<213> ORGANISM: Cucumber

<400> SEQUENCE: 358

```
gaagggatgt atcaacttct tatatttcct caggttatgg tagctctatt gcttccatct    60
tctgtgattc ccctctatcg tgttgcttca tcaagaacaa taatgggtgc cttcaaaata   120
tcgcagcttg tggaatttat agcaattggt atctttattg gaatattagg actgaaaatt   180
```

```
atatttgttg tagagatgat t                                              201
```

<210> SEQ ID NO 359
<211> LENGTH: 201
<212> TYPE: DNA
<213> ORGANISM: Cucumber

<400> SEQUENCE: 359

```
aaattatatt tgttgtagag atgattttg gtaacagtga ttgggtagtt aatttgaggt      60
ggaacatggg gagtggtatg tcaatcccat ttgtggttct ccttattact gcttgttcat   120
cgttttgtct gatgctatgg ttggcagcta ctccattaaa atctgctact actattgccc   180
aattagatgc tgaagtattg a                                              201
```

<210> SEQ ID NO 360
<211> LENGTH: 201
<212> TYPE: DNA
<213> ORGANISM: Cucumber

<400> SEQUENCE: 360

```
tgcccaatta gatgctgaag tattgaactg ggatatgcca gaagttatac ctgattcatc    60
tgaagagagg gaaaacatag atttggggaa aagttcaaac agtgccgaac ctatagaaag   120
tcattctgac ctatctacaa caaagtttga ttttaatttg cctgaaaata ttatggaacc   180
tgatcaggtt cttggttcag t                                              201
```

<210> SEQ ID NO 361
<211> LENGTH: 201
<212> TYPE: DNA
<213> ORGANISM: Cucumber

<400> SEQUENCE: 361

```
gaacctgatc aggttcttgg ttcagttaat caaaacgaga atcgatctag tggtgtagtt    60
ccaagctccc caaatatgt acaagaggaa cttgaatcca ctgaggagtt agtctcatcc    120
tcaactgtga ctcgcgatgt tcctgattca acattggctg acaaaaaggt cttaaaaata   180
gagccagtgg agcccgttga a                                              201
```

<210> SEQ ID NO 362
<211> LENGTH: 201
<212> TYPE: DNA
<213> ORGANISM: Cucumber

<400> SEQUENCE: 362

```
aaatagagcc agtggagccc gttgaaaaga ctgttggact cgatggtgat ttgcgttctg    60
agaaggatga ttatgaggtt gataactggg aggctgaaga gtcaatgaaa gagatttctg   120
ggaatatacc atcctcaaca tctgagggtc ctggttcttt tagaagtatt ggtgggaaaa   180
gcgaagaagg tgggaatggc a                                              201
```

<210> SEQ ID NO 363
<211> LENGTH: 201
<212> TYPE: DNA
<213> ORGANISM: Cucumber

<400> SEQUENCE: 363

```
gaaaagcgaa gaaggtggga atggcactgg tagtctttca aggttagctg gccttgggcg    60
tgctgcaagg cgccaactta ctggaatact tgatgaattt tggggacaat tgtatgattt   120
ccatggggtg gctactcaag atgcaaaggt taagaaacta gatttgttgc tgggtattac   180
```

```
ctctctgaaa ttggatgctg t                                              201
```

<210> SEQ ID NO 364
<211> LENGTH: 201
<212> TYPE: DNA
<213> ORGANISM: Cucumber

<400> SEQUENCE: 364

```
attacctctc tgaaattgga tgctgttggt aaagattttc ctcactcatc acctcttgga     60
tgcaaaacat ctgatccaat ttcttccagt ttgtacgact cccccaagag tcagagggta    120
caaagtgggt tagaaccacc ctatgggata caaaagggga accaaccatt gtggtctaac    180
cacatgcagc tttgggatgc g                                              201
```

<210> SEQ ID NO 365
<211> LENGTH: 201
<212> TYPE: DNA
<213> ORGANISM: Cucumber

<400> SEQUENCE: 365

```
ctaaccacat gcagctttgg gatgcgtatg tgaataattc tagccataat gctctggact     60
ctggagtgaa gcgatattct agtttgcgca gtttgccgtc tactgagagt tgggattatc    120
agcctgccac agtccatggc tatcagctaa cttacctgag tagaatggca aaggacagaa    180
gttctggtaa ttcgaatggt c                                              201
```

<210> SEQ ID NO 366
<211> LENGTH: 201
<212> TYPE: DNA
<213> ORGANISM: Cucumber

<400> SEQUENCE: 366

```
cagaagttct ggtaattcga atggtcagtt ggattcgtca ggctctaaat atcatacctt     60
gggtggtggt ggtgcaggct tgcgagactc agttgcattt gcaatggggc aaaagttgca    120
aaatggctta ggtgcttgtc agcaggctgc tcccccagga ttttccaaca tcaaagtatc    180
caggaaacct tcttccgaat c                                              201
```

<210> SEQ ID NO 367
<211> LENGTH: 201
<212> TYPE: DNA
<213> ORGANISM: Cucumber

<400> SEQUENCE: 367

```
gtatccagga aaccttcttc cgaatctgaa aggcaatatt atgatctttc tccttctgga     60
actggtgaga atttagtgag tgtatctaac acaaagaaat accatagctt gccggatatt    120
caccgtgatc agcacacatc agataagagt tctcagtggg ataatgcaac tgtttatgga    180
acatcaattg gtaaaataac a                                              201
```

<210> SEQ ID NO 368
<211> LENGTH: 201
<212> TYPE: DNA
<213> ORGANISM: Cucumber

<400> SEQUENCE: 368

```
atggaacatc aattggtaaa ataacagctc gtggagtgtc ctttgcaaat tctggatcaa     60
gatcagtcgc tcctttagca tttgatgaac tatctcctgc aaatgtctac agtggtgcat    120
```

```
tatcaccaca aatgaatcct catttggatt ctggatcttt ctggcataga cagccttctg      180
agcaatttgg cttggataaa a                                                201

<210> SEQ ID NO 369
<211> LENGTH: 201
<212> TYPE: DNA
<213> ORGANISM: Cucumber

<400> SEQUENCE: 369
ttctgagcaa tttggcttgg ataaaaatag caactccgag agtaaaggaa ttgggaggct      60
gcattcaatt agtcaagaag cttctttcgt tgttaattca gaggccaggc ttctccagtc    120
cttcagagac tgcattgtca aacttcttaa attggaagga tcagactggt tatttgggca    180
aagtgatggt actgacgagg a                                              201

<210> SEQ ID NO 370
<211> LENGTH: 201
<212> TYPE: DNA
<213> ORGANISM: Cucumber

<400> SEQUENCE: 370
gggcaaagtg atggtactga cgaggaacta attgactgtg tagctgccag ggagaaattt      60
ctttatgaag ctgaggcaag ggagatgggt cgggtggtcc gtatgaaaga atctccttca    120
ttttctcctg ataggagacc aggttctgga atgaagaacg atacaaattt ctccaatgtt    180
tctatatcct ctgtacctca t                                              201

<210> SEQ ID NO 371
<211> LENGTH: 201
<212> TYPE: DNA
<213> ORGANISM: Cucumber

<400> SEQUENCE: 371
atgtttctat atcctctgta cctcattgtg gagaaggttg tatttggaga tcagatctga      60
ttgtaagttt tggtgtatgg tgcattcacc gaattctgga tctctcactt atggaaagtc    120
ggcctgaact gtggggaaaa tatacctatg tactcaatcg tcttcagggt attatcgatc    180
ctgcattttc gaagcctcgt g                                              201

<210> SEQ ID NO 372
<211> LENGTH: 201
<212> TYPE: DNA
<213> ORGANISM: Cucumber

<400> SEQUENCE: 372
cgatcctgca ttttcgaagc ctcgtgtacc aatgccgcca tgcttctgcc ttcaaattcc      60
ccaagcattc cagcagaggt caagcccaca aattgcaaac ggaatgttgc ctcctgctgc    120
aaaacctggc aagggaaaat gcaccactgc ggcaatgctt ctggatatgg tcaaggatgt    180
ggagatagcc atctcttgcc g                                              201

<210> SEQ ID NO 373
<211> LENGTH: 201
<212> TYPE: DNA
<213> ORGANISM: Cucumber

<400> SEQUENCE: 373
gatgtggaga tagccatctc ttgccgaaaa ggccgaactg gtacagctgc cggtgacgta      60
gctttcccaa aggggaagga gaacttggct tcagtcctca aacgctacaa gcgtcgatta    120
```
tccaataaac cagttgccac tcacgaagta tcatctatct cacgcaagct ttcagcaaca    180
tccgttcctt atagctcata g                                              201

<210> SEQ ID NO 374
<211> LENGTH: 201
<212> TYPE: DNA
<213> ORGANISM: Cucumber

<400> SEQUENCE: 374
caacatccgt tccttatagc tcatagtatt tacccaaaaa tggtgatcaa atcacccagc    60
tgtttaattt tggaaagcag ctcatggttc ggaacgagat gccctcatct tggtctttac    120
tctctctctc aaaacattat caaggctctt tgctgcgaat tttcttctca catgttaaaa    180
atgattagga tgtgactcaa t                                              201

<210> SEQ ID NO 375
<211> LENGTH: 201
<212> TYPE: DNA
<213> ORGANISM: Cucumber

<400> SEQUENCE: 375
taaaaatgat taggatgtga ctcaatggac ccttagttgc agcaaaactc aggaaactgg    60
tgcaaaccca agttgattg ttatggtggt tgcactagtt acttgtatca agtaattgc     120 tggaggagag atcacaaggt gactttgaaa agttcaaaaa aaaaaaatg ttagtatata    180 gcagacagag gctaatgtgc t                                              201

<210> SEQ ID NO 376
<211> LENGTH: 201
<212> TYPE: DNA
<213> ORGANISM: Cucumber

<400> SEQUENCE: 376
atggaatcta cgacattgca tacaactcat cagtcgggtg ctattcatag gtttatacct    60
ttcattgcac ctgcacttct agtttcaatt agttatgttg accctggaaa gtgggctgca    120
actgttgaag gaggtgctcg gtttggcttt gatttgtttg tgttagtgct tcttttcaat    180
cttgctgcta ttttatgcca g                                              201

<210> SEQ ID NO 377
<211> LENGTH: 201
<212> TYPE: DNA
<213> ORGANISM: Cucumber

<400> SEQUENCE: 377
tcaatcttgc tgctatttta tgccagtatc tctcagctag cattggtgtg gtcactggaa    60
gaggtcttgc ccagatatgc aacgaggagt atgataagtg tacatgtttc ttcctgggaa    120
tccaagcaga ggcttctgtg attctgttag accttaacat gatcttgggc atttcaaatg    180
gacttaatct tctacttggg t                                              201

<210> SEQ ID NO 378
<211> LENGTH: 201
<212> TYPE: DNA
<213> ORGANISM: Cucumber

<400> SEQUENCE: 378
aaatggactt aatcttctac ttgggtggga cctcttcaca tgtgtccttt tgacgggtgt    60

```
tgctgctgct ttatttcctc cttttgctga ccttctggaa gatggcaggg caaagttcct    120
ctatatatgt atggcgggat ttgtactgct ctctttggtt cttggagtat taatcagtca    180
acctgaaatc ccactttcca t                                              201
```

<210> SEQ ID NO 379
<211> LENGTH: 201
<212> TYPE: DNA
<213> ORGANISM: Cucumber

<400> SEQUENCE: 379

```
agtcaacctg aaatcccact ttccatgaat ctcatgccga caaggttaaa tggggaaagt    60
gcctttactc ttatgagtct tcttggagca agtgtcatgc cacacaattt ttatgtgcat    120
tcttctattg tgcagcagca ccagagtcca ccaaatattt ccaaagaagt ttcgtgttat    180
aatcatttgt ttgctatttt c                                              201
```

<210> SEQ ID NO 380
<211> LENGTH: 201
<212> TYPE: DNA
<213> ORGANISM: Cucumber

<400> SEQUENCE: 380

```
gttataatca tttgtttgct attttctgca tattcagtgg aatttatgtg gtgaataacg    60
ttctcatgaa ctcagctgca aatgtattct atagcagtgg tcttgctttg cacacccttta   120 cagatgcatt gtctttaatg gagcaggtat ttgggagctc agtggtatat gttctcttct    180
tacttgtttt gtttctatca a                                              201
```

<210> SEQ ID NO 381
<211> LENGTH: 201
<212> TYPE: DNA
<213> ORGANISM: Cucumber

<400> SEQUENCE: 381

```
cttcttactt gttttgtttc tatcaaatca aatcacagct ctcacatgga gtcttggtgg    60
tcaactggtt ctgaccaatt tcttaaaatt agatattcct ggttggctcc attgtgctac    120
aattaggatt attgccatta ttccagcact atgctgtgtc tggagttcgg gtgctgaagg    180
gatgtatcaa cttcttatat t                                              201
```

<210> SEQ ID NO 382
<211> LENGTH: 201
<212> TYPE: DNA
<213> ORGANISM: Cucumber

<400> SEQUENCE: 382

```
gaagggatgt atcaacttct tatattttct caggttatgg tagctctatt gcttccatct    60
tctgtgattc ccctctatcg tgttgcttca tcaagaacaa taatgggtgc cctcaaaata    120
tcgcagcttg tggaatttat agcaattggt atctttattg gaatattagg actgaaaatt    180
atatttgttg tagagatgat t                                              201
```

<210> SEQ ID NO 383
<211> LENGTH: 201
<212> TYPE: DNA
<213> ORGANISM: Cucumber

<400> SEQUENCE: 383

```
aaattatatt tgttgtagag atgattttg gtaacagtga ttgggtagtt aacttgaggt     60
```
ggaacatggg gagtggtatg tcaatcccat ttgtggttct tcttattact gcttgttcat    120
cgttttgtct gatgctatgg ttggcagcta ccccattaaa atctgctact actattgccc    180
aattagatgc tcaagtattg a                                              201

<210> SEQ ID NO 384
<211> LENGTH: 201
<212> TYPE: DNA
<213> ORGANISM: Cucumber

<400> SEQUENCE: 384
tgcccaatta gatgctcaag tattgaactg ggatatggca gaggttagac ccgattcatc     60
tgaagagagg gaaaacatag atttggggaa aagttcatac agtgccgagc ctatagaaag    120
tcattctgac ctatcttcaa caaagtttga ttttaatttg cctgaaaata ttatggaacc    180
tgatcaggtt cttggttcag t                                              201

<210> SEQ ID NO 385
<211> LENGTH: 201
<212> TYPE: DNA
<213> ORGANISM: Cucumber

<400> SEQUENCE: 385
gaacctgatc aggttcttgg ttcagttaat caaaacgaga atcgatctag tactgtagtt     60
ccaagctccc caaatatgt acaagaggaa cttgaatcca ctgaggagtt agtctcatcc     120
tcaattgtga ctcacgatgt tcctgattca acattggctg acaaaaaggt cttaaaaata    180
gagtcagtgg aggccgttga a                                              201

<210> SEQ ID NO 386
<211> LENGTH: 201
<212> TYPE: DNA
<213> ORGANISM: Cucumber

<400> SEQUENCE: 386
aaatagagtc agtggaggcc gttgaaaaga ctgttggact cgatggtgat ttgcgttctg     60
agaaggatga ttatgaggtt gataactggg aggctgaaga gtcactgaaa gagatctctg    120
ggaatatacc atcctcaaca tctgagggtc ctggttcttt tagaagtatt ggtgggagaa    180
gtgaagaagg tgggaatgga a                                              201

<210> SEQ ID NO 387
<211> LENGTH: 201
<212> TYPE: DNA
<213> ORGANISM: Cucumber

<400> SEQUENCE: 387
gagaagtgaa gaaggtggga atggaactgg tagtctttca aggttagctg gcctcgggcg     60
tgctgcaagg cgccaactta ctggaattct tgatgaattt ggggacaat tgtatgattt     120 ccatggggtg cctactcaag atgcaaaggt taagaaacta gatttgttac tgggttttac    180
ctctctgaaa ttggatgctg t                                              201

<210> SEQ ID NO 388
<211> LENGTH: 201
<212> TYPE: DNA
<213> ORGANISM: Cucumber

<400> SEQUENCE: 388

```
tttacctctc tgaaattgga tgctgttggt aaagattttc ctcactcatc acctattgga    60
tgcaaaacat ccgatccaat ttcttctagt ttgtacgact cccccaagag tcagagggta   120
caaagtgggt tagaaccacc ctatgggata caaaaggggc accagccatt gtggtctaac   180
cacatgcagc attgggatgc a                                             201

<210> SEQ ID NO 389
<211> LENGTH: 201
<212> TYPE: DNA
<213> ORGANISM: Cucumber

<400> SEQUENCE: 389
ctaaccacat gcagcattgg gatgcatatg tgaataattc tagccataat gctctggact    60
ctggagtgaa gcgatattct agtttgcgca gtttgccttc tactgagagt tgggattatc   120
agcctgccac agtccatggc tatcagttaa cttatctgag tagaatggca aaggacagaa   180
gttctggtaa ttcgaacggt c                                             201

<210> SEQ ID NO 390
<211> LENGTH: 201
<212> TYPE: DNA
<213> ORGANISM: Cucumber

<400> SEQUENCE: 390
cagaagttct ggtaattcga acggtcagtt ggattcatca ggctctaaat atcataccttt    60 gggtggtggt ggtgcaggct tgcgagactc agttgcattt gcaatggggc aaaagttgca   120
aaatggcttg ggtgcttgtc agcaggcggc tcccccaggt ttttccaaca tcacagtatc   180
caggaaacct tcttccgaat c                                             201

<210> SEQ ID NO 391
<211> LENGTH: 201
<212> TYPE: DNA
<213> ORGANISM: Cucumber

<400> SEQUENCE: 391
gtatccagga aaccttcttc cgaatctgaa aggaaatatt atgatcattc tctttctgga    60
actggtgaga atttagtgag tgtatctaac acaaagaaat accatagctt accggatatt   120
caccgtgatc agcacacatc agataagagt tctcagtggg ataatgtgag tggttatgga   180
acatctattg gtagaataac a                                             201

<210> SEQ ID NO 392
<211> LENGTH: 201
<212> TYPE: DNA
<213> ORGANISM: Cucumber

<400> SEQUENCE: 392
atggaacatc tattggtaga ataacagctc gtggagtgtc cacaaattct ggatcaagat    60
tagtttctcc tttagcattt gatgaactat ctcctgcaaa tgtctacagt ggtgcattat   120
caccacaaat gaatcctcat ctggattctg gatctttctg gcatagacag ccttctgagc   180
aatttggctt ggacaaaaat a                                             201

<210> SEQ ID NO 393
<211> LENGTH: 201
<212> TYPE: DNA
<213> ORGANISM: Cucumber

<400> SEQUENCE: 393
```

```
tgagcaattt ggcttggaca aaaatagcaa ctccgagagt aaaggaattg ggaggctgca    60
ttcaattagt cacgaagctt cttttgttgt taattcagag gccaggcttc tccagtcctt   120
cagagactgc attgtcaaac ttctgaaatt agaaggatca gactggttat ttgggcaaag   180
tgatggtgct gacgaggagc t                                             201
```

<210> SEQ ID NO 394
<211> LENGTH: 201
<212> TYPE: DNA
<213> ORGANISM: Cucumber

<400> SEQUENCE: 394

```
caaagtgatg gtgctgacga ggagctaatt gattgtgtag ctgccaggga gaaatttctt    60
tatgaagctg aggcaaggga gatgggtcgg gtggtccgca tgaaagaatc tccttcattt   120
tctcctgata ggagaccagg ttctggaatg aagaatgata caaatttctc caatgtttct   180
atttcctctg tacctcattg t                                             201
```

<210> SEQ ID NO 395
<211> LENGTH: 201
<212> TYPE: DNA
<213> ORGANISM: Cucumber

<400> SEQUENCE: 395

```
tttctatttc ctctgtacct cattgtggag aaggctgtat ttggagatca gatttgattg    60
gtattatcga tcctgcattt tcgaagcctc gtataccgat gccaccatgc ttctgcctcc   120
aaattcccca agcattccag cagaggtcaa gcccacaaat tgcaaatgga atgttgcctc   180
ctgctgcaaa acctggcaag g                                             201
```

<210> SEQ ID NO 396
<211> LENGTH: 201
<212> TYPE: DNA
<213> ORGANISM: Cucumber

<400> SEQUENCE: 396

```
gcctcctgct gcaaaacctg gcaagggaaa atgcaccact gctgcaatgc ttctggatat    60
ggtcaaggat gtggagatag ccatctcttg ccgaaaaggt cgaactggta cagcagccgg   120
cgacgtagct ttcccaaagg ggaaggagaa cttggcttca gtcctcaaac gctacaagcg   180
ccgattatcc aataaaccag t                                             201
```

<210> SEQ ID NO 397
<211> LENGTH: 201
<212> TYPE: DNA
<213> ORGANISM: lettuce

<400> SEQUENCE: 397

```
gagaagaggt attacagtat gccagatatt gccggggttga ttcgtaatcg ggagtctaaa    60
gttctacccg aaagagagag cgggtcgaga tacccccccc tgggtatccg ggcccaggat   120
caggcccagg cccaggcccg gtgtacaggt ccgggacaat ctcgggttat ggcgggttgt   180
cttattctaa tttgtcccgg g                                             201
```

<210> SEQ ID NO 398
<211> LENGTH: 201
<212> TYPE: DNA
<213> ORGANISM: lettuce

<400> SEQUENCE: 398

```
gttgtcttat tctaatttgt cccgggatgc tgctgcttac caacccgttt ccagttacgg      60
gccagggatt gggttagggg tagggttcgg gtcggggtca gacacgtggt caatgtggtc     120
aaaacaaccg tctgaacaat ttggtgtggc tgaaaaggtt aatttgaaca ctcaagaagc     180
ttttattaca tctggagtag a                                                201
```

<210> SEQ ID NO 399
<211> LENGTH: 201
<212> TYPE: DNA
<213> ORGANISM: lettuce

<400> SEQUENCE: 399

```
gaagctttta ttacatctgg agtagatgct gaagcaaatc ttttgaagtc atttaggttg      60
tgtattgtaa aactgttgaa gcttgaaggg tctgaatggt tgtttaagca gaatggtggg     120
ttagatgagg atcttgttga ccgggtggct gcccgggaga gatttctgta tgaaattgag     180
ggcaatgagg tgacccgggc a                                                201
```

<210> SEQ ID NO 400
<211> LENGTH: 201
<212> TYPE: DNA
<213> ORGANISM: lettuce

<400> SEQUENCE: 400

```
ttgagggcaa tgaggtgacc cgggcagctg cccgtggtgg tggggccaaa gttgatgaag      60
ctgaatacaa taagtattta gtgacatcgg ttccaaattg tggtgagggt tgtgtatgga     120
gaattgagtt gataaaaagc tttggtgttt ggtgtataca tagaattctc gagctttctt     180
taatggaaag taggcccgaa c                                                201
```

<210> SEQ ID NO 401
<211> LENGTH: 201
<212> TYPE: DNA
<213> ORGANISM: lettuce

<400> SEQUENCE: 401

```
ttctttaatg gaaagtaggc ccgaactttg ggggaataca catatgttct caatcgtctt      60
cagggaataa ttgagccgtc attctcgaaa cctcgtacac catcaagtcc cgtgtttctg     120
tcttcagctt ccggaagcat accacctgcg atcatctccg cccaaatcca tcaccagtct     180
gccgcctccg gtgaaacaga g                                                201
```

<210> SEQ ID NO 402
<211> LENGTH: 201
<212> TYPE: DNA
<213> ORGANISM: lettuce
<220> FEATURE:
<221> NAME/KEY: unsure
<222> LOCATION: (1)..(201)
<223> OTHER INFORMATION: unsure at all n locations

<400> SEQUENCE: 402

```
agtctgccgc ctccggtgaa acagagcaga gggaaaacca ccaccgccgc cagtctgttg      60
gacatagtaa aagacgtgga gaccgccatc tcttgccgga aaggccgacc gggtactgcc     120
gccggtgacg tggcgttccc gaaagggaaa gaaaacctgg cgtctgttct ncaaagatac     180
aagcggcggt tgatggcggt g                                                201
```

<210> SEQ ID NO 403
<211> LENGTH: 201
<212> TYPE: DNA
<213> ORGANISM: Rice

<400> SEQUENCE: 403

```
acagttccac taaaaaaatc cacttcacct agcagccgct ctcacctcca cgcgctctcc      60
gccaccggag cacgagcgcg actgccacca cctccaccgg attcatctcc gcctcttgcc     120
gcggcaaagc ccccccagct tggattcctc tgtttttttt tccttttttgc gtacgaatct    180
cttgtatatc cctctcctgt a                                               201
```

<210> SEQ ID NO 404
<211> LENGTH: 201
<212> TYPE: DNA
<213> ORGANISM: Rice

<400> SEQUENCE: 404

```
aatctcttgt atatccctct cctgtatgtt gcgagaaatc aatctagtcc gaatggtgtg      60
ctcctgcgtg ctggagtagt ctaggtatac cagttttgtt ctccaaagca tttgggattg     120
ggttgaatgg aacatctatg gtccacgcta ggtccgcccc tggctgtgat ggatggagct     180
tagagcaggg gcaacctaga t                                               201
```

<210> SEQ ID NO 405
<211> LENGTH: 201
<212> TYPE: DNA
<213> ORGANISM: Rice

<400> SEQUENCE: 405

```
gagcttagag caggggcaac ctagatcagg ggtgtctccc tgggggggttt tcatggtgct      60
gtggatgttc actagctttg gagggtttga ttagggcctc ttgggtcata acaggagggt     120
tttaagggac ctggatttgg taaagcattt ttcaggcatg tgatgcttct tggggaggat     180
ttcatggtgt tgtggatgtt c                                               201
```

<210> SEQ ID NO 406
<211> LENGTH: 201
<212> TYPE: DNA
<213> ORGANISM: Rice

<400> SEQUENCE: 406

```
aggatttcat ggtgttgtgg atgttcacca gctttggagg gtttgattag ggctgcttgg      60
gtcacaacag gagggcttta gggatctgaa tttggtagtc atttcaggca tgtgatgctt     120
cttggggagg atttcatggt gttgtggatg gatgtccccc aggtttggat ggttagactt     180
cttcgatcac cacaagagct t                                               201
```

<210> SEQ ID NO 407
<211> LENGTH: 201
<212> TYPE: DNA
<213> ORGANISM: Rice

<400> SEQUENCE: 407

```
gacttcttcg atcaccacaa gagctttgaa gagacctgag tggataagca tttgatcctt      60
cttggaggtg tttcatggtg ttctagatgt tcaccagctt cggagggttt gattagactg     120
cttgagttaa cagtgttcaa gggactgaat ttgataagca tgtcgggcat ttgatccagt     180
ggtgtggatt cgtatccatc t                                               201
```

<210> SEQ ID NO 408
<211> LENGTH: 201
<212> TYPE: DNA
<213> ORGANISM: Rice

<400> SEQUENCE: 408

```
ccagtggtgt ggattcgtat ccatcttttg ttgttataag atttgctgcc acaaaaaatg      60
gaaggtgtgc acggtataga atctctggct actggagatg gttggcatca tctttcccgt     120
acccttggac cggtgctcct gatctcgatg gggtatattg accttgggaa gtgggtggaa     180
acgatagatg ccgggtctcg g                                                201
```

<210> SEQ ID NO 409
<211> LENGTH: 201
<212> TYPE: DNA
<213> ORGANISM: Rice

<400> SEQUENCE: 409

```
tggaaacgat agatgccggg tctcggtttg gctatgatct cgtaatactg gtgttgcttt      60
tcaacttgtc ggccattctg tgccagtatc tgtcgatgtg tatcggcatg gtcactggga     120
aaaatcttgc ggagatttgc cgcgaggagt acagtccatc aatatgtgtc atccttggta     180
ttcaggcagg attgtccttg c                                                201
```

<210> SEQ ID NO 410
<211> LENGTH: 201
<212> TYPE: DNA
<213> ORGANISM: Rice

<400> SEQUENCE: 410

```
tggtattcag gcaggattgt ccttgctaac cgcggaacta accatgcttt caggcatatc      60
agtcggattc aacctggtct ttgaatatga tgatcctatc gcaggcttat attttgctag     120
tgttgtggtc aatttgctac cttacactat gtcttatctg gcaaacgga tggctgggac      180
attgaatgca tgcgtagcag g                                                201
```

<210> SEQ ID NO 411
<211> LENGTH: 201
<212> TYPE: DNA
<213> ORGANISM: Rice

<400> SEQUENCE: 411

```
gggacattga atgcatgcgt agcaggcttt gcacttcttt gttttgtgct tggtttatta      60
gtcagtcaac caaaaattcc agttgatatg aatgcaatgt tccccaagtt gagtggtgaa     120
agtgcttatt ccttgatggc gcttcttggc ggaaatgtaa tagcgcacaa ttttatgtt     180
cattcatcag ttgtacaggg c                                                201
```

<210> SEQ ID NO 412
<211> LENGTH: 201
<212> TYPE: DNA
<213> ORGANISM: Rice

<400> SEQUENCE: 412

```
atgttcattc atcagttgta cagggccaaa gacaatctac aactctttcc cttggtgctc      60
tgttccacga tcacctgttc tcaatattgt ttattttcac tggggttttc cttgtgaatt     120
atgtcctgat gggctcagca gcagttgaat ccaataatac tctggttact tttcaagatt     180
ctgtagattt aatgaaccag a                                                201
```

<210> SEQ ID NO 413
<211> LENGTH: 201
<212> TYPE: DNA
<213> ORGANISM: Rice

<400> SEQUENCE: 413
agattctgta gatttaatga accagatgtt catgaatccg atggcaccaa ttgttttttt        60
agtgatcctt atcttttcga gtcatgtcat ctcattgaca tctattattg gcagccacgc       120
aattttgaag aatttctttg gtgtaaactt gcctcattct gctcatcatc tgctactaaa       180
ggccgttgcc atggttccta c                                                 201

<210> SEQ ID NO 414
<211> LENGTH: 201
<212> TYPE: DNA
<213> ORGANISM: Rice

<400> SEQUENCE: 414
ctaaaggccg ttgccatggt tcctactatg tactatgcaa aggttgcagg ttctgaaggg        60
atatatcagt tactcattat ctgcccagtt atccaagcta tgttccttcc ttcatctgtt       120
attcctgttt tccgtgtttc ctcatcaaga gttataatga gcagatataa aatatctttg       180
tacgttgaaa tattggccat c                                                 201

<210> SEQ ID NO 415
<211> LENGTH: 201
<212> TYPE: DNA
<213> ORGANISM: Rice

<400> SEQUENCE: 415
ctttgtacgt tgaaatattg gccatcctag catttcttct tttgctgttc acaaatatca        60
tttttgctgc ggaaatcctg tttggtgata gtacctggac aaacaacttg aaagggaaca       120
ctggaagccc tgttgtactt ccgcatgcca ttgtagttct aatttcttgt gcatcaatta       180
cttttacgct gttcctggct g                                                 201

<210> SEQ ID NO 416
<211> LENGTH: 201
<212> TYPE: DNA
<213> ORGANISM: Rice

<400> SEQUENCE: 416
aattactttt acgctgttcc tggctgtcac tccactgaag tcagcaagta atgaacctga        60
aactcaggag ctatctgagc actctcagag agaagatcca gatactactt atcaaagaga       120
agcaagtaat gaacctgaaa ctcaggagct atctgagcac tctcagagag aagatccaga       180
tactacttat caaatagaag t                                                 201

<210> SEQ ID NO 417
<211> LENGTH: 201
<212> TYPE: DNA
<213> ORGANISM: Rice

<400> SEQUENCE: 417
ccagatacta cttatcaaat agaagtaagt aatgaacgtg aaactcagca gctatctgag        60
cactctcaga tagaagatcc agatactttt tatcatagag aggagctttc tctggttgaa       120
cagaaagaag atcatacgac ttctactatt aatgctattc ccaggatttc atcagaaagt       180
tatcaaacat cagctttgga g    201

<210> SEQ ID NO 418
<211> LENGTH: 201
<212> TYPE: DNA
<213> ORGANISM: Rice

<400> SEQUENCE: 418
aaagttatca aacatcagct ttggagcata atgactttcc tgacatcact gtggagtctg    60
gtcatggcac tcagcagctt actgcttttg tgccaattat tccggaggtc tcatcgtcta    120
tcaaacataa ggaaccaaaa tcagtagtta ttgaccagac ggaaccagtg ccaaaggttt    180
gtactgccac agtagtagaa c    201

<210> SEQ ID NO 419
<211> LENGTH: 201
<212> TYPE: DNA
<213> ORGANISM: Rice

<400> SEQUENCE: 419
ggtttgtact gccacagtag tagaacataa cactgctgag aacatcaaaa tgaagagtac    60
aacttcaaag catgtccaag aagaagcagg agctagcatg gactatgata ctgaggcttc    120
ttataatgcg gaagtcagca agtcttctgg aaacaaggca cctccaattt ctgatgaccc    180
aacatctctt actttgagca a    201

<210> SEQ ID NO 420
<211> LENGTH: 201
<212> TYPE: DNA
<213> ORGANISM: Rice

<400> SEQUENCE: 420
gacccaacat ctcttacttt gagcaagggg agagactctg atgctggtta tcgtggcagt    60
aacctctcaa gactgcctgg tttgggtcgt gcagcaagga ggcaattagc agcgattctt    120
gatgagttct ggggacatct ctttgattat catggtaagc taacgcaaga agctaatgca    180
ggaaggttca actttctgct a    201

<210> SEQ ID NO 421
<211> LENGTH: 201
<212> TYPE: DNA
<213> ORGANISM: Rice

<400> SEQUENCE: 421
atgcaggaag gttcaacttt ctgctaggac catacccgaa agcagttaga agtgataacc    60
aagccatcga agcttctagg agccccttga tgagagatgc aatacgagga tcagctacca    120
tacagaaatc atgggactca cgtgctaagg aagtctctag tccaggcttt aattttgtgc    180
ttcagatggg tcgcattgga t    201

<210> SEQ ID NO 422
<211> LENGTH: 201
<212> TYPE: DNA
<213> ORGANISM: Rice

<400> SEQUENCE: 422
tgtgcttcag atgggtcgca ttggatcatc aaactggtct gagagcatgc gtttatctaa    60
tgctgacatc ccaaggccaa ctagcacctt gtttgaacaa atactcagt tttattcaaa    120 ttataatgtc ccatcttacc ctgacaatca gttctatcaa cctgctacca ttcatggcta    180

```
tcacctggca acctctttga a                                              201

<210> SEQ ID NO 423
<211> LENGTH: 201
<212> TYPE: DNA
<213> ORGANISM: Rice

<400> SEQUENCE: 423
ggctatcacc tggcaacctc tttgaaaagt atgaatgcaa gtcacagcac gcactccagc     60
atttcactag atccacggcg acttcctaga tcatctgaat ctgctggttc taactacgca    120
gattctgcaa ggtatgctcg taaccaagat gtaattggtt cacagggaac cgcttcgcaa    180
aacacaacaa tgagctgttt a                                              201

<210> SEQ ID NO 424
<211> LENGTH: 201
<212> TYPE: DNA
<213> ORGANISM: Rice

<400> SEQUENCE: 424
cgcaaaacac aacaatgagc tgtttagata caatgacagt ggagagagct ttttacaatc     60
ctgcctctgt taatgagatt gaaggggttg gttcatctgc ttactcaaag aagtaccata    120
gttcacctga catatctgca ctaattgctg caagtaggaa ttatttgcca aatgaagtaa    180
atttgggagg tgctgctgga a                                              201

<210> SEQ ID NO 425
<211> LENGTH: 201
<212> TYPE: DNA
<213> ORGANISM: Rice

<400> SEQUENCE: 425
agtaaatttg ggaggtgctg ctggaagcag ttcatacttc agtaatttgg catgtgaaag     60
atcacaatat gtgaacttgg gatccagttc cacagctcaa tttgcactta gcaagcactc    120
acaacctaat ttccatagag acacatcatc tatgcagtca agtgtgaacc caagtactga    180
atccatttgg gcccagcagc c                                              201

<210> SEQ ID NO 426
<211> LENGTH: 201
<212> TYPE: DNA
<213> ORGANISM: Rice

<400> SEQUENCE: 426
actgaatcca tttgggccca gcagccgttt gaacaattac tcggtgtatc aagagcagag     60
ttgaataagg gcgagggtaa caccgaccag agatcaagtg gtgtcaccaa acacgatttc    120
tctaacaaag aatatgaggt gaaacttctt caatcactca gattttgcat catgaagctc    180
ttgaaactgg aaggatcagg a                                              201

<210> SEQ ID NO 427
<211> LENGTH: 201
<212> TYPE: DNA
<213> ORGANISM: Rice

<400> SEQUENCE: 427
agctcttgaa actggaagga tcaggatggc tctttgagca aaatggtggc tgtgatgaaa     60
aattaattga tcaagttgct gtagctgaga gagtttcaca acataccact gaaaatcagt    120
```

```
tatctgctga tctccagctc catagttctg atgaagactt gcagccactg caaaggaatg      180
ataacaggga tgccaattgc a                                                201

<210> SEQ ID NO 428
<211> LENGTH: 201
<212> TYPE: DNA
<213> ORGANISM: Rice

<400> SEQUENCE: 428
gaatgataac agggatgcca attgcatgag cctactgccc aagtgtggag atgattgtgt      60
ttggcaggcc ccctgattg tcagttttgg tgtttggtgc atccgccaga ttctgaacct      120
gtgccttgtc gaaagtaggc cagaactttg gggcaagtat acatatgttc ttaatcgtct     180
ccagggaata cttgatcctg c                                                201

<210> SEQ ID NO 429
<211> LENGTH: 201
<212> TYPE: DNA
<213> ORGANISM: Rice

<400> SEQUENCE: 429
cgtctccagg gaatacttga tcctgcattt tccaagcctc agaaacccat gaaaggatgc      60
gtatgccttc aaaaagttgc caagcccatc tctggtactt tcaccactgc tggtatgatc     120
ttggagatga ttaaagacgt ggaacaagcc atttctagcc gcaagggccg aagcggcaca     180
gcagcaggag acgttgcttt t                                                201

<210> SEQ ID NO 430
<211> LENGTH: 201
<212> TYPE: DNA
<213> ORGANISM: Rice

<400> SEQUENCE: 430
gcacagcagc aggagacgtt gcttttccca aagggaagga gaacctagct tctgtcctta      60
agcgatacaa gcgtaggctc tcgaacaaga catctgcagg acaatagcgt ggcagcgagc     120
tttcttttgt tcttgtttg tatagggttc ttggggctgc tccacaaagt tctgtttttt     180
tgtgctcctc aaaccttggg t                                                201

<210> SEQ ID NO 431
<211> LENGTH: 201
<212> TYPE: DNA
<213> ORGANISM: Rice

<400> SEQUENCE: 431 tttttttgtgc tcctcaaacc ttgggttttt tcgatgcaca cgatctccag agtgcctgag     60
agcttcttga tctttggtca ttttttgcaca tgttgtttat gaagtggcca agggtgaatg    120
gtataccttg tttattcatc ttatcagcga gatctcaaca gtagatgata tttgctggag    180
cagcaacatt gtaaagttct t                                                201

<210> SEQ ID NO 432
<211> LENGTH: 201
<212> TYPE: DNA
<213> ORGANISM: Rice

<400> SEQUENCE: 432
ggtttccccc aatttcctcc cgcaatttct acttgttctt ggctcctctc tgctgttctt      60
agcctcgccg cgatggcgta gtcttggaga agatcagatc catctcgagt tcgattgggg    120
```

```
tttttttttt ctctcttgag atttccatga ttggtggtgg agttcatcgg caaggaattc      180
agcagaagag atcagattct g                                                201
```

<210> SEQ ID NO 433
<211> LENGTH: 201
<212> TYPE: DNA
<213> ORGANISM: Rice

<400> SEQUENCE: 433

```
aattcagcag aagagatcag attctgtaca cagttcgtct tcttgctcgg tgactaagct      60
gggttaggag aggaggaaaa gaaaatcttt tttttttttt ttgcggcgcc atggatgggc      120
agcagctacg tagctcggaa tctccggcga gcggcggcgg cggagtcacc ggcggcggcg      180
cgccacatct gttccacgcg c                                                201
```

<210> SEQ ID NO 434
<211> LENGTH: 201
<212> TYPE: DNA
<213> ORGANISM: Rice

<400> SEQUENCE: 434

```
cggcgcgcca catctgttcc acgcgctcgg gccggcgctg ctgatctcga ttgggtacat      60
tgacctcggg aaatgggtgg ccgcggtgga ggcagggtca cggttcggcc ttgacctcgt      120
gctgctggcc ctcctcttca acttcatggc catcctgtgc cagtatctcg cggcttgcat      180
tggcacggtc accgggagga g                                                201
```

<210> SEQ ID NO 435
<211> LENGTH: 201
<212> TYPE: DNA
<213> ORGANISM: Rice

<400> SEQUENCE: 435

```
tgcattggca cggtcaccgg gaggagcctc gccgagatct gccaccaaga atacagcagg      60
ccaacatgca tctttctggg tgttcaagca ggattgtcct tgttgacatc agaattgacg      120 atgattttg ggatagcact tggattcaat cttctatttg aatatgatga tctcatcact        180
gggatatgtt ttgcaaccgt t                                                201
```

<210> SEQ ID NO 436
<211> LENGTH: 201
<212> TYPE: DNA
<213> ORGANISM: Rice

<400> SEQUENCE: 436

```
tcactgggat atgttttgca accgttgttc ctaatctgct accatatgct atatcacacc      60
tgggaaagaa gatggtgggg acattaaatg cttgcattgc aggctttgcg cttctttgct      120
acgttcttgg tttattggtc agccaaccac aaattcctct gacaacgaat gtaattttcc      180
ccaagctcag tggtgaaagt g                                                201
```

<210> SEQ ID NO 437
<211> LENGTH: 201
<212> TYPE: DNA
<213> ORGANISM: Rice

<400> SEQUENCE: 437

```
tttccccaag ctcagtggtg aaagtgctta ttctctgatg gctcttcttg gtgcaaacgt      60
```

```
aatggcacac aacttttaca tccattcatc agttgttcag ggtcagaaaa gatctgcctt    120
tgctgttggt gccttatttc atgatcactt gttttcagta ttatttattt ttactggaat    180
ttttctggtg aatcatgttc t                                              201
```

<210> SEQ ID NO 438
<211> LENGTH: 201
<212> TYPE: DNA
<213> ORGANISM: Rice

<400> SEQUENCE: 438

```
ggattttttc tggtgaatca tgttctaatg aactctgcag cagctgattc cactaacacc    60
cttcttctca ccttccaaga tgttgtagaa ctaatgaacc agatatttgt aaaccctatg    120
gctccaacta tatttctagt ggttcttctc ttctctagcc acatcatctc gttgacatct    180
gctattggta gccaagtgat t                                              201
```

<210> SEQ ID NO 439
<211> LENGTH: 201
<212> TYPE: DNA
<213> ORGANISM: Rice

<400> SEQUENCE: 439

```
catctgctat tggtagccaa gtgatttcgc agcatttgtt tggcattaat cttcctctct    60
ctggacatca tctgatactg aaggcttttg ccatagttcc tgctctgtac tgtgctaagg    120
ttgcaggtgc tgaaggaata taccaattac tgataatctg ccagattatc caggccatgc    180
tccttccatc atcagtcgtg c                                              201
```

<210> SEQ ID NO 440
<211> LENGTH: 201
<212> TYPE: DNA
<213> ORGANISM: Rice

<400> SEQUENCE: 440

```
catgctcctt ccatcatcag tcgtgccact cttccgtgtt gcctcatcaa gattgataat    60
gggtgcccac agagtgtctt tgcatctgga gatattaaca tttcttgcat ttctcctcat    120
gctgttttcg aatatcatct ttatggcaga aatgctgttt ggtgacagtg gttggctgaa    180
cactctgaaa gggaatactg g                                              201
```

<210> SEQ ID NO 441
<211> LENGTH: 201
<212> TYPE: DNA
<213> ORGANISM: Rice

<400> SEQUENCE: 441

```
ctgaacactc tgaaagggaa tactggaagc cctgtggtgt ttccatctac ggttctcatc    60
acggtggctt gtgtctctgt tgcattttca ctctacatgg ctgttacacc actgaaatca    120
ggaagccatg aagctgaatt gcagcaggaa tggtctgtgc cttctcagaa agagctcttg    180
aatactactc aagacagaga a                                              201
```

<210> SEQ ID NO 442
<211> LENGTH: 201
<212> TYPE: DNA
<213> ORGANISM: Rice

<400> SEQUENCE: 442

```
tcttgaatac tactcaagac agagaagaga cttgtgcggg caatgttacc tatgaggaag    60
```

```
atcagagatc tgatgttgtc ccttctccta ggattcagcc tgtggattgt ctgaaatcag    120
ctctggacta cattgatagt tcggacacag ctatagaatc tgatcatgat tctcaacatt    180
ccactgctca tacatctacc g                                              201
```

<210> SEQ ID NO 443
<211> LENGTH: 201
<212> TYPE: DNA
<213> ORGANISM: Rice

<400> SEQUENCE: 443

```
acattccact gctcatacat ctaccgctcc tgaatcctgt cactctccat cattcattcc    60
tgaagagtca aaatcagttg ttgctgttga ctggccagag cctctggagc caatttctaa    120
tgctattgtg gctgaggaaa gtacagtaga gagtgtggac tccaagagca caggcgaaag    180
ggatattgaa gtagaaccag c                                              201
```

<210> SEQ ID NO 444
<211> LENGTH: 201
<212> TYPE: DNA
<213> ORGANISM: Rice

<400> SEQUENCE: 444

```
gaaagggata ttgaagtaga accagctctt tgatggaca atgataagga ggctccaaat     60
attctagagt ctgacaacaa gccacttgga ggcaataatc cttcctgtgc atcggatgat    120
ggcccaccat ctcttacctt cagcagggg aaaggctcag atgcaggcaa tggcagcggg    180
agtctctcga ggttatctgg t                                              201
```

<210> SEQ ID NO 445
<211> LENGTH: 201
<212> TYPE: DNA
<213> ORGANISM: Rice

<400> SEQUENCE: 445

```
gcgggagtct ctcgaggtta tctggtttgg gccgtgcagc aaggaggcaa ctagcagcca    60
tacttgatga gttctggggg catctctttg attaccatgg gaaactcact caagaagcta    120
gctctaaaag gtttgacatc ttgcttgggc tagacgtaag aacacctagc tcaactgtaa    180
gagcagacag tcaagctaat g                                              201
```

<210> SEQ ID NO 446
<211> LENGTH: 201
<212> TYPE: DNA
<213> ORGANISM: Rice

<400> SEQUENCE: 446

```
tgtaagagca gacagtcaag ctaatgaaat cccgaagagt cccatggtac gagacaattt    60
acaagggtct gccttcttgg gaagttcaag ggatctgatg tctactaaga atgagatgtc    120
gaatttggat ctgacatatg ggcttcagat gggcaataac attgggtcat cagcctggtc    180
tcagggcatg cagttaccaa g                                              201
```

<210> SEQ ID NO 447
<211> LENGTH: 201
<212> TYPE: DNA
<213> ORGANISM: Rice

<400> SEQUENCE: 447

```
tggtctcagg gcatgcagtt accaagtacc caactgcaga gttcaagcaa cagcttactc    60
gatcaaggtg caagattaaa ttcaaatttt agcacgccat catacgcaga caacaaccaa   120
ttctaccaac ctgcaacgat tcatgggtat cagctcgcat catacctaaa acagatgaat   180
gctaatcgaa atccttactc t                                             201

<210> SEQ ID NO 448
<211> LENGTH: 201
<212> TYPE: DNA
<213> ORGANISM: Rice

<400> SEQUENCE: 448
tgaatgctaa tcgaaatcct tactctagca tgccattgga cccacagcga cttccaaaat    60
cttctgcatc ggctgtgcca acctatgtcg attctgtcat gcatgctcgt aaccagaact   120
tgcttgcttc attgggagct actccttcac agatcgcagc aacatcccgg ataggtacta   180
tgatggcaga aagatcctat t                                             201

<210> SEQ ID NO 449
<211> LENGTH: 201
<212> TYPE: DNA
<213> ORGANISM: Rice

<400> SEQUENCE: 449
tactatgatg gcagaaagat cctattatgt cccttccact cttgacggga atgaaaatgc    60
tggttcatca gcttactcaa agaagtacca cagctcacca gacatatctg cactgattgc   120
tgcaagcagg agtgctctgt tgaatgaatc aaagttgggt ggtggtacca ttggatccca   180
gtcgtacctt agcaggcttg c                                             201

<210> SEQ ID NO 450
<211> LENGTH: 201
<212> TYPE: DNA
<213> ORGANISM: Rice

<400> SEQUENCE: 450
tcccagtcgt accttagcag gcttgcatcg gaaagatctc agtatacaaa ctcggtggcc    60
aggcctgcag ctcccttggc gttttgatgag ctctctccac ctaagctccc aggggatatc   120
ttctcaatgc aacaaagccc aaacccaagt gcaagatccc tttgggctaa gcaacctttt   180
gagcagctgt ttggtgtgtc g                                             201

<210> SEQ ID NO 451
<211> LENGTH: 201
<212> TYPE: DNA
<213> ORGANISM: Rice

<400> SEQUENCE: 451
cttttgagca gctgtttggt gtgtcgagtg cggagctcac taaaagcgag ttcaaccctg    60
caggcagatc gggtggcatg accaaggatg atttctctta caaggagtct gaggcgaagc   120
ttcttcagtc tcttagattc tgcatctcga agctcctgaa gctagaagga tcagggtggc   180
tgttcaagca aaatggtggc a                                             201

<210> SEQ ID NO 452
<211> LENGTH: 201
<212> TYPE: DNA
<213> ORGANISM: Rice

<400> SEQUENCE: 452
```

```
gtggctgttc aagcaaaatg gtggcagcga cgaagatctg attgatcaag ttgctgcggt    60
agagaagcta ttgcaacaag gaaccagtga caaccaactg ctgcttggtg atactcagca   120
accaccatgt gataaggcag acatccagta catgcgcgta ctgcctaact gcggagacga   180
ctgcatctgg cgcgcctccc t                                             201
```

<210> SEQ ID NO 453
<211> LENGTH: 201
<212> TYPE: DNA
<213> ORGANISM: Rice

<400> SEQUENCE: 453

```
gacgactgca tctggcgcgc ctccctcgtt gtcagcttcg gtgtctggtg catccgccgg    60
gtgctagacc tgtctctggt ggaaagcagg ccagaacttt ggggcaagta tacctatgtt   120
ctcaaccgtc ttcagggcat cctggatcct gcattctcca gcctcggag tgctctcagc   180 gcgtgtgcgt gccttcacag a                                             201
```

<210> SEQ ID NO 454
<211> LENGTH: 201
<212> TYPE: DNA
<213> ORGANISM: Rice

<400> SEQUENCE: 454

```
tcagcgcgtg tgcgtgcctt cacagagata tccgggtgct caacagcctg cgccacagta    60
gcctggtagc aacaaactcc attccaaggc aaatccgagg ttccttcacc accgcatctg   120
tggtcctgga gatgatcaag gatgtggaga ccgcagtctc agggcgcaag ggcaggagtg   180
gcaccgcagc tggggatgtc g                                             201
```

<210> SEQ ID NO 455
<211> LENGTH: 201
<212> TYPE: DNA
<213> ORGANISM: Rice

<400> SEQUENCE: 455

```
gagtggcacc gcagctgggg atgtcgcctt ccccaagggg aaggagaacc tggcctccgt    60
gctgaagcga tacaagcgga ggctctcgag caagggacaa caataataag gcatctgggc   120
agcgtgatcc tgtcgcgttt taggggact tgaccattg ttcttcaagg atggcagcca    180
gccatggtgg cttgccctcc c                                             201
```

<210> SEQ ID NO 456
<211> LENGTH: 201
<212> TYPE: DNA
<213> ORGANISM: Rice

<400> SEQUENCE: 456

```
agccagccat ggtggcttgc cctccctgag ccctggattt tttcgttgca caacgtttgc    60
agggacctga ggaattggcc aacacttctg gtcccttcca tcatatttcg ttttttttg    120 tttctttctt gttttttttt ttttttttgc atgtgatgtg ttgtataatg gtaactgttc   180
atgtgccaga agaacaacca c                                             201
```

<210> SEQ ID NO 457
<211> LENGTH: 201
<212> TYPE: DNA
<213> ORGANISM: Rice

<400> SEQUENCE: 457

```
tgttcatgtg ccagaagaac aaccaccaaa atgtacaaca gatgtagtca gctgatgcac    60
cattgtaaag tttagtctct gcattttaac ctttttttg ggggtcattg acaaactgaa    120
tgaatgccct gtgtaatctc tcttcagaga ggatgccaag actgagaaaa agcttttgcc   180
agatttccag attccttgtg t                                              201
```

<210> SEQ ID NO 458
<211> LENGTH: 201
<212> TYPE: DNA
<213> ORGANISM: Rice

<400> SEQUENCE: 458

```
ttgccagatt tccagattcc ttgtgttcat ctaatatctg tcatgtctct cacattttct    60
ccagcttatg atcttttgt ctcgttggca tttgatagcg tgtgctggag atgtctaccg   120
tatatgtgga ttactgtatt aagcttctgg gaccggtgta tatatataat ttgtatggat   180
agagataaag aaatactaac t                                              201
```

<210> SEQ ID NO 459
<211> LENGTH: 201
<212> TYPE: DNA
<213> ORGANISM: Rice

<400> SEQUENCE: 459

```
aaaatgtaaa aattatatga atagatttgt cttgaaaaat actttcataa aagtatacat    60
atatcacttt tcaatgaata tttttatata aataagaagt caaagttgtg ttttggagac   120
cgtgtcgata tcctaaacga cttcctttat gagtatggag ggagtatgtg aataggcatg   180
gtggtaatgg gacatgccac c                                              201
```

<210> SEQ ID NO 460
<211> LENGTH: 201
<212> TYPE: DNA
<213> ORGANISM: Rice

<400> SEQUENCE: 460

```
gcatggtggt aatgggacat gccaccagca ttaaatctaa aggcctaaag tctgagcgca    60
catggtggta atgggacatg ccaccagcat taaacctaaa ggcctaaagt ctaagcgcac   120
attgatgaca aggacgatga acgtcactgg acccatggcc tcctcaactc cccgtcctcc   180
gtctcatgct taaggcatga c                                              201
```

<210> SEQ ID NO 461
<211> LENGTH: 201
<212> TYPE: DNA
<213> ORGANISM: Rice

<400> SEQUENCE: 461

```
cctccgtctc atgcttaagg catgacgatg tgcaccggat ttgactctca tgcagaaaag    60
aggcaaacaa ggagaattga taccgaccgg cacgaattcc tcctcccata aattgtcatt   120
ggtgatggaa aaggagacca tgaggctgct atatatggag ctttgattgg cacctaacat   180
ggtgaagcga tcatgtttct c                                              201
```

<210> SEQ ID NO 462
<211> LENGTH: 201
<212> TYPE: DNA
<213> ORGANISM: Rice

<400> SEQUENCE: 462
aacatggtga agcgatcatg tttctcaccc accttatgtg taggtacgtc atatgacaca    60
tcatctggtt agtacccata ggtaacaact agtgttgttg cttataacac cgtgtcctag   120
cacctagcca tcaacatcga tattgaccgt tgccacgatc tcctcctagt gatgttatcg   180
tgcttcattg ttgacgggtg g                                             201

<210> SEQ ID NO 463
<211> LENGTH: 201
<212> TYPE: DNA
<213> ORGANISM: Rice

<400> SEQUENCE: 463
tatcgtgctt cattgttgac gggtggcttt gctcaggggc gtccttaggc ccatgcgggc    60
tgtgcgaccg aacagggccc ccaaatttca agggccctaa aatattaagt atacccaata   120
tataataata ttaaatgctt caattttagt aaaactaagc ccccaaaaca atgcaaaagg   180
tgaatgatcc attttccaat t                                             201

<210> SEQ ID NO 464
<211> LENGTH: 201
<212> TYPE: DNA
<213> ORGANISM: Rice

<400> SEQUENCE: 464
aaaggtgaat gatccatttt ccaatttcca tcgtacagtc gtccgtgtcg tcgaagtccc    60
aacgccacgt cgcttcgtct cctctcctca gttactaggc cactaggatc cattttaata   120
tttcgcacgg ggacccaatt tgtccgggat gcccctggct ttgctcatga caaagacacg   180
agtgtgtgtc gtgggcgtgg g                                             201

<210> SEQ ID NO 465
<211> LENGTH: 201
<212> TYPE: DNA
<213> ORGANISM: Rice

<400> SEQUENCE: 465
acacgagtgt gtgtcgtggg cgtgggatgc tgccaaactc acgaggagga ggcaccataa    60
tcctgcgacc tagcatgggc tgctgccgac tgattttctc gtgtcgtctc gtctgcaagc   120
tcatcctggt gggagcacag cacagcagag agctagacga actcacaacc ccaggtgaac   180
gtggtcaagt tgctcaacat a                                             201

<210> SEQ ID NO 466
<211> LENGTH: 201
<212> TYPE: DNA
<213> ORGANISM: Rice

<400> SEQUENCE: 466
tgaacgtggt caagttgctc aacatacacg tgcaaagcta ctttagctcc tagaggtttt    60
gcatgggttt aagggtgcct ctcctacgca cgacgacgac gaaaacagga aagggtgggt   120
gggcacgctt ttgcagctga actccccgag atagagcggt tgatggaacc cgagagaca    180 aaggagacaa cggcgtgtgt t                                             201

<210> SEQ ID NO 467
<211> LENGTH: 201
<212> TYPE: DNA

<213> ORGANISM: Rice

<400> SEQUENCE: 467

```
agacaaagga gacaacggcg tgtgtttggt taattcggca gcatcttcgg cacgggacca    60
ggcgtagtat cgcgtatatg ccctcgtctc gactccgccg taatctgatt cggccgcggt   120
cttcttctgg agaatattat gcttgctcat tttatgctgt gtttagttgg tgaaaagaaa   180
atttttaagt gtcacattaa a                                             201
```

<210> SEQ ID NO 468
<211> LENGTH: 201
<212> TYPE: DNA
<213> ORGANISM: Rice

<400> SEQUENCE: 468

```
agaaaatttt taagtgtcac attaaacttt tgattggatg ttaaaatgag ttctcagaca    60
cgattaaaaa actaatttca taacttggtt ggaaaccgcg agatgaattt attaagtcta   120
attaatcttt cattagcaca tatatgttac tgtagcactt atgattaatc atggattaat   180
taaactcaaa atattcgtat c                                             201
```

<210> SEQ ID NO 469
<211> LENGTH: 201
<212> TYPE: DNA
<213> ORGANISM: Rice

<400> SEQUENCE: 469

```
ttaattaaac tcaaaatatt cgtatcgcga ttttcataca aactgtataa ttaatttttt    60
ttaatttata tttaatgctt atatatgtgt ctaaaatttg atgggaattt tttgagaaaa   120
aaagtttagg gaactaaggt gtccctcctt tccaaacacc acctaaacag gcctttacaa   180
tctacaaaaa aggcacgggc a                                             201
```

<210> SEQ ID NO 470
<211> LENGTH: 201
<212> TYPE: DNA
<213> ORGANISM: Rice

<400> SEQUENCE: 470

```
gatcctaatg aacatatgta cggttcagcc gtgcttcatg catatgccat cgtttgatcg    60
actgatatga tcccaaaatt cccaattaag gtttattcga tttcaatcaa tattagtgta   120
gcttaatact gtgtatttga tttatttct tgaattatag tgagccaata ggtacaattg   180
ttgtgaacta gtgatatgta t                                             201
```

<210> SEQ ID NO 471
<211> LENGTH: 201
<212> TYPE: DNA
<213> ORGANISM: Rice

<400> SEQUENCE: 471

```
aattgttgtg aactagtgat atgtatttct cgcgacgtga ttgactagta actttatgct    60
tgatatgtgc taccaccttt tctctcaggt aatgctacca tagccagcga cctttcctcg   120
cttttattag tacaatgtag ttttattgat cactgttgcc aatttcatat atttatttca   180
aaaattgtat ttattactag c                                             201
```

<210> SEQ ID NO 472
<211> LENGTH: 201

```
<212> TYPE: DNA
<213> ORGANISM: Rice

<400> SEQUENCE: 472
tttcaaaaat tgtatttatt actagctgat tattcttttt tggggaaaac tctgactgat      60
tgtgaatcat atatatcatg catggcgcca tgattctttt agagctaagg aggcttaaaa     120
cagttaaccc cgacatctag tttttaatag tcttacaaaa accatttcaa ttgattttca     180
acagttttgc aagtcggccg a                                                201

<210> SEQ ID NO 473
<211> LENGTH: 201
<212> TYPE: DNA
<213> ORGANISM: Rice

<400> SEQUENCE: 473
tttcaacagt tttgcaagtc ggccgattga tattttggct tgaagacata aaccagtagt      60
gattttctct tatctctaaa aagattcata accatgaaag tttagaggtt atttttttg     120 gtaaagtgta ctttcattaa ttgtgtttaa accgtcatta atgaccttat ctaattattg     180
cacgaattgt tagagatgac t                                                201

<210> SEQ ID NO 474
<211> LENGTH: 201
<212> TYPE: DNA
<213> ORGANISM: Rice

<400> SEQUENCE: 474
tattgcacga attgttagag atgactgcta caaattaatc atcagaggtt gccttttttt      60
ataatattga gtgagacttc cggttgagct cttaataaat tttcagattc agatcaaaat     120
atttaacaaa ctcattaaat cccaaaacta tgtcacggaa aaaagatcc ttcattcaat     180 ttcatacaac aacaatacaa a                                                201

<210> SEQ ID NO 475
<211> LENGTH: 201
<212> TYPE: DNA
<213> ORGANISM: Rice

<400> SEQUENCE: 475
tcaatttcat acaacaacaa tacaaacttt catctcatgc cttccaaaaa taagaaaaa      60 atgcatatcc aaaacgtggg aatgcgaaaa gtagcctatg ccaaacagca ttactactgt     120
caacctcaaa gctagcttgc aaattaaaag gattggccac gttgacactt tcaagtcctc     180
tccaacagtg aaagcacaac a                                                201

<210> SEQ ID NO 476
<211> LENGTH: 201
<212> TYPE: DNA
<213> ORGANISM: Rice

<400> SEQUENCE: 476
tcctctccaa cagtgaaagc acaacatggg caaagtacca ataaaaagtg ataatgttat      60
aatcttgttg ctttgctatg caaccttgct tatttctaat taataacagt gccttttgaa     120
ttattggaga gcaccatcac accacaccac acatggtagc aagttcatta ccatacttca     180
attgctgaaa gtcttccatg t                                                201

<210> SEQ ID NO 477
```

```
<211> LENGTH: 201
<212> TYPE: DNA
<213> ORGANISM: Rice

<400> SEQUENCE: 477
cttcaattgc tgaaagtctt ccatgtcttt gacttaatta gacactgtta agtgatagtt      60
gtattagtac tagttacatc cattgttggt gactgagaag ccataaaagt aaagtcacat     120
tattcccaag agggacttct catttaggct tccttctttt cagttgaacg aactcagctc     180
attctaatag ggtaatgaag a                                               201

<210> SEQ ID NO 478
<211> LENGTH: 201
<212> TYPE: DNA
<213> ORGANISM: Rice

<400> SEQUENCE: 478
agctcattct aatagggtaa tgaagataac cattaatgca taattactta agtggagtac      60
ttactattat aaagtatttt ttttaaaaaa atatttaata ttaacaaaac ttgtaagtag     120
aaactttta tataaaatat aaggtttgac aattcagaaa acatgctaac attaaacaaa     180
gggagtagta ctagcatgta g                                               201

<210> SEQ ID NO 479
<211> LENGTH: 201
<212> TYPE: DNA
<213> ORGANISM: Rice

<400> SEQUENCE: 479
acaaagggag tagtactagc atgtaggact atcactgact ggtgcatgga ccaagtccat      60
ccactgctga acatggggaa caacactaca cagtaagcac agaatcttcc aaataatata     120
aacaaaaaga tcagaaattt ttttaagaaa acaaaaaaaa ataaaaaaaa tagtgaagaa     180
aaagagctag ggagaggaga g                                               201

<210> SEQ ID NO 480
<211> LENGTH: 201
<212> TYPE: DNA
<213> ORGANISM: Rice

<400> SEQUENCE: 480
aagaaaaaga gctagggaga ggagagagaa agagagaaag ctgaaagctg tgaaagaaaa      60
gcctctgctg ctctctgcta gcttcttctc ctcctcctcc tcccccttct ccccgtagat     120
aaggaggacc cggggaaaaa ggggaggcaa aaagctgcga ttttccgcta attaaccccg     180
gggattagct gcccaagaac a                                               201

<210> SEQ ID NO 481
<211> LENGTH: 201
<212> TYPE: DNA
<213> ORGANISM: Soy

<400> SEQUENCE: 481
ggtggttaat cttaatctga gtgtgtgaga tctacttagt agtggtagtg gcagatgaag      60
aagagagaag aagcagtgaa ggatttgaga agttcgagtg ggaagtgatg atgatggatg     120
tgtttgggaa ccctttttga aattgagaat cgccagagct gtttatgaag tttggcctca     180
aattggattg attttcagtc a                                               201
```

<210> SEQ ID NO 482
<211> LENGTH: 201
<212> TYPE: DNA
<213> ORGANISM: Soy

<400> SEQUENCE: 482

```
cctcaaattg gattgatttt cagtcatgtt gaggagatga atggaatttt taatagtggt      60
gtgttgtgaa aagatttgt gatggtatac cttgacttga tcgaaaacct cggtcttgtt      120
agtatcggat gtgctatatg ttcaactttt tgcaagttgc aagtgatttt agcagcttag     180
tttatatttg aagctgctaa c                                                201
```

<210> SEQ ID NO 483
<211> LENGTH: 201
<212> TYPE: DNA
<213> ORGANISM: Soy

<400> SEQUENCE: 483

```
cttagtttat atttgaagct gctaacatat ctatgattgt aataaataaa taaatacaat      60
cttttgatag aaatatagtt aagttgcagt tatggaattg tctatgggtc attaggtttt     120
agctacttca aagtggttgt cctgtcctga gtatcatatt tttccagtag ccttattgtt    180
gctagtatgg tatcgaagag t                                                201
```

<210> SEQ ID NO 484
<211> LENGTH: 201
<212> TYPE: DNA
<213> ORGANISM: Soy

<400> SEQUENCE: 484

```
ttgttgctag tatggtatcg aagagtaaaa tggaagcagg acattgagt cctaaccacc      60 ctccttgctt tcttcgtcag tcacttcctg ctgttgcacc tatgcttctg atttcaacag    120
gatatgttga ccctggaaag tgggtagcca ctgttgaagg tggtgcacgg tttgggtttg    180
atctgatggc tgtcatgctt a                                                201
```

<210> SEQ ID NO 485
<211> LENGTH: 201
<212> TYPE: DNA
<213> ORGANISM: Soy

<400> SEQUENCE: 485

```
gtttgatctg atggctgtca tgcttatttt caattttgct gctatcttct gtcagtacat      60
atctgcaagg attggtgcga ttactggaaa aagtctagct cagatttgca gtgatgagta    120
tgatacatgg acatgcatgc tccttggagt tcaaacagaa ctttcagtga taatgctaga    180
ccttaacatg atcttgggca t                                                201
```

<210> SEQ ID NO 486
<211> LENGTH: 201
<212> TYPE: DNA
<213> ORGANISM: Soy

<400> SEQUENCE: 486

```
ctagacctta acatgatctt gggcatggca caaggattaa atcttatttt tgggtgggac      60
ttgttcactt gtgtcttttt aactgctact ggtgctgttt ttcatatact tctctcagtt     120
ctccttgaca ttgagaaggc aaaaatccta ggaccgtttg ttgctggttt tgtattgctt    180
gcttttatac ttggactgct t                                                201
```

<210> SEQ ID NO 487
<211> LENGTH: 201
<212> TYPE: DNA
<213> ORGANISM: Soy

<400> SEQUENCE: 487
tgcttgcttt tatacttgga ctgcttatca atcaaccgga aattccattt tccatgaatg     60
gaataccaac aaggttgagt ggggagagtg catttgtgct aatgagtctt ctaggagcaa    120
atcttgtacc tcacaacttt taccttcatt cctctattgt acagtggcat cagggattga    180
caagcatttc taagaatgct t                                              201

<210> SEQ ID NO 488
<211> LENGTH: 201
<212> TYPE: DNA
<213> ORGANISM: Soy

<400> SEQUENCE: 488
attgacaagc atttctaaga atgctttgtg tcataaccac ttttggcca tattatgtgt      60 ttccagtggt ctttatttgg taaataatat gctgatgacc gcctcagcaa atgagttcta   120
cagtacagat cctgttctgc ttacttttca ggatgcattg tcacccatgg aacaggtctt   180
acgtagccca atagctctgc t                                              201

<210> SEQ ID NO 489
<211> LENGTH: 201
<212> TYPE: DNA
<213> ORGANISM: Soy

<400> SEQUENCE: 489
gtcttacgta gcccaatagc tctgcttggg tttttgctca ttttgtttct tgcaaatcaa     60
accacagcat taacttggag tttaggcgga gaagtagtag tgcgtaattt cttaaaattg   120
gatattccag gttggcttca ttatgctaca attagagtga ttgctgtttt gcctgccctt   180
tattgtgtct ggagttcagg a                                              201

<210> SEQ ID NO 490
<211> LENGTH: 201
<212> TYPE: DNA
<213> ORGANISM: Soy

<400> SEQUENCE: 490
ccctttattg tgtctggagt tcaggagctg aggggatgta tcagctacta ttatccacac     60
aagttttggt agctctgcaa cttccatctt ttgtgatccc tcttttcga gttgccacat    120 ctagatcaat aatgggtgta cacaagatat cccagtttct ggaacttttg gcatcgatca   180
tattcattgg tatgcttggc t                                              201

<210> SEQ ID NO 491
<211> LENGTH: 201
<212> TYPE: DNA
<213> ORGANISM: Soy

<400> SEQUENCE: 491
gatcatattc attggtatgc ttggcttgaa tattgtcttc gtggtagaaa tgatattcgg     60
caatagtgac tgggcaagtg atttgagatg gaatgttggg agtggtgtgt ctgtctcata   120
tttagttctt cttaccgctg ctattacatc gttatgtttg atgctttggt tagccgccac   180
acctttaaga tctgccagtg t                                              201

<210> SEQ ID NO 492
<211> LENGTH: 201
<212> TYPE: DNA
<213> ORGANISM: Soy

<400> SEQUENCE: 492
gccacacctt taagatctgc cagtgtccaa ttagatgctc agacatggaa ctgggatatg    60
ccagagactc tgccaactcc tccagttgtt ggggaggaat tgtatttaac tgaaaaaaag   120
tgtcatgaag atgtatctaa gcatgtggag gaacacacac cagctgtagc aaaaagcttg   180
gactactcag atgtatcact t                                             201

<210> SEQ ID NO 493
<211> LENGTH: 201
<212> TYPE: DNA
<213> ORGANISM: Soy

<400> SEQUENCE: 493
gcttggacta ctcagatgta tcacttccaa gttttcatcc tgatctacct gaatctttaa    60
tggaacctga accccatgtg aatgctgtaa gggataatta ttctcttata tcgacttcca   120
catcagagtt agaggcagta tatgctgtag ttaatgagac ttctgattct tgtttggaag   180
acaccaaaac cataacaatg g                                             201

<210> SEQ ID NO 494
<211> LENGTH: 201
<212> TYPE: DNA
<213> ORGANISM: Soy

<400> SEQUENCE: 494
ggaagacacc aaaaccataa caatggaaac aaacgctgaa agggatgacg atgattcatg    60
ggaaactgaa gaaccttctg gagtggtatc agccagtgtt ccatcttcaa catcagatgg   120
ccctgcatca ttcaggagtc ttaatggcaa aagtgatgaa ggagggaata gctgtggaag   180
tctttcaaga atagaaggct t                                             201

<210> SEQ ID NO 495
<211> LENGTH: 201
<212> TYPE: DNA
<213> ORGANISM: Soy

<400> SEQUENCE: 495
ggaagtcttt caagaataga aggcttaggg cgtgcagcaa ggcgtcagct agctactgtt    60
cttaatgaat tctggggaca actatatgat ttgcatggac aagtaaccca ggaggcaaag   120
gctgggaaaa ttgacctttt gctgggagtg ggtgtagatt caaggcccac cagttccttg   180
caaaaagtgg atgcatgtgg a                                             201

<210> SEQ ID NO 496
<211> LENGTH: 201
<212> TYPE: DNA
<213> ORGANISM: Soy

<400> SEQUENCE: 496
ccttgcaaaa agtggatgca tgtggaaagg attattctga atacttagta tctgtcagag    60
gtagagcttc tgacgcatta atgaactctg cttcatatga ttcttccaag cagcctatga   120
tgcaaagtaa ttcagagtct tatggccttc aaaggagttc ttcctcaatg tgggcaaatc   180

```
ccatccaatt attggatgca t                                              201
```

<210> SEQ ID NO 497
<211> LENGTH: 201
<212> TYPE: DNA
<213> ORGANISM: Soy

<400> SEQUENCE: 497

```
aaatcccatc caattattgg atgcatatgt acagaactct agccacaatc tcctcgattc     60
tggtgagagg cgctattcaa gtgtgcgtaa tctacattca tcagaagctt gggattatca    120
accagctacc atacatggtt atcagactgc atcctatctt agccggcttg gtaaagacag    180
aaattctgct aacttaaatt g                                              201
```

<210> SEQ ID NO 498
<211> LENGTH: 201
<212> TYPE: DNA
<213> ORGANISM: Soy

<400> SEQUENCE: 498

```
gacagaaatt ctgctaactt aaattgtcag gtggacttgt catcactgaa atccccttcc     60
atagttaata caaagtacag ggattcactt gcatttgctt tggggaaaag gttgcaaagt    120
ggctcaggtg tgggccaacc cccagggttc ccaaatgtag ctgtctctag agattcccaa    180
ttacaatctg agaggtttta t                                              201
```

<210> SEQ ID NO 499
<211> LENGTH: 201
<212> TYPE: DNA
<213> ORGANISM: Soy

<400> SEQUENCE: 499

```
cccaattaca atctgagagg ttttattatg acttatgctc ttctggatct gcagataata     60
cagtcaattc agttaatact aaaaagtacc acagtttgcc agacatttca ggatactcca    120
tcccccacag ggctggttat gtgtctgata aaaatgctcc aagggatggt tctgttggat    180
atggatcttt tgctagtagg a                                              201
```

<210> SEQ ID NO 500
<211> LENGTH: 201
<212> TYPE: DNA
<213> ORGANISM: Soy

<400> SEQUENCE: 500

```
tggatatgga tcttttgcta gtaggacgtg ctatgaccaa tcattatatt taaattctgg     60
atcaagaaca ggaggtcatt tggccttcaa tgaacttcct ttgtctgaag tttacaacaa    120
ggcactctct tcacagttga gttctggttt tgatactgga tccctccggt ctagattgcc    180
ttatgagcag tttggggtag c                                              201
```

<210> SEQ ID NO 501
<211> LENGTH: 201
<212> TYPE: DNA
<213> ORGANISM: Soy

<400> SEQUENCE: 501

```
ttgccttatg agcagtttgg ggtagctgag aaaattccta atgttgcaat ggaagctgtt     60
ggaaataggc ctaatgcaat tgctcaagaa actacttcat ttgtggatat agaggggaaa    120
cttcttcagt ctattagact ttgcattgtg aagctcttga aactggatgg gtctgattgg    180
```

```
ttgtttagac agaatggtgg a                                              201

<210> SEQ ID NO 502
<211> LENGTH: 201
<212> TYPE: DNA
<213> ORGANISM: Soy

<400> SEQUENCE: 502
attggttgtt tagacagaat ggtggagccg atgaggatct gatagattct gttgctgcaa     60
gggagaagtt gttttatgaa attgaaacca gggagatgaa tcaggtcatt catatggatg    120
aagctcatta ttttccttct gataggaaat ttggttcttc aatgaagagt aatggggcat    180
attcttcagg ttttcggtg t                                               201

<210> SEQ ID NO 503
<211> LENGTH: 201
<212> TYPE: DNA
<213> ORGANISM: Soy

<400> SEQUENCE: 503
ggcatattct tcaggttttt cggtgtcttc ggttccaaat tgcgggcagg gatgtatatg     60
gaaaacagat ttaataataa gctttggagt atggtgtatc cacagtattc ttaacctctc    120
aattgtagaa agccggccgg agctttgggg gaaatacacc tatgttctca atcgcctcca    180
gggcatcatt gatccagctt t                                              201

<210> SEQ ID NO 504
<211> LENGTH: 201
<212> TYPE: DNA
<213> ORGANISM: Soy

<400> SEQUENCE: 504
ctccagggca tcattgatcc agctttcctt aagcctcgga gtcccttggc tccatgcttc     60
tgccttcaag ttcagcaaaa gttaagcccc catctttcaa atgggatact accccccaacg   120 actacaaaac caggccaggg caaatgcaca actgcatcaa cgttgcttga acttatcaag    180
gaagtggagc ttgccatctc t                                              201

<210> SEQ ID NO 505
<211> LENGTH: 201
<212> TYPE: DNA
<213> ORGANISM: Soy

<400> SEQUENCE: 505
tcaaggaagt ggagcttgcc atctctggca ggaaaggacg taccggaact gccgcaggcg     60
atgtggcttt ccctatgggg aaggaaaatt tggcgtctgt tctcaaacgg tacaagcgga    120
ggctatctaa caagcccgtt ggcactaatg gagggacagg ttcacgcaag atccccacat    180
tagcaccata caaccaataa t                                              201

<210> SEQ ID NO 506
<211> LENGTH: 201
<212> TYPE: DNA
<213> ORGANISM: Soy

<400> SEQUENCE: 506
cacattagca ccatacaacc aataatagca ttttgcgtta acaaaatcag cgttagttgg     60
gctgttttgt aatttatttt ctttagcagc tcatgctgtc aaagaatgtt gtcttctccg    120
```

```
tgtatcatat tccattccct gctgacattg tagcaaattt atccacgta tgttacatac      180 acgtagggca aatgtacta t                                                 201

<210> SEQ ID NO 507
<211> LENGTH: 201
<212> TYPE: DNA
<213> ORGANISM: Soy

<400> SEQUENCE: 507
taacatcttg gtggatgact tgtaaattgt aatagatgga atgttttgct agtaatatag      60
tatttatcta gcagcaatat aatttatggc tcgctgagca ttggtacttc caattgcttg     120
tagacctaat cctggtggta ctagtagaag aggaagaatg gaagcagaga ctttgaacgc     180
aaatcaccct cccggttttc t                                                201

<210> SEQ ID NO 508
<211> LENGTH: 201
<212> TYPE: DNA
<213> ORGANISM: Soy

<400> SEQUENCE: 508
aacgcaaatc accctcccgg ttttcttcac cggtcgcttc ctgctgttgt gcctatgctt      60
ttgatttcaa taggatatgt tgaccctgga aagtgggtgg caattgctga aggaggtgca     120
cgatttgggt tcgatctgat ggccttcaca cttatcttta atcttgctgc catcttctgt     180
cagtacatag cagcaaaaat t                                                201

<210> SEQ ID NO 509
<211> LENGTH: 201
<212> TYPE: DNA
<213> ORGANISM: Soy

<400> SEQUENCE: 509
tctgtcagta catagcagca aaaattggtg ttatcacagg aaaagatctt gctcagattt      60
gcagtgatga gtacgataat tggacgtgca tgcttcttgg agttcaagca gaactttcgg     120
tgattatgct agaccttaac atgatattgg gcatggcaca tggattaaat attctttttg     180
ggtgggactt gttcacttgt g                                                201

<210> SEQ ID NO 510
<211> LENGTH: 201
<212> TYPE: DNA
<213> ORGANISM: Soy

<400> SEQUENCE: 510
ttttgggtgg gacttgttca cttgtgtctt tttaactgct actggtgctg ttttccatct      60
ccttcttttt gtcatccttg acattgagaa ggcaaagatc ctgggactgt tgtgtcagg      120 ttttgtattt ctttcatttg tacttggaac actcattaat caaccagaca ttccattatc     180
cattaatgga atactaacaa a                                                201

<210> SEQ ID NO 511
<211> LENGTH: 201
<212> TYPE: DNA
<213> ORGANISM: Soy

<400> SEQUENCE: 511
ttatccatta atggaatact aacaaagttg aatggggaga gtgcatttgt gctgatgagt      60
ctattaggag caattcttgt gcctcacaac ttctaccttc attcctctat tgtacagtgg     120
```
catcagggat caactaccat ttctaaggat gctttgtgtc ataaccattt tttggccatc     180
atgtgtgtct tcagtggcct t                                              201

<210> SEQ ID NO 512
<211> LENGTH: 201
<212> TYPE: DNA
<213> ORGANISM: Soy

<400> SEQUENCE: 512
ccatcatgtg tgtcttcagt ggcctttatt tggtcaataa tgtgctgatg aatgctgcag     60
caaatgagtt ctacagtatg ggtcttgttt tgactacttt tcaggacgca ttatcgccaa    120
tggaacaggt gttgcgtagt ccaatagcca tgcttgcttt tttactcatt ctgtttttt     180 caaatcaaac cacagcatta a                                              201

<210> SEQ ID NO 513
<211> LENGTH: 201
<212> TYPE: DNA
<213> ORGANISM: Soy

<400> SEQUENCE: 513
tttttcaaat caaaccacag cattaacttg gagtttcggt ggagaagtag tagtgcgaaa     60
tttcttaaaa ttggatattc cgggttggct tcattatgct acaattagag taattgctgt    120
tctgcctgcc ctttattgcg tttggaattc aggagctgaa gggatgtatc aactacttat    180
attcactcag attgtggtag c                                              201

<210> SEQ ID NO 514
<211> LENGTH: 201
<212> TYPE: DNA
<213> ORGANISM: Soy

<400> SEQUENCE: 514
cttatattca ctcagattgt ggtagctctg caacttcctt cttctgtgat ccccctttt     60 cggatcgcct catctagatc aataatgggg gtacacaaga tccctcaatt tgtggaattt    120
ttggcattga tcatattcat tgggatgctt ggcttgaata ttgtctttgt tgtagaaatg    180
gtatttggca gtagtgattg g                                              201

<210> SEQ ID NO 515
<211> LENGTH: 201
<212> TYPE: DNA
<213> ORGANISM: Soy

<400> SEQUENCE: 515
aaatggtatt tggcagtagt gattgggtgg gcaatttgag atggaatgtg gagactggtg     60
tgtctctctc ttatttggtc cttctgtgca ctgcttttgc atctttctgt ctgatgcttt    120
ggttagctgc cacaccttta aaatctgcaa gtgttcaatt ggatgatcag gcatggaact    180
gggacatgcc acaagccata c                                              201

<210> SEQ ID NO 516
<211> LENGTH: 201
<212> TYPE: DNA
<213> ORGANISM: Soy

<400> SEQUENCE: 516
gaactgggac atgccacaag ccataccaaa gtcacggatt gataacgagg aaacagattt     60

```
aaaagaaaca agatatcatg gagatgcatc agttcaggtg aaggaaccat caccagttct    120
agcaaggacc ctggaatact cagatgtacc aattgcaagt tttcatcatg atctacctga    180
aactatcatg gagcctgatg t                                              201

<210> SEQ ID NO 517
<211> LENGTH: 201
<212> TYPE: DNA
<213> ORGANISM: Soy

<400> SEQUENCE: 517
cctgaaacta tcatggagcc tgatgttcct gtgactactg taagggagac tcatccattt    60
acatcatttc ctttctcccc aacttctgtt gttaaggaat cagcttccac ttcagaatca    120
gaggcagtac cagctgtaag taatgagact tctgatatta tattgggaga ttccaaaact    180
ttgaaaacag aaactactgc c                                              201

<210> SEQ ID NO 518
<211> LENGTH: 201
<212> TYPE: DNA
<213> ORGANISM: Soy

<400> SEQUENCE: 518
aaactttgaa aacagaaact actgcccctg ttgagaaaac tgtagaagtt gagggagatt    60
caaatgccga aagggatgat gattatggag attcatggga aactgaagaa ataccaaaag    120
tggtctcact agccccatct tcagcatcag atggcccagc atcattcagg agccttagtg    180
ggaaaagtga tgatggaggg a                                              201

<210> SEQ ID NO 519
<211> LENGTH: 201
<212> TYPE: DNA
<213> ORGANISM: Soy

<400> SEQUENCE: 519
tagtgggaaa agtgatgatg gagggaatag cattggaagt ctttcaagat tagcaggttt    60
agggcgcggt gcaagacgtc aactagctgc tattcttgat gaattctggg gacaactttt    120
tcatttccat ggtcaatta cccaggaagc taaggccaag aaacttgatg ttttactggg    180
agtagattca acactcactg g                                              201

<210> SEQ ID NO 520
<211> LENGTH: 201
<212> TYPE: DNA
<213> ORGANISM: Soy

<400> SEQUENCE: 520
ctgggagtag attcaacact cactggttct ttgcaaaaaa tggattcatg taaggcatgt    60
tatgaatact tcaaatctgt aggaagtaga gctccagata ctttaatgaa ctctgctcca    120
tatgaatctc ccaggctgaa taggatgcaa agtaatttag aggcttcctt tgggcctcaa    180
aggagttctt cctcactgca g                                              201

<210> SEQ ID NO 521
<211> LENGTH: 201
<212> TYPE: DNA
<213> ORGANISM: Soy

<400> SEQUENCE: 521
ctcaaaggag ttcttcctca ctgcaggcaa atcctgtcca gtttatggat gaatatgttc    60
```
agacctccag ccgcaatctc cttgatgctg gtgaaaggcg ctattttagt gtgcacaatc      120
tacctacatc tgcagcctgg gattatcagc cagctaccat acatggttat caggtttcat      180
catatattaa tcaagttggt a                                                 201

<210> SEQ ID NO 522
<211> LENGTH: 201
<212> TYPE: DNA
<213> ORGANISM: Soy

<400> SEQUENCE: 522
ttcatcatat attaatcaag ttggtaaaga cacaaattct gataaattaa atggtctgag       60
ggaatcccct tccatgggta atacaaacaa ctacaggaat tctattgcat ttgctttggg      120
taaaaagttg caaaacggtt ctggtttaag ccaaccccca ggattcccga acattgctgt      180
ctctaagaat agccaattgc c                                                 201

<210> SEQ ID NO 523
<211> LENGTH: 201
<212> TYPE: DNA
<213> ORGANISM: Soy

<400> SEQUENCE: 523
gctgtctcta agaatagcca attgccatct gagaggtcct attatgattc tcgcccttcc       60
ggacctgtgg atagtacagt cagttcagtc tatgctaaga agttccacag cttgccagac      120
atttcaggat atgccatccc tcacagggat gtttacctgt ctgataaaag tgctccatgg      180
gatgattctg ttggtggata t                                                 201

<210> SEQ ID NO 524
<211> LENGTH: 201
<212> TYPE: DNA
<213> ORGANISM: Soy

<400> SEQUENCE: 524
catgggatga ttctgttggt ggatatagat cttctgcaag taggactcat tatgaaccgt       60
cattatattc aaattctgga tcaagtacag gagctccttt agcctttgat gtactctctc      120
catcaaaagt ctacggtggt gtactttctt ctcagttgag ttctggtttt ggcactggat      180
ccctctggtc cagacagcct t                                                 201

<210> SEQ ID NO 525
<211> LENGTH: 201
<212> TYPE: DNA
<213> ORGANISM: Soy

<400> SEQUENCE: 525
tggatccctc tggtccagac agccttttga gcagtttggg gtggatgata aaattcataa       60
tgctgcaaca gaagatgttg gaaataggcc tagtgcaact actcatgaaa ttacttcagt      120
tgtggatatt gatggcaagc ttcttcaatc ttttagacaa tgtatttttga aactcttaaa     180 attggaaggg tctgattggt t                                                 201

<210> SEQ ID NO 526
<211> LENGTH: 201
<212> TYPE: DNA
<213> ORGANISM: Soy

<400> SEQUENCE: 526

```
ttaaaattgg aagggtctga ttggttgttt aaacagaatg atggggctga tgaagatctg      60
attgaccgtg ttgctgcaag ggagaaattt gtttatgaaa ttgaaaccac agagatgaac     120
cgcaatcata tgggagaaac tcgatatctt tcttctgatg gaaggcttg ttcttcaatg      180 aagaataatg aggcaaattg g                                               201

<210> SEQ ID NO 527
<211> LENGTH: 201
<212> TYPE: DNA
<213> ORGANISM: Soy

<400> SEQUENCE: 527
caatgaagaa taatgaggca aattggtcta gttttctgt aacctcaatc cctaactgtg       60
gggaaggatg tgtttggaga gcagatataa taataagctt tggagtgtgg tgtatcaaac     120
gtgttctgga cctctcccta atggagagcc gaccagagct gtggggaag tacacttatg      180 tactcaatcg cctccagggc a                                               201

<210> SEQ ID NO 528
<211> LENGTH: 201
<212> TYPE: DNA
<213> ORGANISM: Soy

<400> SEQUENCE: 528
ttatgtactc aatcgcctcc agggcatcat tgatctggct ttctccaagc ctcgtagtcc      60
catgacccca tgcttttgcc ttcaagttcc catgacttac cagcagaagt caagctcgcc     120
tccttccaat gggatgctgc ccctgcgtc aaaaccgggc cgtggaaaat gcacaactgc      180
atcagtggtg tttgagatgg t                                               201

<210> SEQ ID NO 529
<211> LENGTH: 201
<212> TYPE: DNA
<213> ORGANISM: Soy

<400> SEQUENCE: 529
actgcatcag tggtgtttga gatggtcaag gatgtggaga tagcaatctc cagccggaaa      60
ggtcgcacag gaaccgctgc tggtgacgta gccttcccaa agggaaagga gaatttggca     120
tctgttctca acggtataa gcgtagatta ccaacaaac cagttggcac tactcaagaa       180
gggattcgca agatatactt g                                               201

<210> SEQ ID NO 530
<211> LENGTH: 201
<212> TYPE: DNA
<213> ORGANISM: Soy

<400> SEQUENCE: 530
aagaagggat tcgcaagata tacttgtagc attttgcctt tcactacgca ttaacataag      60
cagtgttcct tgggctgttt tgatttgtga agcagttcat gctgtagatc aaaggattac     120
cataggaagt tcctcgccac aagactgctg tctccgtgta ccaatcctca ctgcagattt     180
tatttccttg taatgttata t                                               201

<210> SEQ ID NO 531
<211> LENGTH: 201
<212> TYPE: DNA
<213> ORGANISM: Soy

<400> SEQUENCE: 531
```

```
gattttattt ccttgtaatg ttatatacac atagggttag agttactata tgtaattgca        60
acaaaaaatc aaaggaaaaa gatggttaga tggaaactga cttctaccat tttggcttat       120
ttttcattac ttcactcgct actgcatgca aggtggggaa acaaatggg aagaaaattg        180 tcgacatctt gtcatcttaa c                                                 201
```

```
<210> SEQ ID NO 532
<211> LENGTH: 201
<212> TYPE: DNA
<213> ORGANISM: Soy

<400> SEQUENCE: 532
atggaagcag agactttgaa tgcaaatcac cctcccggtt tcttcaccg gtcgctcccc         60 gctgttgtgc ctatcctttt gatttcaata ggatatgttg accctggaaa gtgggtggca       120
attgctgaag gaggtgcacg atttgggttc gatctgatgg ccttcatgct tatctttaat       180
tttgcagcca tcttctgtca g                                                 201
```

```
<210> SEQ ID NO 533
<211> LENGTH: 201
<212> TYPE: DNA
<213> ORGANISM: Soy

<400> SEQUENCE: 533
ttaattttgc agccatcttc tgtcagtaca tatcagcaaa aattggtgtt atcacaggaa        60
aggatcttgc tcagatttgc agtgatgagt acgataattg gacatgcatg cttcttggag       120
ttcaggcaga actttcggtg attatgctag accttaacat gatattgggc atggcacatg      180
gattaaatat tcttttttggg t                                                201
```

```
<210> SEQ ID NO 534
<211> LENGTH: 201
<212> TYPE: DNA
<213> ORGANISM: Soy

<400> SEQUENCE: 534
acatggatta aatattcttt tgggtgggga cttgttcact tgtgtctttt taattgctac        60
tggtgctgtt ttccatctcc ttcttttttgc cctcctggac attgagaagg tgaagatcct      120
gggcctgttt gtgtcaggtt ttgtatttct ttcgtttgta cttggaacac tcattaatca      180
accagacatt ccattatcca t                                                 201
```

```
<210> SEQ ID NO 535
<211> LENGTH: 201
<212> TYPE: DNA
<213> ORGANISM: Soy

<400> SEQUENCE: 535
aatcaaccag acattccatt atccattaat ggaatactaa caaagttgag tggggagagt        60
gcatttgtgc tgatgagtct attaggagca actcttgtgc ctcacaactt ctaccttcat      120
tcctctattg tacagtggca tcaggatca actaccattt ctaaggatgc tttatgtcat       180 aaccatttttt tggccatcat g                                                201
```

```
<210> SEQ ID NO 536
<211> LENGTH: 201
<212> TYPE: DNA
<213> ORGANISM: Soy
```

-continued

<400> SEQUENCE: 536

```
gtcataacca ttttttggcc atcatgtgtg tcttcagtgg cctttatttg gtaaataatg    60
tgctgatgaa tgctgcagca aatgagttct acagtatggg tcttgttttg actactttc   120
aggatgcatt atcaccaatg gaacaggtgt tgcgtagtcc aatagccatg cttgctttt   180
tactcattct gttttttca a                                              201
```

<210> SEQ ID NO 537
<211> LENGTH: 201
<212> TYPE: DNA
<213> ORGANISM: Soy

<400> SEQUENCE: 537

```
tttttactc attctgtttt tttcaaatca aaccacagca ttaacttgga gttttggtgg    60
agaagtagtt gtgcaaagtt tcttaaaatt ggatattccg ggttggcttc attatgctac  120
aattagagta attgctgttc tgcctgccct ttattgtgtt tggagttcag gagctgaagg  180
gatgtatcaa ctacttatat t                                             201
```

<210> SEQ ID NO 538
<211> LENGTH: 201
<212> TYPE: DNA
<213> ORGANISM: Soy

<400> SEQUENCE: 538

```
gaagggatgt atcaactact tatattcact cagattgttg tagctctgca acttccatct    60
tctgtgatcc ccctttttcg gatcgcctca tctagatcaa taatgggggt acacaagatc  120
cctcaatttg tggaattttt ggcattgatc atattcattg ggatgcttgg cttgaatatt  180
gtctttgttg tagaaatgat a                                             201
```

<210> SEQ ID NO 539
<211> LENGTH: 201
<212> TYPE: DNA
<213> ORGANISM: Soy

<400> SEQUENCE: 539

```
atattgtctt tgttgtagaa atgatatttg gcagtagtga ttgggtgggc aatttgagat    60
ggaatgtggg gactggtgtg tctctctctt atttggttct tctttgcact gcgtttgcat  120
cattctgtct gatgctttgg ttagctgcca cacctttaaa gtctgctagt gttcaattgg  180
atgatcagca atggaactgg g                                             201
```

<210> SEQ ID NO 540
<211> LENGTH: 201
<212> TYPE: DNA
<213> ORGANISM: Soy

<400> SEQUENCE: 540

```
attggatgat cagcaatgga actgggacat gccacaggcc gtaccaaaat cacggattga    60
taacgaggaa acagatttaa aagaaacaag atatcaagga gatgcatcag ttcagggaa   120
ggaaccatca ccagctctag caaggaccct ggaatattca gatgtaccag ttgcaagttt  180
tcatcttgat ctacctgaaa c                                             201
```

<210> SEQ ID NO 541
<211> LENGTH: 201
<212> TYPE: DNA
<213> ORGANISM: Soy

<400> SEQUENCE: 541
agttttcatc ttgatctacc tgaaactatc atggagcctg atgttcctgt gactactgta  60
agggagactc atccatttac atcatttcct tgctccccaa catctgttaa ggaatcagct  120
tccacttcag aatcggaggc agtaccagct gtaagtaatg agacttctga tattatattg  180
ggacattcca aaactttgaa a  201

<210> SEQ ID NO 542
<211> LENGTH: 201
<212> TYPE: DNA
<213> ORGANISM: Soy

<400> SEQUENCE: 542
tattgggaca ttccaaaact ttgaaaacag aaactactgc ccctgttgag aaaactgtag  60
aaattgaggg agattcaaat gccgaaaggg atgatgatga tggagattca tgggaaactg  120
aagaaataca aaaagtggtc tcactagccc catcttcagc atcagatggc ccagcatcat  180
tcaggagcct tagtgggaaa a  201

<210> SEQ ID NO 543
<211> LENGTH: 201
<212> TYPE: DNA
<213> ORGANISM: Soy

<400> SEQUENCE: 543
atcattcagg agccttagtg ggaaaagtga tgatggaggg aatagcattg gtagtctttc  60
gagattagca ggtttagggc gcggtgcaag acgtcaacta gctgctattc ttgatgaatt  120
ctggggacaa ctttatggtt tccatggtca atttacccag gaagctaagg ccaagaaact  180
tgatgtttta ctgggaatag a  201

<210> SEQ ID NO 544
<211> LENGTH: 201
<212> TYPE: DNA
<213> ORGANISM: Soy

<400> SEQUENCE: 544
aaacttgatg ttttactggg aatagattca agactcactg gttctttgca aagaatggat  60
ccatgtggaa aggaatattc tgaatattta atatctgtag gaagtagagc tccagatact  120
ttaatgaact ctgctccata tgaatctccc aggcagaata ggatccaaag taatttagat  180
gcttcctatg ggcctcaaag g  201

<210> SEQ ID NO 545
<211> LENGTH: 201
<212> TYPE: DNA
<213> ORGANISM: Soy

<400> SEQUENCE: 545
tagatgcttc ctatgggcct caaggagtt cttcctcact gcgggcaaat cctgtccagt  60
ttatggatga atatgttcag acctccagcc gcaatctcct cgatgctggt gaaaggcgct  120
attccagtgt gcgcaattta cctacgtctg cagcctggga ttatcagcca gctactatac  180
atggttatca ggtttcatcg t  201

<210> SEQ ID NO 546
<211> LENGTH: 201
<212> TYPE: DNA

```
<213> ORGANISM: Soy

<400> SEQUENCE: 546
tatacatggt tatcaggttt catcgtatat taatcaggtt ggtaaagaca caaattctga        60
taacttaaat ggtctgaggg aatcccttc catgggtaat acgaaccact acaggaattc        120
tatgggtaat acgaactaca ggaattctat tgcatttgct ttgggtaaaa agttgcaaaa       180
tggttcaggt ttaagccaac c                                                  201

<210> SEQ ID NO 547
<211> LENGTH: 201
<212> TYPE: DNA
<213> ORGANISM: Soy

<400> SEQUENCE: 547
caaaatggtt caggtttaag ccaacccca gggttccaga acattgctgt ctctaagaat        60
agccaattgc catctgagag gtcctattat gattctcgcc cttccggacc tgtggatagt       120
acagtcagtt cagtcaatgc taaaaagtac cacagcttgc cagatatttc aggatatgcc       180
attcctcaca gggatgttta c                                                  201

<210> SEQ ID NO 548
<211> LENGTH: 201
<212> TYPE: DNA
<213> ORGANISM: Soy

<400> SEQUENCE: 548
atgccattcc tcacagggat gtttacatgt ctgataagag tgctccatgg gatggttctg        60
ttggtggata tagatcttct gcaagtagga ctcattatga accgtcatta tattcaaact       120
ctggatcaag gacaggagct cctttagcct ttgatgtact ctctccatca aaagcctaca       180
gtgatgaact ttcttctcag t                                                  201

<210> SEQ ID NO 549
<211> LENGTH: 201
<212> TYPE: DNA
<213> ORGANISM: Soy

<400> SEQUENCE: 549
ctacagtgat gaactttctt ctcagttgag ttctggtttt ggcactggat ccctctggtc        60
cagacagcct tttgagcagt ttggggtgga tgataaaatt cataatgctg caacagaaga       120
tgttggaaat aggcctagtg caactactca agaaactact tcagtggtgg atatagatgg       180
caaacttctt caatctttta g                                                  201

<210> SEQ ID NO 550
<211> LENGTH: 201
<212> TYPE: DNA
<213> ORGANISM: Soy

<400> SEQUENCE: 550
gatggcaaac ttcttcaatc ttttagacaa tgtatttga aactcttaaa attggaaggg        60
tctgattggt tgtttaaaca gaatgatggg gctgatgaag atctgattga tcgtgttgct       120
gcaagggaga aatttgttta tgaaattgaa accacagaga tgaaccgcaa tcatatggga       180
gaaactcgat atctttcttc t                                                  201

<210> SEQ ID NO 551
<211> LENGTH: 201
```

```
<212> TYPE: DNA
<213> ORGANISM: Soy

<400> SEQUENCE: 551
tgggagaaac tcgatatctt tcttctgatg ggaattttc cgtaacctca atccctaact    60
gtggagatgg atgtgtatgg agagcagaca taataataag ctttggggtg tggtgtatca   120
aacgtgttct tgacctctca ttaatggaga gccggccaga gctgtggggg aagtacactt   180
atgtactcaa tcgcctccag g                                             201

<210> SEQ ID NO 552
<211> LENGTH: 201
<212> TYPE: DNA
<213> ORGANISM: Soy

<400> SEQUENCE: 552
cacttatgta ctcaatcgcc tccagggcat cattgatctg gctttctcca gcctcgtag    60
tcccatgacc ccatgctttt gccttcaagt tccatgact taccagcaga agtcaggctc   120
acctccttcc aatgggatgc tgcccctgc atcaaaacca ggccgtggaa aatgcacaac   180
tgcgtcagtg gtgtttgaga t                                             201

<210> SEQ ID NO 553
<211> LENGTH: 201
<212> TYPE: DNA
<213> ORGANISM: Soy

<400> SEQUENCE: 553
acaactgcgt cagtggtgtt tgagatggtc aaggatgtgg agatagcaat ctctagccgg    60
aaaggtcgca caggaactgc tgctggtgat gtagctttcc caagggaaa ggagaatttg   120
gcatctgttc tcaaacggta taagcgtaga ttatccaata aaccagttgg cactactcaa   180
gaagggattc gcaagattcc c                                             201

<210> SEQ ID NO 554
<211> LENGTH: 201
<212> TYPE: DNA
<213> ORGANISM: Soy

<400> SEQUENCE: 554
agacacctca ctgttttaaa actgcataac ataatccaaa atatgaatct ctgtagaagg    60
agatagggta ctaagggtag caatttctag ttcaggatca tgtcaacaaa ttcagcaaca   120
acagttagtt agattattag aagaagacca ataggaataa gaatggctac aaaactaggc   180
cctatcggta gaggacagag a                                             201

<210> SEQ ID NO 555
<211> LENGTH: 201
<212> TYPE: DNA
<213> ORGANISM: Soy

<400> SEQUENCE: 555
taggccctat cggtagagga cagagagagt gaggaacaag agtatcagaa agaaaccgcc    60
accataataa taaataatta tttatttata aatatataaa aatatggata atacttttc   120
agacaaccga tttaattatt atctcttta attgaaaatt gaggtgtgat ctggtttaag   180
aatgaagtca tgaatatttt a                                             201

<210> SEQ ID NO 556
```

```
<211> LENGTH: 201
<212> TYPE: DNA
<213> ORGANISM: Soy

<400> SEQUENCE: 556
ttaagaatga agtcatgaat attttacctt gaagagctta acagacaata ttaattgaat      60
accaaataaa attcataata tcttgttatg ctaaaataaa taaataaatt tgaatgaaaa     120
tgaatataaa aacaaataaa ggtaagagaa aaaaaaatac tagttggact aaaagactgt     180
taatagcaat tttttataga g                                                201

<210> SEQ ID NO 557
<211> LENGTH: 201
<212> TYPE: DNA
<213> ORGANISM: Soy

<400> SEQUENCE: 557
actgttaata gcaattttttt atagagactt tttggaacac atttatgaaa tgaaactttt      60
ctttctttgt ttcttttctg gcttcattca ctcatgcttt ctctctcttg aatgtggcct     120
agaaagttga aaccctccac ccatgtcata aattttcttt tttcttttcc ttagctgctc     180
tctctccatg ttcacataag t                                                201

<210> SEQ ID NO 558
<211> LENGTH: 201
<212> TYPE: DNA
<213> ORGANISM: Soy

<400> SEQUENCE: 558
tgctctctct ccatgttcac ataagttagt agtagcactt acatcattaa atatgctaaa      60
ttattaaaca ataaattaat atataattta tttaatgttt atatacatga tcccgtgaga     120
tctactttgc aggagtaaat agcatagctg ggatagagac ttgtggcagc tgaaaagaaa     180
ttcagagaaa ggtaaagatt t                                                201

<210> SEQ ID NO 559
<211> LENGTH: 201
<212> TYPE: DNA
<213> ORGANISM: Soy

<400> SEQUENCE: 559
agaaattcag agaaaggtaa agatttcaga accctaataa ccactctcag actctttagg      60
aactgttctg ttgtacggtc ttcttaattc attctcagtc ctgaaacccc catcatcgtc     120
cttgtcgaaa ttcgtgcaac tgttttttttt cttcctcttt tctctttctt ctttcttctt     180
cttcgtgtgt ttcttcttgc a                                                201

<210> SEQ ID NO 560
<211> LENGTH: 201
<212> TYPE: DNA
<213> ORGANISM: Soy

<400> SEQUENCE: 560
ttcttcttcg tgtgtttctt cttgcaacag atccacgcca acgctttcag ttcctctttt      60
tatctatttc atgaccgtac acgccgtagg gttttttgttt tgtttcttcg tttctcagca     120 ttttttttagc gttttgtttt cttctaaaga tctatttttgt tgttgttatt actatttatg     180
attattataa ttataattat a                                                201
```

```
<210> SEQ ID NO 561
<211> LENGTH: 201
<212> TYPE: DNA
<213> ORGANISM: Soy

<400> SEQUENCE: 561
ttatgattat tataattata attataatta taattattta actatggtgg atgctgtaat       60
ttgttgtttt ggtggttttt ttttgtttgt taaagcaaat tcaagaaaga taaatgatt       120 ttgttgcgtt ggttttttat tttcttgtaa tcaaccgttg tgctgatgaa ttttaaggt       180 atttgttgtt tctattggta t                                                201

<210> SEQ ID NO 562
<211> LENGTH: 201
<212> TYPE: DNA
<213> ORGANISM: Soy

<400> SEQUENCE: 562
aaggtatttg ttgtttctat tggtatggtg gctgtgttat tgttgtttac gtgaactaat       60
tcgatgcagg atttgaggag tccaaggagg ttgatttatc agggggtgct tgctggatt       120 agcattgaga gtctcaagag ggtgtttggt ttgggaagtt tgagatggat tggattggct      180
ttcagtcatg tgaaggagat g                                                201

<210> SEQ ID NO 563
<211> LENGTH: 201
<212> TYPE: DNA
<213> ORGANISM: Soy

<400> SEQUENCE: 563
tggctttcag tcatgtgaag gagatgagtg gaataatttg taagactgta gtgaagaaat       60
tttggtatgg cgtgcaggtt gactttagtg ataagtcaga tttgtgtctg acatagtatc      120
acagttaatg ttggaacatc actggctggt tgatgctggg atacgaggtg gagaagctag      180
ttgttgaatt gttgaaggtg t                                                201

<210> SEQ ID NO 564
<211> LENGTH: 201
<212> TYPE: DNA
<213> ORGANISM: Soy

<400> SEQUENCE: 564
gctagttgtt gaattgttga aggtgtcttg gactggcttg caggttgaaa gtcctttgtc       60
ttttaattat ctttgaagcg gctaacatct tggtgatgac ttgtaaattg tagtagatag      120
aatgtttgct agtaataatg gtatttatct agcagtaata taatttatgt ctctctgagt      180
attggtgctt ccaagtgttt c                                                201

<210> SEQ ID NO 565
<211> LENGTH: 201
<212> TYPE: DNA
<213> ORGANISM: Soy

<400> SEQUENCE: 565
ggattacatt acgaatatta acactagcat tgataaaatc cacaatcatc atttattgta       60
gacacctcac tgttttagta aaattgcata ataatacatt ttttttattt ataaatatat      120
aaataaattt tataaaagat aacaatgaga tattgattac aggagcacta gattcaattc      180
tcatgtttga atgtgaatga a                                                201
```

<210> SEQ ID NO 566
<211> LENGTH: 201
<212> TYPE: DNA
<213> ORGANISM: Soy

<400> SEQUENCE: 566
aattctcatg tttgaatgtg aatgaaaata gtaattgaaa atcatcaaa tttagtccat      60 caattttttt taatggagat tgcttactaa taaaagcgag tagatattcc ttatgaataa    120
tatgataacc aattttttat taaaaaatta gacataagta ataattaaga attaaaattg    180
tgatggtaga atattaattg a                                              201

<210> SEQ ID NO 567
<211> LENGTH: 201
<212> TYPE: DNA
<213> ORGANISM: Soy

<400> SEQUENCE: 567
aattgtgatg gtagaatatt aattgagtgt gaaatagaag ttttaaatat ctttcggtta     60
aaataaaaaa gacaaataaa agagaaaaat actaaaaaac gttaatagcg ttttcgttt    120 tttgagatac ttattggaac acattatga aatatgaaac ttttctttcc ttcttttctc    180
gcttcattca ctcacacttt c                                              201

<210> SEQ ID NO 568
<211> LENGTH: 201
<212> TYPE: DNA
<213> ORGANISM: Soy

<400> SEQUENCE: 568
ttctcgcttc attcactcac actttctctc tcttcaatgt ggcctagaaa gttgaaaccc     60
ttcacccatg ccataaattt tcttttttct ttcttagctt tctctcagct ttccgggaaa    120
atctctctct ccattttcac ataagttagt agtagtacct tacatcatta cctatgctaa    180
attattaaac aatgaattaa t                                              201

<210> SEQ ID NO 569
<211> LENGTH: 201
<212> TYPE: DNA
<213> ORGANISM: Soy

<400> SEQUENCE: 569
gctaaattat taaacaatga attaattaat ttgatttaat gtttatatat atgatccgtg     60
agatctactt tgcaggagta aatagcacag ctgagacaga gacttgtggc agctgaaaag    120
aaattcagag aaaaggtaga gagatttcag aaccctaata caaactactc tcagactctg    180
gtgaaactgt ttttctgttg t                                              201

<210> SEQ ID NO 570
<211> LENGTH: 201
<212> TYPE: DNA
<213> ORGANISM: Soy

<400> SEQUENCE: 570
ctctggtgaa actgttttc tgttgtattg tacggtcttt ttaattctta gtcgtgaaac      60
cccaatcatc gtcctcgtcg aaattcgtgc ttctgttttt ccccttatt ttctctttct    120 tcttccttct tcctgtgttt cttcttgcat cagatccacg ccaactcttt cagttcctct    180 ttttttatc tatttcatga c                                              201

<210> SEQ ID NO 571
<211> LENGTH: 201
<212> TYPE: DNA
<213> ORGANISM: Soy

<400> SEQUENCE: 571 cctcttttttt ttatctattt catgaccgta cacagggtag ggttttttgtt ttgcttccaa    60
gtttctcaac atttttttagc gttttgtttt cttctagaga tctaattttt tgttgttgtt   120
aattatgtaa ctttttttttt tataaaaaat attaattatt agtttgttag cagagactaa   180
gaagatagaa tccaccattt t                                              201

<210> SEQ ID NO 572
<211> LENGTH: 201
<212> TYPE: DNA
<213> ORGANISM: Soy

<400> SEQUENCE: 572
actaagaaga tagaatccac cattttttttc tccttccttt tttaaccacc caaccaacct    60
tatatctcct tgataaattg gtaattattt aactgtggtg gatgctgtaa actttgttgc   120
tgtggtggtc tttttgttac cgttttttttt tggtgcttttt taaatcaaat ttaagaaaga   180
taaaatgatt tttttttgtg t                                              201

<210> SEQ ID NO 573
<211> LENGTH: 201
<212> TYPE: DNA
<213> ORGANISM: Soy

<400> SEQUENCE: 573
aaagataaaa tgattttttt ttgtgttgtt gatggatttt tttcactgta atttgttatt    60
tctattatgg cggttgtgtt gttgtttatg tgaactaatt cgatgcagga tttgaggagt   120
tcgaggaggt tgatttatca tggagtgctt tgttttggaa gtttgagatg gattggattg   180
atttatcaat gagtggaatc a                                              201

<210> SEQ ID NO 574
<211> LENGTH: 201
<212> TYPE: DNA
<213> ORGANISM: Soy

<400> SEQUENCE: 574
gattgattta tcaatgagtg gaatcatttg taaggttgtg gtgaagagat tttgggatgg    60
gaagcaggtt gactttacta atgaagtcag atttatgcat gatatatgat catagttgat   120
gttggaacat catccgctgg gttgctgttg gggtacgagg aagagaagct agttgttgaa   180
ttgttgaagg tgtcttggac t                                              201

<210> SEQ ID NO 575
<211> LENGTH: 201
<212> TYPE: DNA
<213> ORGANISM: Soy

<400> SEQUENCE: 575
ttgaattgtt gaaggtgtct tggactggct tgcaagttga aagtcctttg tcctttaatt    60
atatggatta ttatggttaa tgtttgaagc tgctaacatc ttggtggatg acttgtaaat   120
tgtaatagat ggaatgtttt gctagtaata tagtatttat ctagcagcaa tataatttat   180

```
ggctcgctga gcattggtac t                                               201

<210> SEQ ID NO 576
<211> LENGTH: 201
<212> TYPE: DNA
<213> ORGANISM: Soy

<400> SEQUENCE: 576
cgtttgtaaa attgttcttt atttaactta atcttaatta aaacaacaac agaaacaaaa     60
caaaaattat caaattatct gcaggatcta ttttctatat gtttatttgc aactttacta    120
aatgaaaact ccattcaaaa ataatttata ttgaccatga ctatttacta ttcagagtat    180
cctctctggc actacaacta c                                              201

<210> SEQ ID NO 577
<211> LENGTH: 201
<212> TYPE: DNA
<213> ORGANISM: Soy

<400> SEQUENCE: 577
agtatcctct ctggcactac aactaccaat ttgacttttg tatcttattg ctaggaaaga     60
atctatatcc accctattta aaccattaat atacaaatac acttacgcac aaacattcaa    120
aagagtattc aaaacataat tcaacataaa aaaaaatgta tctaatatgt agtgtgtttt    180
ggatcaacat tgacaactca t                                              201

<210> SEQ ID NO 578
<211> LENGTH: 201
<212> TYPE: DNA
<213> ORGANISM: Soy

<400> SEQUENCE: 578
gttttggatc aacattgaca actcattata ctttaatgat ttaaagtctc aaattatata     60
aaaaaaaggc ggaaactaat atatttaaca catctacctg gatggacgaa tgtccaagca    120
tggagatgga ttgctcttta cttgtgaaag gtttccttca aatatggtaa aaattgttaa    180
tagaataaac aacaaacatt a                                              201

<210> SEQ ID NO 579
<211> LENGTH: 201
<212> TYPE: DNA
<213> ORGANISM: Soy

<400> SEQUENCE: 579
gttaatagaa taaacaacaa acattatttt gatgtgagtg aaatgactga tttttttta     60 agtaaagtcc ctaataaaga agaagaaaaa cttctaaaaa tgactaatta gattttctag    120
taaataaata ttaataacgg acaaagtata acgataaata gccgacacat acagaaaata    180
taaataagat gtcatttaat a                                              201

<210> SEQ ID NO 580
<211> LENGTH: 201
<212> TYPE: DNA
<213> ORGANISM: Soy

<400> SEQUENCE: 580
aaatataaat aagatgtcat ttaatactca atggacattt cataaattcg gctgagacag     60
ttaaattgta atctttgtat ttatccattt cccttatct ctaaacttta gagagaataa    120
tgaatatttt tggaaaatgg cgaagaagaa tatattttaa acatttcccc cccttttgg    180
```
aagagaagtg cgaatgagat a                                                    201

<210> SEQ ID NO 581
<211> LENGTH: 201
<212> TYPE: DNA
<213> ORGANISM: Soy

<400> SEQUENCE: 581
tttggaagag aagtgcgaat gagatagagg cagctataaa taaatgaaac agtaagtgtc      60 gttttagga gttacagtta ctagcctcct tttgaagatt ctcatccttt ctctctcctc      120
gtgttcaccc ataccttaca taataatacc cggtttactt tcccagaacc tcctctctct     180
taatatgaat ataaaaattt a                                                    201

<210> SEQ ID NO 582
<211> LENGTH: 201
<212> TYPE: DNA
<213> ORGANISM: Soy

<400> SEQUENCE: 582
tctcttaata tgaatataaa aatttaaaaa tatatatact attatttatc tgaatgtatg      60
aatggtggtt aatcttaatc tgagtgtgtg agatctactt agtagtggta gtggcagatg      120
aagaagagag aagaagcagt gaaggtaaac atttcttcag aaccctaact gtacggtcat     180
catcatcgtc cttgaatttc g                                                    201

<210> SEQ ID NO 583
<211> LENGTH: 201
<212> TYPE: DNA
<213> ORGANISM: Soy

<400> SEQUENCE: 583
gtcatcatca tcgtccttga atttcgtgct aaatgttcct tcctaaggct tcatcagatc      60
cacgccaacg ttttcattac ttcttgaact tttccattca gtgagggttc aggcttttt     120 acctctcttt cttattctcc ttgggattcc ggagctgagt tctgtttcgc tacttgtctt     180 atggttttg gttgcttgcg t                                                    201

<210> SEQ ID NO 584
<211> LENGTH: 201
<212> TYPE: DNA
<213> ORGANISM: Soy

<400> SEQUENCE: 584
gtcttatggt ttttggttgc ttgcgtgcta tttgttaccg ctttctactg ttaattaatt      60
aattgtaacg aagatagtgt gaatataaag tttctgtttt tactttggtg ctaatgttgt      120
tacattggtc aatttgatga tgcaggattt gagaagttcg agtgggaagt gatgatgatg     180
gatgtgtttg ggaacccttt t                                                    201

<210> SEQ ID NO 585
<211> LENGTH: 201
<212> TYPE: DNA
<213> ORGANISM: Soy

<400> SEQUENCE: 585
tgatggatgt gtttgggaac ccttttgaa attgagaatc gccagagctg tttatgaagt       60
ttggcctcaa attggattga ttttcagtca tgttgaggag atgaatggaa tttttaatag     120

```
tggtgtgttg tgaaaagatt ttgtgatggt ataccttgac ttgatcgaaa acctcggtct    180
tgttagtatc ggatgtgcta t                                              201

<210> SEQ ID NO 586
<211> LENGTH: 201
<212> TYPE: DNA
<213> ORGANISM: Soy

<400> SEQUENCE: 586
ggtcttgtta gtatcggatg tgctatatgt tcaactttttt gcaagttgca agtgatttta    60
gcagcttagt ttatatttga agctgctaac atatctatga ttgtaataaa taaataaata   120
caatcttttg atagaaatat agttaagttg cagttatgga attgtctatg ggtcattagg   180
ttttagctac ttcaaagtgg t                                              201

<210> SEQ ID NO 587
<211> LENGTH: 201
<212> TYPE: DNA
<213> ORGANISM: Tomato

<400> SEQUENCE: 587
cttgttcatg tcaaatgggt tgctaagtga tgctgtagtg ctagtttact gcgatctctg    60
ggcttgctaa ccatttaaat caaataatgg agtctgaaac tctgactaga aatataggc   120 agcccagcat gcttcagcga gtactttctg cttctgtgcc aatgctgttg attgcagttg   180
gctatgttga tcctgggaaa t                                              201

<210> SEQ ID NO 588
<211> LENGTH: 201
<212> TYPE: DNA
<213> ORGANISM: Tomato

<400> SEQUENCE: 588
agttggctat gttgatcctg ggaaatgggc tgcaatggtt gatggaggag cccgatttgg    60
gtttgatttg gtcatgctag tactcttgtt caattttgct gccattctgt gccagtatct   120
gtctgcttgt atagccttgg ttacagaccg agatcttgcg cagatttgca gtgaagaata   180
tgacaaagtt acatgcatat t                                              201

<210> SEQ ID NO 589
<211> LENGTH: 201
<212> TYPE: DNA
<213> ORGANISM: Tomato

<400> SEQUENCE: 589
gaatatgaca aagttacatg catattccta ggaattcaag ctgaggtttc gatgattgct    60
ttggacctca caatggtttt gggcactgcc catgggctta atgttgtgtt tggagttgac   120
ctgtttagct gtgttttcct gactgcaacc ggtgccattt gtttccact gcttgcttct   180 ctctttgaca atggcagtgc a                                              201

<210> SEQ ID NO 590
<211> LENGTH: 201
<212> TYPE: DNA
<213> ORGANISM: Tomato

<400> SEQUENCE: 590
cttctctctt tgacaatggc agtgcaaaat tcttatgtat tggctgggca agctctgtac    60
tgctctctta tgttttgga gtggttataa ctctacctga aactccattc tccattggtg   120
```

```
gtgtgctgaa taagtttagt ggagagagtg catttgcatt gatgagtctt cttggagcaa      180
gtattatgcc tcacaattt t                                                 201

<210> SEQ ID NO 591
<211> LENGTH: 201
<212> TYPE: DNA
<213> ORGANISM: Tomato

<400> SEQUENCE: 591
agcaagtatt atgcctcaca atttttacct ccattcttct attgtacagc aaggtaagga      60
atcaacagag ctttccaggg gagctctgtg tcaggaccat ttttttgcca ttgttttcat     120
attcagtggc attttcctgg tcaactatgc cgcgatgaat tcagcagcga atgtgtctta     180
cagtactggc cttttgttgc t                                                201

<210> SEQ ID NO 592
<211> LENGTH: 201
<212> TYPE: DNA
<213> ORGANISM: Tomato

<400> SEQUENCE: 592
tcttacagta ctggcctttt gttgctgaca tttcaggaca cattgtcatt gctcgatcag      60
gttttcagaa gctcagttgc accattcacc ataatgctgg ttacatttat ttccaatcaa    120
gttacaccac taacttggga tcttggtaga caagcagttg tgcatgactt atttggaatg    180
gacatcccag gctggcttca t                                                201

<210> SEQ ID NO 593
<211> LENGTH: 201
<212> TYPE: DNA
<213> ORGANISM: Tomato

<400> SEQUENCE: 593
gaatggacat cccaggctgg cttcatcatg tgacgatcag agttatttcc attgtcccag      60
ctctttattg tgtatggagt tcaggagctg aaggcctata tcagttactt atactgacac    120
aggttgtggt ggctcttgtc cttccatctt ctgtcatacc cctgttcaga gttgcttctt    180
ccagatcaat tatgggtatc c                                                201

<210> SEQ ID NO 594
<211> LENGTH: 201
<212> TYPE: DNA
<213> ORGANISM: Tomato

<400> SEQUENCE: 594
ttcttccaga tcaattatgg gtatccacaa aatttctcag ttaatggagt tcttatctct      60
tggcacattt attggcttac ttggcctaaa gattatattt gtcatagaga tgatatttgg    120
aaatagtgat tgggttaata atttgaagtg gaatattggg agtagtgtgt ctactccata    180 tgttttctc ctcatcgcag c                                                 201

<210> SEQ ID NO 595
<211> LENGTH: 201
<212> TYPE: DNA
<213> ORGANISM: Tomato

<400> SEQUENCE: 595
ccatatgttt ttctcctcat cgcagcctct ttatgtcttt gtctgatgct gtggttagca      60
```
gttactcctc tgaaatctgc aagttccagg ttcgatgctc aggcgtttct gcaaacgcat    120
gtgcctgagc catattcaga gtgtaatcaa cttggtgcga gtaatgctat gtttggtcta    180
gtagaaggat cctcccaaaa g    201

<210> SEQ ID NO 596
<211> LENGTH: 201
<212> TYPE: DNA
<213> ORGANISM: Tomato

<400> SEQUENCE: 596
gtctagtaga aggatcctcc caaaagcaag aaggtgcatt tcatgtggaa aaatccttgg    60
taacccatcc agatttatca actaaagatc ctgatcaact cttgccagaa tctctcttgg    120
attttgaaaa ggtccatcag ttggctacta ttgatgagag caaatctgaa acaacatttt    180
cagctcctgc tgtcgttcat c    201

<210> SEQ ID NO 597
<211> LENGTH: 201
<212> TYPE: DNA
<213> ORGANISM: Tomato

<400> SEQUENCE: 597
attttcagct cctgctgtcg ttcatcctga ggtacctgta tcagcaggag caagtcccag    60
tgtgaaaagt gtttgtaatg aggtttctgg tgttgtatca gtggatacca gtgtcttcaa    120
tactgaaact gtggatgtcg cagagaagac tctcagaatt gaaggggaca tggcaaatga    180
cagggatgat ggagattcgt g    201

<210> SEQ ID NO 598
<211> LENGTH: 201
<212> TYPE: DNA
<213> ORGANISM: Tomato

<400> SEQUENCE: 598
aatgacaggg atgatggaga ttcgtgggaa gagcctgaag aggcaatcaa aggagtatct    60
gagaacgctc aatctttat ttctgatggt ccggggtcat acaaaagtct aagtggaaaa    120
ctagaggaca cggggagtgg tacaggaagt ctatcaagat tagcaggtct tggtcgtgca    180
gctaggaggc agttaacaga a    201

<210> SEQ ID NO 599
<211> LENGTH: 201
<212> TYPE: DNA
<213> ORGANISM: Tomato

<400> SEQUENCE: 599
gtgcagctag gaggcagtta acagaagctc taaatgagtt ttgggggcag cttttttgatt    60 accatggcat ggcaacagca gaagcgaagt ccaagaaact ggatataata cttggtctgg    120
attcaaagat gaatccaaaa cctgcccctg catcattaaa agttgaaagc agtgcgtata    180
ttccatcggg gagtgcaagg a    201

<210> SEQ ID NO 600
<211> LENGTH: 201
<212> TYPE: DNA
<213> ORGANISM: Tomato

<400> SEQUENCE: 600
gtatattcca tcggggagtg caaggatacc agagcctctg atcaactcgc atgtgtactc    60

```
tcccaagcag caatttgcgt ctaacattgt ggactctgct tatagagtcc caaggagcc    120 atcttcgaca tcttctatgt ggtctaacca tatgaaatta gtaggtgcat atgtgcaaag    180
ttccaacagc aacatgcttg a                                              201
```

<210> SEQ ID NO 601
<211> LENGTH: 201
<212> TYPE: DNA
<213> ORGANISM: Tomato

<400> SEQUENCE: 601

```
caaagttcca acagcaacat gcttgactca ggggagaggc gctattctag tatgcggatt    60
ccagcgactt ctgctggcta tgatcagcag cctgccactg tgcatggata tcagattact   120
gcttacctta atcaacttgc gaaagaaaga ggatctgatt atttaaatgg gcaactggag   180
tcaccatctc ctcgttctgt a                                              201
```

<210> SEQ ID NO 602
<211> LENGTH: 201
<212> TYPE: DNA
<213> ORGANISM: Tomato

<400> SEQUENCE: 602

```
tggagtcacc atctcctcgt tctgtatcat cactgacgtc aaactatgca gaaccattgg    60
ctcgtgtttc ggggcaaaaa cctcagagtg gagtcagtag tcgagcacca cctggttttg   120
gaaatgtccc tgtaggccga ataattcga tgcagcccac taacactact tctgtcgacc    180
atagctctac tgaaactgct g                                              201
```

<210> SEQ ID NO 603
<211> LENGTH: 201
<212> TYPE: DNA
<213> ORGANISM: Tomato

<400> SEQUENCE: 603

```
cgaccatagc tctactgaaa ctgctgaaag cgtggctggt tcagccaact ctaagaagta    60
ctacagcttg cctgatatct cagggcgcta tgttcctcgc caagattcta tagtgtcaga   120
tgcgagagct caatggtaca attccatggg attcggacaa tctggtggtc gatctacata   180
cgaacaagcc tatatgagtg g                                              201
```

<210> SEQ ID NO 604
<211> LENGTH: 201
<212> TYPE: DNA
<213> ORGANISM: Tomato

<400> SEQUENCE: 604

```
acatacgaac aagcctatat gagtggttca ctaagggcag gtggtcctca gaggtatgaa    60
cattctccta aagtctgcag agatgcattc tccttgcagt acagtccaa ttcagggact    120 ggatccctgt ggtctagaca gccttttgag caatttggtg tagctggtaa gccagatgtt   180
ggtagcggcg atcatggaac t                                              201
```

<210> SEQ ID NO 605
<211> LENGTH: 201
<212> TYPE: DNA
<213> ORGANISM: Tomato

<400> SEQUENCE: 605

```
atgttggtag cggcgatcat ggaactgtgc tgagttcctc tgctcaagag agtacatcta    60
cggttgactt ggaagctaag ctgcttcagt ctttcagaag ttgtattgtg aaacttttga   120
aactggaagg atctgagtgg ttatttaggc aagatgatgg ggctgatgag gatcttatag   180
gtcggattgc tgcaagagag a                                             201
```

<210> SEQ ID NO 606
<211> LENGTH: 201
<212> TYPE: DNA
<213> ORGANISM: Tomato

<400> SEQUENCE: 606

```
tataggtcgg attgctgcaa gagagaaatt tctctatgaa gctgaaacta gggagataag    60
tagattgacc aacattggtg aatcacactt ctcttccaac aggaaacccg gttctgcccc   120
aaaacctgaa gagatggatt acaccaagtt cttggtgatg tcagttcccc actgcggaga   180
aggttgtgtt tggaaagtag a                                             201
```

<210> SEQ ID NO 607
<211> LENGTH: 201
<212> TYPE: DNA
<213> ORGANISM: Tomato

<400> SEQUENCE: 607

```
ggagaaggtt gtgtttggaa agtagatctg attataagct tcggtgtgtg gtgcattcac    60
agaattcttg agctttcact tatggaaagt aggccagagt tgtggggcaa atatacctat   120
gttctcaacc gtcttcaggg catagtagat ctggcatttt caaagcccca ttctccgacg   180
agccattgtt tttgtcttca a                                             201
```

<210> SEQ ID NO 608
<211> LENGTH: 201
<212> TYPE: DNA
<213> ORGANISM: Tomato

<400> SEQUENCE: 608

```
cgacgagcca ttgttttttgt cttcaaattc cggctggccg ccagcaaaag gcaagccccc    60
ctccaatttc taatggaaac ttgccgccac aagcaaaaca gggtcgagga aaatgcacga   120
ctgcagcaat gctcttagag atgatcaaag acgtggagac agcaatttcc tgtcgaaagg   180
gacgaacggg cactgcagca g                                             201
```

<210> SEQ ID NO 609
<211> LENGTH: 201
<212> TYPE: DNA
<213> ORGANISM: Tomato

<400> SEQUENCE: 609

```
aaagggacga acgggcactg cagcagggga tgtagccttt cctaaaggaa aagagaacct    60
ggcatccgtc ctcaagcgct ataaacgtcg attatccaat aagccggtag gaaaccagga   120
ggtggctgga gtcgccggac cgcgcaaagt aacgctgtct gcctcatcac ccccttttcgt   180 cttgtaacgc tcttttctca g                                             201
```

<210> SEQ ID NO 610
<211> LENGTH: 201
<212> TYPE: DNA
<213> ORGANISM: Tomato

<400> SEQUENCE: 610

```
ttcgtcttgt aacgctcttt tctcagttca tagcaaatga ctggtgagat caccattgtt      60
agacttgttc ttagtttctg tgaattatcc ccccctcccc aactatacct cccttgcacc     120
tcatgtgtat tttgaatctt tgcagcttat tcaccccat cccttgtacc tcaatctgta      180
tacataggat aaaatgttgt a                                                201
```

<210> SEQ ID NO 611
<211> LENGTH: 201
<212> TYPE: DNA
<213> ORGANISM: Tomato

<400> SEQUENCE: 611

```
cttggcaggt aaaactgaac gaaaaggata caaacgagaa atatagtaat aaaacgagag      60
atacgacaat aaaaccaaaa acccaactaa ctagcgcgcg aaattctgaa cttggcaggt     120
aaaactgaac gaaaaaatac aaatgaaaaa tatagtaata aaacaacttt taccgaattt     180
cttcgacata attctctcaa a                                                201
```

<210> SEQ ID NO 612
<211> LENGTH: 201
<212> TYPE: DNA
<213> ORGANISM: Tomato

<400> SEQUENCE: 612

```
aatttcttcg acataattct ctcaaaacac cttaatatac tgtatttat ttacgtatgt       60 atctatgctg aatataatgg agaaaaaaac cgattaaaaa actatctttt tagttcactt     120
ttctccttca tagcttttgg actcacatta gtgaagtgaa actctcaact ttttctctct     180
ctctccaaga tagctttaag a                                                201
```

<210> SEQ ID NO 613
<211> LENGTH: 201
<212> TYPE: DNA
<213> ORGANISM: Tomato

<400> SEQUENCE: 613

```
tctctctctc caagatagct ttaagaccct acccaccccc ttacatgacc ccttttccc       60 cataatatat atataaatac agtaatatat atgtatatat atagtttc tctctctaca      120 gtagtcacag ctcacacacc ataactctcc atctctctag gatatgtatt atgtacaggt    180
tcctctcttt atctcttagt a                                                201
```

<210> SEQ ID NO 614
<211> LENGTH: 201
<212> TYPE: DNA
<213> ORGANISM: Tomato

<400> SEQUENCE: 614

```
caggttcctc tctttatctc ttagtagtat atatagatat tagagcttcc ttaaaagctt      60
ctgatctgaa ctctgagcac tgaaatttat agagaagaag actgaagaaa acccatccag    120
aaaaggaagg aaaactattt gaagaaggta taaaaagaa atggaaaacc ctaatggtct     180
acacacccac ttgggtaaat t                                                201
```

<210> SEQ ID NO 615
<211> LENGTH: 201
<212> TYPE: DNA
<213> ORGANISM: Tomato

<400> SEQUENCE: 615

```
ggtctacaca cccacttggg taaattttat cattttttt aatttactg ttatgggtat      60
gtttagatat aggtataagg attatatgtt ttggaatctt gaaataaaaa tttggtcttt    120
ataggatatg tttgtatcag atccgatgaa gtgggtattg agttttttgc tgattgtttt   180
gatttgttgt attgggttgt g                                              201
```

<210> SEQ ID NO 616
<211> LENGTH: 201
<212> TYPE: DNA
<213> ORGANISM: Tomato

<400> SEQUENCE: 616

```
gttttgattt gttgtattgg gttgtgttaa aaaggttgga gaagtgttat ttatggggtt    60
ttggttttg ggttggaaaa agatttgatc ttctttata taaatttgat ggggttttgt    120
agttttgtgt aataaagatc tggatggttg aggaggagaa ggtgtttcat ttgcagttct   180
cttctttct ttttgaaaag t                                              201
```

<210> SEQ ID NO 617
<211> LENGTH: 201
<212> TYPE: DNA
<213> ORGANISM: Tomato

<400> SEQUENCE: 617

```
gttctcttct tttcttttg aaaagtggta ttgcttttga agtcaagttg atgtttttt     60
ttgtttcaaa atgcaggata ttttgttaa agcaatcatg tttagtttta gatgccaggc   120
tgtaacatgg agtttactga gtgttttaat tattttttg ggcaagttga ctaattttga  180
aatatatgaa taatgctgga t                                             201
```

<210> SEQ ID NO 618
<211> LENGTH: 201
<212> TYPE: DNA
<213> ORGANISM: Tomato

<400> SEQUENCE: 618

```
tttgaaatat atgaataatg ctggattggt ttgtgaattg tgatctcagt gaaggtttgc    60
caaattttg tgttccatgt ttctcgcgct acaggacact gtgatgtatg ttaggtcgtg   120
aaagatccaa ttttttctg ttgggtagtt tatcaacttc agcattttg tcttttaact   180
ggaattaaca tgtatatagt t                                             201
```

<210> SEQ ID NO 619
<211> LENGTH: 201
<212> TYPE: DNA
<213> ORGANISM: Tomato

<400> SEQUENCE: 619

```
taactggaat taacatgtat atagttttag tttggatata atgctttctc cagctgtttt    60
aagtgtttga tagtcatggt tacctagttt tttctgtaac tacaatttga atacttgact  120
gaagttttgg tatttaactc aattcagaaa tcagaatcgg caatcggatt attgacggat  180
gcaaaggtgt taatgcggtg t                                             201
```

<210> SEQ ID NO 620
<211> LENGTH: 201
<212> TYPE: DNA
<213> ORGANISM: Tomato

<400> SEQUENCE: 620

| | | | | | |
|---|---|---|---|---|---|
| cggatgcaaa | ggtgttaatg | cggtgtattt | ggttggagtt | ggtggattta | gcaactcgaa | 60 |
| aagacttcca | tctttataag | gcgcacttct | caaagttatt | gttcgaagtt | ggttgatttt | 120 |
| agcagcttga | aaagactctt | aataaattgc | ttttgtcaag | ttcttcatgt | ccattgcttt | 180 |
| tgggtgcaaa | cttgctcaaa | a | | | | 201 |

<210> SEQ ID NO 621
<211> LENGTH: 201
<212> TYPE: DNA
<213> ORGANISM: Tomato

<400> SEQUENCE: 621

| | | | | | |
|---|---|---|---|---|---|
| gcttttgggt | gcaaacttgc | tcaaaattct | ccagagataa | cgaggggttt | tggtatcctg | 60 |
| ttctaactgt | gctacattga | gctacagtct | acagttggag | ctgcagctgc | tacatagaaa | 120 |
| agctgtgtgg | tcggaacttg | gaacttcact | ggttggattg | tgagcttgtt | catgtcaaat | 180 |
| gggttgctaa | gtgatgctgt | a | | | | 201 |

<210> SEQ ID NO 622
<211> LENGTH: 3872
<212> TYPE: DNA
<213> ORGANISM: Cucumis sativus

<400> SEQUENCE: 622

| | | | | | |
|---|---|---|---|---|---|
| atggaatcta | cgacattgca | tacaactcat | cagtcgggtg | ctattcatag | gtttataccct | 60 |
| ttcattgcac | ctgcacttct | agtttcaatt | agttatgttg | accctggaaa | gtgggctgca | 120 |
| actgttgaag | gaggtgctcg | gtttggcttt | gatttgtttg | tgttagtgct | tcttttcaat | 180 |
| cttgctgcta | ttttatgcca | gtatctctca | gctagcattg | gtgtggtcac | tggaagaggt | 240 |
| cttgcccaga | tatgcaacga | ggagtatgat | aagtgtacat | gtttcttcct | gggaatccaa | 300 |
| gcagaggctt | ctgtgattct | gttagacctt | aacatgatct | tgggcatttc | aaatggactt | 360 |
| aatcttctac | ttgggtggga | cctcttcaca | tgtgtccttt | tgacgggtgt | tgctgctgct | 420 |
| ttatttcctc | cttttgctga | ccttctggaa | gatggcaggg | caaagttcct | ctatatatgt | 480 |
| atggcgggat | ttgtactgct | ctcttttggtt | cttggagtat | taatcagtca | acctgaaatc | 540 |
| ccactttcca | tgaatctcat | gccgacaagg | ttaaatgggg | aaagtgcctt | tactcttatg | 600 |
| agtcttcttg | gagcaagtgt | catgccacac | aatttttatg | tgcattcttc | tattgtgcag | 660 |
| cagcaccaga | gtccaccaaa | tatttccaaa | gaagtttcgt | gttataatca | tttgtttgct | 720 |
| attttctgca | tattcagtgg | aattatgtgg | tgaataacgt | tctcatgaac | tcagctgcaa | 780 |
| atgtattcta | tagcagtggt | cttgctttgc | acacctttac | agatgcattg | tctttaatgg | 840 |
| agcaggtatt | tgggagctca | gtggtatatg | ttctcttctt | acttgttttg | tttctatcaa | 900 |
| atcaaatcac | agctctcaca | tggagtcttg | gtggtcaact | ggttctgacc | aatttcttaa | 960 |
| aattagatat | tcctggttgg | ctccattgtg | ctacaattag | gattattgcc | attattccag | 1020 |
| cactatgctg | tgtctggagt | tcgggtgctg | aagggatgta | tcaacttctt | atattttctc | 1080 |
| aggttatggt | agctctattg | cttccatctt | ctgtgattcc | cctctatcgt | gttgcttcat | 1140 |
| caagaacaat | aatgggtgcc | tcaaaatat | cgcagcttgt | ggaatttata | gcaattggta | 1200 |
| tctttattgg | aatattagga | ctgaaaatta | tatttgttgt | agagatgatt | tttggtaaca | 1260 |
| gtgattgggt | agttaacttg | aggtggaaca | tggggagtgg | tatgtcaatc | ccatttgtgg | 1320 |

```
ttcttcttat tactgcttgt tcatcgtttt gtctgatgct atggttggca gctacccccat    1380 taaaatctgc tactactatt gcccaattag atgctcaagt attgaactgg gatatggcag    1440
aggttagacc cgattcatct gaagagaggg aaaacataga tttggggaaa agttcataca    1500
gtgccgagcc tatagaaagt cattctgacc tatcttcaac aaagtttgat tttaatttgc    1560
ctgaaaatat tatggaacct gatcaggttc ttggttcagt taatcaaaac gagaatcgat    1620
ctagtactgt agttccaagc tccccaaaat atgtacaaga ggaacttgaa tccactgagg    1680
agttagtctc atcctcaatt gtgactcacg atgttcctga ttcaacattg gctgacaaaa    1740
aggtcttaaa aatagagtca gtggaggccg ttgaaaagac tgttggactc gatggtgatt    1800
tgcgttctga gaaggatgat tatgaggttg ataactggga ggctgaagag tcactgaaag    1860
agatctctgg gaatatacca tcctcaacat ctgagggtcc tggttctttt agaagtattg    1920
gtgggagaag tgaagaaggt gggaatggaa ctggtagtct ttcaaggtta gctggcctcg    1980
ggcgtgctgc aaggcgccaa cttactgaaa ttcttgatga attttgggga caattgtatg    2040
atttccatgg ggtgcctact caagatgcaa aggttaagaa actagatttg ttactgggtt    2100
ttacctctct gaaattggat gctgttggta aagattttcc tcactcatca cctattggat    2160
gcaaaacatc cgatccaatt tcttctagtt tgtacgactc ccccaagagt cagagggtac    2220
aaagtgggtt agaaccaccc tatgggatac aaaaggggca ccagccattg tggtctaacc    2280
acatgcagca ttgggatgca tatgtgaata attctagcca taatgctctg gactctggag    2340
tgaagcgata ttctagtttg cgcagtttgc cttctactga gagttgggat tatcagcctg    2400
ccacagtcca tggctatcag ttaacttatc tgagtagaat ggcaaaggac agaagttctg    2460
gtaattcgaa cggtcagttg gattcatcag gctctaaata tcataccttg ggtggtggtg    2520
gtgcaggctt gcgagactca gttgcatttg caatggggca aaagttgcaa aatggcttgg    2580
gtgcttgtca gcaggcggct ccccaggtt tttccaacat cacagtatcc aggaaaacctt    2640 cttccgaatc tgaaaggaaa tattatgatc attctctttc tggaactggt gagaatttag    2700
tgagtgtatc taacacaaag aaataccata gcttaccgga tattcaccgt gatcagcaca    2760
catcagataa gagttctcag tgggataatg tgagtggtta tggaacatct attggtagaa    2820
taacagctcg tggagtgtcc acaaattctg gatcaagatt agtttctcct ttagcatttg    2880
atgaactatc tcctgcaaat gtctacagtg gtgcattatc accacaaatg aatcctcatc    2940
tggattctgg atctttctgg catagacagc cttctgagca atttggcttg gacaaaaata    3000
gcaactccga gagtaaagga attgggaggc tgcattcaat tagtcacgaa gcttcttttg    3060
ttgttaattc agaggccagg cttctccagt ccttcagaga ctgcattgtc aaacttctga    3120
aattagaagg atcagactgg ttatttgggc aaagtgatgg tgctgacgag gagctaattg    3180
attgtgtagc tgccagggag aaatttcttt atgaagctga ggcaagggag atgggtcggg    3240
tggtccgcat gaaagaatct ccttcatttt ctcctgatag gagaccaggt tctgaatga    3300 agaatgatac aaatttctcc aatgtttcta tttcctctgt acctcattgt ggagaaggct    3360
gtatttggag atcagatttg attgtaagtt ttggtgtatg gtgcattcac cgtattctag    3420
atctctcact tatggaaagt cggcctgaac tatggggaaa atatacctat gtactcaatc    3480
gtcttcaggg tattatcgat cctgcatttt cgaagcctcg tataccgatg ccaccatgct    3540
tctgcctcca aattccccaa gcattccagc agaggtcaag cccacaaatt gcaaatggaa    3600
tgttgcctcc tgctgcaaaa cctggcaagg gaaaatgcac cactgctgca atgcttctgg    3660
atatggtcaa ggatgtggag atagccatct cttgccgaaa aggtcgaact ggtacagcag    3720
```

-continued

| | | |
|---|---|---|
| ccggcgacgt agctttccca aaggggaagg agaacttggc ttcagtcctc aaacgctaca | 3780 |
| agcgccgatt atccaataaa ccagttgcca ctcacgaagt atcatctatt tcacgcaaga | 3840 |
| tttcagcaac atccgttcct tatagctcat ag | 3872 |

<210> SEQ ID NO 623
<211> LENGTH: 2001
<212> TYPE: DNA
<213> ORGANISM: Cucumis sativus

<400> SEQUENCE: 623

| | |
|---|---|
| tatatatgca tataaatact attattcata aatttaagat ttattgaagc acttcttatg | 60 |
| gaatctctat ttttagaatg aaatatgatg ttttgaattt gaatttgatt aaaaaagaca | 120 |
| tgttaagtgt taaataaaaa tacaaaattt tatttatgag ggtgaaatta gaattgaaga | 180 |
| aatataaaaa agaaaaaaaa atgaaaagat aggttgagaa gagagaagga agaaggagaa | 240 |
| aaggggatga aaaaagaga gagagagaaa ttgggagtgt ggaagcaaaa gcagtctatc | 300 |
| actctcatca gctataaatg aaaaaggtta aattttttat ttttgggtgt gggagtttct | 360 |
| gcactttctc acacacaaac tctctcctcc agatgagctt caaagcccac cagtgacttt | 420 |
| tatctaaaaa atttcccttt tttctctctc tccctatcat cttcccccct aaaaaaactc | 480 |
| tgttccctct ttctctttct ctttctcttt ctatatataa agcttatgca attaactctc | 540 |
| tggcgttact gaagcatcta tgagatctac tgtccacact gaattcatgg attcaatgag | 600 |
| atttcctacg aattaagcca gtacggaaaa cccaggtgaa tatcaaaaga agtagaacag | 660 |
| caatgaaatc aacaaacaat tttacaaccc tatctccttt tttttctttt tctttttttgt | 720 |
| tcagcttcat gtgggtttct tttgtttatc cataacctct cttaaaatct gtgttttga | 780 |
| agcttgggtt ttaattcctt ttcttttctt caccttttagc ttgcatcgga tccgtggttt | 840 |
| tttattctga tcttcatttc tcgtggccaa tttcttttgg gagagtaggt tttgggttct | 900 |
| gggttctggg ttgggcttta ttttaggtgt atgtcccaat tttgagatac ccttttgtgt | 960 |
| tcgatgaaag tccccggtat tttttttatt ttttattttt tctgttttttc tggattttga | 1020 |
| ctgtctaggg tttgaattgt aatggggctc tattaatttt gaactatagg tatgcattta | 1080 |
| ggttgttgac tttctataag gagaaataaa aaataggcgg taaggtaagg ccgaaccagg | 1140 |
| attatttatt attagaatta ctcatggtag ttaacatgta gaattcttgt acctccctaa | 1200 |
| atcgagtttt cttaattgct aaactgattt cgtggggaat tagctgcttt ttcagtttgt | 1260 |
| ttagtcaaca tctgattttg attcctaaaa atttatccta tgcatgattt cacaattttg | 1320 |
| ttgtctttat agtaaagttt tgattctgga ctttcggttt ctactttatt attgtaattt | 1380 |
| tgagatccta tcatcaccta ttgtttctca tagatttctt ttaccaaaaa tctattattt | 1440 |
| ctttgaatgt attgcataaa caactatttt gttctgcatt accgttgtct ccttctctga | 1500 |
| tgctaatgga tatgctttca ttgatttagg cgagggggtgg cacagaatat tcttttcgga | 1560 |
| gcaggcacta aattaataag ttatcaagat cactctagag tgccattcaa ttggcattca | 1620 |
| ttctaagaat gctaaggaag ataaccacag ctatcgttcg aggattttcg tggcgttagg | 1680 |
| actgagggat tgagcacata taatgtgcta gaaggatatt tgttgaagca aggatggatg | 1740 |
| ttcatgttat atttgcacaa tataatggaa caggggttat ttacaatgga tgattttttgt | 1800 |
| tcttttttcc ttttttcttc ggttgtagaa attttttactt tctagttagt aaaagagtgg | 1860 |
| tagttgcaga gaacacaaac acctgatgta aattgtttat ctcgatgctt attaggaagt | 1920 |

```
ttgtagtttt ctggacttgt tagccacgct ttacacactg ctccattccg actattttgt    1980
ggaaaatctc catttatacc a                                              2001

<210> SEQ ID NO 624
<211> LENGTH: 193
<212> TYPE: DNA
<213> ORGANISM: Solanum lycopersicum

<400> SEQUENCE: 624
gagaggcgct attctagtat gcggattcca gcgacttctg ctggctatga tcagcagcct      60
gccactgtgc atggatatca gattactgct taccttaatc aacttgcgaa agaaagagga    120
tctgattatt taaatgggca actggagtca ccatctcctc gttctgtatc atcactgacg    180
tcaaactatg cag                                                       193

<210> SEQ ID NO 625
<211> LENGTH: 387
<212> TYPE: DNA
<213> ORGANISM: Solanum lycopersicum

<400> SEQUENCE: 625
atggagtctg aaactctgac tagagaatat aggcagccca gcatgcttca gcgagtactt     60
tctgcttctg tgccaatgct gttgattgca gttggctatg ttgatcctgg gaatgggct    120 gcaatggttg atggaggagc ccgatttggg tttgatttgg tcatgctagt actcttgttc    180
aattttgctg ccattctgtg ccagtatctg tctgcttgta tagccttggt tacagaccga    240
gatcttgcgc agatttgcag tgaagaatat gacaaagtta catgcatatt cctaggaatt    300
caagctgagg tttcgatgat tgctttggac ctcacaatgg ttttgggcac tgcccatggg    360
cttaatgttg tgtttggagt tgacctg                                        387

<210> SEQ ID NO 626
<211> LENGTH: 462
<212> TYPE: DNA
<213> ORGANISM: Solanum lycopersicum

<400> SEQUENCE: 626
tttagctgtg ttttcctgac tgcaaccggt gccattttgt ttccactgct tgcttctctc     60
tttgacaatg gcagtgcaaa attcttatgt attggctggg caagtctgt actgctctct    120 tatgttttg gagtggttat aactctacct gaaactccat tctccattgg tggtgtgctg    180
aataagttta gtggagagag tgcatttgca ttgatgagtc ttcttggagc aagtattatg    240
cctcacaatt tttacctcca ttcttctatt gtacagcaag gtaaggaatc aacagagctt    300
tccaggggag ctctgtgtca ggaccatttt tttgccattg ttttcatatt cagtggcatt    360
ttcctggtca actatgccgc gatgaattca gcagcgaatg tgtcttacag tactggcctt    420
ttgttgctga catttcagga cacattgtca ttgctcgatc ag                       462

<210> SEQ ID NO 627
<211> LENGTH: 25
<212> TYPE: DNA
<213> ORGANISM: Cucumis sativus

<400> SEQUENCE: 627
ctgatagcca tggactgtgg caggc                                           25

<210> SEQ ID NO 628
<211> LENGTH: 25
```

<212> TYPE: DNA
<213> ORGANISM: Cucumis sativus

<400> SEQUENCE: 628
agcctgatga atccaactga ccgtt    25

<210> SEQ ID NO 629
<211> LENGTH: 25
<212> TYPE: DNA
<213> ORGANISM: Cucumis sativus

<400> SEQUENCE: 629
ctgcaccacc accacccaag gtatg    25

<210> SEQ ID NO 630
<211> LENGTH: 25
<212> TYPE: DNA
<213> ORGANISM: Cucumis sativus

<400> SEQUENCE: 630
caagcaccca agccattttg caact    25

<210> SEQ ID NO 631
<211> LENGTH: 25
<212> TYPE: DNA
<213> ORGANISM: Cucumis sativus

<400> SEQUENCE: 631
acactccacg agctgttatt ctacc    25

<210> SEQ ID NO 632
<211> LENGTH: 25
<212> TYPE: DNA
<213> ORGANISM: Cucumis sativus

<400> SEQUENCE: 632
taaagaaatt tctccctggc agcta    25

<210> SEQ ID NO 633
<211> LENGTH: 25
<212> TYPE: DNA
<213> ORGANISM: Cucumis sativus

<400> SEQUENCE: 633
cccgacccat ctcccttgcc tcagc    25

<210> SEQ ID NO 634
<211> LENGTH: 25
<212> TYPE: DNA
<213> ORGANISM: Cucumis sativus

<400> SEQUENCE: 634
aatgaaggag attctttcat gcgga    25

<210> SEQ ID NO 635
<211> LENGTH: 25
<212> TYPE: DNA
<213> ORGANISM: Cucumis sativus

<400> SEQUENCE: 635
ttcattccag aacctggtct cctat    25

<210> SEQ ID NO 636

<211> LENGTH: 25
<212> TYPE: DNA
<213> ORGANISM: Cucumis sativus

<400> SEQUENCE: 636
ccccatagtt caggccgact ttcca 25

<210> SEQ ID NO 637
<211> LENGTH: 25
<212> TYPE: DNA
<213> ORGANISM: Cucumis sativus

<400> SEQUENCE: 637
atacgaggct tcgaaaatgc aggat 25

<210> SEQ ID NO 638
<211> LENGTH: 25
<212> TYPE: DNA
<213> ORGANISM: Cucumis sativus

<400> SEQUENCE: 638
tttggaggca gaagcatggt ggcat 25

<210> SEQ ID NO 639
<211> LENGTH: 25
<212> TYPE: DNA
<213> ORGANISM: Cucumis sativus

<400> SEQUENCE: 639
ttgacctctg ctggaatgct tgggg 25

<210> SEQ ID NO 640
<211> LENGTH: 25
<212> TYPE: DNA
<213> ORGANISM: Cucumis sativus

<400> SEQUENCE: 640
cttgccaggt tttgcagcag gaggc 25

<210> SEQ ID NO 641
<211> LENGTH: 25
<212> TYPE: DNA
<213> ORGANISM: Cucumis sativus

<400> SEQUENCE: 641
tccagaagca ttgcagcagt ggtgc 25

<210> SEQ ID NO 642
<211> LENGTH: 25
<212> TYPE: DNA
<213> ORGANISM: Cucumis sativus

<400> SEQUENCE: 642
ggcaagagat ggctatctcc acatc 25

<210> SEQ ID NO 643
<211> LENGTH: 25
<212> TYPE: DNA
<213> ORGANISM: Cucumis sativus

<400> SEQUENCE: 643
gattccataa gaagtgcttc aataa 25

<210> SEQ ID NO 644
<211> LENGTH: 25
<212> TYPE: DNA
<213> ORGANISM: Cucumis sativus

<400> SEQUENCE: 644
caattctaat ttcaccctca taaat                                    25

<210> SEQ ID NO 645
<211> LENGTH: 25
<212> TYPE: DNA
<213> ORGANISM: Cucumis sativus

<400> SEQUENCE: 645
tctctctctt tttttcatcc cctttt                                   25

<210> SEQ ID NO 646
<211> LENGTH: 25
<212> TYPE: DNA
<213> ORGANISM: Cucumis sativus

<400> SEQUENCE: 646
ctgcttttgc ttccacactc ccaat                                    25

<210> SEQ ID NO 647
<211> LENGTH: 25
<212> TYPE: DNA
<213> ORGANISM: Cucumis sativus

<400> SEQUENCE: 647
agatgcttca gtaacgccag agagt                                    25

<210> SEQ ID NO 648
<211> LENGTH: 25
<212> TYPE: DNA
<213> ORGANISM: Cucumis sativus

<400> SEQUENCE: 648
tgaatccatg aattcagtgt ggaca                                    25

<210> SEQ ID NO 649
<211> LENGTH: 25
<212> TYPE: DNA
<213> ORGANISM: Cucumis sativus

<400> SEQUENCE: 649
tattcacctg ggttttccgt actgg                                    25

<210> SEQ ID NO 650
<211> LENGTH: 25
<212> TYPE: DNA
<213> ORGANISM: Cucumis sativus

<400> SEQUENCE: 650
agaaaaaaaa aggagatagg gttgt                                    25

<210> SEQ ID NO 651
<211> LENGTH: 25
<212> TYPE: DNA
<213> ORGANISM: Cucumis sativus

<400> SEQUENCE: 651
aaaaccacgg atccgatgca agcta                                    25

<210> SEQ ID NO 652
<211> LENGTH: 25
<212> TYPE: DNA
<213> ORGANISM: Cucumis sativus

<400> SEQUENCE: 652
agaaattggc cacgagaaat gaaga                                25

<210> SEQ ID NO 653
<211> LENGTH: 25
<212> TYPE: DNA
<213> ORGANISM: Cucumis sativus

<400> SEQUENCE: 653
cccaacccag aacccagaac ccaaa                                25

<210> SEQ ID NO 654
<211> LENGTH: 25
<212> TYPE: DNA
<213> ORGANISM: Cucumis sativus

<400> SEQUENCE: 654
aaaaaatacc ggggactttc atcga                                25

<210> SEQ ID NO 655
<211> LENGTH: 25
<212> TYPE: DNA
<213> ORGANISM: Cucumis sativus

<400> SEQUENCE: 655
tcaaaattaa tagagcccca ttaca                                25

<210> SEQ ID NO 656
<211> LENGTH: 25
<212> TYPE: DNA
<213> ORGANISM: Cucumis sativus

<400> SEQUENCE: 656
ctggttcggc cttaccttac cgcct                                25

<210> SEQ ID NO 657
<211> LENGTH: 25
<212> TYPE: DNA
<213> ORGANISM: Cucumis sativus

<400> SEQUENCE: 657
aagaaaactc gatttaggga ggtac                                25

<210> SEQ ID NO 658
<211> LENGTH: 25
<212> TYPE: DNA
<213> ORGANISM: Cucumis sativus

<400> SEQUENCE: 658
gcagctaatt ccccacgaaa tcagt                                25

<210> SEQ ID NO 659
<211> LENGTH: 25

```
<212> TYPE: DNA
<213> ORGANISM: Aequoria victoria

<400> SEQUENCE: 659
gttgtagttg tactccatct tattg                                         25
```

METHODS AND COMPOSITIONS FOR DELAYING SENESCENCE AND IMPROVING DISEASE TOLERANCE AND YIELD IN PLANTS

CROSS-REFERENCE TO RELATED APPLICATIONS

This non-provisional U.S. patent application claims the benefit under 35 U.S.C. §119(e) of U.S. Provisional Patent Application No. 61/534,351, filed on Sep. 13, 2011 and incorporated herein by reference in its entirety.

INCORPORATION OF SEQUENCE LISTING

The sequence listing that is contained in the file named "40_77(58620).txt", which is 259,094 bytes (measured in operating system MS-Windows), created on Sep. 11, 2012, is filed herewith by electronic submission and incorporated herein by reference in its entirety. The sequence listing contains SEQ ID NO: 1-659.

INCORPORATION BY REFERENCE OF TABLES OF PROVISIONAL APPLICATION

A "Table 1" was provided as a part of Provisional U.S. Patent Application No. 61/534,351 in a file named "40_77_58620_A_TAB1.txt" which was 57,572 bytes in size (measured in MS-Windows®) and that comprised SEQ ID NO:1-18. "Table 1" of Provisional U.S. Patent Application No. 61/534,351 is incorporated herein by reference in its entirety.

A "Table 2" was provided as a part of Provisional U.S. Patent Application No. 61/534,351, in file named "40_77_58620 A_TAB2.txt" which was 83,568 bytes in size (measured in MS-Windows®) and that comprised SEQ ID NO:19-331. "Table 2" of Provisional U.S. Patent Application No. 61/534,351 is incorporated herein by reference in its entirety.

A "Table 3" was provided as a part of Provisional U.S. Patent Application No. 61/534,351, in file named "40_77_58620_A_TAB3.txt" which was 12,078 bytes in size (measured in MS-Windows®) and that comprised SEQ ID NO:332-621. "Table 3" of Provisional U.S. Patent Application No. 61/534,351 is incorporated herein by reference in its entirety.

BACKGROUND OF THE INVENTION

Leaf senescence occurs at the end of the plant life cycle, and is controlled by a number of internal factors such as plant hormones and developmental stage, and can be accelerated by environmental stresses (Lim, Kim et al. 2007). Ethylene is a plant hormone with a key role in control of leaf senescence. Application of exogenous ethylene can induce leaf senescence, and suppression of ethylene biosynthesis or response can delay leaf senescence (Lim, Kim et al. 2007). Leaf senescence that has been delayed by reduced ethylene levels or response will eventually be initiated, and it will then proceed normally.

An example of the role of ethylene on crop productivity in field conditions was reported for soybean. Stressful high temperature conditions will reduce yield in soy and other crops. Ethylene production was shown to increase in soybean leaves in response to high temperature, and triggered premature leaf senescence (Djanaguiraman and Prasad 2010). However, prevention of ethylene response by use of the inhibitor 1-methyl cyclopropene (1-MCP) in plants grown at high temperature reduced leaf senescence and allowed increased yield compared to untreated controls also grown at high temperature. 1-MCP is a gas, and not appropriate for application in open fields. Therefore, other methods to delay leaf senescence are needed.

Ethylene also plays a major role in the ripening of fruits and vegetables. Ripening is an important phase of fruit development involving changes in fruit cellular metabolism leading to the development of a soft and edible ripe fruit with desirable quality. However, the softening that accompanies excessive ripening increases postharvest losses and reduces the shelf life of fruits and vegetables during handling, transportation, and storage. Ethylene, as a fruit ripening phytohormone, triggers many events of cell metabolism including initiation of ripening and senescence in fruits and vegetables, particularly in climacteric fruits (reviewed by (Lin, Zhong et al. 2009; Bapat, Trivedi et al. 2010)). Two systems, system 1 and 2 of ethylene production have been described in plants (McMurchie, McGlasson et al. 1972). System 1 operates during normal growth and development and during stress responses while system 2 functions during floral senescence and fruit ripening. System 2 is autocatalytic and it is stimulated by ethylene. Manipulation of ethylene biosynthesis, especially the system 2, in fruits and vegetables can be of strategic importance to enhance the shelf life and to reduce the postharvest losses of these crops.

The ethylene signal transduction pathway is relatively well understood (Lin, Zhong et al. 2009). Ethylene is perceived by a family of two-component histidine kinase-like receptors encoded by the ETHYLENE RESPONSE 1 (ETR1) and related genes. The CONSTITUTIVE TRIPLE RESPONSE 1 (CTR1) gene encodes a Raf-like serine/threonine kinase that has been shown to interact with ethylene receptors. ETHYLENE INSENSITIVE 2 (EIN2) is a positive regulator of ethylene signaling and has been placed downstream of the ethylene-receptor/CTR1 complex. The N-terminus of EIN2 has homology with NRAMP ion transporters, but its exact function in ethylene signaling is not understood. Further downstream of EIN2 are transcription factors, including EIN3-encoded proteins, that regulate genes in response to ethylene.

Mutants of EIN2 have delayed senescence in *Arabidopsis*, without an effect on flowering time or development (Aeong Oh, Park et al. 1997).

Ethylene insensitivity has been shown to provide improvements in tolerance to certain diseases in certain plants as well as reduced disease tolerance to certain diseases in certain plants (van Loon, L. C., et al. Trends in Plant Sci. 11(4): 184, 2006).

SUMMARY OF THE INVENTION

Provided herein are compositions and methods that provide for delayed leaf senescence, improved disease tolerance, and increased crop yield that results from suppression of EIN2 expression. In certain embodiments, delayed leaf senescence and increased crop yield that results from suppression of EIN2 expression is obtained by topical applications of compositions comprising polynucleotides and transfer agents to plants. For the purpose of extending functional stay-green, the ability to control the timing of application so that EIN2 genes are suppressed only during grain fill or under environmentally stressed conditions makes the compositions and methods provided herein particularly useful. Many crops will derive benefit from this method, including but are not limited to, corn, wheat, rice, soybean, cotton, Canola, tomato, alfalfa, melon, lettuce, cucumber, and broccoli.

Also provided herein are methods and compositions that provide for reductions in expression of EIN2 target polynucleotide and protein molecules in at least the cells of a plant root for improved resistance to nematodes. Nematodes that can be controlled by the methods and compositions provided herein include, but are not limited to, root knot nematodes (such as *Meloidogyne* sp.), cyst nematodes (such as *Globodera* sp. and *Heterodera* sp.), lesion nematodes (such as *Pratylenchus* sp.), and the like. In certain embodiments, EIN2 expression is reduced in plant root cells from which nematodes feed by providing topically to plant leaves, shoots, roots and/or seeds compositions comprising polynucleotides that comprise at least 18 contiguous nucleotides that are essentially identical or essentially complementary to an EIN2 gene or to a transcript of the EIN2 gene; and a transfer agent.

Also provided herein are compositions and methods for controlling plant fungal diseases. Plant fungal diseases that can be controlled with the methods and compositions provided herein include, but are not limited to, obligate biotrophic powdery mildew, downy mildew, and rust fungal infestations in plants. Plant fungal diseases that can be controlled with the methods and compositions provided herein also include, but are not limited to, fungal pathogens such as those causing anthracnose stalk rot, *Diplodia* Stalk or Ear Rot, *Gibberella* Stalk or Ear Rot, and *Fusarium* Stalk Rot in corn, or causing Take-all in wheat, *Fusarium* head blight in barley and wheat, or causing rice blast. In certain embodiments, methods and compositions for reducing expression of one or more host plant EIN2 polynucleotide and/or protein molecules in one or more cells or tissues of the plant such that the plant is rendered less susceptible to fungal infections from the order Erysiphales, the family Peronosporaceae or the order Pucciniales, are provided. In certain embodiments, nucleotide and amino acid sequences of plant EIN2 genes which can be downregulated by methods and compositions provided herein to increase plant resistance to powdery mildew, downy mildew, rust infection, or fungal pathogens such as those causing anthracnose stalk rot, *Diplodia* Stalk or Ear Rot, *Gibberella* Stalk or Ear Rot, and *Fusarium* Stalk Rot in corn, or causing Take-all in wheat, *Fusarium* head blight in barley and wheat, or causing rice blast are disclosed. Exemplary powdery mildew fungi of the order Erysiphales which are controlled by the compositions and methods provided herein include, but are not limited to, *Blumeria graminis* f. sp. *hordei*, *Blumeria graminis forma specialis* (f. sp.) *tritici*, *Golovinomyces orontii*, *Golovinomyces cichoracearum*, *Oidium neolycopersici*, *Oidium lycopersici*, *Erysiphe pisi*, *Erisyphe necator* and *Sphaerotheca fuliginea* among others. Exemplary downy mildew of the family Peronosporaceae include *Pseudoperonospora humuli*, *Pseudoperonospora cubensis*, *Plasmopara viticola*, *Peronospora tabacina*, *Bremia lactucae*, and *Plasmopara halstedii*. Exemplary rusts of the order Pucciniales which are controlled by the compositions and methods provided herein include, but are not limited to, *Phakopsora meibomiae*, *Phakopsora pachyrhizi*, *Puccinia graminis*, *Puccinia recondita*, *Uromyces phaseoli* and *Uromyces appendeculatus*. Other exemplary fungal pathogens which are controlled by the compositions and methods provided herein include, but are not limited to, *Colletotrichum graminicola*, *Stenocarpella* (or *Diplodia*) *maydis*, *Gibberella zeae*, *Fusarium moniliforme*, *Gaeumannomyces graminis*, *Fusarium graminearum*, *Magnaporthe grisea* (also known as *Pyricularia grisea* or *Pyricularia oryzae*), *Septoria nodorum*, and *Septoria tritici*.

Also provided herein are compositions and methods for controlling plant bacterial diseases. Plant bacterial diseases that can be controlled with the methods and compositions provided herein include, but are not limited to, Disease Pathogen Bacterial leaf blight and stalk rot *Pseudomonas avenae* subsp. *avenae*, Bacterial leaf spot *Xanthomonas campestris* pv. *Holcicola*, Bacterial stalk rot *Enterobacter dissolvens=Erwinia dissolvens*, Bacterial stalk and top rot *Erwinia carotovora* subsp. *carotovora*, *Erwinia chrysanthemi* pv. *zeae*, Bacterial stripe *Pseudomonas andropogonis*, Chocolate spot *Pseudomonas syringae* pv. *coronafaciens*, Goss's bacterial wilt and blight *Clavibacter michiganensis* subsp. (leaf freckles and wilt) *nebraskensis=Corynebacterium michiganense* pv. *andnebraskense*, Holcus spot *Pseudomonas syringae* pv. *syringae*, Purple leaf sheath Hemiparasitic bacteria Seed rot-seedling blight *Bacillus subtilis*, Stewart's disease (bacterial wilt) *Pantoea stewartii=Erwinia stewartii*, Corn stunt (achapparramiento, *Spiroplasma kunkelii* maize stunt, Mesa Central or Rio Grande maize stunt). In certain embodiments, methods and compositions for reducing expression of one or more host plant EIN2 polynucleotide and/or protein molecules in one or more cells or tissues of the plant such that the plant is rendered less susceptible to any of the aforementioned bacterial diseases.

Also provided herein are compositions and methods that provide for delayed fruit senescence that results from suppression of EIN2 expression by topical applications of compositions comprising polynucleotides and transfer agents to plants. For the purpose of delaying fruit senescence, the ability to control the timing of application so that EIN2 genes are suppressed only during fruit ripening and/or only in detached fruit makes the compositions and methods provided herein particularly useful. Ethylene has many roles in growth and development and response to the environment that we do not want to otherwise disrupt. Many crops will derive benefit from this method, including, but not limited to, tomato, alfalfa, melon, lettuce, cucumber, and broccoli. Polynucleotides that can be used to suppress EIN2 include, but are not limited to, any of: i) polynucleotides comprising at least 18 contiguous nucleotides that are essentially identical or essentially complementary to an EIN2 gene or to a transcript of the gene of Table 2 (SEQ ID NO:1-18, or 622-623); ii) polynucleotides comprising at least 18 contiguous nucleotides that are essentially identical or essentially complementary to a polynucleotide of SEQ ID NO:19-331, or 624-658, or, iii) polynucleotides comprising at least 18 contiguous nucleotides that are essentially identical or essentially complementary to a polynucleotide of SEQ ID NO: 332-621.

In an aspect of the invention, the polynucleotide molecules are provided in compositions that can permeate or be absorbed into living plant tissue to initiate systemic gene inhibition or regulation. In certain embodiments of the invention, the polynucleotide molecules ultimately provide to a plant, or allow the in planta production of, RNA that is capable of hybridizing under physiological conditions in a plant cell to RNA transcribed from a target endogenous EIN2 gene or target EIN2 transgene in the plant cell, thereby effecting regulation of the target gene. In other embodiments of the invention, the polynucleotide molecules disclosed herein are useful for ultimately providing to a plant, or allowing the in planta production of, RNA that is capable of hybridizing under physiological conditions to RNA transcribed from a EIN2 target gene of the plant, thereby effecting regulation of the target gene. In certain embodiments, regulation of the target genes, such as by silencing or suppression of the target gene, leads to the upregulation of another gene that is itself affected or regulated by the target gene's expression.

In certain aspects or embodiments of the invention, the topical application of a composition comprising an exogenous polynucleotide and a transfer agent to a plant or plant part according to the methods described herein does not necessarily result in nor require the exogenous polynucleotide's integration into a chromosome of the plant. In certain aspects or embodiments of the invention, the topical application of a composition comprising an exogenous polynucleotide and a transfer agent to a plant or plant part according to the methods described herein does not necessarily result in nor require transcription of the exogenous polynucleotide from DNA integrated into a chromosome of the plant. In certain embodiments, topical application of a composition comprising an exogenous polynucleotide and a transfer agent to a plant according to the methods described herein also does not require that the exogenous polynucleotide be physically bound to a particle, such as in biolistic mediated introduction of polynucleotides associated with gold or tungsten particles into internal portions of a plant, plant part, or plant cell. An exogenous polynucleotide used in certain methods and compositions provided herein can optionally be associated with an operably linked promoter sequence in certain embodiments of the methods provided herein. However, in other embodiments, an exogenous polynucleotide used in certain methods and compositions provided herein is not associated with an operably linked promoter sequence. Also, in certain embodiments, an exogenous polynucleotide used in certain methods and compositions provided herein is not operably linked to a viral vector.

In certain embodiments, methods for delaying senescence, improving disease tolerance, and/or improving yield in a plant comprising topically applying compositions comprising a polynucleotide and a transfer agent that suppress the target EIN2 gene are provided. In certain embodiments, methods for selectively suppressing the target EIN2 gene by topically applying the polynucleotide composition to a plant surface at one or more selected seed, vegetative, or reproductive stage(s) of plant growth are provided. Such methods can provide for EIN2 gene suppression in a plant or plant part on an as needed or as desired basis. In certain embodiments, methods for selectively suppressing the target EIN2 gene by topically applying the polynucleotide composition to a plant surface at one or more pre-determined seed, vegetative, or reproductive stage(s) of plant growth are also provided. Such methods can provide for EIN2 gene suppression in a plant or plant part that obviates any undesired or unnecessary effects of suppressing the EIN2 genes expression at certain seed, vegetative, or reproductive stage(s) of plant development.

In certain embodiments, methods for selectively delaying senescence, improving disease tolerance, and/or improving yield in a plant by topically applying the polynucleotide composition to the plant surface at one or more selected seed, vegetative, or reproductive stage(s) are provided. Such methods can provide for a delayed senescence, improving disease tolerance, and/or improved yield in a plant or plant part on an as needed or as desired basis. In certain embodiments, methods for selectively delaying senescence, improving disease tolerance, and/or improving yield in a plant by topically applying the polynucleotide composition to the plant surface at one or more predetermined seed, vegetative, or reproductive stage(s) are provided. Such methods can provide for the delayed senescence, improving disease tolerance, and/or improved yield in a plant or plant part that obviates any undesired or unnecessary effects of providing the delayed senescence and/or improved yield at certain seed, vegetative, or reproductive stage(s) of plant development.

Polynucleotides that can be used to suppress an EIN2 gene include, but are not limited to, any of: i) polynucleotides comprising at least 18 contiguous nucleotides that are essentially identical or essentially complementary to EIN2 gene or to a transcript of the gene comprising or consisting of a sequence of SEQ ID NO:1-18, 622, or 623 in the sequence listing; ii) polynucleotides comprising at least 18 contiguous nucleotides that are essentially identical or essentially complementary to a polynucleotide comprising or consisting of a sequence of SEQ ID NO:19-331 or SEQ ID NO: 624-658 in the sequence listing; or, iii) polynucleotides comprising at least 18 contiguous nucleotides that are essentially identical or essentially complementary to a polynucleotide comprising or consisting of a sequence of SEQ ID NO:332-613 in the sequence listing Provided herein are compositions and methods that provide for delayed leaf senescence, improving disease tolerance, and increased crop yield that results from suppression of EIN2 expression by topical applications of compositions comprising polynucleotides and transfer agents. For the purpose of extending functional stay-green, the ability to control the timing of application so that EIN2 genes are suppressed only during grain fill or under environmentally stressed conditions makes the compositions and methods provided herein especially effective. In certain embodiments, methods and compositions provided herein can delay leaf senescence during optimal growing conditions for a crop to improve yield. In certain embodiments, methods and compositions provided herein can delay premature leaf senescence caused various stresses including drought, heat and nutrient limitation can promote leaf senescence prematurely, and thus enhance crop yields under environmentally stressed conditions. Ethylene has certain roles in growth and development and response to the environment where suppression of EIN2 may be undesirable. The controlled suppression of EIN2 permitted by methods and compositions provided herein can avoid such undesirable suppression. Many crops will derive benefit from this method, including, but not limited to, corn, wheat, rice, soybean, cotton, Canola, tomato, alfalfa, melon, lettuce, cucumber and broccoli. Certain embodiments of the invention are directed to methods for producing a plant exhibiting delayed senescence, improving disease tolerance, and/or improved yield comprising topically applying to a plant surface a composition that comprises:

a. at least one polynucleotide that comprises at least 18 contiguous nucleotides that are essentially identical or essentially complementary to a EIN2 gene or to a transcript of the gene; and b. a transfer agent, wherein the plant exhibits an improvement in delayed senescence and/or improved yield that results from suppression of the EIN2 gene. In certain embodiments, the polynucleotide molecule comprises sense ssDNA, sense ssRNA, dsRNA, dsDNA, a double stranded DNA/RNA hybrid, anti-sense ssDNA, or anti-sense ssRNA. In certain embodiments, the polynucleotide is selected from the group consisting of SEQ ID NO:19-621, 624-657, and 658, or wherein the polynucleotide comprises at least 18 contiguous nucleotides that are essentially identical or essentially complementary to SEQ ID NO:1-18, 622, or 623.

In certain embodiments: (a) the plant is a corn plant, the gene or the transcript is a corn EIN2 gene or transcript, and the polynucleotide molecule is selected from the group consisting SEQ ID NO: 27-60, and 61 or the polynucleotide comprises at least 18 contiguous nucleotides that are essentially identical or essentially complementary to SEQ ID NO:2 or SEQ ID NO:3; (b) the plant is a soy plant, the gene or the transcript is a soy EIN2 gene or transcript, and the polynucleotide molecule is selected from the group consisting of SEQ ID NO:191-295, and 296, or the polynucleotide comprises at least 18 contiguous nucleotides that are essentially identical or essentially complementary to any one of SEQ ID NO:11-16; (c) the plant is a Canola plant, the gene or the transcript is a Canola EIN2 gene or transcript, and the polynucleotide molecule is selected from the group consisting of SEQ ID NO: 19-25, and 26, or the polynucleotide comprises at least 18 contiguous nucleotides that are essentially identical or essentially complementary to SEQ ID NO:1; (d) the plant is a cucumber plant, the gene or the transcript is a cucumber EIN2 gene or transcript, and the polynucleotide molecule is selected from the group consisting of SEQ ID NO:62-106, 627-657, and 658, or the polynucleotide comprises at least 18 contiguous nucleotides that are essentially identical or essentially complementary to SEQ ID NO:4, SEQ ID NO:5, SEQ ID NO: 622, or SEQ ID NO:623; (e) the plant is a lettuce plant, the gene or the transcript is a lettuce EIN2 gene or transcript, and the polynucleotide molecule is selected from the group consisting of SEQ ID NO:107-111, and 112, or the polynucleotide comprises at least 18 contiguous nucleotides that are essentially identical or essentially complementary to SEQ ID NO:6; (f) the plant is a rice plant, the gene or the transcript is a rice EIN2 gene or transcript, and the polynucleotide molecule is selected from the group consisting of SEQ ID NO:113-189, and 190, or the polynucleotide comprises at least 18 contiguous nucleotides that are essentially identical or essentially complementary to any one of SEQ ID NO:7-10; (g) the plant is a tomato plant the gene or the transcript is a tomato EIN2 gene or transcript, and the polynucleotide molecule is selected from the group consisting of SEQ ID NO:297-331, 624, 625, and 626, or the polynucleotide comprises at least 18 contiguous nucleotides that are essentially identical or essentially complementary to any one of SEQ ID NO:17-18; (h) the plant is a corn or rice plant and the polynucleotide comprises a sequence selected from the group consisting of SEQ ID NO: 332-560, and 561; (i) the plant is a cucumber or soy plant and the polynucleotide comprises a sequence selected from the group consisting of SEQ ID NO: 562-588, and 589; (j) the plant is a cucumber or tomato plant of and the polynucleotide comprises a sequence selected from the group consisting of SEQ ID NO:590, and 591; or, (k) the plant is a rice or tomato plant and the polynucleotide comprises a sequence selected from the group consisting SEQ ID NO: 592-620, and 621. In certain embodiments, the composition comprises any combination of two or more polynucleotide molecules. In certain embodiments, the polynucleotide is at least 18 to about 24, about 25 to about 50, about 51 to about 100, about 101 to about 300, about 301 to about 500, or at least about 500 or more residues in length. In certain embodiments, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments, the composition further comprises a non-polynucleotide herbicidal molecule and the plant is resistant to the herbicidal molecule. In certain embodiments, the transfer agent comprises an organosilicone preparation. In certain embodiments, the polynucleotide is not operably linked to a viral vector. In certain embodiments, the polynucleotide is not integrated into the plant chromosome.

Further embodiments of the invention are directed to: a plant made according to the above-described method; progeny of the plant that exhibits improvement in delayed senescence, improved disease tolerance, and/or improved yield; seed of the plant, wherein seed from the plant exhibits improvement in delayed senescence, improved disease tolerance, and/or improved yield; and a processed product of the plant, the progeny plant, or the seed, wherein the processed product exhibits improvement in delayed senescence, improved disease tolerance, and/or improved yield. In certain embodiments, the processed product exhibits an improved attribute relative to a processed product of an untreated control plant and wherein the improved attribute results from the delayed senescence, improved disease tolerance, and/or improved yield. An improved attribute of a processed product can include, but is not limited to, decreased mycotoxin content, improved nutritional content, improved storage characteristics, improved flavor, improved consistency, and the like when compared to a processed product obtained from an untreated plant or plant part.

An additional embodiment of the invention is directed to a composition comprising a polynucleotide molecule that comprises at least 18 contiguous nucleotides that are essentially identical or essentially complementary to a EIN2 gene or transcript of the gene, wherein the polynucleotide is not operably linked to a promoter; and, a transfer agent. In certain embodiments, the polynucleotide is selected from the group consisting of wherein the polynucleotide is selected from the group consisting of SEQ ID NO:19-621, 624-657, and 658, or wherein the polynucleotide comprises at least 18 contiguous nucleotides that are essentially identical or essentially complementary to SEQ ID NO:1-18, 622, or 623. In certain embodiments, the polynucleotide is at least 18 to about 24, about 25 to about 50, about 51 to about 100, about 101 to about 300, about 301 to about 500, or at least about 500 or more residues in length. In certain embodiments, the composition further comprises a non-polynucleotide herbicidal molecule, a polynucleotide herbicidal molecule, a polynucleotide that suppresses an herbicide target gene, an insecticide, a fungicide, a nematocide, or a combination thereof. In certain embodiments, the transfer agent is an organosilicone preparation. In certain embodiments, the polynucleotide is not physically bound to a biolistic particle. Another embodiment of the invention is directed to a method of making a composition comprising the step of combining at least: a) a polynucleotide molecule comprising at least 18 contiguous nucleotides that are essentially identical or essentially complementary to a EIN2 gene or a transcript of the gene, wherein the polynucleotide is not operably linked to a promoter or a viral vector; and, b) a transfer agent. In certain embodiments, the polynucleotide is obtained by in vivo biosynthesis, in vitro enzymatic synthesis, or chemical synthesis. In certain embodiments, the method further comprises combining with the polynucleotide and the transfer agent at least one of a non-polynucleotide herbicidal molecule, a polynucleotide herbicidal molecule, an insecticide, a fungicide, and/or a nematocide. In certain embodiments, the transfer agent is an organosilicone preparation. In certain embodiments, the polynucleotide is selected from the group consisting of wherein the polynucleotide is selected from the group consisting of SEQ ID NO:19-621, 624-657, and 658, or wherein the polynucleotide comprises at least 18 contiguous nucleotides that are essentially identical or essentially complementary to SEQ ID NO:1-18, 622, or 623.

Yet another embodiment of the invention is directed to a method of identifying a polynucleotide for delaying senescence, improving disease tolerance, and/or improving yield in a plant comprising: a) selecting a population of polynucleotides that are essentially identical or essentially complementary to a EIN2 gene or transcript of the gene; b) topically applying to a surface of at least one of the plants a composition comprising at least one polynucleotide from the population and a transfer agent to obtain a treated plant; and, c) identifying a treated plant that exhibits suppression of the EIN2 gene or exhibits delayed senescence and/or improved yield, thereby identifying a polynucleotide that delays senescence and/or improves yield in a plant. In certain embodiments, the polynucleotide is selected from the group consisting of wherein the polynucleotide is selected from the group consisting of SEQ ID NO:19-621, 624-657, and 658, or the polynucleotide comprises at least 18 contiguous nucleotides that are essentially identical or essentially complementary to SEQ ID NO:1-18, 622, or 623. In certain embodiments: (a) the plant is a corn plant, the gene or the transcript is a corn EIN2 gene or transcript, and the polynucleotide molecule is selected from the group consisting SEQ ID NO: 27-60, and 61 or the polynucleotide comprises at least 18 contiguous nucleotides that are essentially identical or essentially complementary to SEQ ID NO:2 or SEQ ID NO:3; (b) the plant is a soy plant, the gene or the transcript is a soy EIN2 gene or transcript, and the polynucleotide molecule is selected from the group consisting of SEQ ID NO:191-295, and 296, or the polynucleotide comprises at least 18 contiguous nucleotides that are essentially identical or essentially complementary to any one of SEQ ID NO:11-16; (c) the plant is a Canola plant, the gene or the transcript is a Canola EIN2 gene or transcript, and the polynucleotide molecule is selected from the group consisting of SEQ ID NO: 19-25, and 26, or the polynucleotide comprises at least 18 contiguous nucleotides that are essentially identical or essentially complementary to SEQ ID NO:1; (d) the plant is a cucumber plant, the gene or the transcript is a cucumber EIN2 gene or transcript, and the polynucleotide molecule is selected from the group consisting of SEQ ID NO:62-106, 627-657, and 658, or the polynucleotide comprises at least 18 contiguous nucleotides that are essentially identical or essentially complementary to SEQ ID NO:4, SEQ ID NO:5, SEQ ID NO: 622, or SEQ ID NO:623; (e) the plant is a lettuce plant, the gene or the transcript is a lettuce EIN2 gene or transcript, and the polynucleotide molecule is selected from the group consisting of SEQ ID NO:107-111, and 112, or the polynucleotide comprises at least 18 contiguous nucleotides that are essentially identical or essentially complementary to SEQ ID NO:6; (f) the plant is a rice plant, the gene or the transcript is a rice EIN2 gene or transcript, and the polynucleotide molecule is selected from the group consisting of SEQ ID NO:113-189, and 190, or the polynucleotide comprises at least 18 contiguous nucleotides that are essentially identical or essentially complementary to any one of SEQ ID NO:7-10; (g) the plant is a tomato plant the gene or the transcript is a tomato EIN2 gene or transcript, and the polynucleotide molecule is selected from the group consisting of SEQ ID NO:297-331, 624, 625, and 626, or the polynucleotide comprises at least 18 contiguous nucleotides that are essentially identical or essentially complementary to any one of SEQ ID NO:17-18; (h) the plant is a corn or rice plant and the polynucleotide comprises a sequence selected from the group consisting of SEQ ID NO: 332-560, and 561; (i) the plant is a cucumber or soy plant and the polynucleotide comprises a sequence selected from the group consisting of SEQ ID NO: 562-588, and 589; (j) the plant is a cucumber or tomato plant of and the polynucleotide comprises a sequence selected from the group consisting of SEQ ID NO:590, and 591; or, (k) the plant is a rice or tomato plant and the polynucleotide comprises a sequence selected from the group consisting SEQ ID NO: 592-620, and 621.

A further embodiment of the invention is directed to a plant comprising an exogenous polynucleotide that comprises at least 18 contiguous nucleotides that are essentially identical or essentially complementary to a EIN2 gene or transcript of the gene, wherein the exogenous polynucleotide is not operably linked to a promoter or to a viral vector, is not integrated into the chromosomal DNA of the plant, and is not found in a non-transgenic plant; and, wherein the plant exhibits delayed senescence and/or improved yield that results from suppression of the EIN2 gene. In certain embodiments, the plant further comprises an organosilicone compound, or a metabolite thereof, or a component thereof. In certain embodiments, the polynucleotide is selected from the group consisting of wherein the polynucleotide is selected from the group consisting of SEQ ID NO:19-621, 624-657, and 658, or the polynucleotide comprises at least 18 contiguous nucleotides that are essentially identical or essentially complementary to SEQ ID NO:1-18, 622, or 623. In certain embodiments: (a) the plant is a corn plant, the gene or the transcript is a corn EIN2 gene or transcript, and the polynucleotide molecule is selected from the group consisting SEQ ID NO: 27-60, and 61 or the polynucleotide comprises at least 18 contiguous nucleotides that are essentially identical or essentially complementary to SEQ ID NO:2 or SEQ ID NO:3; (b) the plant is a soy plant, the gene or the transcript is a soy EIN2 gene or transcript, and the polynucleotide molecule is selected from the group consisting of SEQ ID NO:191-295, and 296, or the polynucleotide comprises at least 18 contiguous nucleotides that are essentially identical or essentially complementary to any one of SEQ ID NO:11-16; (c) the plant is a Canola plant, the gene or the transcript is a Canola EIN2 gene or transcript, and the polynucleotide molecule is selected from the group consisting of SEQ ID NO: 19-25, and 26, or the polynucleotide comprises at least 18 contiguous nucleotides that are essentially identical or essentially complementary to SEQ ID NO:1; (d) the plant is a cucumber plant, the gene or the transcript is a cucumber EIN2 gene or transcript, and the polynucleotide molecule is selected from the group consisting of SEQ ID NO:62-106, 627-657, and 658, or the polynucleotide comprises at least 18 contiguous nucleotides that are essentially identical or essentially complementary to SEQ ID NO:4, SEQ ID NO:5, SEQ ID NO: 622, or SEQ ID NO:623; (e) the plant is a lettuce plant, the gene or the transcript is a lettuce EIN2 gene or transcript, and the polynucleotide molecule is selected from the group consisting of SEQ ID NO:107-111, and 112, or the polynucleotide comprises at least 18 contiguous nucleotides that are essentially identical or essentially complementary to SEQ ID NO:6; (f) the plant is a rice plant, the gene or the transcript is a rice EIN2 gene or transcript, and the polynucleotide molecule is selected from the group consisting of SEQ ID NO:113-189, and 190, or the polynucleotide comprises at least 18 contiguous nucleotides that are essentially identical or essentially complementary to any one of SEQ ID NO:7-10; (g) the plant is a tomato plant the gene or the transcript is a tomato EIN2 gene or transcript, and the polynucleotide molecule is selected from the group consisting of SEQ ID NO:297-331, 624, 625, and 626, or the polynucleotide comprises at least 18 contiguous nucleotides that are essentially identical or essentially complementary to any one of SEQ ID NO:17-18; (h) the plant is a corn or rice plant and the polynucleotide comprises a sequence selected from the group consisting of SEQ ID NO: 332-560, and 561; (i) the plant is a cucumber or soy plant and the polynucleotide comprises a sequence selected from the group consisting of SEQ ID NO: 562-588, and 589; (j) the plant is a cucumber or tomato plant of and the polynucleotide comprises a sequence selected from the group consisting of SEQ ID NO:590, and 591; or, (k) the plant is a rice or tomato plant and the polynucleotide comprises a sequence selected from the group consisting SEQ ID NO: 592-620, and 621.

An additional embodiment of the invention is directed to a plant part comprising an exogenous polynucleotide that comprises at least 18 contiguous nucleotides that are essentially identical or essentially complementary to a EIN2 gene or transcript of the gene, wherein the exogenous polynucleotide is not operably linked to a promoter or to a viral vector and is not found in a non-transgenic plant; and, wherein the plant part exhibits delayed senescence, improved disease tolerance, and/or improved yield that results from suppression of the EIN2 gene. In certain embodiments, the plant part further comprises an organosilicone compound or a metabolite thereof. In certain embodiments, the polynucleotide is selected from the group consisting of wherein the polynucleotide is selected from the group consisting of SEQ ID NO:19-621, 624-657, and 658, or the polynucleotide comprises at least 18 contiguous nucleotides that are essentially identical or essentially complementary to SEQ ID NO:1-18, 622, or 623. In certain embodiments: (a) the plant part is a corn plant part, the gene or the transcript is a corn EIN2 gene or transcript, and the polynucleotide molecule is selected from the group consisting SEQ ID NO: 27-60, and 61 or the polynucleotide comprises at least 18 contiguous nucleotides that are essentially identical or essentially complementary to SEQ ID NO:2 or SEQ ID NO:3; (b) the plant part is a soy plant part, the gene or the transcript is a soy EIN2 gene or transcript, and the polynucleotide molecule is selected from the group consisting of SEQ ID NO:191-295, and 296, or the polynucleotide comprises at least 18 contiguous nucleotides that are essentially identical or essentially complementary to any one of SEQ ID NO:11-16; (c) the plant part is a Canola plant part, the gene or the transcript is a Canola EIN2 gene or transcript, and the polynucleotide molecule is selected from the group consisting of SEQ ID NO: 19-25, and 26, or the polynucleotide comprises at least 18 contiguous nucleotides that are essentially identical or essentially complementary to SEQ ID NO:1; (d) the plant part is a cucumber plant part, the gene or the transcript is a cucumber EIN2 gene or transcript, and the polynucleotide molecule is selected from the group consisting of SEQ ID NO:62-106, 627-657, and 658, or the polynucleotide comprises at least 18 contiguous nucleotides that are essentially identical or essentially complementary to SEQ ID NO:4, SEQ ID NO:5, SEQ ID NO: 622, or SEQ ID NO:623; (e) the plant part is a lettuce plant part, the gene or the transcript is a lettuce EIN2 gene or transcript, and the polynucleotide molecule is selected from the group consisting of SEQ ID NO:107-111, and 112, or the polynucleotide comprises at least 18 contiguous nucleotides that are essentially identical or essentially complementary to SEQ ID NO:6; (f) the plant part is a rice plant part, the gene or the transcript is a rice EIN2 gene or transcript, and the polynucleotide molecule is selected from the group consisting of SEQ ID NO:113-189, and 190, or the polynucleotide comprises at least 18 contiguous nucleotides that are essentially identical or essentially complementary to any one of SEQ ID NO:7-10; (g) the plant part is a tomato plant part the gene or the transcript is a tomato EIN2 gene or transcript, and the polynucleotide molecule is selected from the group consisting of SEQ ID NO:297-331, 624, 625, and 626, or the polynucleotide comprises at least 18 contiguous nucleotides that are essentially identical or essentially complementary to any one of SEQ ID NO:17-18; (h) the plant part is a corn or rice plant part and the polynucleotide comprises a sequence selected from the group consisting of SEQ ID NO: 332-560, and 561; (i) the plant part is a cucumber or soy plant part and the polynucleotide comprises a sequence selected from the group consisting of SEQ ID NO: 562-588, and 589; (j) the plant part is a cucumber or tomato plant part of and the polynucleotide comprises a sequence selected from the group consisting of SEQ ID NO:590, and 591; or, (k) the plant part is a rice or tomato plant part and the polynucleotide comprises a sequence selected from the group consisting SEQ ID NO: 592-620, and 621. Another embodiment of the invention is directed to a plant that exhibits delayed senescence, improved disease tolerance, and/or improved yield, wherein the plant was topically treated with a composition that comprises: (a) at least one polynucleotide that comprises at least 18 contiguous nucleotides that are essentially identical or essentially complementary to a EIN2 gene or to a transcript of the gene; and, (b) a transfer agent; and, wherein the plant exhibits delayed senescence, improved disease tolerance, and/or improved yield that results from suppression of the EIN2 gene. Ion certain embodiments, the transfer agent comprises an organosilicone preparation.

DETAILED DESCRIPTION

I. Definitions

Figure 1A:
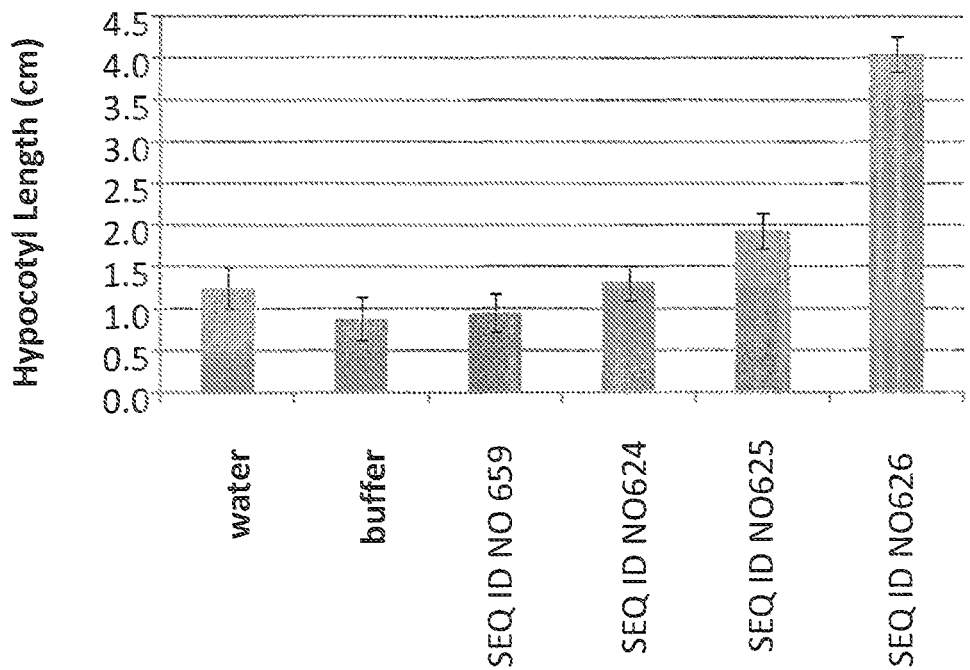
FIG. 1 A, B. Illustrates the hypocotyl lengths of tomato seedlings treated with EIN2 triggers or control treatments, and grown in the presence of 100 µm ACC in the dark. SEQ ID NO: 624, 625, and 626 are double-stranded RNAs containing sequences from the EIN2 transcript (Table 3). SEQ ID NO:659 is a control double-stranded RNA sequence from the jelly-fish green fluorescent protein (GFP). Two independent experiments are shown in FIGS. 1A and 1B. N=15-44 seedlings. Error bars represent 95% confidence intervals.

The following definitions and methods are provided to better define the present invention and to guide those of ordinary skill in the art in the practice of the present invention. Unless otherwise noted, terms are to be understood according to conventional usage by those of ordinary skill in the relevant art.

Where a term is provided in the singular, the inventors also contemplate aspects of the invention described by the plural of that term.

As used herein, the terms "DNA," "DNA molecule," and "DNA polynucleotide molecule" refer to a single-stranded DNA or double-stranded DNA molecule of genomic or synthetic origin, such as, a polymer of deoxyribonucleotide bases or a DNA polynucleotide molecule.

As used herein, the terms "DNA sequence," "DNA nucleotide sequence," and "DNA polynucleotide sequence" refer to the nucleotide sequence of a DNA molecule.

As used herein, the term "gene" refers to any portion of a nucleic acid that provides for expression of a transcript or encodes a transcript. A "gene" thus includes, but is not limited to, a promoter region, 5' untranslated regions, transcript encoding regions that can include intronic regions, and 3' untranslated regions.

As used herein, the terms "RNA," "RNA molecule," and "RNA polynucleotide molecule" refer to a single-stranded RNA or double-stranded RNA molecule of genomic or synthetic origin, such as, a polymer of ribonucleotide bases that comprise single or double stranded regions.

Unless otherwise stated, nucleotide sequences in the text of this specification are given, when read from left to right, in the 5' to 3' direction. The nomenclature used herein is that required by Title 37 of the United States Code of Federal Regulations §1.822 and set forth in the tables in WIPO Standard ST.25 (1998), Appendix 2, Tables 1 and 3.

As used herein, a "plant surface" refers to any exterior portion of a plant. Plant surfaces thus include, but are not limited to, the surfaces of flowers, stems, tubers, fruit, anthers, pollen, leaves, roots, or seeds. A plant surface can be on a portion of a plant that is attached to other portions of a plant or on a portion of a plant that is detached from the plant.

As used herein, the phrase "polynucleotide is not operably linked to a promoter" refers to a polynucleotide that is not covalently linked to a polynucleotide promoter sequence that is specifically recognized by either a DNA dependent RNA polymerase II protein or by a viral RNA dependent RNA polymerase in such a manner that the polynucleotide will be transcribed by the DNA dependent RNA polymerase II protein or viral RNA dependent RNA polymerase. A polynucleotide that is not operably linked to a promoter can be transcribed by a plant RNA dependent RNA polymerase.

As used herein, SEQ ID NO:19-331, though displayed in the Sequence Listing in the form of ssDNA, encompass dsDNA equivalents, dsRNA equivalents, ssRNA equivalents, ssRNA complements, ssDNA as shown, and ssDNA complements.

As used herein, SEQ ID NO: 332-621, and 624-659, though displayed in the Sequence Listing in the form of ssDNA, encompass dsDNA equivalents, dsRNA equivalents, ssRNA equivalents, a ssRNA complement, ssDNA as shown, and ssDNA complements.

As used herein, a first nucleic-acid sequence is "operably" connected or "linked" with a second nucleic acid sequence when the first nucleic acid sequence is placed in a functional relationship with the second nucleic acid sequence. For instance, a promoter is operably linked to an RNA and/or protein-coding sequence if the promoter provides for transcription or expression of the RNA or coding sequence. Generally, operably linked DNA sequences are contiguous and, where necessary to join two protein-coding regions, are in the same reading frame.

As used herein, the phrase "organosilicone preparation" refers to a liquid comprising one or more organosilicone compounds, wherein the liquid or components contained therein, when combined with a polynucleotide in a composition that is topically applied to a target plant surface, enable the polynucleotide to enter a plant cell. Exemplary organosilicone preparations include, but are not limited to, preparations marketed under the trade names "Silwet®" or "BREAK-THRU®" and preparations provided in Table 1. In certain embodiments, an organosilicone preparation can enable a polynucleotide to enter a plant cell in a manner permitting a polynucleotide mediated suppression of target gene expression in the plant cell.

As used herein, the phrases "delayed senescence and/or improved yield" or "delaying senescence or improving yield" refer to any measurable delay in the onset or progress of a senescence process and/or any measurable improvement in yield. In certain embodiments, a delay in a senescence process and/or an improvement in yield in a plant or plant part can be determined in a comparison to a control plant or plant part that has not been treated with a composition comprising a polynucleotide and a transfer agent. When used in this context, a control plant is a plant that has not undergone treatment with polynucleotide and a transfer agent. Such control plants would include, but are not limited to, untreated plants or mock treated plants.

As used herein, the phrase "improved disease tolerance" refer to any measurable increase in a plants resistance to fungal-, bacterial-, and/or nematode-induced damage. In certain embodiments, an improvement in fungal-, bacterial-, and/or nematode-resistance in a plant or plant part can be determined in a comparison to a control plant or plant part that has not been treated with a composition comprising a polynucleotide and a transfer agent. When used in this context, a control plant is a plant that has not undergone treatment with polynucleotide and a transfer agent. Such control plants would include, but are not limited to, untreated plants or mock treated plants.

As used herein, a "senescence process" refers to any pre- or post-harvest process whereby any visual, physical, and/or biochemical property of a plant or plant part changes as a result of aging.

As used herein, the phrase "provides for a reduction", when used in the context of a transcript or a protein in a plant or plant part, refers to any measurable decrease in the level of transcript or protein in a plant or plant part. In certain embodiments, a reduction of the level of a transcript or protein in a plant or plant part can be determined in a comparison to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the phrase "wherein said plant does not comprise a transgene" refers to a plant that lacks either a DNA molecule comprising a promoter that is operably linked to a polynucleotide or a recombinant viral vector.

As used herein, the phrase "suppressing expression" or "suppression", when used in the context of a gene, refers any measurable decrease in the amount and/or activity of a product encoded by the gene. Thus, expression of a gene can be suppressed when there is a reduction in levels of a transcript from the gene, a reduction in levels of a protein encoded by the gene, a reduction in the activity of the transcript from the gene, a reduction in the activity of a protein encoded by the gene, any one of the preceding conditions, or any combination of the preceding conditions. In this context, the activity of a transcript includes, but is not limited to, its ability to be translated into a protein and/or to exert any RNA-mediated biologic or biochemical effect. In this context, the activity of a protein includes, but is not limited to, its ability to exert any protein-mediated biologic or biochemical effect. In certain embodiments, a suppression of gene expression in a plant or plant part can be determined in a comparison of gene product levels or activities in a treated plant to a control plant or plant part that has not been treated with a composition comprising a polynucleotide and a transfer agent. When used in this context, a control plant or plant part is a plant or plant part that has not undergone treatment with polynucleotide and a transfer agent. Such control plants or plant parts would include, but are not limited to, untreated or mock treated plants and plant parts.

As used herein, the term "transcript" corresponds to any RNA that is produced from a gene by the process of transcription. A transcript of a gene can thus comprise a primary transcription product which can contain introns or can comprise a mature RNA that lacks introns.

As used herein, the term "liquid" refers to both homogeneous mixtures such as solutions and non-homogeneous mixtures such as suspensions, colloids, micelles, and emulsions.

II. Overview

Provided herein are certain methods and polynucleotide compositions that can be applied to living plant cells/tissues to suppress expression of target EIN2 genes and that provide delayed senescence, improved disease tolerance, and/or improved yield to a crop plant in need of the benefit. Also provided herein are plants and plant parts exhibiting delayed senescence and/or improved yield as well as processed products of such plants or plant parts. The compositions may be topically applied to the surface of a plant, such as to the surface of a leaf, and include a transfer agent. Aspects of the method can be applied to various crops, for example, including but not limited to: i) row crop plants including, but not limited to, corn, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) include fruit trees and plants. Fruit trees produced by such processes include, but are not limited to, citrus and apple trees. Plants produced by such processes include, but are not limited to, avocados, tomatoes, eggplant, cucumber, melons, watermelons, and grapes as well as various ornamental plants.

Examples of the fungal plant diseases controlled by materials and compositions provided herein include, but are not limited to, diseases caused by phytopathogenic fungi (in particular of the classes of Ascomycetes, Deuteromycetes, Oomycetes and Basidiomycetes) such as *Magnaporthe grisea, Cochliobolus miyabeanus, Rhizoctonia solani* and *Gibberella fujikuroi* on rice; *Erysiphe graminis, Fusarium graminearum, F. avenacerum, F. culmorum, Microdochium nivale, Puccinia striiformis, P. graminis, P. recondita, P. hordei, Typhula* sp., *Micronectriella nivalis, Ustilago tritici, U. nuda, Tilletia caries, Pseudocercosporella herpotrichoides, Rhynchosporium secalis, Septoria tritici, Leptosphaeria nodorum* and *Pyrenophora teres* on wheat and barley; *Diaporthe citri, Elsinoe fawcetti, Penicillium digitatum, P. italicum, Phytophthora parasitica* and *Phytophthora citrophthora* on citrus; *Monilinia mali, Valsa ceratosperma, Podosphaera leucotricha, Alternaria alternata* apple pathotype, *Venturia inaequalis, Colletotrichum acutatum* and *Phytophtora cactorum* on apple; *Venturia nashicola, V. pirina, Alternaria alternata* Japanese pear pathotype, *Gymnosporangium haraeanum* and *Phytophthora cactorum* on pear; *Monilinia fructicola, Cladosporium carpophilum* and *Phomopsis* sp. on peach; *Elsinoe ampelina, Glomerella cingulata, Uncinula necator, Phakopsora ampelopsidis, Guignardia bidwellii* and *Plasmopara viticola* on grape; *Gloeosporium kaki, Cercospora kaki* and *Mycosphaerella nawae* on persimmon; *Colletotrichum lagenarium, Sphaerotheca fuliginea, Mycosphaerella melonis, Fusarium oxysporum, Pseudoperonospora cubensis* and *Phytophthora* sp. on Cucurbitales vegetables; *Alternaria solani, Cladosporium fulvum* and *Phytophthora infestans* on tomato; *Phomopsis vexans* and *Erysiphe cichoracearum* on eggplant; *Alternaria japonica, Cercosporella brassicae, Plasmodiophora brassicae* and *Peronospora parasitica* on Brassicaceae vegetables; *Puccinia allii* and *Peronospora destructor* on leek; *Cercospora kikuchii, Elsinoe glycines, Diaporthe phaseolorum* var. *sojae, Phakopsora pachyrhizi* and *Phytophthora sojae* on soybean; *Colletotrichum lindemuthianum* of kidney bean; *Cercospora personata, Cercospora arachidicola* and *Sclerotium rolfsii* on peanut; *Erysiphe pisi* on pea; *Alternaria solani, Phytophthora infestans, Phytophthora erythroseptica* and *Spongospora subterranean* f sp. subterranean on potato; *Sphaerotheca humuli* and *Glomerella cingulata* on strawberry; *Exobasidium reticulatum, Elsinoe leucospila, Pestalotiopsis* sp. and *Colletotrichum theae-sinensis* on tea; *Alternaria longipes, Erysiphe cichoracearum, Colletotrichum tabacum, Peronospora tabacina* and *Phytophthora nicotianae* on tobacco; *Cercospora beticola, Thanatephorus cucumeris,* and *Aphanidermatum cochlioides* on sugar beet; *Diplocarpon rosae, Sphaerotheca pannosa* and *Peronospora sparsa* on rose; *Bremia lactucae, Septoria chrysanthemi-indici* and *Puccinia horiana* on chrysanthemum and Compositae vegetables; *Alternaria brassicicola* on radish; *Sclerotinia homeocarpa* and *Rhizoctonia solani* on turf; *Mycosphaerella fijiensis* and *Mycosphaerella musicola* on banana; *Plasmopara halstedii* on sunflower; and various diseases on crops caused by *Pythium* spp. (e.g., *Pythium aphanidermatum, Pythium debaryanum, Pythium graminicola, Pythium irregulare, Pythium ultimum*), *Botrytis cinerea, Sclerotinia sclerotiorum, Aspergillus* spp., *Penicillium* spp., *Fusarium* spp., *Gibberella* spp., *Trichoderma* spp., *Thielaviopsis* spp., *Rhizopus* spp., *Mucor* spp., *Corticium* spp., *Phoma* spp., *Rhizoctonia* spp., *Diplodia* spp., *Polymyxa* spp. and *Olpidium* spp.

Exemplary plants protected from plant-parasitic nematodes species associated with them by the methods and compositions provided herein include, but are not limited to: alfalfa: *Pratylenchus* spp., *Meloidogyne hapla, Meloidogyne incognita, Meloidogyne javanica, Ditylenchus dipsaci, Paratylenchus* spp., *Xiphinema* spp.; banana: *Pratylenchus coffeae, Meloidogyne incognita, Meloidogyne arenaria, Meloidogyne javanica, Radopholus similis, Helicotylenchus multicinctus, Rotylenchulus reniformis*; cereals (barley, wheat, rye): *Pratylenchus* spp., *Meloidogyne naasi*; chickpea: *Pratylenchus* spp., *Meloidogyne* spp., *Heterodera cajani, Rotylenchulus reniformis, Hoplolaimus seinhorsti*; citrus: *Pratylenchus* spp., *Meloidogyne* spp., *Tylenchulus*

*semipenetrans, Radopholus similis, Radopholus citrophilus, Hemicycliophora arenaria, Bolonolaimus longicaudatus, Trichodorus* spp., *Paratrichodorus* spp., *Xiphinema* spp.; clover: *Pratylenchus* spp., *Meloidogyne* spp., *Heterodera trifolii*; corn: *Pratylenchus brachyurus, Pratylenchus hexincisus, Pratylenchus penetrans, Pratylenchus scribneri, Pratylenchus zeae, Meloidogyne incognita, Paratrichodorus minor, Longidorus* spp., *Hoplolaimus columbus*; cotton: *Pratylenchus* spp., *Meloidogyne incognita, Belonolaimus longicaudatus, Rotylenchulus reniformis, Hoplolaimus galeatus, Tylenchorhynchus* spp., *Paratrichodorus* minor; grapes: *Pratylenchus vulnus, Meloidogyne* spp., *Xiphinema* spp., *Tylenchulus semipenetrans, Rotylenchulus reniformis*; grasses: *Pratylenchus* spp., *Longidorus* spp., *Paratrichodorus christiei, Xiphinema* spp., *Ditylenchus* spp.; peanut: *Pratylenchus* spp., *Meloidogyne hapla, Meloidogyne arenaria, Criconemella* spp., *Belonolaimus longicaudatus*; pigeon pea: *Pratylenchus* spp., *Meloidogyne* spp., *Heterodera cajani, Rotylenchulus reniformis, Hoplolaimus seinhorsti*; potato: *Pratylenchus* spp., *Meloidogyne* spp., *Globodera rostochiensis, Globodera pallida, Trichodorus primitivus, Ditylenchus* spp., *Paratrichodorus* spp., *Nacobbus aberrans*; rice: *Pratylenchus* spp., *Meloidogyne* spp., Aphelenchiodes *besseyi, Ditylenchus angustus, Hirchmanniella* spp., *Heterodera oryzae*; small fruits: *Pratylenchus* spp., *Meloidogyne* spp.; *Xiphinema* spp., *Longidorus* spp., *Paratrichodorus christiei, Aphelenchoides* spp.; soybean: *Pratylenchus* spp., *Meloidogyne incognita, Meloidogyne javanica, Heterodera glycines, Belonolaimus* spp., *Hoplolaimus columbus*; sugar beet: *Pratylenchus* spp., *Meloidogyne* spp., *Heterodera schachtii, Ditylenchus dipsaci, Nacobbus aberrans, Trichodorus* spp., *Longidorus* spp., *Paratrichodorus* spp.; sugar cane: *Pratylenchus* spp., *Meloidogyne* spp., *Radopholus* spp., *Heterodera* spp., *Hoplolaimus* spp., *Helicotylenchus* spp., *Scutellonema* spp., *Belonolaimus* spp., *Tylenchorhynchus* spp., *Xiphinema* spp., *Longidorus* spp., *Paratrichodorus* spp.; tobacco: *Pratylenchus* spp., *Meloidogyne* spp., *Tylenchorhynchus claytoni, Globodera tabacum, Trichodorus* spp., *Xiphinema americanum, Ditylenchus dipsaci, Paratrichodorus* spp.; and tomato: *Pratylenchus* spp., *Meloidogyne* spp.

Materials and compositions provided herein also provide for improved tolerance to bacterial diseases including but not limited to: Disease Pathogen Bacterial leaf blight and stalk rot *Pseudomonas avenae* subsp. *avenae*, Bacterial leaf spot *Xanthomonas campestris* pv. *Holcicola*, Bacterial stalk rot *Enterobacter dissolvens=Erwinia dissolvens*, Bacterial stalk and top rot *Erwinia carotovora* subsp. *carotovora, Erwinia chrysanthemi* pv. *zeae*, Bacterial stripe *Pseudomonas andropogonis*, Chocolate spot *Pseudomonas syringae* pv. *coronafaciens*, Goss's bacterial wilt and blight *Clavibacter michiganensis* subsp. (leaf freckles and wilt) *nebraskensis=Corynebacterium michiganense* pv. *andnebraskense, Holcus* spot *Pseudomonas syringae* pv. *syringae*, Purple leaf sheath Hemiparasitic bacteria Seed rot-seedling blight *Bacillus subtilis*, Stewart's disease (bacterial wilt) *Pantoea stewartii=Erwinia stewartii*, and Corn stunt (achapparramiento, *Spiroplasma kunkelii* maize stunt, Mesa Central or Rio Grande maize stunt).

Without being bound by theory, the compositions and methods of the present invention are believed to operate through one or more of the several natural cellular pathways involved in RNA-mediated gene suppression as generally described in Brodersen and Voinnet (2006), *Trends Genetics*, 22:268-280; Tomari and Zamore (2005) *Genes & Dev.*, 19:517-529; Vaucheret (2006) *Genes Dev.*, 20:759-771; Meins et al. (2005) *Annu. Rev. Cell Dev. Biol.*, 21:297-318; and Jones-Rhoades et al. (2006) *Annu. Rev. Plant Biol.*, 57:19-53. RNA-mediated gene suppression generally involves a double-stranded RNA (dsRNA) intermediate that is formed intra-molecularly within a single RNA molecule or inter-molecularly between two RNA molecules. This longer dsRNA intermediate is processed by a ribonuclease of the RNAase III family (Dicer or Dicer-like ribonuclease) to one or more shorter double-stranded RNAs, one strand of which is incorporated into the RNA-induced silencing complex ("RISC"). For example, the siRNA pathway involves the cleavage of a longer double-stranded RNA intermediate to small interfering RNAs ("siRNAs"). The size of siRNAs is believed to range from about 19 to about 25 base pairs, but the most common classes of siRNAs in plants include those containing 21 to 24 base pairs (See, Hamilton et al. (2002) *EMBO J.*, 21:4671-4679).

Polynucleotides

As used herein, "polynucleotide" refers to a DNA or RNA molecule containing multiple nucleotides and generally refers both to "oligonucleotides" (a polynucleotide molecule of 18-25 nucleotides in length) and longer polynucleotides of 26 or more nucleotides. Embodiments of this invention include compositions including oligonucleotides having a length of 18-25 nucleotides (18-mers, 19-mers, 20-mers, 21-mers, 22-mers, 23-mers, 24-mers, or 25-mers), or medium-length polynucleotides having a length of 26 or more nucleotides (polynucleotides of 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, about 65, about 70, about 75, about 80, about 85, about 90, about 95, about 100, about 110, about 120, about 130, about 140, about 150, about 160, about 170, about 180, about 190, about 200, about 210, about 220, about 230, about 240, about 250, about 260, about 270, about 280, about 290, or about 300 nucleotides), or long polynucleotides having a length greater than about 300 nucleotides (e. g., polynucleotides of between about 300 to about 400 nucleotides, between about 400 to about 500 nucleotides, between about 500 to about 600 nucleotides, between about 600 to about 700 nucleotides, between about 700 to about 800 nucleotides, between about 800 to about 900 nucleotides, between about 900 to about 1000 nucleotides, between about 300 to about 500 nucleotides, between about 300 to about 600 nucleotides, between about 300 to about 700 nucleotides, between about 300 to about 800 nucleotides, between about 300 to about 900 nucleotides, or about 1000 nucleotides in length, or even greater than about 1000 nucleotides in length, for example up to the entire length of a target EIN2 gene including coding or non-coding or both coding and non-coding portions of the target EIN2 gene). Where a polynucleotide is double-stranded, its length can be similarly described in terms of base pairs.

Polynucleotide compositions used in the various embodiments of this invention include compositions including oligonucleotides, polynucleotides, or a mixture of both, including: RNA or DNA or RNA/DNA hybrids or chemically modified oligonucleotides or polynucleotides or a mixture thereof. In certain embodiments, the polynucleotide may be a combination of ribonucleotides and deoxyribonucleotides, for example, synthetic polynucleotides consisting mainly of ribonucleotides but with one or more terminal deoxyribonucleotides or synthetic polynucleotides consisting mainly of deoxyribonucleotides but with one or more terminal dideoxyribonucleotides. In certain embodiments, the polynucleotide includes non-canonical nucleotides such as inosine, thiouridine, or pseudouridine. In certain embodiments, the polynucleotide includes chemically modified nucleotides. Examples of chemically modified oligonucleotides or polynucleotides are well known in the art; see, for example, U.S. Patent Publication 2011/0171287, U.S. Patent Publication 2011/0171176, U.S. Patent Publication 2011/0152353, U.S. Patent Publication 2011/0152346, and U.S. Patent Publication 2011/0160082, which are herein incorporated by reference. Illustrative examples include, but are not limited to, the naturally occurring phosphodiester backbone of an oligonucleotide or polynucleotide which can be partially or completely modified with phosphorothioate, phosphorodithioate, or methylphosphonate internucleotide linkage modifications, modified nucleoside bases or modified sugars can be used in oligonucleotide or polynucleotide synthesis, and oligonucleotides or polynucleotides can be labeled with a fluorescent moiety (e. g., fluorescein or rhodamine) or other label (e. g., biotin).

Polynucleotides can be single- or double-stranded RNA, single- or double-stranded DNA, double-stranded DNA/RNA hybrids, and modified analogues thereof. In certain embodiments of the invention, the polynucleotides that provide single-stranded RNA in the plant cell may be: (a) a single-stranded RNA molecule (ssRNA), (b) a single-stranded RNA molecule that self-hybridizes to form a double-stranded RNA molecule, (c) a double-stranded RNA molecule (dsRNA), (d) a single-stranded DNA molecule (ssDNA), (e) a single-stranded DNA molecule that self-hybridizes to form a double-stranded DNA molecule, (f) a single-stranded DNA molecule including a modified Pol III gene that is transcribed to an RNA molecule, (g) a double-stranded DNA molecule (dsDNA), (h) a double-stranded DNA molecule including a modified Pol III gene that is transcribed to an RNA molecule, and (i) a double-stranded, hybridized RNA/DNA molecule, or combinations thereof. In certain embodiments, these polynucleotides can comprise both ribonucleic acid residues and deoxyribonucleic acid residues. In certain embodiments, these polynucleotides include chemically modified nucleotides or non-canonical nucleotides. In certain embodiments of the methods, the polynucleotides include double-stranded DNA formed by intramolecular hybridization, double-stranded DNA formed by intermolecular hybridization, double-stranded RNA formed by intramolecular hybridization, or double-stranded RNA formed by intermolecular hybridization. In certain embodiments where the polynucleotide is a dsRNA, the anti-sense strand will comprise at least 18 nucleotides that are essentially complementary to the target EIN2 gene. In certain embodiments the polynucleotides include single-stranded DNA or single-stranded RNA that self-hybridizes to form a hairpin structure having an at least partially double-stranded structure including at least one segment that will hybridize to RNA transcribed from the gene targeted for suppression. Not intending to be bound by any mechanism, it is believed that such polynucleotides are or will produce single-stranded RNA with at least one segment that will hybridize to RNA transcribed from the gene targeted for suppression. In certain embodiments, the polynucleotides can be operably linked to a promoter—generally a promoter functional in a plant, for example, a pol II promoter, a pol III promoter, a pol IV promoter, or a pol V promoter.

The polynucleotide molecules of the present invention are designed to modulate expression by inducing regulation or suppression of an endogenous EIN2 gene in a plant and are designed to have a nucleotide sequence essentially identical or essentially complementary to the nucleotide sequence of an endogenous EIN2 gene of a plant or to the sequence of RNA transcribed from an endogenous EIN2 gene of a plant, which can be coding sequence or non-coding sequence. These effective polynucleotide molecules that modulate expression are referred to herein as "a trigger, or triggers". By "essentially identical" or "essentially complementary" it is meant that the trigger polynucleotides (or at least one strand of a double-stranded polynucleotide) have sufficient identity or complementarity to the endogenous gene or to the RNA transcribed from the endogenous EIN2 gene (e.g. the transcript) to suppress expression of the endogenous EIN2 gene (e.g. to effect a reduction in levels or activity of the gene transcript and/or encoded protein). In certain embodiments, the trigger polynucleotides provided herein can be directed to an EIN2 transgene present in the plant. Polynucleotides of the methods and compositions provided herein need not have 100 percent identity to a complementarity to the endogenous EIN2 gene or to the RNA transcribed from the endogenous EIN2 gene (i.e. the transcript) to suppress expression of the endogenous EIN2 gene (i.e. to effect a reduction in levels or activity of the gene transcript or encoded protein). Thus, in certain embodiments, the polynucleotide or a portion thereof is designed to be essentially identical to, or essentially complementary to, a sequence of at least 18 or 19 contiguous nucleotides in either the target gene or messenger RNA transcribed from the target gene (e.g. the transcript). In certain embodiments, an "essentially identical" polynucleotide has 100 percent sequence identity or at least about 83, 84, 85, 86, 87, 88, 89, 90, 91, 92, 93, 94, 95, 96, 97, 98, or 99 percent sequence identity when compared to the sequence of 18 or more contiguous nucleotides in either the endogenous target gene or to an RNA transcribed from the target gene (e.g. the transcript). In certain embodiments, an "essentially complementary" polynucleotide has 100 percent sequence complementarity or at least about 83, 84, 85, 86, 87, 88, 89, 90, 91, 92, 93, 94, 95, 96, 97, 98, or 99 percent sequence complementarity when compared to the sequence of 18 or more contiguous nucleotides in either the target gene or RNA transcribed from the target gene.

In certain embodiments, polynucleotides used in the methods and compositions provided herein can be essentially identical or essentially complementary to any of: i) conserved regions of EIN2 genes of both monocot and dicot plants; ii) conserved regions of EIN2 genes of monocot plants; or iii) conserved regions of EIN2 genes of dicot plants. Such polynucleotides that are essentially identical or essentially complementary to such conserved regions can be used to improve delayed senescence and/or improved yield by suppressing expression of EIN2 genes in various dicot Polynucleotides containing mismatches to the target gene or transcript can thus be used in certain embodiments of the compositions and methods provided herein. In certain embodiments, a polynucleotide can comprise at least 19 contiguous nucleotides that are essentially identical or essentially complementary to said gene or said transcript or comprises at least 19 contiguous nucleotides that are essentially identical or essentially complementary to the target gene or target gene transcript. In certain embodiments, a polynucleotide of 19 continuous nucleotides that is essentially identical or essentially complementary to the endogenous target gene or to an RNA transcribed from the target gene (e.g. the transcript) can have 1 or 2 mismatches to the target gene or transcript. In certain embodiments, a polynucleotide of 20 or more nucleotides that contains a contiguous 19 nucleotide span of identity or complementarity to the endogenous target gene or to an RNA transcribed from the target gene can have 1 or 2 mismatches to the target gene or transcript. In certain embodiments, a polynucleotide of 21 continuous nucleotides that is essentially identical or essentially complementary to the endogenous target gene or to an RNA transcribed from the target gene (e.g. the transcript) can have 1, 2, or 3 mismatches to the target gene or transcript. In certain embodiments, a polynucleotide of 22 or more nucleotides that contains a contiguous 21 nucleotide span of identity or complementarity to the endogenous target gene or to an RNA transcribed from the target gene can have 1, 2, or 3 mismatches to the target gene or transcript. In designing polynucleotides with mismatches to an endogenous target gene or to an RNA transcribed from the target gene, mismatches of certain types and at certain positions that are more likely to be tolerated can be used. In certain exemplary embodiments, mismatches formed between adenine and cytosine or guanosine and uracil residues are used as described by Du et al. Nucleic Acids Research, 2005, Vol. 33, No. 5 1671-1677. In certain exemplary embodiments, mismatches in 19 base pair overlap regions can be at the low tolerance positions 5, 7, 8 or 11 (from the 5' end of a 19 nucleotide target) with well tolerated nucleotide mismatch residues, at medium tolerance positions 3, 4, and 12-17, and/or at the high tolerance nucleotide positions at either end of the region of complementarity (i.e. positions 1, 2, 18, and 19) as described by Du et al. Nucleic Acids Research, 2005, Vol. 33, No. 5 1671-1677. It is further anticipated that tolerated mismatches can be empirically determined in assays where the polynucleotide is applied to the plants via the methods provided herein and the treated plants assayed for suppression of EIN2 gene expression or appearance of delayed senescence and/or improved yield.

In certain embodiments, polynucleotide molecules are designed to have 100 percent sequence identity with or complementarity to one allele or one family member of a given target EIN2 gene coding or non-coding sequence. Target EIN2 genes include both the EIN2 genes of Table 2 (i.e. SEQ ID NO:1-18, 622, and 623) as well as orthologous EIN2 genes obtainable from other crops. In other embodiments, the polynucleotide molecules are designed to have 100 percent sequence identity with or complementarity to multiple alleles or family members of a given target gene.

In certain embodiments, polynucleotide compositions and methods provided herein typically effect regulation or modulation (e. g., suppression) of gene expression during a period during the life of the treated plant of at least 1 week or longer and typically in systemic fashion. For instance, within days of treating a plant leaf with a polynucleotide composition of this invention, primary and transitive siRNAs can be detected in other leaves lateral to and above the treated leaf and in apical tissue. In certain embodiments, methods of systemically suppressing expression of a gene in a plant, the methods comprising treating said plant with a composition comprising at least one polynucleotide and a transfer agent, wherein said polynucleotide comprises at least 18 or at least 19 contiguous nucleotides that are essentially identical or essentially complementary to a gene or a transcript encoding an EIN2 gene of the plant are provided, whereby expression of the gene in said plant or progeny thereof is systemically suppressed in comparison to a control plant that has not been treated with the composition.

Compositions used to suppress a target gene can comprise one or more polynucleotides that are essentially identical or essentially complementary to multiple genes, or to multiple segments of one or more genes. In certain embodiments, compositions used to suppress a target gene can comprise one or more polynucleotides that are essentially identical or essentially complementary to multiple consecutive segments of a target gene, multiple non-consecutive segments of a target gene, multiple alleles of a target gene, or multiple target genes from one or more species.

In certain embodiments, the polynucleotide includes two or more copies of a nucleotide sequence (of 18 or more nucleotides) where the copies are arranged in tandem fashion. In another embodiment, the polynucleotide includes two or more copies of a nucleotide sequence (of 18 or more nucleotides) where the copies are arranged in inverted repeat fashion (forming an at least partially self-complementary strand). The polynucleotide can include both tandem and inverted-repeat copies. Whether arranged in tandem or inverted repeat fashion, each copy can be directly contiguous to the next, or pairs of copies can be separated by an optional spacer of one or more nucleotides. The optional spacer can be unrelated sequence (i. e., not essentially identical to or essentially complementary to the copies, nor essentially identical to, or essentially complementary to, a sequence of 18 or more contiguous nucleotides of the endogenous target gene or RNA transcribed from the endogenous target gene). Alternatively the optional spacer can include sequence that is complementary to a segment of the endogenous target gene adjacent to the segment that is targeted by the copies. In certain embodiments, the polynucleotide includes two copies of a nucleotide sequence of between about 20 to about 30 nucleotides, where the two copies are separated by a spacer no longer than the length of the nucleotide sequence.

Tiling

Polynucleotide trigger molecules can be identified by "tiling" gene targets in random length fragments, e.g. 200-300 polynucleotides in length, with partially overlapping regions, e.g. 25 or so nucleotide overlapping regions along the length of the target gene. Multiple gene target sequences can be aligned and polynucleotide sequence regions with homology in common are identified as potential trigger molecules for multiple targets. Multiple target sequences can be aligned and sequence regions with poor homology are identified as potential trigger molecules for selectively distinguishing targets. To selectively suppress a single gene, trigger sequences may be chosen from regions that are unique to the target gene either from the transcribed region or the non-coding regions, e.g., promoter regions, 3' untranslated regions, introns and the like.

Polynucleotides fragments are designed along the length of the full length coding and untranslated regions of a EIN2 gene or family member as contiguous overlapping fragments of 200-300 polynucleotides in length or fragment lengths representing a percentage of the target EIN2 gene. These fragments are applied topically (as sense or anti-sense ssDNA or ssRNA, dsRNA, or dsDNA) to determine the relative effectiveness in providing the delayed senescence and/or improved yield phenotype. Fragments providing the desired activity may be further subdivided into 50-60 polynucleotide fragments which are evaluated for providing the delayed senescence and/or improved yield phenotype. The 50-60 base fragments with the desired activity may then be further subdivided into 19-30 base fragments which are evaluated for providing the delayed senescence and/or improved yield phenotype. Once relative effectiveness is determined, the fragments are utilized singly, or in combination in one or more pools to determine effective trigger composition or mixture of trigger polynucleotides for providing the delayed senescence and/or improved yield phenotype.

Coding and/or non-coding sequences of EIN2 gene families in the crop of interest are aligned and 200-300 polynucleotide fragments from the least homologous regions amongst the aligned sequences are evaluated using topically applied polynucleotides (as sense or anti-sense ssDNA or ssRNA, dsRNA, or dsDNA) to determine their relative effectiveness in providing the delayed senescence and/or improved yield phenotype. The effective segments are further subdivided into 50-60 polynucleotide fragments, prioritized by least homology, and reevaluated using topically applied polynucleotides. The effective 50-60 polynucleotide fragments are subdivided into 19-30 polynucleotide fragments, prioritized by least homology, and again evaluated for induction of the delayed senescence and/or improved yield phenotype. Once relative effectiveness is determined, the fragments are utilized singly, or again evaluated in combination with one or more other fragments to determine the trigger composition or mixture of trigger polynucleotides for providing the yield/quality phenotype.

Coding and/or non-coding sequences of EIN2 gene families in the crop of interest are aligned and 200-300 polynucleotide fragments from the most homologous regions amongst the aligned sequences are evaluated using topically applied polynucleotides (as sense or anti-sense ssDNA or ssRNA, dsRNA, or dsDNA) to determine their relative effectiveness in inducing the delayed senescence and/or improved yield phenotype. The effective segments are subdivided into 50-60 polynucleotide fragments, prioritized by most homology, and reevaluated using topically applied polynucleotides. The effective 50-60 polynucleotide fragments are subdivided into 19-30 polynucleotide fragments, prioritized by most homology, and again evaluated for induction of the delayed senescence and/or improved yield phenotype. Once relative effectiveness is determined, the fragments may be utilized singly, or in combination with one or more other fragments to determine the trigger composition or mixture of trigger polynucleotides for providing the delayed senescence and/or improved yield phenotype.

Also, provided herein are methods for identifying a preferred polynucleotide for providing delayed senescence and/or improved yield in a plant. Populations of candidate polynucleotides that are essentially identical or essentially complementary to a EIN2 gene or transcript of the EIN2 gene can be generated by a variety of approaches, including but not limited to, any of the tiling, least homology, or most homology approaches provided herein. Such populations of polynucleotides can also be generated or obtained from any of the polynucleotides or genes provided herewith in Table 2. Such populations of polynucleotides can also be generated or obtained from any genes that are orthologous to the genes provided herewith in Table 2. Such polynucleotides can be topically applied to a surface of plants in a composition comprising at least one polynucleotide from said population and a transfer agent to obtain treated plants. Treated plants that exhibit suppression of the EIN2 gene and/or exhibit an improvement in delayed senescence and/or improved yield are identified, thus identifying a preferred polynucleotide that improves delayed senescence and/or improved yield in a plant. Suppression of the EIN2 gene can be determined by any assay for the levels and/or activity of a EIN2 gene product (i.e. transcript or protein). Suitable assays for transcripts include, but are not limited to, semi-quantitative or quantitative reverse transcriptase PCR® (qRT-PCR) assays. Suitable assays for proteins include, but are not limited to, semi-quantitative or quantitaive immunoassays, biochemical activity assays, or biological activity assays. In certain embodiments, the polynucleotides can be applied alone. In other embodiments, the polynucleotides can be applied in pools of multiple polynucleotides. When a pool of polynucleotides provides for suppression of the EIN2 gene and/or an improvement in delayed senescence and/or improved yield are identified, the pool can be de-replicated and retested as necessary or desired to identify one or more preferred polynucleotide(s) that improve delayed senescence and/or improved yield in a plant.

Methods of making polynucleotides are well known in the art. Such methods of making polynucleotides can include in vivo biosynthesis, in vitro enzymatic synthesis, or chemical synthesis. In certain embodiments, RNA molecules can be made by either in vivo or in vitro synthesis from DNA templates where a suitable promoter is operably linked to the polynucleotide and a suitable DNA-dependent RNA polymerase is provided. DNA-dependent RNA polymerases include, but are not limited to, E. coli or other bacterial RNA polymerases as well as the bacteriophage RNA polymerases such as the T7, T3, and SP6 RNA polymerases. Commercial preparation of oligonucleotides often provides two deoxyribonucleotides on the 3' end of the sense strand. Long polynucleotide molecules can be synthesized from commercially available kits, for example, kits from Applied Biosystems/Ambion (Austin, Tex.) have DNA ligated on the 5' end that encodes a bacteriophage T7 polymerase promoter that makes RNA strands that can be assembled into a dsRNA. Alternatively, dsRNA molecules can be produced from expression cassettes in bacterial cells that have regulated or deficient RNase III enzyme activity. Long polynucleotide molecules can also be assembled from multiple RNA or DNA fragments. In some embodiments design parameters such as Reynolds score (Reynolds et al. *Nature Biotechnology* 22, 326-330 (2004) and Tuschl rules (Pei and Tuschl, Nature Methods 3(9): 670-676, 2006) are known in the art and are used in selecting polynucleotide sequences effective in gene silencing. In some embodiments random design or empirical selection of polynucleotide sequences is used in selecting polynucleotide sequences effective in gene silencing. In some embodiments the sequence of a polynucleotide is screened against the genomic DNA of the intended plant to minimize unintentional silencing of other genes.

While there is no upper limit on the concentrations and dosages of polynucleotide molecules that can be useful in the methods and compositions provided herein, lower effective concentrations and dosages will generally be sought for efficiency. The concentrations can be adjusted in consideration of the volume of spray or treatment applied to plant leaves or other plant part surfaces, such as flower petals, stems, tubers, fruit, anthers, pollen, leaves, roots, or seeds. In one embodiment, a useful treatment for herbaceous plants using 25-mer polynucleotide molecules is about 1 nanomole (nmol) of polynucleotide molecules per plant, for example, from about 0.05 to 1 nmol polynucleotides per plant. Other embodiments for herbaceous plants include useful ranges of about 0.05 to about 100 nmol, or about 0.1 to about 20 nmol, or about 1 nmol to about 10 nmol of polynucleotides per plant. In certain embodiments, about 40 to about 50 nmol of a ssDNA polynucleotide is applied. In certain embodiments, about 0.5 nmol to about 2 nmol of a dsRNA is applied. In certain embodiments, a composition containing about 0.5 to about 2.0 mg/mL, or about 0.14 mg/mL of dsRNA or ssDNA (21-mer) is applied. In certain embodiments, a composition of about 0.5 to about 1.5 mg/mL of a long dsRNA polynucleotide (i.e. about 50 to about 200 or more nucleotides) is applied. In certain embodiments, about 1 nmol to about 5 nmol of a dsRNA is applied to a plant. In certain embodiments, the polynucleotide composition as topically applied to the plant contains the at least one polynucleotide at a concentration of about 0.01 to about 10 milligrams per milliliter, or about 0.05 to about 2 milligrams per milliliter, or about 0.1 to about 2 milligrams per milliliter. Very large plants, trees, or vines may require correspondingly larger amounts of polynucleotides. When using long dsRNA molecules that can be processed into multiple oligonucleotides, lower concentrations can be used. To illustrate embodiments of the invention, the factor 1×, when applied to oligonucleotide molecules is arbitrarily used to denote a treatment of 0.8 nmol of polynucleotide molecule per plant; 10×, 8 nmol of polynucleotide molecule per plant; and 100×, 80 nmol of polynucleotide molecule per plant.

The polynucleotide compositions of this invention are useful in compositions, such as liquids that comprise polynucleotide molecules, alone or in combination with other components either in the same liquid or in separately applied liquids that provide a transfer agent. As used herein, a transfer agent is an agent that, when combined with a polynucleotide in a composition that is topically applied to a target plant surface, enables the polynucleotide to enter a plant cell. In certain embodiments, a transfer agent is an agent that conditions the surface of plant tissue, e. g., seeds, leaves, stems, roots, flowers, or fruits, to permeation by the polynucleotide molecules into plant cells. The transfer of polynucleotides into plant cells can be facilitated by the prior or contemporaneous application of a polynucleotide-transferring agent to the plant tissue. In some embodiments the transferring agent is applied subsequent to the application of the polynucleotide composition. The polynucleotide transfer agent enables a pathway for polynucleotides through cuticle wax barriers, stomata and/or cell wall or membrane barriers into plant cells. Suitable transfer agents to facilitate transfer of the polynucleotide into a plant cell include agents that increase permeability of the exterior of the plant or that increase permeability of plant cells to oligonucleotides or polynucleotides. Such agents to facilitate transfer of the composition into a plant cell include a chemical agent, or a physical agent, or combinations thereof. Chemical agents for conditioning or transfer include (a) surfactants, (b) an organic solvent or an aqueous solution or aqueous mixtures of organic solvents, (c) oxidizing agents, (d) acids, (e) bases, (f) oils, (g) enzymes, or combinations thereof. Embodiments of the method can optionally include an incubation step, a neutralization step (e.g., to neutralize an acid, base, or oxidizing agent, or to inactivate an enzyme), a rinsing step, or combinations thereof. Embodiments of agents or treatments for conditioning of a plant to permeation by polynucleotides include emulsions, reverse emulsions, liposomes, and other micellar-like compositions. Embodiments of agents or treatments for conditioning of a plant to permeation by polynucleotides include counter-ions or other molecules that are known to associate with nucleic acid molecules, e. g., inorganic ammonium ions, alkyl ammonium ions, lithium ions, polyamines such as spermine, spermidine, or putrescine, and other cations. Organic solvents useful in conditioning a plant to permeation by polynucleotides include DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions). Naturally derived or synthetic oils with or without surfactants or emulsifiers can be used, e. g., plant-sourced oils, crop oils (such as those listed in the 9$^{th}$ Compendium of Herbicide Adjuvants, publicly available on the worldwide web (internet) at herbicide-.adjuvants.com can be used, e. g., paraffinic oils, polyol fatty acid esters, or oils with short-chain molecules modified with amides or polyamines such as polyethyleneimine or N-pyrrolidine. Transfer agents include, but are not limited to, organosilicone preparations.

In certain embodiments, an organosilicone preparation that is commercially available as Silwet® L-77 surfactant having CAS Number 27306-78-1 and EPA Number: CAL. REG.NO. 5905-50073-AA, and currently available from Momentive Performance Materials, Albany, N.Y. can be used to prepare a polynucleotide composition. In certain embodiments where a Silwet L-77 organosilicone preparation is used as a pre-spray treatment of plant leaves or other plant surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation comprising Silwet L-77 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided. In certain embodiments of the methods and compositions provided herein, a composition that comprises a polynucleotide molecule and an organosilicone preparation comprising Silwet L-77 in the range of about 0.3 to about 1 percent by weight (wt percent) or about 0.5 to about 1% by weight (wt percent) is used or provided. In certain embodiments, any of the commercially available organosilicone preparations provided in the following Table 1 can be used as transfer agents in a polynucleotide composition. In certain embodiments where an organosilicone preparation of Table 1 is used as a pre-spray treatment of plant leaves or other surfaces, freshly made concentrations in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) are efficacious in preparing a leaf or other plant surface for transfer of polynucleotide molecules into plant cells from a topical application on the surface. In certain embodiments of the methods and compositions provided herein, a composition that comprises a polynucleotide molecule and an organosilicone preparation of Table 1 in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

TABLE 1

| Name | CAS number | Manufacturer[1,2] |
|---|---|---|
| BREAK-THRU ® S 321 | na | Evonik Industries AG |
| BREAK-THRU ® S 200 | 67674-67-3 | Evonik Industries AG |
| BREAK-THRU ® OE 441 | 68937-55-3 | Evonik Industries AG |
| BREAK-THRU ® S 278 | 27306-78-1 | Evonik Industries AG |
| BREAK-THRU ® S 243 | na | Evonik Industries AG |

TABLE 1-continued

| Name | CAS number | Manufacturer[1,2] |
| --- | --- | --- |
| Silwet ® L-77 | 27306-78-1 | Momentive Performance Materials |
| Silwet ® HS 429 | na | Momentive Performance Materials |
| Silwet ® HS 312 | na | Momentive Performance Materials |
| BREAK-THRU ® S 233 | 134180-76-0 | Evonik Industries AG |
| Silwet ® HS 508 | | Momentive Performance Materials |
| Silwet ® HS 604 | | Momentive Performance Materials |

[1]Evonik Industries AG, Essen, Germany
[2]Momentive Performance Materials, Albany, New York Organosilicone preparations used in the methods and compositions provided herein can comprise one or more effective organosilicone compounds. As used herein, the phrase "effective organosilicone compound" is used to describe any organosilicone compound that is found in an organosilicone preparation that enables a polynucleotide to enter a plant cell. In certain embodiments, an effective organosilicone compound can enable a polynucleotide to enter a plant cell in a manner permitting a polynucleotide mediated suppression of target gene expression in the plant cell. In general, effective organosilicone compounds include, but are not limited to, compounds that can comprise: i) a trisiloxane head group that is covalently linked to, ii) an alkyl linker including, but not limited to, an n-propyl linker, that is covalently linked to, iii) a poly glycol chain, that is covalently linked to, iv) a terminal group. Trisiloxane head groups of such effective organosilicone compounds include, but are not limited to, heptamethyltrisiloxane. Alkyl linkers can include, but are not limited to, an n-propyl linker. Poly glycol chains include, but are not limited to, polyethylene glycol or polypropylene glycol. Poly glycol chains can comprise a mixture that provides an average chain length "n" of about "7.5". In certain embodiments, the average chain length "n" can vary from about 5 to about 14. Terminal groups can include, but are not limited to, alkyl groups such as a methyl group. Effective organosilicone compounds are believed to include, but are not limited to, trisiloxane ethoxylate surfactants or polyalkylene oxide modified heptamethyl trisiloxane.

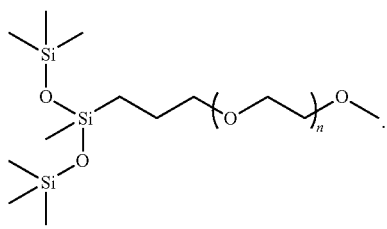

(Compound I: polyalkyleneoxide heptamethyltrisiloxane, average n = 7.5)

One organosilicone compound believed to be ineffective comprises the formula:

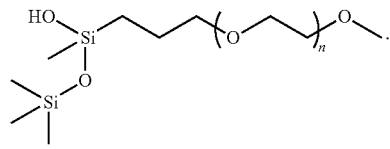

In certain embodiments, an organosilicone preparation that comprises an organosilicone compound comprising a trisiloxane head group is used in the methods and compositions provided herein. In certain embodiments, an organosilicone preparation that comprises an organosilicone compound comprising a heptamethyltrisiloxane head group is used in the methods and compositions provided herein. In certain embodiments, an organosilicone composition that comprises Compound I is used in the methods and compositions provided herein. In certain embodiments, an organosilicone composition that comprises Compound I is used in the methods and compositions provided herein. In certain embodiments of the methods and compositions provided herein, a composition that comprises a polynucleotide molecule and one or more effective organosilicone compound in the range of about 0.015 to about 2 percent by weight (wt percent) (e. g., about 0.01, 0.015, 0.02, 0.025, 0.03, 0.035, 0.04, 0.045, 0.05, 0.055, 0.06, 0.065, 0.07, 0.075, 0.08, 0.085, 0.09, 0.095, 0.1, 0.2, 0.3, 0.4, 0.5, 0.6, 0.7, 0.8, 0.9, 1.0, 1.1, 1.2, 1.3, 1.4, 1.5, 1.6, 1.7, 1.8, 1.9, 2.0, 2.1, 2.2, 2.3, 2.5 wt percent) is used or provided.

In certain embodiments, the polynucleotide compositions that comprise an organosilicone preparation can comprise a salt such as ammonium chloride, tetrabutylphosphonium bromide, and/or ammonium sulfate. Ammonium chloride, tetrabutylphosphonium bromide, and/or ammonium sulfate can be provided in the polynucleotide composition at a concentration of about 0.5% to about 5% (w/v). An ammonium chloride, tetrabutylphosphonium bromide, and/or ammonium sulfate concentration of about 1% to about 3%, or about 2% (w/v) can also be used in the polynucleotide compositions that comprise an organosilicone preparation. In certain embodiments, the polynucleotide compositions can comprise an ammonium salt at a concentration greater or equal to 300 millimolar. In certain embodiments, the polynucleotide compositions that comprise an organosilicone preparation can comprise ammonium sulfate at concentrations from about 80 to about 1200 mM or about 150 mM to about 600 mM.

In certain embodiments, the polynucleotide compositions can also comprise a phosphate salt. Phosphate salts used in the compositions include, but are not limited to, calcium, magnesium, potassium, or sodium phosphate salts. In certain embodiments, the polynucleotide compositions can comprise a phosphate salt at a concentration of at least about 5 millimolar, at least about 10 millimolar, or at least about 20 millimolar. In certain embodiments, the polynucleotide compositions will comprise a phosphate salt in a range of about 1 mM to about 25 mM or in a range of about 5 mM to about 25 mM. In certain embodiments, the polynucleotide compositions can comprise sodium phosphate at a concentration of at least about 5 millimolar, at least about 10 millimolar, or at least about 20 millimolar. In certain embodiments, the polynucleotide compositions can comprise sodium phosphate at a concentration of about 5 millimolar, about 10 millimolar, or about 20 millimolar. In certain embodiments, the polynucleotide compositions will comprise a sodium phosphate salt in a range of about 1 mM to about 25 mM or in a range of about 5 mM to about 25 mM. In certain embodiments, the polynucleotide compositions will comprise a sodium phosphate salt in a range of about 10 mM to about 160 mM or in a range of about 20 mM to about 40 mM. In certain embodiments, the polynucleotide compositions can comprise a sodium phosphate buffer at a pH of about 6.8.

In certain embodiments, other useful transfer agents or adjuvants to transfer agents that can be used in polynucleotide compositions provided herein include surfactants and/or effective molecules contained therein. Surfactants and/or effective molecules contained therein include, but are not limited to, sodium or lithium salts of fatty acids (such as tallow or tallowamines or phospholipids) and organosilicone surfactants. In certain embodiments, the polynucleotide compositions that comprise a transfer agent are formulated with counter-ions or other molecules that are known to associate with nucleic acid molecules. Illustrative examples include, tetraalkyl ammonium ions, trialkyl ammonium ions, sulfonium ions, lithium ions, and polyamines such as spermine, spermidine, or putrescine. In certain embodiments, the polynucleotide compositions are formulated with a non-polynucleotide herbicide. Non-polynucleotide herbicidal molecules include, but are not limited to, glyphosate, auxin-like benzoic acid herbicides including dicamba, chloramben, and TBA, glufosinate, auxin-like herbicides including phenoxy carboxylic acid herbicide, pyridine carboxylic acid herbicide, quinoline carboxylic acid herbicide, pyrimidine carboxylic acid herbicide, and benazolin-ethyl herbicide, sulfonylureas, imidazolinones, bromoxynil, delapon, cyclohezanedione, protoporphyrinogen oxidase inhibitors, and 4-hydroxyphenyl-pyruvate-dioxygenase inhibiting herbicides.

In certain embodiments, the polynucleotides used in the compositions that are essentially identical or essentially complementary to the target gene or transcript will comprise the predominant nucleic acid in the composition. Thus in certain embodiments, the polynucleotides that are essentially identical or essentially complementary to the target gene or transcript will comprise at least about 50%, 75%, 95%, 98%, or 100% of the nucleic acids provided in the composition by either mass or molar concentration. However, in certain embodiments, the polynucleotides that are essentially identical or essentially complementary to the target gene or transcript can comprise at least about 1% to about 50%, about 10% to about 50%, about 20% to about 50%, or about 30% to about 50% of the nucleic acids provided in the composition by either mass or molar concentration. Also provided are compositions where the polynucleotides that are essentially identical or essentially complementary to the target gene or transcript can comprise at least about 1% to 100%, about 10% to 100%, about 20% to about 100%, about 30% to about 50%, or about 50% to a 100% of the nucleic acids provided in the composition by either mass or molar concentration.

Polynucleotides comprising ssDNA, dsDNA, ssRNA, dsRNA, or RNA/DNA hybrids that are essentially identical or complementary to certain plant target genes or transcripts and that can be used in compositions containing transfer agents that include, but are not limited to, organosilicone preparations, to suppress those target genes when topically applied to plants are disclosed in co-assigned U.S. patent application Ser. No. 13/042,856. Various polynucleotide herbicidal molecules, compositions comprising those polynucleotide herbicidal molecules and transfer agents that include, but are not limited to, organosilicone preparations, and methods whereby herbicidal effects are obtained by the topical application of such compositions to plants are also disclosed in co-assigned U.S. patent application Ser. No. 13/042,856, and those polynucleotide herbicidal molecules, compositions, and methods are incorporated herein by reference in their entireties. Genes encoding proteins that can provide tolerance to an herbicide and/or that are targets of a herbicide are collectively referred to herein as "herbicide target genes". Herbicide target genes include, but are not limited to, a 5-enolpyruvylshikimate-3-phosphate synthase (EPSPS), a glyphosate oxidoreductase (GOX), a glyphosate decarboxylase, a glyphosate-N-acetyl transferase (GAT), a dicamba monooxygenase, a phosphinothricin acetyltransferase, a 2,2-dichloropropionic acid dehalogenase, an acetohydroxyacid synthase, an acetolactate synthase, a haloarylnitrilase, an acetyl-coenzyme A carboxylase (ACCase), a dihydropteroate synthase, a phytoene desaturase (PDS), a protoporphyrin IX oxygenase (PPO), a hydroxyphenylpyruvate dioxygenase (HPPD), a para-aminobenzoate synthase, a glutamine synthase, a cellulose synthase, a beta tubulin, and a serine hydroxymethyltransferase gene. The effects of applying certain compositions comprising polynucleotides that are essentially identical or complementary to certain herbicide target genes and transfer agents on plants containing the herbicide target genes was shown to be potentiated or enhanced by subsequent application of an herbicide that targets the same gene as the polynucleotide in co-assigned U.S. patent application Ser. No. 13/042,856. For example, compositions comprising polynucleotides targeting the EPSPS herbicide target gene were potentiated by glyphosate in experiments disclosed in co-assigned U.S. patent application Ser. No. 13/042,856.

In certain embodiments of the compositions and methods disclosed herein, the composition comprising a polynucleotide and a transfer agent can thus further comprise a second polynucleotide comprising at least 19 contiguous nucleotides that are essentially identical or essentially complementary to a transcript to a protein that confers resistance to a herbicide. In certain embodiments, the second polynucleotide does not comprise a polynucleotide that is essentially identical or essentially complementary to a transcript encoding a protein of a target plant that confers resistance to said herbicidal molecule. Thus, in an exemplary and non-limiting embodiment, the second polynucleotide could be essentially identical or essentially complementary to a transcript encoding a protein that confers resistance to a herbicide in a weed (such as an EPSPS encoding transcript) but would not be essentially identical or essentially complementary to a transcript encoding a protein that confers resistance to that same herbicide in a crop plant.

In certain embodiments, the polynucleotide compositions that comprise a transfer agent can comprise glycerin. Glycerin can be provided in the composition at a concentration of about 0.1% to about 1% (w/v or v/v). A glycerin concentration of about 0.4% to about 0.6%, or about 0.5% (w/v or v/v) can also be used in the polynucleotide compositions that comprise a transfer agent.

In certain embodiments, the polynucleotide compositions that comprise a transfer agent can further comprise organic solvents. Such organic solvents include, but are not limited to, DMSO, DMF, pyridine, N-pyrrolidine, hexamethylphosphoramide, acetonitrile, dioxane, polypropylene glycol, other solvents miscible with water or that will dissolve phosphonucleotides in non-aqueous systems (such as is used in synthetic reactions).

In certain embodiments, the polynucleotide compositions that comprise a transfer agent can further comprise naturally derived or synthetic oils with or without surfactants or emulsifiers. Such oils include, but are not limited to, plant-sourced oils, crop oils (such as those listed in the 9th Compendium of Herbicide Adjuvants, publicly available on the world wide web at herbicide.adjuvants.com, paraffinic oils, polyol fatty acid esters, or oils with short-chain molecules modified with amides or polyamines such as polyethyleneimine or N-pyrrolidine.

In aspects of the invention, methods include one or more applications of the composition comprising a polynucleotide and a transfer agent or one or more effective components contained therein. In certain embodiments of the methods, one or more applications of a transfer agent or one or more effective components contained therein can precede one or more applications of the composition comprising a polynucleotide and a transfer agent. In embodiments where a transfer agent and/or one or more effective molecules contained therein is used either by itself as a pre-treatment or as part of a composition that includes a polynucleotide, embodiments of the polynucleotide molecules are double-stranded RNA oligonucleotides, single-stranded RNA oligonucleotides, double-stranded RNA polynucleotides, single-stranded RNA polynucleotides, double-stranded DNA oligonucleotides, single-stranded DNA oligonucleotides, double-stranded DNA polynucleotides, single-stranded DNA polynucleotides, chemically modified RNA or DNA oligonucleotides or polynucleotides or mixtures thereof.

Compositions and methods of the invention are useful for modulating or suppressing the expression of an endogenous target gene or transgenic target gene in a plant cell or plant. In certain embodiments of the methods and compositions provided herein, expression of EIN2 target genes can be suppressed completely, partially and/or transiently to result in delayed senescence and/or improved yield. In various embodiments, a target gene includes coding (protein-coding or translatable) sequence, non-coding (non-translatable) sequence, or both coding and non-coding sequence. Compositions of the invention can include polynucleotides and oligonucleotides designed to target multiple genes, or multiple segments of one or more genes. The target gene can include multiple consecutive segments of a target gene, multiple non-consecutive segments of a target gene, multiple alleles of a target gene, or multiple target genes from one or more species. Examples of target genes of the present invention include endogenous EIN2 genes and EIN2 transgenes.

Target EIN2 genes and plants containing those target EIN2 genes can be obtained from: i) row crop plants including, but not limited to, corn, soybean, cotton, canola, sugar beet, alfalfa, sugarcane, rice, and wheat; ii) vegetable plants including, but not limited to, tomato, potato, sweet pepper, hot pepper, melon, watermelon, cucumber, eggplant, cauliflower, broccoli, lettuce, spinach, onion, peas, carrots, sweet corn, Chinese cabbage, leek, fennel, pumpkin, squash or gourd, radish, Brussels sprouts, tomatillo, garden beans, dry beans, or okra; iii) culinary plants including, but not limited to, basil, parsley, coffee, or tea; iv) fruit plants including but not limited to apple, pear, cherry, peach, plum, apricot, banana, plantain, table grape, wine grape, citrus, avocado, mango, or berry; v) a tree grown for ornamental or commercial use, including, but not limited to, a fruit or nut tree; or, vi) an ornamental plant (e. g., an ornamental flowering plant or shrub or turf grass). The methods and compositions provided herein can also be applied to plants produced by a cutting, cloning, or grafting process (i. e., a plant not grown from a seed) include fruit trees and plants that include, but are not limited to, citrus, apples, avocados, tomatoes, eggplant, cucumber, melons, watermelons, and grapes as well as various ornamental plants. Such row crop, vegetable, culinary, fruit, tree, or ornamental plants exhibiting improvements in that result from suppressing expression of EIN2 are provided herein. Such row crop, vegetable, culinary, fruit, tree, or ornamental plant parts or processed plant products exhibiting improvements in Delayed senescence and/or improved yield that result from suppressing expression of EIN2 are also provided herein. Such plant parts can include, but are not limited to, flowers, stems, tubers, fruit, anthers, meristems, ovules, pollen, leaves, or seeds. Such processed plant products obtained from the plant parts can include, but are not limited to, a meal, a pulp, a feed, or a food product.

Without seeking to be limited by theory, it is believed that in certain embodiments that delays in leaf senescence provided by suppression of EIN2 can provide for improved yield in plants. It is believed that in certain embodiments, delays in senescence provided by suppression of EIN2 can enhance source capacity by delaying leaf senescence and extending the period during grain fill that the source leaves are actively photosynthesizing and exporting sugar. Even a small delay in senescence can significantly improve yield. It was calculated that a 2-day delay in senescence of *Lolium temulentum* would increase the amount of carbon fixed by 11% over the life of the plant (Thomas and Howarth 2000). In fact, in corn increased leaf longevity was associated with improvements of hybrid corn through breeding (Rajcan and Tollenaar 1999). Genetic analysis using a cross of a stay-green inbred corn with a normal inbred showed that there were 14 quantitative trait loci (QTL) for stay-green traits and that these traits were correlated with grain yield (Zheng, Wu et al. 2009). Correlation of stay-green phenotype with yield has also been demonstrated for rice (Fu, Yan et al. 2011).

An aspect of the invention provides a method for modulating expression of an EIN2 gene in a plant including (a) conditioning of a plant to permeation by polynucleotides and (b) treatment of the plant with the polynucleotide molecules, wherein the polynucleotide molecules include at least one segment of 18 or more contiguous nucleotides cloned from or otherwise identified from the target EIN2 gene in either anti-sense or sense orientation, whereby the polynucleotide molecules permeate the interior of the plant and induce modulation of the target EIN2 gene. The conditioning and polynucleotide application can be performed separately or in a single step. When the conditioning and polynucleotide application are performed in separate steps, the conditioning can precede or can follow the polynucleotide application within minutes, hours, or days. In some embodiments more than one conditioning step or more than one polynucleotide molecule application can be performed on the same plant. In embodiments of the method, the segment can be cloned or identified from (a) coding (protein-encoding), (b) non-coding (promoter and other gene related molecules), or (c) both coding and non-coding parts of the target EIN2 gene. Non-coding parts include DNA, such as promoter regions or the RNA transcribed by the DNA that provide RNA regulatory molecules, including but not limited to: introns, 5' or 3' untranslated regions, and microRNAs (miRNA), trans-acting siRNAs, natural anti-sense siRNAs, and other small RNAs with regulatory function or RNAs having structural or enzymatic function including but not limited to: ribozymes, ribosomal RNAs, t-RNAs, aptamers, and riboswitches. In certain embodiments where the polynucleotide used in the composition comprises a promoter sequence essentially identical to, or essentially complementary to at least 18 contiguous nucleotides of the promoter of the endogenous target EIN2 gene, the promoter sequence of the polynucleotide is not operably linked to another sequence that is transcribed from the promoter sequence.

Compositions comprising a polynucleotide and a transfer agent provided herein can be topically applied to a plant or plant part by any convenient method, e.g., spraying or coating with a powder, or with a liquid composition comprising any of an emulsion, suspension, or solution. Such topically applied sprays or coatings can be of either all or of any a portion of the surface of the plant or plant part. Similarly, the compositions comprising a transfer agent or other pre-treatment can in certain embodiments be applied to the plant or plant part by any convenient method, e. g., spraying or wiping a solution, emulsion, or suspension. Compositions comprising a polynucleotide and a transfer agent provided herein can be topically applied to plant parts that include, but are not limited to, flowers, stems, tubers, meristems, ovules, fruit, anthers, pollen, leaves, or seeds.

Application of compositions comprising a polynucleotide and a transfer agent to seeds is specifically provided herein. Seeds can be contacted with such compositions by spraying, misting, immersion, and the like.

In certain embodiments, application of compositions comprising a polynucleotide and a transfer agent to plants, plant parts, or seeds in particular can provide for the delayed senescence and/or improved yield in progeny plants, plant parts, or seeds derived from those treated plants, plant parts, or seeds. In certain embodiments, progeny plants, plant parts, or seeds derived from those treated plants, plant parts, or seeds will exhibit an improvement in delayed senescence and/or improved yield that result from suppressing expression of EIN2. In certain embodiments, the methods and compositions provided herein can provide for an improvement in delayed senescence and/or improved yield in progeny plants or seeds as a result of epigenetically inherited suppression of EIN2 gene expression. In certain embodiments, such progeny plants exhibit an improvement in delayed senescence and/or improved yield from epigenetically inherited suppression of EIN2 gene expression that is not caused by a transgene where the polynucleotide is operably linked to a promoter, a viral vector, or a copy of the polynucleotide that is integrated into a non-native location in the chromosomal DNA of the plant. Without seeking to be limited by theory, progeny plants or seeds derived from those treated plants, plant parts, or seeds can exhibit an improvement in delayed senescence and/or improved yield through an epigenetic mechanism that provides for propagation of an epigenetic condition where suppression of EIN2 gene expression occurs in the progeny plants, plant parts, or plant seeds. In certain embodiments, progeny plants or seeds exhibiting an improvement in delayed senescence and/or improved yield as a result of epigenetically inherited suppression of EIN2 gene expression can also exhibit increased methylation, and in particular, increased methylation of cytosine residues, in the endogenous EIN2 gene of the plant. Plant parts, including seeds, of the progeny plants that exhibit an improvement in the delayed senescence and/or improved yield as a result of epigenetically inherited suppression of EIN2 gene expression, can also in certain embodiments exhibit increased methylation, and in particular, increased methylation of cytosine residues, in the endogenous EIN2 gene. In certain embodiments, DNA methylation levels in DNA encoding the endogenous EIN2 gene can be compared in plants that exhibit the delayed senescence and/or improved yield and control plants that do not exhibit the delayed senescence and/or improved yield to correlate the presence of the delayed senescence and/or improved yield to epigenetically inherited suppression of EIN2 gene expression and to identify plants that comprise the epigenetically inherited delayed senescence and/or improved yield.

Various methods of spraying compositions on plants or plant parts can be used to topically apply to a plant surface a composition comprising a polynucleotide that comprises a transfer agent. In the field, a composition can be applied with a boom that extends over the crops and delivers the composition to the surface of the plants or with a boomless sprayer that distributes a composition across a wide area. Agricultural sprayers adapted for directional, broadcast, or banded spraying can also be used in certain embodiments. Sprayers adapted for spraying particular parts of plants including, but not limited to, leaves, the undersides of leaves, flowers, stems, male reproductive organs such as tassels, meristems, pollen, ovules, and the like can also be used. Compositions can also be delivered aerially, such as by a crop dusting airplane. In certain embodiments, the spray can be delivered with a pressurized backpack sprayer calibrated to deliver the appropriate rate of the composition. In certain embodiments, such a backpack sprayer is a carbon dioxide pressurized sprayer with a 11015 flat fan or equivalent spray nozzle with a customized single nozzle assembly (to minimize waste) at a spray pressure of about 0.25 MPa and/or any single nozzle sprayer providing an effective spray swath of 60 cm above the canopy of 3 to 12 inch tall growing plants can be used. Plants in a greenhouse or growth chamber can be treated using a track sprayer or laboratory sprayer with a 11001XR or equivalent spray nozzle to deliver the sample solution at a determined rate. An exemplary and non-limiting rate is about 140 L/ha at about 0.25 MPa pressure.

In certain embodiments, it is also contemplated that a plant part can be sprayed with the composition comprising a polynucleotide that comprises a transfer agent. Such plant parts can be sprayed either pre- or post-harvest to provide delayed senescence and/or improved yield in the plant part that results from suppression of EIN2 gene expression. Compositions can be topically applied to plant parts attached to a plant by a spray as previously described. Compositions can be topically applied to plant parts that are detached from a plant by a spray as previously described or by an alternative method. Alternative methods for applying compositions to detached parts include, but are not limited to, passing the plant parts through a spray by a conveyor belt or trough, or immersing the plant parts in the composition.

Compositions comprising polynucleotides and transfer agents can be applied to plants or plant parts at one or more developmental stages as desired and/or as needed. Application of compositions to pre-germination seeds and/or to post-germination seedlings is provided in certain embodiments. Seeds can be treated with polynucleotide compositions provided herein by methods including, but not limited to, spraying, immersion, or any process that provides for coating, imbibition, and/or uptake of the polynucleotide composition by the seed. Seeds can be treated with polynucleotide compositions using seed batch treatment systems or continuous flow treatment systems. Seed coating systems are at least described in U.S. Pat. Nos. 6,582,516, 5,891,246, 4,079,696, and 4,023,525. Seed treatment can also be effected in laboratory or commercial scale treatment equipment such as a tumbler, a mixer, or a pan granulator. A polynucleotide composition used to treat seeds can contain one or more other desirable components including, but not limited to liquid diluents, binders to serve as a matrix for the polynucleotide, fillers for protecting the seeds during stress conditions, and plasticizers to improve flexibility, adhesion and/or spreadability of the coating. In addition, for oily polynucleotide compositions containing little or no filler, drying agents such as calcium carbonate, kaolin or bentonite clay, perlite, diatomaceous earth or any other adsorbent material can be added. Use of such components in seed treatments is described in U.S. Pat. No. 5,876,739. Additional ingredients can be incorporated into the polynucleotide compositions used in seed treatments. Such ingredients include but are not limited to: conventional sticking agents, dispersing agents such as methylcellulose (Methocel A15LV or Methocel A15C, for example, serve as combined dispersant/sticking agents for use in seed treatments), polyvinyl alcohol (e.g., Elvanol 51-05), lecithin (e.g., Yelkinol P), polymeric dispersants (e.g., polyvinylpyrrolidone/vinyl acetate PVPNA S-630), thickeners (e.g., clay thickeners such as Van Gel B to improve viscosity and reduce settling of particle suspensions), emulsion stabilizers, surfactants, antifreeze compounds (e.g., urea), dyes, colorants, and the like that can be combined with compositions comprising a polynucleotide and a transfer agent. Further ingredients used in compositions that can be applied to seeds can be found in McCutcheon's, vol. 1, "Emulsifiers and Detergents," MC Publishing Company, Glen Rock, N.J., U.S.A., 1996 and in McCutcheon's, vol. 2, "Functional Materials," MC Publishing Company, Glen Rock, N.J., U.S.A., 1996. Methods of applying compositions to seeds and pesticidal compositions that can be used to treat seeds are described in US Patent Application publication 20080092256, which is incorporated herein by reference in its entirety.

Application of the compositions in early, mid-, and late vegetative stages of plant development is provided in certain embodiments. Application of the compositions in early, mid-, and late reproductive stages is also provided in certain embodiments. Application of the compositions to plant parts at different stages of maturation is also provided.

LITERATURE CITED

Aeong Oh, S., J.-H. Park, et al. (1997). "Identification of three gerietic loci controlling leaf senescence in *Arabidopsis thaliana*." The Plant Journal 12(3): 527-535.
Bapat, V. A., P. K. Trivedi, et al. (2010). "Ripening of fleshy fruit: Molecular insight and the role of ethylene." Biotechnology Advances 28(1): 94-107.
Djanaguiraman, M. and P. V. V. Prasad (2010). "Ethylene production under high temperature stress causes premature leaf senescence in soybean." Functional Plant Biology 37(11): 1071-1084.
Fu, J.-D., Y.-F. Yan, et al. (2011). "Population-specific quantitative trait loci mapping for functional stay-green trait in rice (*Oryza sativa* L.)." Genome 54(3): 235-243.
Ghosh, S., V. S. Meli, et al. (2011). "The N-glycan processing enzymes α-mannosidase and β-D-N-acetylhexosaminidase are involved in ripening-associated softening in the non-climacteric fruits of *capsicum*." Journal of Experimental Botany 62(2): 571-582.
Hu, Z., L. Deng, et al. (2011). Biologia Plantarum 55(1): 27-34. Lim, P. O., H. J. Kim, et al. (2007). "Leaf Senescence." Annual Review of Plant Biology 58(1): 115-136.
McMurchie, E. J., W. B. McGlasson, et al. (1972). "Treatment of Fruit with Propylene gives Information about the Biogenesis of Ethylene." Nature 237(5352): 235-236.
Meli, V. S., S. Ghosh, et al. (2010). "Enhancement of fruit shelf life by suppressing N-glycan processing enzymes." Proceedings of the National Academy of Sciences.
Rajcan, I. and M. Tollenaar (1999). "Source:sink ratio and leaf senescence in maize:—I. Dry matter accumulation and partitioning during grain filling." Field Crops Research 60(3): 245-253.
Thomas, H. and C. J. Howarth (2000). "Five ways to stay green." Journal of Experimental Botany 51: 329-337.
Wellburn, A. R. (1994). "The spectral determination of chlorophylls a and b, as well as total carotenoids, using various solvents with spectrophotometers of different resolution." Journal of Plant Physiology 144: 307-313.
Zheng, H. J., A. Z. Wu, et al. (2009). "QTL mapping of maize (*Zea mays*) stay-green traits and their relationship to yield." Plant Breeding 128(1): 54-62.

The following examples are included to demonstrate examples of certain preferred embodiments of the invention. It should be appreciated by those of skill in the art that the techniques disclosed in the examples that follow represent approaches the inventors have found function well in the practice of the invention, and thus can be considered to constitute examples of preferred modes for its practice. However, those of skill in the art should, in light of the present disclosure, appreciate that many changes can be made in the specific embodiments that are disclosed and still obtain a like or similar result without departing from the spirit and scope of the invention.

EXAMPLES

Example 1. EIN2 Target Genes Target Gene Sequences

The EIN2 genes provided in Table 4 and the sequence listing, or their corresponding transcripts, can be used as targets of polynucleotide compositions comprising a polynucleotide that of at least 18 contiguous nucleotides that are essentially identical or essentially complementary to those genes or transcripts. The genes provided in Table 2 and the sequence listing, protein sequences encoded by those genes, or sequences contained within those genes can also be used to obtain orthologous EIN2 genes from plants not listed in Table 2 and the sequence listing. Such orthologous genes and their transcripts can then serve as targets of polynucleotides provided herein or as a source of polynucleotides that are specifically designed to target the orthologous genes or transcripts.

TABLE 2

Target EIN2 genes

| SEQ ID NO | Source | Name\|Reference | Gene | Type | Length |
|---|---|---|---|---|---|
| 1 | Canola | BRANA-03JUN08-CLUS4975_1 | EIN2 | cDNA | 1473 |
| 2 | Corn | Zm_B73_CR03.G24460.1.cdna | EIN2 | cDNA | 4315 |

TABLE 2-continued

Target EIN2 genes

| SEQ ID NO | Source | Name\|Reference | Gene | Type | Length |
|---|---|---|---|---|---|
| 3 | Corn | Zm_B73_CR03.G24460.1.2kbPromoter | EIN2 | Promoter | 2003 |
| 4 | Cucumber | CumMe_WSH_CR08.G13373580.1.cdna | EIN2 | cDNA | 4372 |
| 5 | Cucumber | CumSa_CL_CR06.G4545310.1.cdna | EIN2 | cDNA | 3768 |
| 6 | lettuce | TC23690 | EIN2 | cDNA | 1189 |
| 7 | Rice | LOC_Os03g49400.1_CDNA | EIN2 | cDNA | 5154 |
| 8 | Rice | LOC_Os07g06130.3_cDNA | EIN2 | cDNA | 4791 |
| 9 | Rice | LOC_Os03g49400.1_2KB_Promoter | EIN2 | Promoter | 2000 |
| 10 | Rice | LOC_Os07g06130.3_2Kb_Promoter | EIN2 | Promoter | 2000 |
| 11 | Soy | Gm_W82_CR03.G375100.1.cdna | EIN2 | cDNA | 4629 |
| 12 | Soy | Gm_W82_CR10.G25060.1.cdna | EIN2 | cDNA | 4525 |
| 13 | Soy | Gm_W82_CR13.G158730.1.cdna | EIN2 | cDNA | 4005 |
| 14 | Soy | Gm_W82_CR13.G158730.1.2kbPromoter | EIN2 | Promoter | 2003 |
| 15 | Soy | Gm_W82_CR10.G25060.1.2kbPromoter | EIN2 | Promoter | 2003 |
| 16 | Soy | Gm_W82_CR03.G375100.1.2kbPromoter | EIN2 | Promoter | 2003 |
| 17 | Tomato | Sl_H1706_CR09.G245610.1.cdna | EIN2 | cDNA | 4294 |
| 18 | Tomato | Sl_H1706_CR09.G245610.1.2KbPromoter | EIN2 | Promoter | 2000 |
| 622 | Cucumber | *Cucumis sativus* EIN2 coding sequence | EIN2 | coding | 3872 |
| 623 | Cucumber | *Cucumis sativus* EIN2 5'UTR | EIN2 | 5'UTR | 2001 |

The sequence listing contains the target DNA sequences from plant species for EIN2 genes listed in Table 2. For each gene having a DNA sequence provided in the sequence listing and listed in listed in Table 2 single stranded or double stranded DNA or RNA fragments in sense or anti-sense orientation or both are mixed with an organosilicone preparation that comprises the compositions of the topical application method. This composition is topically applied to plants to effect expression of the target genes in the specified plant to obtain the desired delays in senescence and/or improvements in yield.

Example 2. Polynucleotides that can be Used to Suppress EIN2 Expression in Various Plants An exemplary set of polynucleotides that can be used to suppress expression of EIN2 genes in various plants is provided herewith in the sequence listing as SEQ ID NOS: 19-331. The SEQ ID NOS: 19-331 describe polynucleotide sequences from a variety of dicot and monocot plants as indicated that are useful for downregulating EIN2 expression using methods described here. The SEQ ID NOS: 19-331 describe polynucleotide sequences that can be applied to plants as ssDNA, ssRNA, dsDNA, dsRNA, and/or as DNA/RNA hybrids to provide for delayed senescence and/or improved yield. Subfragments of at least 18 contiguous nucleotides of the SEQ ID NOS: 19-331 polynucleotide sequences can also be applied to plants as ssDNA, ssRNA, dsDNA, dsRNA, and/or as DNA/RNA hybrids to provide for delayed senescence and/or improved yield. Other regions of EIN2 genes can also be targeted to modify expression including the use of antisense DNA oligonucleotides against coding regions and/or targeting promoter regions using sense/antisense dsRNA, sense or antisense ssDNA as well as sense/antisense double stranded DNA. For example, a polynucleotide that comprises at least 18 contiguous nucleotides that are essentially identical or essentially complementary to SEQ ID NO: 1-18 can be used to downregulate expression of those EIN2 genes.

Example 3. Method for Identifying Preferred Polynucleotides

A method for testing the entire sequence of each gene for selecting effective trigger molecules is described. Polynucleotides fragments are designed to cover the full length coding and untranslated regions of the gene in Table 2 and the sequence listing as full-length sequences or as contiguous overlapping fragments of 200-300 bases length. These fragments are applied topically as sense or anti-sense ssDNA or ssRNA, dsRNA, or dsDNA to determine the relative effectiveness in providing the trait phenotype. Fragments providing the desired activity are further subdivided into 50-60 polynucleotide fragments which are evaluated for providing the trait phenotype. The 50-60 base fragments with the desired activity are subdivided into 19-30 base fragments which are evaluated for providing the trait phenotype. Fragments are tested singly, or in combination in one or more pools to determine effective trigger formulations for generation of the trait phenotype. Exemplary triggers developed in this manner are provided herewith in the sequence listing as SEQ ID NO:19-331 and as SEQ ID NO: 614-659.

Example 4. Method for Identifying Conserved Preferred Polynucleotides

Triggers can also be developed to simultaneously suppress multiple EIN2 gene family members by alignment of coding and/or non-coding sequences of gene families in the crop of interest (Table 2), and choosing 200-300 base fragments from the most similar regions of the aligned sequences for evaluation in the topical application method (as sense or anti-sense ssDNA or ssRNA, dsRNA, or dsDNA) to determine their relative effectiveness in inducing the trait phenotype. The effective segments are subdivided into 50-60 base fragments, prioritized by greatest similarity, and re-evaluated in a topical application method. The effective 50-60 base fragments are subdivided into 19-30 base fragments, prioritized by greatest similarity, and again evaluated for induction of the trait/benefit phenotype. Once relative effectiveness is determined, the fragments may be utilized singly, or in combination with one or more other fragments to determine the trigger formulation for providing the trait phenotype. Exemplary triggers developed in this manner are provided herewith in the sequence listing as SEQ ID NO:332-613.

Example 5 Methods for Topical Application of Polynucleotide Molecules that Suppress EIN2

Tomato plants at the 2-leaf stage grown in a peat moss, composted bark and perlite soil mix are spotted with polynucleotides, either ssDNA and/or dsRNA oligos or long dsRNAs directed to the promoter and/or targeting the coding region of the EIN2 gene or gene family. The nucleotide solution applied consists of 40-50 nmoles of each ssDNA oligonucleotide or 0.5-2 nmoles dsRNA, 0.3% Silwet L77, 5 mM $Na_2HPO_4$ and 2% ammonium sulfate in a final volume of 40 μL. Two mature leaves are spotted with 20 μL of the nucleotide solution for a total of 40 μL per plant.

Corn plants are germinated in potting medium and grown in the greenhouse for approximately 10 days. ssDNA and/or dsRNA polynucleotides directed to the promoter and/or targeting the coding region of the EIN2 gene or gene family are spotted onto the first and second leaves. The nucleotide solution applied consists of 40-50 nmoles of each ssDNA oligonucleotide or 0.5-2 nmoles dsRNA, 0.5% Silwet L77, 20 mM $Na_2HPO_4$ and 2% ammonium sulfate in a final volume of 50 μL. Two mature leaves are spotted with 25 μL each of the nucleotide solution for a total of 50 μL per plant.

Alternatively, corn plants grown in the greenhouse are treated 20 days after pollination by spraying leaves with a solution containing 0.14 mg/mL of dsRNA or ssDNA (21-mer) or 0.5 to 1.5 mg/mL long dsRNA polynucleotides targeted to the EIN2 gene or gene family with 0.5% Silwet L77, 20 mM $Na_2HPO_4$ and 2% ammonium sulfate.

To delay fruit ripening, tomato and melon plants grown in the greenhouse are treated at the stage before fruit production by spraying leaves with a solution containing 0.14 mg/L ssDNA oligonucleotide or dsRNA polynucleotides targeted to the EIN2 gene or gene family with 0.5% Silwet L77, 20 mM $Na_2HPO_4$ and 2% $(NH_4)_2SO4$.

Example 6. Assay for Delayed Leaf Senescence

Various methods are used to demonstrate efficacy of polynucleotide triggers that target EIN2 genes as follows:

Method 1: After treatment with topical polynucleotides targeting the EIN2 gene or with a non-efficacious control polynucleotide, corn plants are kept in the greenhouse under optimal growing conditions or with limiting water and grown to maturity. Yellowing of leaves is assessed at approximately 40 days after pollination, and the percentage of each leaf that has turned yellow is recorded. Leaves are then sampled, and chlorophyll is extracted and quantified (Wellburn 1994). Plants treated with efficacious polynucleotides have leaves that have a higher percentage of green leaf area and more chlorophyll per leaf weight compared with plants treated with non-efficacious control polynucleotides. Photosynthesis of comparable leaves of each of these plants is then measured using a LiCor or PAM fluorescence monitor. Leaves of plants treated with efficacious polynucleotides have a higher rate of photosynthesis compared to controls.

Method 2: One week after topical application of the EIN2 polynucleotides, a hole punch is used to sample treated leaves or leaves from above the treatment site. These leaf discs are placed on 3 layers of wet Whatman No. 1 filter paper and placed in the dark at 25 C (Hu, Deng et al. 2011). One week after sampling, chlorophyll is extracted from the leaf pieces and measured spectrophotometrically using standard methods (Wellburn 1994). Leaf pieces from plants treated with efficacious polynucleotides have a higher concentration of chlorophyll compared with plants treated with non-efficacious control polynucleotides.

To examine the effect of suppression of the EIN2 gene on leaf senescence that occurs in response to drought stress, water is with-held from plants after they have been sprayed with the solution described above containing the EIN2 trigger sequences or with a control solution containing a non-efficacious control polynucleotide. Samples are taken from leaves after drought symptoms are visible to compare chlorophyll content using methods described above. In addition, photosynthesis of comparable leaves of each of these plants is measured using a LiCor or PAM fluorescence monitor. Leaves of plants treated with efficacious polynucleotides contain a higher concentration of chlorophyll and have a higher rate of photosynthesis compared to controls.

Example 7. Assays for Delayed Fruit Ripening that Results from EIN2 Suppression Fruit Shelf Life To assay for delays in fruit ripening that are mediated by application of EIN2 polynucleotides, fruit deterioration will be analyzed by time-lapse photography as described in (Meli, Ghosh et al. 2010) and (Ghosh, Meli et al. 2011). Fruits with topically induced suppression of EIN2 will be stored in various temperatures with control fruits for the analyses.

Textural Analysis:

The impact of topically induced suppression of EIN2 in fruit would be increased firmness. Fruit firmness will be determined using a Texture Analyzer (e.g. TA-XT plus) as described in (Meli, Ghosh et al. 2010) and (Ghosh, Meli et al. 2011).

Cell Wall Structure Analysis:

Topically induced suppression of EIN2 in fruit would delay changes in cell wall structure that are observed in ripening fruit. Cell wall structure in EIN2 polynucleotide treated and control plants will be analyzed by using microscopy. Analysis of cell wall structure by microscopy is as described in (Meli, Ghosh et al. 2010) and (Ghosh, Meli et al. 2011).

Example 8. Additional Methods for Measuring Delayed Leaf Senescence in EIN2 Polynucleotide Treated Plants and Controls The following procedure can be used to measure leaf senescence. Zea mays plants that have been topically treated will be monitored for yellowing of leaves will be visually assessed at approximately 40 days after pollination, and the percentage of each leaf that has turned yellow is recorded. Leaves will be sampled using a hole punch, and chlorophyll will be extracted and quantified using the following method. Each leaf disc is placed in a microcentrifuge tube and 1 ml of ice-cold 80% acetone is added. The tissue is then ground with a blue pestle with sand, until it is completely disintegrated. The tube is centrifuged in a microcentrifuge for 5 minutes at maximum speed at 4° C. The supernatant is removed and absorbance is measured in a spectrophotometer in a 1 ml glass cuvette at 663.2 nm, 646.8 nm and 710 nm. Chlorophyll a and b concentrations (μg/ml) are calculated using the following equations:

$$Chl_a = 12.25*(A_{663.2} - A_{710}) - 2.79*(A_{646.8} - A_{710})$$

$$Chl_b = 21.5*(A_{646.8} - A_{710}) - 5.1*(A_{663.2} - A_{710})$$

Leaves of plants treated with efficacious polynucleotides of SEQ ID NO:19-633, or with efficacious polynucleotides that are essentially complementary or identical to *Zea mays* sequence provided in Table 2 and the sequence listing will have a higher percentage of green leaf area and more chlorophyll per leaf weight compared with plants treated with non-efficacious control polynucleotides. Photosynthesis of comparable leaves of each of these plants will be measured using a LiCor photosynthesis system (LiCor Biosciences) or PAM fluorescence monitor (Heinz Walz GmbH) following the manufacturer's recommended procedures. Leaves of plants treated with efficacious polynucleotides have a higher rate of photosynthesis compared to leaves of plants treated with non-efficacious control polynucleotides.

Chlorophyll will be extracted from leaves one week after topical treatment using a hole punch on treated leaves or leaves from above the treatment site. Leaf discs are placed on 3 layers of wet Whatman No. 1 filter paper and placed in the dark at 25° C. One week after sampling, chlorophyll is extracted from the leaf pieces and measured spectrophotometrically using the method described above. Leaf pieces from plants treated with efficacious polynucleotides have a higher concentration of chlorophyll compared with leaf pieces from plants treated with non-efficacious control polynucleotides.

Example 9. Additional Methods for Measuring Delayed Leaf Senescence in EIN2 Polynucleotide Treated Plants and Controls The following procedure is used for determining the effect of gene regulation on leaf senescence that occurs in response to drought stress. Water is with-held from plants after topical spray application. Samples are taken from leaves after drought symptoms are visible to compare chlorophyll content using methods described above. Photosynthesis of comparable leaves of each of these plants is measured using a LiCor or PAM fluorescence monitor, as described above. Leaves of plants treated with efficacious polynucleotides contain a higher concentration of chlorophyll and will have a higher rate of photosynthesis compared to leaves of plants treated with non-efficacious control polynucleotides.

Example 10. Additional Assays for Delays in Fruit Ripening Mediated by Application of EIN2 Polynucleotides Fruit deterioration will be analyzed by time-lapse photography. Pink tomato fruits with topically induced suppression of EIN2 will be stored at 25° C. with control fruits for the analyses. Analysis will entail taking photographs every 5 days during the storage to record deterioration. Additionally, textural analysis will be performed at 10, 20, 30 and 40 days of storage using texture analyzer (TA-XT) and a 75-mm-wide P75 compression plate that compresses the fruit to a vertical displacement of 5 mm with a test speed of 1 mm/second. The firmness will be defined as the response force to a 5×g applied force. The impact of topically induced suppression of EIN2 will be increased firmness.

Assay for Cell Wall Structure

Cell wall structure in pink fruit and fruit harvested every 2 subsequent days will be analyzed using microscopy. The fruit will be cut into sections, immersed in 0.05% calcofluor and rinsed with distilled water. The stained fruit sections will be mounted in water under a coverslip and photographed using a microscope.

Example 11. Topical Oligonucleotide Application and Fungal Testing Methods

Application of oligonucleotides to leaves for powdery mildew control. Barley seeds are planted in 2 inch pots in the greenhouse. Five days later, barley seedlings are sprayed with nucleotides, either ssDNA and/or dsRNA oligos directed to the promoter and/or targeting the coding region of a target gene of interest such as from Table 2 or Table 3. The nucleotide solution applied consists of 6-20 nm of each ssDNA oligonucleotide or 0.5-4 nm dsRNA, 0.1 to 0.3% L77 silwet, 50 mM NaPO4 in a final volume of 40 uL water. Two to 4 days post spraying seedlings are infected with dry spores of barley powdery mildew (*Blumeria graminis*. 1 sp. *hordei*) and 7 days post infection, disease development is scored for the percentage of leaf area covered with powdery mildew.

Cucumber seeds are planted in a 3-inch square pot and thinned to one plant per pot after emergence. When the first true leaf is fully expanded and the second leaf is opening a nucleotide solution of either ssDNA and/or dsRNA oligos directed to the promoter and/or targeting the coding region of a target gene of interest such as from Table 2 or Table 3 is applied to the first true leaf or the cotyledons. The nucleotide solution applied consists of 6-20 nm of each ssDNA oligonucleotide or 0.5-4 nm dsRNA, 0.1 to 0.3% L77 silwet, 50 mM NaPO4 in a final volume of 40 uL water. Two days later the entire cucumber plant is inoculated with a shower of dry spores of cucumber powdery mildew (*Podosphaera xanthii*) shaken off diseased plants. Disease severity will be evaluated on the treated leaf and succeeding leaves 10 days later and at subsequent intervals.

Tomato seeds are planted in a 3-inch square pot and thinned to one plant per pot after emergence. Two weeks old tomato seedlings are treated with 6-20 nm of each ssDNA oligonucleotide or 0.5-4 nm dsRNA (from one of the polynucleotides from Table 2 or Table 3, 0.2-0.5% L77 silwet, 50 mM NaPO4, 1% ammonium sulfate in a final volume of 30 uL water. Two to 4 days post spraying plants are innoculated with dry spores of tomato powdery mildew (*Oidium neolycopersici*) and 13 days post infection, disease development is scored for the percentage of leaf area covered with powdery mildew.

Application of Oligonucleotides to Leaves for *Phytophthora* Control

Pepper seeds and cucumber seeds are planted in vermiculite in 2 inch pots in the greenhouse. For topical nucleotide treatment, three weeks old pepper seedlings are used and 2 weeks old cucumber seedlings are used.

Seedlings are sprayed with nucleotides, either ssDNA and/or dsRNA oligos directed to the promoter and/or targeting the coding region of a target gene of interest such as from Table 2 or Table 3. The nucleotide solution applied consists of 6-20 nm of each ssDNA oligonucleotide or 0.5-4 nm dsRNA, 0.1 to 0.3% L77 silwet, 50 mM NaPO4 in a final volume of 40 uL water. Two to 4 days post spraying seedlings are infected with zoospores of *Phytophthora capsici*. *Phytophthora capsici* infection will be done either by spraying leaf tissue to test shoot dieback or by flooding soil to check root rot. Ten days post infection and at subsequent intervals, disease development will be scored with disease index ranging from 0 (no disease) to 4 (severe disease).

Zoospore inoculums are prepared with the following procedure. Grow mycelium on V8 agar medium for a week at 25° C., cut medium with mycelium into 4 mm squares, rinse with sterilized water trice at 20 min interval, soak in water in the hood with light on at room temperature for 24 h, transfer plate into 4° C. and keep for 1 h, take out and keep at room temperature for 1 h, check zoospores quantity and quality under dissection microscope. Adjust zoospore concentration to 500/ml with water for inoculation.

Example 12: Topical Oligonucleotide Application and Bacterial Testing Methods Application of Oligonucleotides to Leaves for *Pseudomonas syringae* Control.

Tomato seeds are planted in 2 inch pots in the greenhouse. Two weeks later, tomato seedlings are sprayed with nucleotides, either ssDNA and/or dsRNA oligos directed to the promoter and/or targeting the coding region of a target gene of interest such as from Table 2 or Table 3. The nucleotide solution applied consists of 6-20 nm of each ssDNA oligonucleotide or 0.5-4 nm dsRNA, 0.1 to 0.3% L77 silwet, 50 mM NaPO4, 1% ammonium sulfate in a final volume of 40 uL water. Two to 4 days post nucleotide treatment; plants are inoculated by spraying *Pseudomonas. syringae* pv. tomato suspension until run-off. *P. syringae* suspension is prepared as described below. *P. syringae* pv. tomato DC3000 are grown at 28° C. in liquid LB medium with half strength of salt for overnight. Prior to inoculation, bacterium culture is diluted 50 times with 0.025% silwet 77. Inoculated plants are incubated under mist conditions in the greenhouse with a temperature regime of 28/22° C. (day/night) and natural illumination.

Example 13: Topical Application of Polynucleotide Molecules that Suppress EIN2

Tomato Seed Soak Method

Another trigger application method involved soaking seed in solutions containing the EIN2 trigger molecules, which are then taken up by the germinating seedlings. Approximately 45 tomato seeds (Oregon Spring variety) were soaked in a 1-mL solution containing 1 nmol double-stranded RNA, 5 mM $Na_2HPO_4$ (pH 6.8), and 0.01% Silwet L77 overnight at room temperature. Seeds (approximately 15 per box) were then transferred to seed germination boxes containing 12 mL 100 µM 1-aminocyclopropane-1-carboxylic-acid (ACC), and incubated in the dark for 1 week at 25° C.

Ethylene sensitivity can be tested by measuring the length of hypocotyls of seedlings grown in the dark in the presence of the ethylene precursor, ACC, which is converted by the seedling to ethylene (Lanahan et al., 1994). Seedlings grown in the dark in the absence of ACC or ethylene have long hypocotyls. However, seedlings grown in the presence of ethylene in the dark normally have short hypocotyls. Seedlings that are insensitive to ethylene due to a genetic mutation of the ethylene receptor have long hypocotyls even in the presence of ethylene when grown in the dark.

Figure 1B:
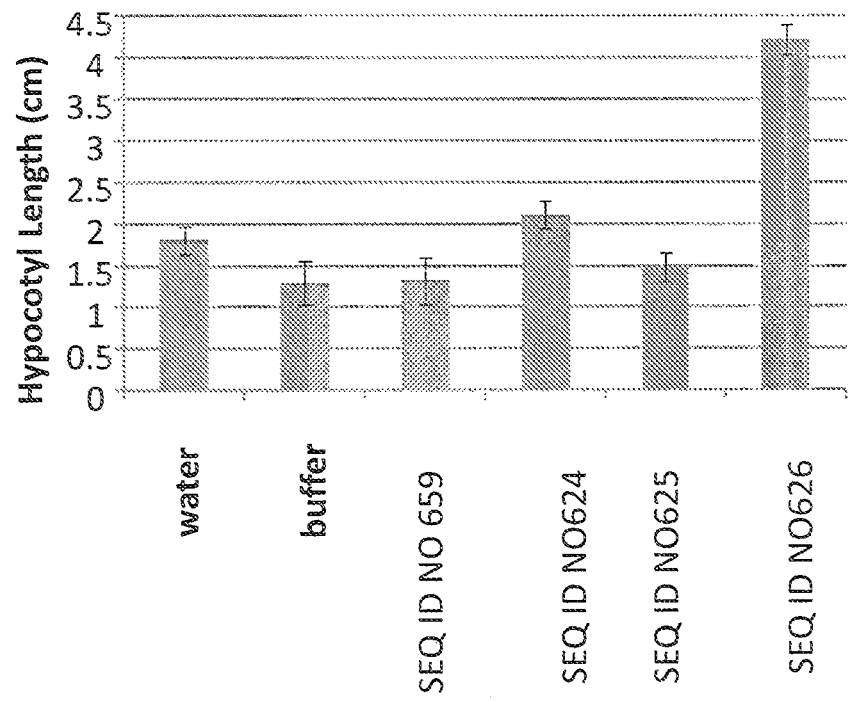
Figure 2A:
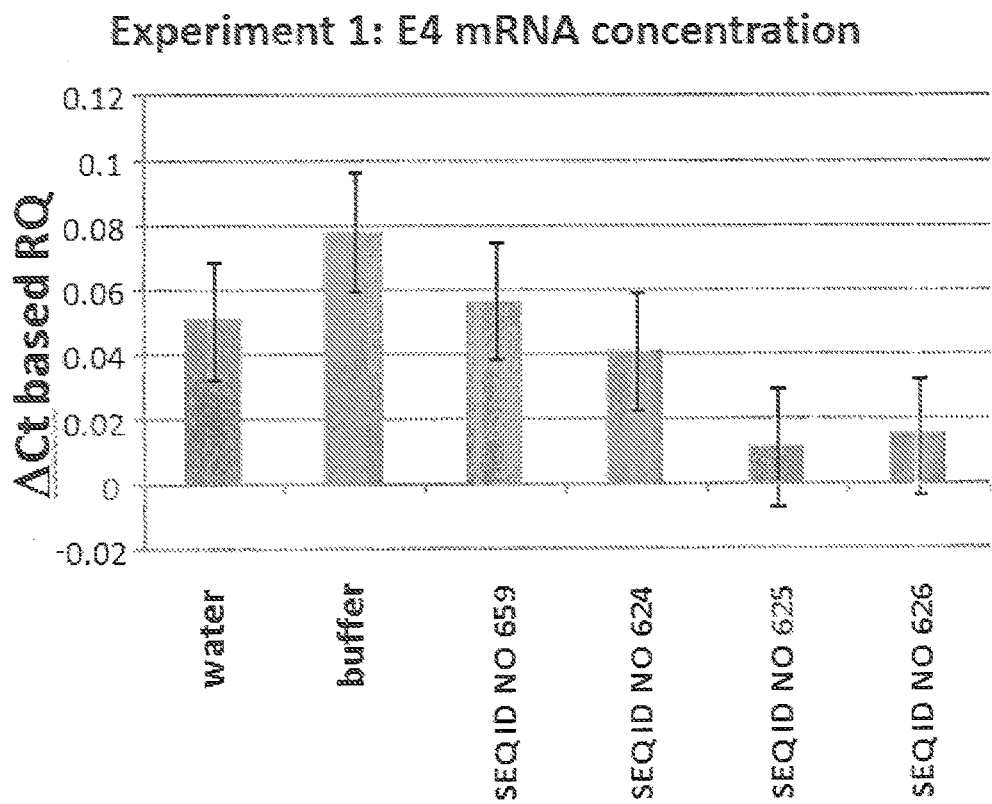
FIGS. 2A and B. Expression of the ethylene-responsive E4 gene in tomato seedlings treated with EIN2 triggers or control treatments, and grown in the presence of 100 µm ACC in the dark. Samples were taken from the experiment shown in FIGS. 1A and 1B. N=3 (FIG. 2A) or 9 (FIG. 2B). Error bars represent the 95% confidence interval.
Figure 2B:
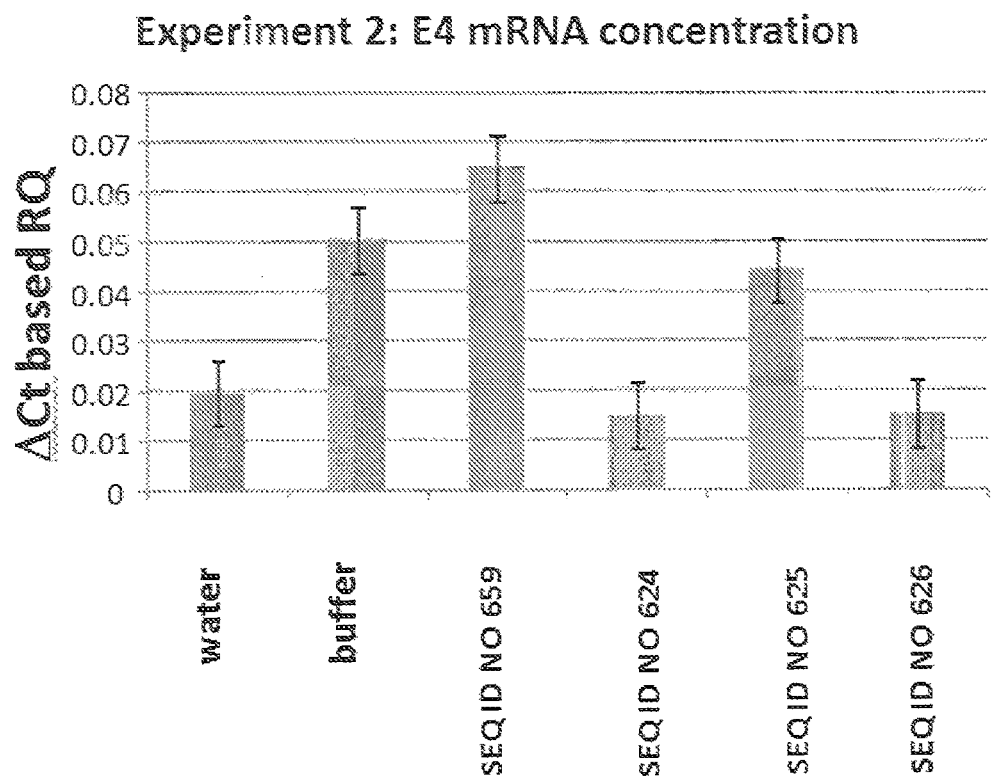

The treatment with dsRNA triggers that target the EIN2 gene also results in longer hypocotyls for seedlings grown in the dark with 100 µM ACC, suggesting these seedlings have become insensitive to ethylene (FIG. 1). The long double-stranded RNA triggers used in these experiments are fragments of the tomato EIN2 cDNA, Sl_H1706_CR09.G245610.1.cDNA (Sequence ID NO 17 in Table 2). The coordinates and sizes of the EIN2 triggers are show in Table 3. A control double-stranded RNA sequence (SEQ ID NO 659) was taken from the green fluorescent protein (GFP). Hypocotyls of the seedlings treated with water, buffer or SEQ ID NO 659 have short hypocotyls, as expected (FIGS. 1A and 1B). However, treatment with either the SEQ ID 624, or SEQ ID 625, or SEQ ID 626 dsRNA molecules that target EIN2 tomato sequence results in longer hypocotyls. The error bars represent 95% confidence intervals. The regulation of gene expression by ethylene in plant tissues has been studied, and this research identified a gene called E4 that is transcriptionally activated by ethylene in both tomato fruit and in leaves (Montgomery et al., 1993). The E4 gene encodes a methionine sulfoxide reductase, an enzyme which likely functions to repair proteins damaged by oxidative stress (Dai and Wang, 2012), but the E4 gene can be used as a marker for ethylene response. RNA was isolated from shoots of seedlings treated as described above, and qPCR was conducted to quantify E4 mRNA. As shown in FIGS. 2A and 2B, E4 gene expression is relatively high in samples from seedlings treated with buffer or the GFP control trigger but is significantly reduced in samples from seedlings treated with EIN2 triggers. There is a fairly good correlation between treatments that produce long hypocotyls (FIG. 1A,B) and those that have reduced E4 expression (FIG. 2A,B). Thus, we observed 2 independent phenotypes that suggest a loss of ethylene sensitivity from treatment with dsRNA triggers targeting the EIN2 gene.

Table 3. Description of long dsRNA triggers tested with seed soak method in tomato. Coordinates of EIN2 dsRNAs are with respect to Sl_H1706_CR09.G245610.1.cDNA (Sequence ID NO:17 in Table 2 and the sequence listing).

TABLE 3

Description of long dsRNA triggers tested with seed soak method in tomato. Coordinates of EIN2 dsRNAs are with respect to Sl_H1706_CR09.G245610.1.cDNA (Sequence ID NO: 17 in Table 2 and the sequence listing).

| Trigger name | Coordinates of EIN2 cDNA in SEQ ID NO: 17 | Size of trigger (bp) | Trigger SEQ ID NO |
|---|---|---|---|
| PCR1 | 2484..2676 | 192 | 624 |
| PCR2 | 87..473 | 356 | 625 |
| PCR3 | 474..935 | 461 | 626 |
| GFP |  | 25 | 659 |

The regulation of gene expression by ethylene in plant tissues has been studied, and this research identified a gene called E4 that is transcriptionally activated by ethylene in both tomato fruit and in leaves (Montgomery et al., 1993). The E4 gene encodes a methionine sulfoxide reductase A enzyme, which likely functions to repair proteins damaged by oxidative stress (Dai and Wang, 2012), but the E4 gene can be used as a marker for ethylene response. RNA was isolated from shoots of seedlings treated as described above, and qPCR was conducted to quantify E4 mRNA. As shown in FIGS. 2A and 2B, E4 gene expression is relatively high in samples from seedlings treated with buffer or the GFP control trigger but is significantly reduced in samples from seedlings treated with EIN2 triggers. There is a fairly good correlation between treatments that produce long hypocotyls (FIGS. 1A and 1B) and those that have reduced E4 expression (FIGS. 2A and 2B).

Thus, we have observed 2 independent phenotypes that suggest a loss of ethylene sensitivity from treatment with dsRNA triggers targeting the EIN2 gene.

Lettuce Seed Soak Method

Absence of the ethylene-induced triple response phenotype has been used to select lettuce lines that were insensitive to ethylene, and these lines then showed reduced ethylene-induced chlorophyll loss in mature heads (Saltveit et al., 2003). We have used the seed soak method to demonstrate suppression of ethylene response by treatment of seeds with dsRNAs containing lettuce EIN2 transcribed sequences.

Dai C., Wang M.-H. (2012) Characterization and functional analysis of methionine sulfoxide reductase A gene family in tomato. Molecular Biology Reports 39:6297-6308. DOI: 10.1007/s11033-012-1451-0. Lanahan M. B., Yen H. C., Giovannoni J. J., Klee H. J. (1994) The never ripe mutation blocks ethylene perception in tomato. The Plant Cell Online 6:521-30. DOI: 10.1105/tpc.6.4.521. Montgomery J., Goldman S., Deikman J., Margossian L., Fischer R. L. (1993) Identification of an ethylene-responsive region in the promoter of a fruit ripening gene. Proceedings of the National Academy of Sciences 90:5939-5943. Saltveit M. E., Ochoa O., Campos-Vargas R., Michelmore R. (2003) Lines of lettuce selected for ethylene insensitivity at the seedling stage displayed variable responses to ethylene or wounding as mature heads. Postharvest Biology and Technology 27:277-283. DOI: 10.1016/s0925-5214(02)00119-9.

Example 14. Topical Oligonucleotide Application and Nematode Testing Methods

Application of Oligonucleotides to Leaves for Nematode Control.

Ten day old cucumber plants grown in sand are spotted with nucleotides, either ssDNA and/or dsRNA oligos directed to the promoter and/or targeting the coding region of a target EIN2 gene of interest such as from Table 2 and the sequence listing. The nucleotide solution applied consists of 6-20 nm of each ssDNA oligonucleotide or 0.5-1 nm dsRNA, 0.1% L77 silwet, 50 mM NaPO4 in a final volume of 40 uL water. Two cotyledon or leaves are spotted with 20 uL of the nucleotide solution for a total of 40 uL per plant. After 6-24 hours, 1000 vermiform eggs or 1000 J2 Meloidogyne incognita (RKN) are inoculated into each pot. Watering of the test plants is then restricted to only water as needed to prevent wilt for a period of 24 hours. After the 24 hour restricted watering, normal sub-irrigation watering is done for the duration of the test. Cucumber plants are harvested approximately 14 days after inoculation by washing sand off the roots. A root gall rating and visual phytotoxicity rating is assigned using the following scales: Gall rating scale (Gall: % root mass galled): 0=0-5%; 1=6-20%; 2=21-50%; and 3=51-100%. Visual phytotoxicity scale is also assigned (Vis. tox; visual reduction in root mass compared to the control): rs1=mild stunting; rs2=moderate stunting; rs3=severe stunting Experiments in soybeans using soy cyst nematodes (SCN) are similar to the cucumber RKN assay except for the following changes. Soybean seeds are planted in 100% sand in two inch square plastic pots. The oligonucleotide solution is applied when the soybeans show the first trifoliate beginning to emerge, about 10 to 12 days after planting. At least six hours after application of the oligonucleotide solution, the nematode soybean cyst nematode (SCN) innoculum (1000 vermiform eggs or 1000 J2s) is applied to the pots. Watering of the test plants is then restricted to only water as needed to prevent wilt for a period of 24 hours. After the 24 hour restricted watering, normal sub-irrigation watering is done for the duration of the test. Twenty eight days after inoculation the plants are harvested and cysts counted. Experiments in corn using lesion nematodes are similar to above except for the following changes. Corn plants growin in a sand:turface mix 2:1 in 4 inch deep pots. Treatment with oligonucleotide solution is done when the plants are approximately 8-10 old. At least six hours after inoculation of the oligonucleotide solution, plants are inoculated with 2 μm of P. scribneri infested corn roots which are then removed from the pot after 7 days. Watering of the test plants is then restricted to only water as needed to prevent wilt for a period of 24 hours. After the 24 hour restricted watering, normal sub-irrigation watering as needed is done for the duration of the test. 12-14 days post inoculation, plants are harvested and nematodes extracted for 6 days from the cut up roots in a mist tent.

Application of Oligonucleotides to Seeds for Nematode Control

Cucumber seeds are soaked approximately 5-72 hours in nucleotides, either ssDNA and/or dsRNA oligos directed to the promoter and/or targeting the coding region of a target of interest such as from Table 2 or Table 3. Seeds can also be soaked in water for a few hours prior to soaking in oligonucleotide solution. Soaking solution consists of 20 nm of each ssDNA nucleotide or 0.03-1 nm dsRNA, 0.1% silwet L77, 50 mM NaPO4 in a final volume 200 uL in water. The radicals of the cucumber seeds emerge within 72 hours, after which the seeds are placed on germination paper until root length is approximately 2 inches. Seedlings are transplanted to sand vials for RKN inoculation 24 hours later. Ten mL dry sand is added to each vial and seedlings are planted by tilting the vial and laying the seedling in the correct orientation so that the cotyledons are just above the sand and then tilting back to cover the radicles with sand. 3.3 ml water is added to each vial and the vials placed in racks under fluorescent light banks. 500 vermiform eggs or 300 J2 RKN are inoculated in each tube in 50 uL of deionized or spring water. Harvest of the cucumber plants is performed 10 to 12 days after inoculation by washing sand off the roots. A root gall rating and visual phytotoxicity rating is assigned using the following scales: Gall rating scale (Gall: % root mass galled): 0=0-5%; 1=6-20%; 2=21-50%; and 3=51-100%. The average of the triplicate gall rating is then calculated: green=0.00-0.33 (no galls); yellow=0.67-1.33 (mild galling); orange=1.67-2.33 (moderate galling); red=2.67-3.00 (severe galling). Visual phytotoxicity scale is also assigned (Vis. tox; visual reduction in root mass compared to the control): rs1=mild stunting; rs2=moderate stunting; rs3=severe stunting.

Experiments in soybeans using soy cyst nematodes (SCN) are similar to RKN assays except for the following changes. After 5-72 hours of soaking soybean seeds are planted in 100% sand in two inch square plastic pots. Seeds can also be soaked in water for a few hours prior to soaking in oligonucleotide solution. Seven days after planting the soybean seed, the nematode soybean cyst nematode (SCN) inoculum (1000 vermiform eggs or 1000 J2s) are applied to the pot. Watering of the test plants is then restricted to only water as needed to prevent wilt for a period of 24 hours. After the 24 hour restricted watering, normal sub-irrigation watering is done for the duration of the test. Twenty eight days after inoculation the test is harvested and cysts counted Experiments in corn using lesion nematodes are similar to above except for the following changes. After 5-72 hours of soaking corn seeds are planted in a sand:turface mix 2:1 in 4 inch deep pots. Seeds can also be soaked in water for a few hours prior to soaking in oligonucleotide solution. Inoculum of 2 μm of roots P. scribneri infested corn roots are applied at seeding and removed from the pot after 7 days. Watering of the test plants is then restricted to only water as needed to prevent wilt for a period of 24 hours after inoculation. After the 24 hour restricted watering, normal sub-irrigation watering as needed is done for the duration of the test. 12-14 days post inoculation, plants are harvested and nematodes extracted for 6 days from the cut up roots in a mist tent.

RKN and SCN J2s are prepared from hatchbowls using the following solutions: RKN solution: 1 L aerated tap water, 1 ml of 50 mg/ml kanamycin, 0.5 ml of 20 mg/ml imazalil sulfate; SCN solution: 1 L aerated tap water, 1 ml of 50 mg/ml kanamycin, 0.5 ml of 20 mg/ml imazalil sulfate, 1430 mg zinc sulfate Hatchbowls are autoclaved 6 oz bowls, lined with screen mesh and paper filter. Approximately 20 ml of appropriate hatch solution is poured into each bowl. Eggs are then place in the bowls and covered with foil. The bowls are then placed in a 25° C. incubator overnight. The next day the hatched J2's are extracted, additional solution added as needed and replaced in the incubator. Each bowl is used for 2 weeks and then disposed.

Example 15. Nematode Control in Cucumber Via Oligonucleotide Application by Seed Soak Cucumber seeds were soaked approximately 72 hours in dsDNA oligos directed to the promoter and/or targeting the coding region of a cucumber EIN2 gene. Soaking solution consists of 20 nm of each ssDNA nucleotide or 0.03-1 nm dsRNA, 0.1% silwet L77, 50 mM NaPO4 in a final volume 200 uL in water. The radicals of the cucumber seeds emerge within 72 hours, after which the seeds were placed on germination paper until root length is approximately 2 inches. Seedlings are transplanted to sand vials for Root Knot Nematode (RKN) inoculation 24 hours later. Ten mL dry sand is added to each vial and seedlings are planted by tilting the vial and laying the seedling in the correct orientation so that the cotyledons are just above the sand and then tilting back to cover the radicles with sand. 3.3 ml water is added to each vial and the vials were placed in racks under fluorescent light banks. 500 vermiform eggs or 300 J2 RKN are inoculated in each tube in 50 uL of deionized or spring water. Harvest of the cucumber plants is performed 10 to 12 days after inoculation by washing sand off the roots. A root gall rating and visual phytotoxicity rating was assigned using the following scales: Gall rating scale (Gall: % root mass galled): 0=0-5%; 1=6-20%; 2=21-50%; and 3=51-100%. The average of the triplicate gall rating was then calculated: green=0.00-0.33 (no galls); yellow=0.67-1.33 (mild galling); orange=1.67-2.33 (moderate galling); red=2.67-3.00 (severe galling). Visual phytotoxicity scale was also assigned (Vis. tox; visual reduction in root mass compared to the control): rs1=mild stunting; rs2=moderate stunting; rs3=severe stunting.

The results of this experiment shown in Table 6 indicate that certain EIN2 oligonucleotide pools exhibited RKN control.

TABLE 4

Treatment regimens.

| Treatment Number # | Description: | Nucleotide ID | Oligos | NaPO4 | water | total |
|---|---|---|---|---|---|---|
| 1 | Ein2 Pool 1 asDNA CDS 80 nmol | T8140-43 | 4 × 10 | 40 | 120 | 200 |
| 2 | Ein2 Pool 2 asDNA CDS 80 nmol | T8144-47 | 4 × 10 | 40 | 120 | 200 |
| 3 | Ein2 Pool 3 asDNA CDS 80 nmol | T8148-51 | 4 × 10 | 40 | 120 | 200 |
| 4 | Ein2 Pool 4 asDNA CDS 80 nmol | T8152-55 | 4 × 10 | 40 | 120 | 200 |
| 5 | Ein2 Pool 1 asDNA prom 80 nmol | T8156-59 | 4 × 10 | 40 | 120 | 200 |
| 6 | Ein2 Pool 2 asDNA prom 80 nmol | T8160-63 | 4 × 10 | 40 | 120 | 200 |
| 7 | Ein2 Pool 3 asDNA prom 80 nmol | T8164-67 | 4 × 10 | 40 | 120 | 200 |
| 8 | Ein2 Pool 4 asDNA prom 80 nmol | T8168-71 | 4 × 10 | 40 | 120 | 200 |
| 9 | GFP asDNA | | | 40 | 40 | 120 | 200 |
| 10 | blank | | | 0 | 40 | 160 | 200 |

TABLE 5

Nucleotide Sequences

| Nucleotide ID | SEQ ID NO: | Sequence |
|---|---|---|
| T8140 | 627 | CTGATAGCCATGGACTGTGGCAGGC |
| T8141 | 628 | AGCCTGATGAATCCAACTGACCGTT |
| T8142 | 629 | CTGCACCACCACCACCCAAGGTATG |
| T8143 | 630 | CAAGCACCCAAGCCATTTTGCAACT |
| T8144 | 631 | ACACTCCACGAGCTGTTATTCTACC |
| T8145 | 632 | TAAAGAAATTTCTCCCTGGCAGCTA |
| T8146 | 633 | CCCGACCCATCTCCCTTGCCTCAGC |
| T8147 | 634 | AATGAAGGAGATTCTTTCATGCGGA |
| T8148 | 635 | TTCATTCCAGAACCTGGTCTCCTAT |
| T8149 | 636 | CCCCATAGTTCAGGCCGACTTTCCA |
| T8150 | 637 | ATACGAGGCTTCGAAAATGCAGGAT |
| T8151 | 638 | TTTGGAGGCAGAAGCATGGTGGCAT |
| T8152 | 639 | TTGACCTCTGCTGGAATGCTTGGGG |
| T8153 | 640 | CTTGCCAGGTTTTGCAGCAGGAGGC |
| T8154 | 641 | TCCAGAAGCATTGCAGCAGTGGTGC |
| T8155 | 642 | GGCAAGAGATGGCTATCTCCACATC |
| T8156 | 643 | gattccataagaagtgcttcaataa |
| T8157 | 644 | caattctaatttcaccctcataaat |
| T8158 | 645 | tctctctcttttttttcatcccttt |
| T8159 | 646 | ctgcttttgcttccacactcccaat |
| T8160 | 647 | agatgcttcagtaacgccagagagt |
| T8161 | 648 | tgaatccatgaattcagtgtggaca |
| T8162 | 650 | tattcacctgggttttccgtactgg |
| T8163 | 651 | agaaaaaaaaggagatagggttgt |
| T8164 | 652 | aaaaccacggatccgatgcaagcta |
| T8165 | 653 | agaaattggccacgagaaatgaaga |
| T8166 | 654 | cccaacccagaacccagaacccaaa |
| T8167 | 655 | aaaaaataccggggactttcatcga |
| T8168 | 656 | tcaaaattaatagagcccattaca |

TABLE 5-continued

Nucleotide Sequences

| Nucleotide ID | SEQ ID NO: | Sequence |
| --- | --- | --- |
| T8169 | 657 | ctggttcggccttaccttaccgcct |
| T8170 | 658 | aagaaaactcgatttagggaggtac |
| T8171 | 659 | gcagctaattccccacgaaatcagt |

TABLE 6

Results of Oligonucleotide Treatment on Nematode Resistance

| Trt. No. | Treatment | Rep Score (% root mass galled) | | | | AVG | stdev |
| --- | --- | --- | --- | --- | --- | --- | --- |
| 1 | Ein2 asDNA CDS T8140-43 | 45 | 45 | 45 | 45 | 45.00 | 0.00 |
| 2 | Ein2 asDNA CDS T8144-47 | 30 | 30 | 45 | 45 | 37.50 | 8.66 |
| 3 | Ein2 asDNA CDS T81448-51 | 25 | 35 | 30 | 35 | 31.25 | 4.79 |
| 4 | Ein2 asDNA CDS T8152-55 | 35 | 25 | 40 | | 33.33 | 7.64 |
| 5 | Ein2 asDNA prom T8156-59 | 35 | 35 | 45 | 30 | 36.25 | 6.29 |
| 6 | Ein2 asDNA prom T8160-63 | 45 | 30 | 40 | 25 | 35.00 | 9.13 |
| 7 | Ein2 asDNA prom T8164-67 | 40 | 40 | 35 | 30 | 36.25 | 4.79 |
| 8 | Ein2 asDNA prom T8168-71 | 45 | 40 | 60 | 40 | 46.25 | 9.46 |
| | GFP asDNA | 50 | 55 | 40 | 50 | 48.75 | 6.29 |
| | blank | 45 | 50 | 50 | 55 | 50.00 | 4.08 |
| | | | | | | Anova: Single Factor | |

Similar protocols were also used to test single oligonucleotides for inhibition of RKN in cucumbers. Data shown in Table 7 indicates that certain single oligonucleotides could provide RKN control.

TABLE 7

Single oligonucleotide mediated control of RKN

| Treatment | Rep Score (% root mass galled) | | | | AVG | stdev |
| --- | --- | --- | --- | --- | --- | --- |
| Ein2 CDS T8148 | 55 | 45 | 45 | 45 | 47.50 | 5.00 |
| Ein2 CDS T8149 | 50 | 40 | 60 | 45 | 48.75 | 8.54 |
| Ein2 CDS T8151 | 40 | 45 | 40 | 40 | 41.25 | 2.50 |
| Ein2 CDS T8152 | 40 | 35 | 40 | 45 | 40.00 | 4.08 |
| Ein2 CDS T8153 | 55 | 50 | 55 | 60 | 55.00 | 4.08 |
| Ein2 CDS T8154 | 60 | | | | 60.00 | |
| Ein2 CDS T8155 | 40 | 45 | 35 | 50 | 42.50 | 6.45 |
| Ein2 CDS T8160 | 60 | 60 | 60 | | 60.00 | 0.00 |
| Ein2 CDS T8161 | 50 | 50 | 60 | 45 | 51.25 | 6.29 |
| Ein2 CDS T8162 | 50 | 40 | 45 | 40 | 43.75 | 4.79 |
| Ein2 CDS T8163 | 50 | 50 | 65 | 75 | 60.00 | 12.25 |
| Ein2 CDS T8160-63 | 40 | 40 | 60 | 50 | 47.50 | 9.57 |
| Ein2 CDS T8148-51 | 50 | 45 | 40 | 40 | 43.75 | 4.79 |
| Ein2 CDS T8152-55 | 50 | 50 | 40 | 50 | 47.50 | 5.00 |
| GFP asDNA | 45 | 60 | 50 | 65 | 55.00 | 9.13 |
| blank | 60 | 60 | | | 60.00 | 0.00 |
| | | | | | Anova: Single Factor | |

Example 16. Barley Powdery Mildew Assay Protocol

Barley seeds (Perry variety) are planted about ¼" into soil in 2 inch pots in the growth chamber and grown at 25° C. with a 16 hr light cycle in 50% humidity. Before polynucleotide application the plants are randomized. Application of polynucleotides (either ssDNA oligos and/or dsRNA) is performed by pipet application where 54 of solution containing nucleotides is applied to both sides of the first leaf. The nucleotide solution applied consists of ~3-15 nm of each ssDNA oligonucleotide or ~0.5-1 nm dsRNA, 0.1-0.3% Silwet L-77, 5 mM NaPO4, and 1% AMS in Gibco ultra pure water. Two days post treatment seedlings are infected with barley powdery mildew (*Blumeria graminis* f sp. *hordei*). The growth chamber settings for the infection are as follows: 23° C., with a 12 hr light cycle in 70% humidity. At seven days post infection disease severity is scored for the percentage of leaf area covered with powdery mildew. Data is analyzed using Anova Single Factor Analysis ($\alpha=0.1$). The ½ LSD is calculated and custom error bars created for the bar graphs. Percent disease reduction is compared to formulation blank and nucleic acid control Example 17 Application of Topical Polynucleotides to Leaves or Seed for *Phytophthora* Control Growth Chamber Whole Plant Assay Soybean seeds are planted in vermiculite in 3 inch pots and allowed to grow for 8 to 11 days. Unifoliate leaves are topically treated with 5 L total volume of polynucleotides (either ssDNA oligos and/or dsRNA) in a solution containing ~3-15 nm of each ssDNA oligonucleotide or ~0.5-1 nm dsRNA, 0.1-0.3% Silwet L-77, 5 mM NaPO4, and 1% AMS in Gibco ultra pure water. One day after topical polynucleotide application, pots are inoculated with 3 to 5 ml of ground up inoculum. *P. sojae* inoculum is grown on V8 agar, ground in a Cuisinart blender and pushed through a syringe. Plants are harvested 21 to 26 days after inoculation. Roots are weighed and checked for disease symptoms.

Petri Plate Seedling Assay

Soybean seeds are sterilized with 4 ml of 37% HCL into 100 ml of 100% bleach over a 3 day period. Bleach and HCL is replaced each day. (Sterile soybeans are critical for the assay to be useful.) Sterile seeds are soaked overnight in a solution comprising polynucleotides (either ssDNA oligos and/or dsRNA) in a solution containing ~3-15 nm of each ssDNA oligonucleotide or ~0.5-1 nm dsRNA, 0.1-0.3% Silwet L-77, 5 mM NaPO4, and 1% AMS in Gibco ultra pure water and transferred to a square petri plate with 8 layers of moistened Whatman filter paper. Seeds are germinated in the dark at 25 C for 5 days, then hypocotyls are wounded and inoculated with a small plug of *P. sojae*. Seedlings are kept under lights at room temperature and hypocotyls are checked for disease symptoms at 3 and 6 days.

What is claimed is:

1. A method for producing a tomato plant exhibiting delayed senescence and/or improved disease tolerance, the method comprising topically applying to a tomato plant surface a composition that comprises:
   (a) at least one double-stranded RNA (dsRNA) polynucleotide that comprises at least 18 contiguous nucleotides that are identical or complementary to a tomato EIN2 gene transcript, wherein the said dsRNA polynucleotide is not operably linked to a promoter or to a viral vector; and
   (b) a transfer agent comprising a surfactant comprising an organosilicone preparation that conditions the tomato plant surface to permeation by the dsRNA polynucleotide into cells of the tomato plant;

wherein said tomato plant exhibits delayed senescence and/or improved disease tolerance in comparison to a control plant that has not been treated with a composition comprising a polynucleotide and a transfer agent and wherein the delayed senescence and/or improved disease tolerance results from suppression of said tomato EIN2 gene.

2. The method of claim 1, wherein said dsRNA polynucleotide comprises at least 18 contiguous nucleotides that are identical or complementary to SEQ ID NO:17.

3. The method of claim 1, wherein one strand of said dsRNA polynucleotide molecule is complementary to a sequence selected from the group consisting of SEQ ID NO: 624, 625, and 626.

4. The method of claim 1, wherein said composition further comprises one or more additional dsRNA polynucleotides that are essentially identical or complementary to a different target gene or transcript thereof.

5. The method of claim 1, wherein said dsRNA polynucleotide is at least 18 to about 24, about 25 to about 50, about 51 to about 100, about 101 to about 300, about 301 to about 500, or at least about 500 or more residues in length.

6. The method of claim 1, wherein said composition further comprises a non-polynucleotide herbicidal molecule, a polynucleotide herbicidal molecule, a polynucleotide that suppresses an herbicide target gene, an insecticide, a fungicide, a nematocide, or a combination thereof.

7. The method of claim 1, wherein said composition further comprises a non-polynucleotide herbicidal molecule and said plant is resistant to said herbicidal molecule.

8. The method of claim 1, wherein the improved disease tolerance is tolerance to *Alternaria solani, Cladosporium fulvum, Oidium neolycopersici, Oidium lycopersici, Phytophthora infestans, Pratylenchus* spp., *Meloidogyne* spp., or *Pseudomonas syringae*.

* * * * *